US012466781B2

(12) United States Patent
von Geldern et al.

(10) Patent No.: US 12,466,781 B2
(45) Date of Patent: Nov. 11, 2025

(54) THYROMIMETICS

(71) Applicant: Autobahn Therapeutics, Inc., San Diego, CA (US)

(72) Inventors: Thomas von Geldern, Richmond, IL (US); Bradley Backes, San Francisco, CA (US); Baoku He, Jiangsu (CN); Jason Harris, San Diego, CA (US)

(73) Assignee: AUTOBAHN THERAPEUTICS, INC., San Diego, CA (US)

(*) Notice: Subject to any disclaimer, the term of this patent is extended or adjusted under 35 U.S.C. 154(b) by 679 days.

(21) Appl. No.: 17/780,465

(22) PCT Filed: Nov. 25, 2020

(86) PCT No.: PCT/US2020/062229
§ 371 (c)(1),
(2) Date: May 26, 2022

(87) PCT Pub. No.: WO2021/108549
PCT Pub. Date: Jun. 3, 2021

(65) Prior Publication Data

US 2023/0048992 A1 Feb. 16, 2023

(30) Foreign Application Priority Data

Nov. 29, 2019 (WO) ................ PCT/CN2019/122062
May 1, 2020 (WO) ................ PCT/CN2020/085540

(51) Int. Cl.

| | |
|---|---|
| ***C07C 69/734*** | (2006.01) |
| ***A61P 11/00*** | (2006.01) |
| ***C07C 59/70*** | (2006.01) |
| ***C07C 235/74*** | (2006.01) |
| ***C07C 243/18*** | (2006.01) |
| ***C07C 259/06*** | (2006.01) |
| ***C07D 205/04*** | (2006.01) |
| ***C07D 261/14*** | (2006.01) |

(52) U.S. Cl.
CPC ............ *C07C 69/734* (2013.01); *A61P 11/00* (2018.01); *C07C 59/70* (2013.01); *C07C 235/74* (2013.01); *C07C 243/18* (2013.01); *C07C 259/06* (2013.01); *C07D 205/04* (2013.01); *C07D 261/14* (2013.01)

(58) Field of Classification Search
CPC .............................. C07C 69/734; C07C 59/70
See application file for complete search history.

(56) References Cited

U.S. PATENT DOCUMENTS

| | | | |
|---|---|---|---|
| 3,845,770 | A | 11/1974 | Theeuwes et al. |
| 4,326,525 | A | 4/1982 | Swanson et al. |
| 4,652,441 | A | 3/1987 | Okada et al. |
| 4,675,189 | A | 6/1987 | Kent et al. |
| 4,677,191 | A | 6/1987 | Tanaka et al. |
| 4,723,027 | A | 2/1988 | Stoutamire et al. |
| 4,728,721 | A | 3/1988 | Yamamoto et al. |
| 4,741,897 | A | 5/1988 | Andrews et al. |
| 4,917,893 | A | 4/1990 | Okada et al. |
| 4,992,445 | A | 2/1991 | Lawter et al. |
| 5,001,139 | A | 3/1991 | Lawter et al. |
| 5,023,252 | A | 6/1991 | Hseih |
| 5,466,569 | A | 11/1995 | Eber et al. |
| 5,616,345 | A | 4/1997 | Geoghegan et al. |
| 5,883,294 | A | 3/1999 | Scanlan et al. |
| 6,054,485 | A | 4/2000 | Schwartz et al. |
| 6,107,517 | A | 8/2000 | Scanlan et al. |
| 6,236,946 | B1 | 5/2001 | Scanlan et al. |
| 7,288,571 | B2 | 10/2007 | Hangeland et al. |

(Continued)

FOREIGN PATENT DOCUMENTS

| | | | |
|---|---|---|---|
| CN | 1882327 | A | 12/2006 |
| CN | 101180097 | A | 5/2008 |

(Continued)

OTHER PUBLICATIONS

Actis et al., Small molecule inhibitors of PCNA/PIP-box interaction suppress translesion DNA synthesis. Bioorg Med Chem. 21(7):1972-1977 (2013).
Alonso-Merino et al., Thyroid hormones inhibit TGF-beta signaling and attenuate fibrotic responses. Proc Natl Acad Sci U S A. 113(24):E3451-E3460 (2016).
Ashraf et al., Synthesis, characterization and in vitro hydrolysis studies of ester and amide prodrugs of dexibuprofen. Medicinal Chemistry Research 21:3361-3368 (2012).
Balkwill et al., Smoldering and polarized inflammation in the initiation and promotion of malignant disease. Cancer Cell 7(3):211-217 (2005).
Bastin et al. Salt selection and optimisation procedures for pharmaceutical new chemical entities. Organic Process Research & Development 4.5:427-435 (2000).

(Continued)

*Primary Examiner* — Adam C Milligan
*Assistant Examiner* — Karen Cheng
(74) *Attorney, Agent, or Firm* — WILSON SONSINI GOODRICH & ROSATI

(57) ABSTRACT

Compounds are provided having the structure of Formula (I) or a pharmaceutically acceptable isomer, racemate, hydrate, solvate, isotope, or salt thereof, wherein $R^1$, $R^2$, $X^1$, $X^2$, $Y^1$, and $Y^2$ are as defined herein. Such compounds function as thyromimetics and have utility for treating diseases such as neurodegenerative disorders and fibrotic diseases. Pharmaceutical compositions containing such compounds are also provided, as are methods of their use and preparation.

(I)

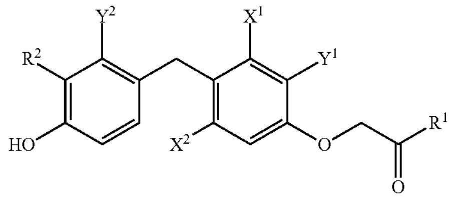

20 Claims, 1 Drawing Sheet

(56) References Cited

U.S. PATENT DOCUMENTS

| | | | |
|---|---|---|---|
| 7,302,347 | B2 | 11/2007 | Baxter et al. |
| 7,915,261 | B2 | 3/2011 | Ishii et al. |
| 7,919,494 | B2 | 4/2011 | Ishii et al. |
| 7,919,495 | B2 | 4/2011 | Ishii et al. |
| 9,562,012 | B2 | 2/2017 | Tanis et al. |
| 9,701,650 | B2 | 7/2017 | Scanlan et al. |
| 10,130,643 | B2 | 11/2018 | Cable et al. |
| 10,226,438 | B2 | 3/2019 | Scanlan et al. |
| 10,392,356 | B2 | 8/2019 | Scanlan et al. |
| 10,544,075 | B2 | 1/2020 | Scanlan et al. |
| 10,870,616 | B2 | 12/2020 | Scanlan et al. |
| 11,104,654 | B2 | 8/2021 | Scanlan et al. |
| 11,325,886 | B2 | 5/2022 | Scanlan et al. |
| 11,510,887 | B2 | 11/2022 | Scanlan et al. |
| 11,578,032 | B2 | 2/2023 | Scanlan |
| 11,613,517 | B2 | 3/2023 | Scanlan et al. |
| 2003/0203898 | A1 | 10/2003 | Haning et al. |
| 2003/0215434 | A1 | 11/2003 | Khan et al. |
| 2005/0282872 | A1 | 12/2005 | Hangeland et al. |
| 2007/0021407 | A1 | 1/2007 | Boyle et al. |
| 2008/0124280 | A1 | 5/2008 | Mousa et al. |
| 2008/0221170 | A1 | 9/2008 | Roberts et al. |
| 2009/0028925 | A1 | 1/2009 | Erion et al. |
| 2009/0062330 | A1 | 3/2009 | Kalafer et al. |
| 2009/0105347 | A1 | 4/2009 | Scanlan et al. |
| 2009/0232879 | A1 | 9/2009 | Cable et al. |
| 2009/0306225 | A1 | 12/2009 | Lichter et al. |
| 2009/0318514 | A1 | 12/2009 | Garcia Collazo et al. |
| 2010/0099608 | A1 | 4/2010 | Browning |
| 2010/0216771 | A1 | 8/2010 | Li |
| 2010/0303934 | A1 | 12/2010 | Soumyanath et al. |
| 2011/0178134 | A1 | 7/2011 | Jaehne et al. |
| 2012/0004166 | A1 | 1/2012 | Keil et al. |
| 2012/0245213 | A1 | 9/2012 | Mosinger et al. |
| 2013/0289024 | A1 | 10/2013 | Johansen et al. |
| 2014/0235676 | A1 | 8/2014 | Landreth |
| 2014/0288077 | A1 | 9/2014 | Fujii et al. |
| 2016/0081955 | A1 | 3/2016 | Scanlan et al. |
| 2016/0244418 | A1 | 8/2016 | Scanlan et al. |
| 2017/0007589 | A1 | 1/2017 | Ding et al. |
| 2017/0226154 | A1 | 8/2017 | Evans et al. |
| 2018/0057472 | A1 | 3/2018 | Scanlan et al. |
| 2019/0175531 | A1 | 6/2019 | Scanlan et al. |
| 2020/0181103 | A1 | 6/2020 | Scanlan et al. |
| 2020/0361849 | A1 | 11/2020 | Von Geldern et al. |
| 2020/0405669 | A1 | 12/2020 | Scanlan et al. |
| 2021/0002208 | A1 | 1/2021 | Scanlan |
| 2021/0053917 | A1 | 2/2021 | Von Geldern et al. |
| 2021/0087137 | A1 | 3/2021 | Scanlan et al. |

FOREIGN PATENT DOCUMENTS

| | | | |
|---|---|---|---|
| CN | 101189248 | A | 5/2008 |
| CN | 101547898 | A | 9/2009 |
| CN | 101600450 | A | 12/2009 |
| CN | 101610774 | A | 12/2009 |
| CN | 101848712 | A | 9/2010 |
| CN | 107848940 | A | 3/2018 |
| EP | 3259246 | A1 | 12/2017 |
| JP | S59116256 | A | 7/1984 |
| JP | H09301917 | A | 11/1997 |
| JP | 2004512303 | A | 4/2004 |
| JP | 2004517037 | A | 6/2004 |
| JP | 2008542301 | A | 11/2008 |
| JP | 2008545711 | A | 12/2008 |
| JP | 2012106996 | A | 6/2012 |
| JP | 2016517884 | A | 6/2016 |
| PE | 20180021 | A1 | 1/2018 |
| RU | 2007148927 | A | 7/2009 |
| WO | WO-9321146 | A1 | 10/1993 |
| WO | WO-9900353 | A1 | 1/1999 |
| WO | WO-0039077 | A2 | 7/2000 |
| WO | WO-0073292 | A1 | 12/2000 |
| WO | WO-0160784 | A1 | 8/2001 |
| WO | WO-0190053 | A1 | 11/2001 |
| WO | WO-0200167 | A2 | 1/2002 |
| WO | WO-0234260 | A1 | 5/2002 |
| WO | WO-02072539 | A1 | 9/2002 |
| WO | WO-02081426 | A1 | 10/2002 |
| WO | WO-2004043939 | A1 | 5/2004 |
| WO | WO-2006031922 | A2 | 3/2006 |
| WO | WO-2006128056 | A2 | 11/2006 |
| WO | WO-2006128058 | A2 | 11/2006 |
| WO | WO-2007110226 | A1 | 10/2007 |
| WO | WO-2008125724 | A1 | 10/2008 |
| WO | WO-2013006734 | A1 | 1/2013 |
| WO | WO-2014078892 | A1 | 5/2014 |
| WO | WO-2014178892 | A1 | 11/2014 |
| WO | WO-2014178931 | A1 | 11/2014 |
| WO | WO-2015188015 | A1 | 12/2015 |
| WO | WO-2016134292 | A1 | 8/2016 |
| WO | WO-2017015360 | A1 | 1/2017 |
| WO | WO-2017201320 | A1 | 11/2017 |
| WO | WO-2018032012 | A1 | 2/2018 |
| WO | WO-2018208707 | A1 | 11/2018 |
| WO | WO-2019160980 | A1 | 8/2019 |
| WO | WO-2020118564 | A1 | 6/2020 |
| WO | WO-2020123861 | A1 | 6/2020 |
| WO | WO-2020180624 | A1 | 9/2020 |
| WO | WO-2021108549 | A1 | 6/2021 |

OTHER PUBLICATIONS

Baxi et al., A selective thyroid hormone beta receptor agonist enhances human and rodent oligodendrocyte differentiation. Glia 62(9):1513-1529 (2014).

Baxter et al., Selective activation of thyroid hormone signaling pathways by GC-1: a new approach to controlling cholesterol and body weight. Trends Endocrinol Metab. 15(4):154-157 (2004).

Baxter et al., Selective modulation of thyroid hormone receptor action. J. Steroid Biochem. Mol. Bio. 76:31-42 (2001).

Belikov. Pharmaceutical Chemistry: Manual. Moscow: MEDpress-inform (pp. 27-29) (2007).

Berge et al. Pharmaceutical Salts. Journal of Pharmaceutical Sciences 66(1):1-19 (Jan. 1977).

Berkenstam et al., The thyroid hormone mimetic compound KB2115 lowers plasma LDL cholesterol and stimulates bile acid synthesis without cardiac effects in humans. Proc Natl Acad Sci U S A 105(2):663-667 (2008).

Bernal et al., Action of thyroid hormone in brain. J Endocrinol Invest. 25(3):268-288 (2002).

Bernal et al., Thyroid hormone receptors in brain development and function. Nat Clin Pract Endocrinol Metab. 3(3):249-259 (2007).

Biondi et al., Hypothyroidism as a risk factor for cardiovascular disease. Endocrine 24: 1-13 (2004).

Boger et al., Fatty acid amide hydrolase substrate specificity. Bioorg Med Chem Lett. 10(23):2613-2616 (2000).

Borngraeber et al. Ligand Selectivity by Seeking Hydrophobicity in Thyroid Hormone Receptor. PNAS USA 100(26):15358-15363 (2003).

Boymond et al., Preparation of highly functionalized grignard reagents by an iodine-magnesium exchange reaction and its application in solid-phase synthesis. Angew Chem Int Ed Engl. 37(12):1701-1703 (1998).

Calza et al., Thyroid hormone and remyelination in adult central nervous system: a lesson from an inflammatory-demyelinating disease. Brain Res Brain Res Rev. 48(2):339-346 (2005).

Chiellini et al., A high-affinity subtype-selective agonist ligand for the thyroid hormone receptor. Chemistry and Biology 5(6):299-306 (1998).

Chiellini et al., Synthesis and biological activity of novel thyroid hormone analogues: 5'-aryl substituted GC-1 derivatives. Bioorg Med Chem. 10(2):333-346 (2002).

Cravatt et al., Supersensitivity to anandamide and enhanced endogenous cannabinoid signaling in mice lacking fatty acid amide hydrolase. Proc Natl Acad Sci U S A 98(16):9371-9376 (2001).

Dell'Acqua et al., Functional and molecular evidence of myelin- and neuroprotection by thyroid hormone administration in experimental allergic encephalomyelitis. Neuropathol Appl Neurobiol. 38(5):454-470 (2012).

(56) References Cited

OTHER PUBLICATIONS

Devereaux et al., Increasing thyromimetic potency through halogen substitution. ChemMedChem. 11(21):2459-2465 (2016).
D'Intino et al., Triiodothyronine administration ameliorates the demyelination/remyelination ratio in a non-human primate model of multiple sclerosis by correcting tissue hypothyroidism. J Neuroendocrinol. 23(9):778-790 (2011).
Doran et al., The impact of P-glycoprotein on the disposition of drugs targeted for indications of the central nervous system: evaluation using the MDR1A/1B knockout mouse model. Drug Metab Dispos. 33(1):165-174 (2005).
Edgar et al., An efficient and selective method for the preparation of iodophenols. Journal of Organic Chemistry 55:5287-5291 (1990).
Engelen et al., X-linked adrenoleukodystrophy (X-ALD): clinical presentation and guidelines for diagnosis, follow-up and management. Orphanet J Rare Dis. 7:51 [1-14] (2012).
Erion et al., Targeting thyroid hormone receptor-beta agonists to the liver reduces cholesterol and triglycerides and improves the therapeutic index. Proc Natl Acad Sci U S A 104(39):15490-15495 (2007).
Ferrara et al., Ester-to-amide rearrangement of ethanolamine-derived prodrugs of sobetirome with increased blood-brain barrier penetration. Bioorg Med Chem. 25(10):2743-2753 (2017).
Fourcade et al., Thyroid hormone induction of the adrenoleukodystrophy-related gene (ABCD2). Mol. Pharmacol. 63:1296-1303 (2003).
Genin et al., Induction of the adrenoleukodystrophy-related gene (ABCD2) by thyromimetics. J Steroid Biochem Mol Biol. 116(1-2):37-43 (2009).
Gold et al. Understanding pathogenesis and therapy of multiple sclerosis via animal models: 70 years of merits and culprits in experimental autoimmune encephalomyelitis research. Brain 129:1953-1971 (2006).
Gould et al. Salt Selection for Basic Drugs. Int J. Pharm. 33:201-217 (1986).
Grover et al., Effects of the thyroid hormone receptor agonist GC-1 on metabolic rate and cholesterol in rats and primates: selective actions relative to 3,5,3'-triiodo-L-thyronine. Endocrinology 145(4):1656-1661 (2004).
Hafer-Macko et al., Immune attack on the Schwann cell surface in acute inflammatory demyelinating polyneuropathy. Ann. Neurol. 39:625-635 (1996).
Hangeland et al., Thyroid receptor ligands. Part 2: Thyromimetics with improved selectivity for the thyroid hormone receptor beta. Bioorg Med Chem Lett 14(13):3549-3553 (2004).
Hartley et al., A thyroid hormone-based strategy for correcting the biochemical abnormality in X-linked adrenoleukodystrophy. Endocrinology 158(5):1328-1338 (2017).
Johnson, Demyelinating diseases, in: The Infectious Etiology of Chronic Diseases: Defining the Relationship, Enhancing the Research, and Mitigating the Effects: Workshop Summary. Institute of Medicine (US) Forum on Microbial Threats; Knobler SL, O'Connor S, Lemon SM, et al., editors. Washington (DC): National Academies Press (US); 45-52 (2004).
Kavirajan et al., Efficacy and adverse effects of cholinesterase inhibitors and memantine in vascular dementia: a meta-analysis of randomised controlled trials. Lancet Neurol. 6(9):782-792 (2007).
Koenning et al., Myelin gene regulatory factor is required for maintenance of myelin and mature oligodendrocyte identity in the adult CNS. J Neurosci. 32(36):12528-12542 (2012).
Krogsgaard-Larsen et al. Chapter 4: Design and application of prodrugs. Textbook of Drug Designing and Discovery, US, Taylor & Francis Inc (3rd Ed.) (pp. P460-P514).
Lee et al., Drug transporters in the central nervous system: brain barriers and brain parenchyma considerations. Pharmacological Review 53(4):569-596 (2001).
Link et al., Photo-caged agonists of the nuclear receptors RARgamma and TRbeta provide unique time-dependent gene expression profiles for light-activated gene patterning. Bioorg Med Chem. 12(22):5949-5959 (2004).
Lu et al., An expedient synthesis of benzyl 2,3,4-tri-O-benzyl-beta-D-glucopyranoside and benzyl 2,3,4-tri-O-benzyl-beta-D-mannopyranoside. Carbohydr Res. 340(6):1213-1217 (2005).
Malm et al., Recent advances in the development of agonists selective for beta1-type thyroid hormone receptor. Mini Rev Med Chem. 7(1):79-86 (2007).
Mandal et al., Pd-C-induced catalytic transfer hydrogenation with triethylsilane. Journal of Organic Chemistry 72(17):6599-6601 (2007).
Martin et al. The proliferating cell nuclear antigen regulates retinoic acid receptor transcriptional activity through direct protein-protein interaction. Nucleic Acids Res. 33(13):4311-21 (2005).
Massague. TGFbeta signalling in context. Nat Rev Mol Cell Biol. 13(10):616-630 (2012).
Meinig et al., Structure-activity relationships of central nervous system penetration by fatty acid amide hydrolase (FAAH)-targeted thyromimetic prodrugs. ACS Med Chem Lett. 10(1):111-116 (2018).
Meinig et al., Targeting fatty-acid amide hydrolase with prodrugs for CNS-selective therapy. ACS Chem Neurosci. 8(11):2468-2476 (2017).
Miller et al., Primary-progressive multiple sclerosis. Lance Neurol. 6:903-912 (2007).
Miyabara et al., Thyroid hormone receptor-beta-selective agonist GC-24 spares skeletal muscle type I to II fiber shift. Cell Tissue Res. 321(2):233-241 (2005).
Montalban et al. Primary progressive multiple sclerosis diagnostic criteria: a reappraisal. Mult Scler 15(12):1459-65 (2009).
Nguyen et al., Hammett analysis of selective thyroid hormone receptor modulators reveals structural and electronic requirements for hormone antagonists. J Am Chem Soc. 127(13):4599-4608 (2005).
Nguyen et al., Rational design and synthesis of a novel thyroid hormone antagonist that blocks coactivator recruitment. J Med Chem. 45(15):3310-3320 (2002).
Ocasio et al., Characterization of thyroid hormone receptor alpha (TRalpha)-specific analogs with varying inner- and outer-ring substituents. Bioorg Med Chem. 16(2):762-770 (2008).
Ocasio et al., Design and characterization of a thyroid hormone receptor alpha (TRalpha)-specific agonist. ACS Chem Biol. 1(9):585-593 (2006).
O'Shea et al., Characterization of skeletal phenotypes of TRalpha1 and TRbeta mutant mice: implications for tissue thyroid status and T3 target gene expression. Nucl Recept Signal 4:e011 [1-5] (2006).
Oppenheimer et al., Molecular basis of thyroid hormone-dependent brain development. Endocrine Reviews 18(4):462-475 (1997).
Patani et al. Bioisosterism: A Rational Approach in Drug Design. Chem. Rev. 96:3147-3176 (1996).
PCT/US2020/062229 International Invitation to Pay Additional Fees dated Jan. 27, 2021.
PCT/US2020/062229 International Search Report and Written Opinion dated Mar. 24, 2021.
Penning et al., Structure-activity relationship studies on 1-[2-(4-Phenylphenoxy)ethyl]pyrrolidine (SC-22716), a potent inhibitor of leukotriene A(4) (LTA(4)) hydrolase. Journal of Medicinal Chemistry 43(4):721-735 (2000).
Placzek et al., New synthetic routes to thyroid hormone analogs: d(6)-sobetirome, (3)H-sobetirome, and the antagonist NH-3. Tetrahedron 71(35):5946-5951 (2015).
Placzek et al., Sobetirome prodrug esters with enhanced blood-brain barrier permeability. Bioorg Med Chem. 24(22):5842-5854 (2016).
PubChem SID 235918886 [https://pubchem.ncbi.nlm.nih.gov/substance/235918886] (2015).
PubChem SID 319635332 [https://pubchem.ncbi.nlm.nih.gov/substance/319635332] (2016).
Reichel et al., The role of blood-brain barrier studies in the pharmaceutical industry. Curr Drug Metab. 7(2):183-203 (2006).
Scanlan. Safety and Pharmacodynamic Study of Sobetirome in X-Linked Adrenoleukodystrophy (X-ALD), available online at ClinicalTrials.gov on Feb. 6, 2013, 3 pages (clinicaltrials.gov/ct2/show/NCT01787578?term=Scanlan&rank=1).
Scanlan. Sobetirome: a case history of bench-to-clinic drug discovery and development. Heart Fail Rev 15:177-182 (2010).

(56) References Cited

OTHER PUBLICATIONS

Shiohara et al., Discovery of novel indane derivatives as liver-selective thyroid hormone receptor beta (TRbeta) agonists for the treatment of dyslipidemia. Bioorg Med Chem 20(11):3622-3634 (2012).
Smith et al., Water soluble prodrug of a COX-2 selective inhibitor suitable for intravenous administration in models of cerebral ischemia. Bioorganic & Medicinal Chemistry Letters 15(13):3197-3200 (2005).
Takahashi et al., Characterisation of liver-specific distribution of a novel 1-benzyl-4-aminoindole-based thyroid hormone receptor beta agonist, SKL-13784: comparison with GC-1. Xenobiotica 46(2):108-116 [1-9] (2016; published online 2015).
Takahashi et al., In vivo evaluation of 1-benzyl-4-aminoindole-based thyroid hormone receptor beta agonists: importance of liver selectivity in drug discovery. Biol Pharm Bull. 37(7):1103-1108 (2014).
Takahashi et al., Synthesis and pharmacological characterization of 1-benzyl-4-aminoindole-based thyroid hormone receptor beta agonists. Bioorg Med Chem. 22(1):488-498 (2014).
Tancevski et al., The resurgence of thyromimetics as lipid-modifying agents. Curr Opin Investig Drugs 10(9):912-918 (2009).
Tangdenpaisal et al., Synthesis of the thyroid hormone analog GC-1 via Bi(OTf)3-catalyzed benzylation. Tetrahedron 70: 6789-6795 (2014).
Taub et al., Lipid lowering in healthy volunteers treated with multiple doses of MGL-3196, a liver-targeted thyroid hormone receptor-beta agonist. Atherosclerosis 230(2):373-380 (2013).
Tegeli et al. Synthesis and evaluation of amide prodrugs of mefenamic acid. International Journal of Chemical Sciences 12(3):1033-1043.
Thyroid. Abstract from poster presented at the 87th Annual Meeting of the American Thyroid Association (Oct. 18-22, 2017).
Trost et al., The thyroid hormone receptor-beta-selective agonist GC-1 differentially affects plasma lipids and cardiac activity. Endocrinology 141(9):3057-3064 (2000).
U.S. Department of Health and Human Services, Health Resources and Services Administration (HRSA), Orphan Drug Designations and Approvals List as of Sep. 3, 2013. http://www.hrsa.gov/opa/programrequirements/orphandrugsexclusion/ [originally accessed 2014/updated Mar. 1, 2021].
Valadares et al. Role of halogen bonds in thyroid hormone receptor selectivity: pharmacophore-based 3D-QSSR studies. J Chem Inf Model 49(11):2606-2616 (2009).
Varga et al., Antitransforming growth factor-beta therapy in fibrosis: recent progress and implications for systemic sclerosis. Curr Opin Rheumatol. 20(6):720-728 (2008).
Vattakatuchery et al., Acetylcholinesterase inhibitors in cognitive impairment in Huntington's disease: A brief review. 3(3):62-64 (2013).
Ye et al, Thyroid receptor ligands. 1. Agonist ligands selective for the thyroid receptor beta1. J Med Chem. 46(9):1580-1588 (2003).
Yen., Physiological and molecular basis of thyroid hormone action. Physiological Reviews 81(3):1097-1142 (2001).
Yoshihara et al., A designed antagonist of the thyroid hormone receptor. Bioorg Med Chem Lett. 11(21):2821-2825 (2001).
Yoshihara et al., Structural determinants of selective thyromimetics. J Med Chem. 46(14):3152-3161 (2003).
Zhang et al., Thyroid hormone potentially benefits multiple sclerosis via facilitating remyelination. Mol Neurobiol. 53(7):4406-4416 (2016).

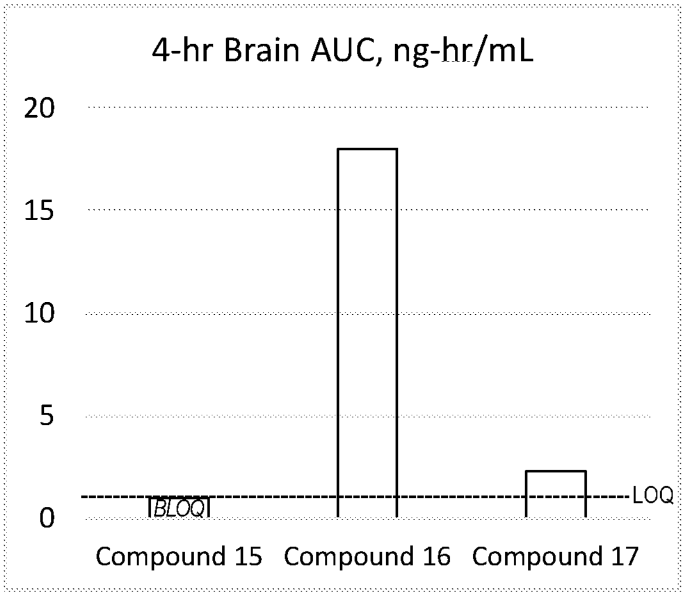
4-hr Brain AUC, ng-hr/mL
20
15
10
5
0
BLOQ
LOQ
Compound 15
Compound 16
Compound 17

THYROMIMETICS

BACKGROUND

Technical Field

The invention relates to thyromimetic compounds and to products containing the same, as well as to methods of their use and preparation.

Description of the Related Art

Thyroid hormone (TH) is a key signal for oligodendrocyte differentiation and myelin formation during development, and also stimulates remyelination in adult models of multiple sclerosis (MS) (Calzà et al., *Brain Res Revs* 48:339-346, 2005). However, TH is not an acceptable long-term therapy due to the limited therapeutic window in which remyelination can be achieved while avoiding the cardiotoxicity and bone demineralization associated with chronic hyperthyroidism. Some thyroid hormone analogs can activate thyroid hormone-responsive genes while avoiding the associated downsides of TH by exploiting molecular and physiological features of thyroid hormone receptors (Malm et al., *Mini Rev Med Chem* 7:79-86, 2007). These receptors are expressed in two major forms with heterogenous tissue distributions and overlapping but distinct sets of target genes (Yen, *Physiol Rev* 81:1097-1142, 2001). TRα is enriched in the heart, brain, and bone while TRβ is enriched in the liver (O'Shea et al., *Nucl Recept Signal* 4:e011, 2006).

It has also been reported that TH can inhibit the transforming growth factor beta (TGF-β) signaling, and, therefore, attenuate fibrotic responses (Alonso-Merino et al., *Proc Natl Acad Sci USA.* 113(24):E3451-60, 2016). TGF-β is a cytokine with pleiotropic effects in tissue homeostasis that plays a key role in pathological processes such as fibrosis (Massague, *Nat Rev Mol Cell Biol.* 13(10):616-630, 2012). By inhibiting TGF-β signalling, TR ligands or agonists could have beneficial effects to block the progression of fibrotic diseases, such as idiopathic pulmonary fibrosis (IPF) or systemic sclerosis (Varga et al., *Curr Opin Rheumatol.* 20(6): 720-728, 2008).

Developing selective thyromimetics has been challenging due to the high sequence homology of thyroid hormone receptor subtypes; namely, only one amino acid residue on the internal surface of the ligand binding domain cavity varies between the α1 and β1 forms. Despite this challenge, several groups have reported TRβ-selective agonists. Scanlan et al. identified GC-1 (sobetirome) as one of the first potent analogs to demonstrate significant TRβ-selectivity in vitro (Chiellini et al., *Chem Biol* 5:299-306, 1998; Yoshihara et al., *J Med Chem* 46:3152-3161, 2003) and in vivo (Trost et al., *Endocrinology* 141:3057-3064, 2000; Grover et al., *Endocrinology* 145:1656-1661, 2004; Baxter et al., *Trends Endocrinol Metab* 15:154-157, 2004). As used herein, the term "sobetirome" refers to a synthetic diarylmethane derivative that was investigated clinically as a potential therapeutic for hypercholesterolemia (see U.S. Pat. No. 5,883,294, which is incorporated by reference herein). Other names for sobetirome found in the literature and regulatory filings include QRX-431 and GC-1. Metabasis employs a similar core with a novel liver-targeting prodrug strategy in MB07811 (Erion et al., *PNAS* 104(39), 15490-15495, 2007). Madrigal has reported TRβ-selective activity in vivo for MGL-3196 (Taub et al., *Atherosclerosis* 230(2):373-380, 2013). KaroBio has reported on eprotirome (KB2115; Berkenstam et al., *PNAS* 105(2):663-668, 2008) and KB-141 (Ye et al., *J Med Chem* 46:1580-1588, 2003), both of which demonstrate improved TRβ-selectivity in vitro. Further studies from this group highlight additional selective compounds (Hangeland et al., BMCL 14:3549-3553, 2004). Two TRβ-selective agonists, identified as SKL-12846 and SKL-13784, have been reported to accumulate in the liver and to reduce cholesterol levels in rodents (Takahashi et al., BMC 22(1):488-498, 2014; *Xenobiotica* 2015, 1-9). Kissei has also reported selective compounds (Shiohara et al., BMC 20(11), 3622-3634, 2012).

While progress has been made in this field, there remains a need in the art for further selective thyromimetic compounds, as well as to products containing the same, and for methods related to their use and preparation.

BRIEF SUMMARY

Disclosed herein are compounds according to Formula I:

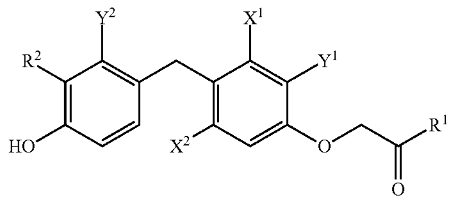

(I)

or a pharmaceutically acceptable isomer, racemate, hydrate, solvate, isotope, or salt thereof, wherein $R^1$, $R^2$, $X^1$, $X^2$, $Y^1$, and $Y^2$ are as defined below.

In an embodiment, a pharmaceutical composition is provided comprising a compound having the structure of Formula (I), or a pharmaceutically acceptable isomer, racemate, hydrate, solvate, isotope, or salt thereof, in combination with a pharmaceutically acceptable carrier, diluent, or excipient. In an embodiment, the pharmaceutical composition is for use in treating a neurodegenerative disorder including neurodegenerative disorders classified as a demyelinating disease such as X-linked adrenoleukodystrophy or multiple sclerosis. In another embodiment, the pharmaceutical composition is for use in treating a medical condition associated increased activity of TGF-β, such as a fibrotic disease.

In an embodiment, a method is provided for treating a neurodegenerative disorder in a subject in need thereof, comprising administering a compound having the structure of Formula (I), or a pharmaceutically acceptable salt or composition comprising the same. In some aspects, the neurodegenerative disorder can be classified as a demyelinating disease such as X-linked adrenoleukodystrophy or multiple sclerosis.

In another embodiment, a method is provided for treating a medical condition associated with over-expression of TGF-β in a subject in need thereof, comprising administering a compound having the structure of Formula (I), or a pharmaceutically acceptable salt or composition comprising the same. In some aspects, the medical condition associated with over-expression of TGF-β is a fibrotic disease.

DRAWINGS

FIG. 1 indicates that the amide prodrugs Compound 16 & 17 provide higher brain levels of the parent acid Compound 15 than are achieved by dosing Compound 15 itself.

DETAILED DESCRIPTION

As mentioned above, the invention relates to thyromimetic compounds, to products comprising the same, and to methods for their use and synthesis.

In one embodiment, compounds are provided having the structure of Formula (I):

(I)

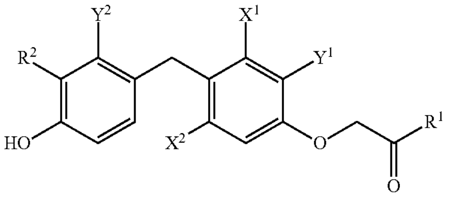

or a pharmaceutically acceptable isomer, racemate, hydrate, solvate, isotope, or salt thereof, wherein:

$X^1$ is lower alkyl, lower alkenyl, lower haloalkyl, or halo;

$X^2$ is lower alkyl, lower alkenyl, lower haloalkyl, or halo;

$Y^1$ and $Y^2$ are each, independently, H, cyano, halogen, lower alkyl, or lower alkoxy, wherein at least one of $Y^1$ and $Y^2$ is not H;

$R^1$ is $-NR^{1a}R^{1b}$ or $-OR^{1c}$;

$R^{1a}$ and $R^{1b}$ are each, independently, H, lower alkyl, lower alkenyl, lower alkynyl, $-OR^a$, $-NR^aR^b$, carbocycle, carbocyclealkyl, heterocycle, or heterocyclealkyl, or $R^{1a}$ and $R^{1b}$ taken together with the nitrogen atom to which they are attached form heterocycle;

$R^{1c}$ is H, lower alkyl, carbocycle, heterocycle, carbocyclealkyl, or heterocyclealkyl; and $R^2$ is lower alkyl, lower alkenyl, carbocycle, heterocycle, carbocyclealkyl, or heterocyclealkyl;

wherein $R^{1a}$, $R^{1b}$, $R^{1c}$, and $R^2$ are each, independently, optionally substituted with one or more halo, lower alkyl, lower haloalkyl, cyano, $-OR'$, $-NR'R''$, $=O$, $=S$, $-S(O)_2R'$ or $-S(O)_2OR'$, wherein R' and R'' are each, independently, H, lower alkyl, or lower haloalkyl.

The acid compounds of the present invention ($R^1=-OR^{1c}$ and $R^{1c}=H$) are active agonists selectively activating the TRβ receptor. The amide compounds of the present invention ($R^1=-NR^{1a}R^{1b}$) may act as substrates for the specific hydrolase enzyme fatty acid-amide hydrolase (FAAH), which cleaves the amide, liberating the thyromimetic. Thus, prodrug conversion to drug is enhanced in tissues that express high levels of FAAH such as the central nervous system. FIG. 1 indicates that the amide prodrugs Compound 16 and 17 provides markedly higher brain levels of the parent acid Compound 15, than can be achieved by dosing Compound 15 itself. The ester compounds of the present invention ($R^1=-OR^{1c}$ and $R^{1c}\neq H$) are also prodrugs, typically processed through the action of esterases which may exist selectively in specific tissues.

As used herein, "lower alkyl" means a straight chain or branched alkyl group having from 1 to 8 carbon atoms, in some embodiments from 1 to 6 carbon atoms, in some embodiments from 1 to 4 carbon atoms, and in some embodiments from 1 to 3 carbon atoms. Examples of straight chain lower alkyl groups include, but are not limited to, methyl, ethyl, n-propyl, n-butyl, n-pentyl-, n-hexyl, n-heptyl, and n-octyl groups. Examples of branched lower alkyl groups include, but are not limited to, isopropyl, iso-butyl, sec-butyl, t-butyl, neopentyl, isopentyl, and 2,2-dimethylpropyl groups.

As used herein, "lower alkenyl" means a straight chain or branched alkenyl group having from 2 to 8 carbon atoms, in some embodiments from 2 to 6 carbon atoms, in some embodiments from 2 to 4 carbon atoms, and in some embodiments from 2 to 3 carbon atoms. Alkenyl groups are unsaturated hydrocarbons that contain at least one carbon-carbon double bond. Examples of lower alkenyl groups include, but are not limited to, vinyl, propenyl, isopropenyl, butenyl, pentenyl, and hexenyl.

As used herein, "lower alkynyl" means a straight chain or branched alkynyl group having from 2 to 8 carbon atoms, in some embodiments from 2 to 6 carbon atoms, in some embodiments from 2 to 4 carbon atoms, and in some embodiments from 2 to 3 carbon atoms. Alkynyl groups are unsaturated hydrocarbons that contain at least one carbon-carbon triple bond. Examples of lower alkynyl groups include, but are not limited to, ethynyl, propynyl, butynyl, pentynyl, and hexynyl.

"Halo" or "halogen" refers to fluorine, chlorine, bromine, and iodine.

"Hydroxy" refers to $-OH$.

"Cyano" refers to $-CN$.

"Lower haloalkyl" refers to a lower alkyl as defined above with one or more hydrogen atoms replaced with halogen. Examples of lower haloalkyl groups include, but are not limited to, $-CF_3$, $-CHF_2$, and the like.

"Lower alkoxy" refers to a lower alkyl as defined above joined by way of an oxygen atom (i.e., —O-(lower alkyl). Examples of lower alkoxy groups include, but are not limited to, methoxy, ethoxy, n-propoxy, n-butoxy, isopropoxy, sec-butoxy, tert-butoxy, and the like.

"Lower haloalkoxy" refers to a lower haloalkyl as defined above joined by way of an oxygen atom (i.e., —O-(lower haloalkyl). Examples of lower haloalkoxy groups include, but are not limited to, $-OCF_3$, $-OCHF_2$, and the like.

"Cycloalkyl" refers to alkyl groups forming a ring structure, which can be substituted or unsubstituted, wherein the ring is either completely saturated, partially unsaturated, or fully unsaturated, wherein if there is unsaturation, the conjugation of the pi-electrons in the ring do not give rise to aromaticity. Examples of cycloalkyl include, but are not limited to, cyclopropyl, cyclobutyl, cyclopentyl, cyclohexyl, cycloheptyl, and cyclooctyl groups.

In some embodiments, the cycloalkyl group has 3 to 8 ring members, whereas in other embodiments the number of ring carbon atoms range from 3 to 5, 3 to 6, or 3 to 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like.

"Cycloalkylalkyl" are alkyl groups as defined above in which a hydrogen or carbon bond of the alkyl group is replaced with a bond to a cycloalkyl group as defined above.

"Aryl" groups are cyclic aromatic hydrocarbons that do not contain heteroatoms. Thus, aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain 6-14 carbons in the ring portions of the groups. The terms "aryl" and "aryl groups" include fused rings wherein at least one ring, but not necessarily all rings, are aromatic, such as fused aromatic-aliphatic ring systems (e.g., indanyl, tetrahydronaphthyl, and the like). In one embodiment, aryl is phenyl or naphthyl, and in another embodiment aryl is phenyl.

"Carbocyclyl," "carbocycle," or "carbocyclic" refers to alkyl groups forming a ring structure, which can be substituted or unsubstituted, wherein the ring is either completely saturated, partially unsaturated, or fully unsaturated, wherein if there is unsaturation, the conjugation of the pi-electrons in the ring may give rise to aromaticity. In one embodiment, carbocycle includes cycloalkyl as defined above. In another embodiment, carbocycle includes aryl as defined above.

"Carbocyclealkyl" are alkyl groups as defined above in which a hydrogen or carbon bond of the alkyl group is replaced with a bond to a carbocycle group as defined above. Examples of carbocyclealkyl groups include, but are not limited to, cyclopropylmethyl, cyclobutylmethyl, benzyl, and the like.

"Heterocyclyl," "heterocycle," or "heterocyclic" refers to aromatic and non-aromatic ring moieties containing 3 or more ring members, of which one or more is a heteroatom such as, but not limited to, N, O, S, or P. In some embodiments, heterocyclyl include 3 to 20 ring members, whereas other such groups have 3 to 15 ring members. At least one ring contains a heteroatom, but every ring in a polycyclic system need not contain a heteroatom. For example, a dioxolanyl ring and a benzdioxolanyl ring system (methylenedioxyphenyl ring system) are both heterocyclyl groups within the meaning herein.

Heterocyclyl groups also include fused ring species including those having fused aromatic and non-aromatic groups. A heterocyclyl group also includes polycyclic ring systems containing a heteroatom such as, but not limited to, quinuclidyl, and also includes heterocyclyl groups that have substituents, including but not limited to alkyl, halo, amino, hydroxy, cyano, carboxy, nitro, thio, or alkoxy groups, bonded to one of the ring members. A heterocyclyl group as defined herein can be a heteroaryl group or a partially or completely saturated cyclic group including at least one ring heteroatom. Heterocyclyl groups include, but are not limited to, pyrrolidinyl, furanyl, tetrahydrofuranyl, dioxolanyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups.

"Heterocyclealkyl" are alkyl groups as defined above in which a hydrogen or carbon bond of the alkyl group is replaced with a bond to a heterocycle group as defined above.

"Heteroaryl" refers to aromatic ring moieties containing 5 or more ring members, of which, one or more is a heteroatom such as, but not limited to, N, O, and S. Heteroaryl groups include, but are not limited to, groups such as pyrrolyl, pyrazolyl, pyridinyl, pyridazinyl, pyrimidyl, pyrazyl, pyrazinyl, pyrimidinyl, thienyl, triazolyl, tetrazolyl, triazinyl, thiazolyl, thiophenyl, oxazolyl, isoxazolyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, tetrahydroisoquinolinyl, quinoxalinyl, and quinazolinyl groups. The terms "heteroaryl" and "heteroaryl groups" include fused ring compounds such as wherein at least one ring, but not necessarily all rings, are aromatic, including tetrahydroquinolinyl, tetrahydroisoquinolinyl, indolyl, and 2,3-dihydro indolyl.

In one embodiment, compounds are provided having the structure of Formula (I), or a pharmaceutically acceptable isomer, racemate, hydrate, solvate, isotope, or salt thereof, wherein $R^2$ is lower alkyl optionally substituted with one or more halo, cyano, —OR', —NR'R", =O, =S, —$S(O)_2R'$ or —$S(O)_2OR'$, wherein R' and R" are each, independently, H, lower alkyl, or lower haloalkyl. In another embodiment, $R^2$ is unsubstituted lower alkyl. In a more specific embodiment, $R^2$ is methyl, ethyl, propyl, isopropyl, or butyl.

In one embodiment, compounds are provided having the structure of Formula (II):

(II)

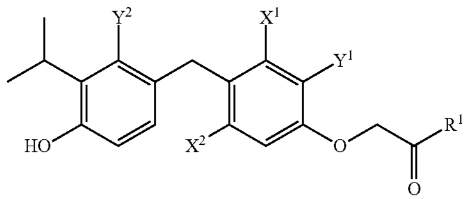

or a pharmaceutically acceptable isomer, racemate, hydrate, solvate, isotope, or salt thereof, wherein:

$X^1$ is lower alkyl, lower alkenyl, lower haloalkyl, or halo;

$X^2$ is lower alkyl, lower alkenyl, lower haloalkyl, or halo;

$Y^1$ and $Y^2$ are each, independently, H, cyano, halogen, lower alkyl, or lower alkoxy, wherein at least one of $Y^1$ and $Y^2$ is not H;

$R^1$ is —$NR^{1a}R^{1b}$ or —$OR^{1c}$;

$R^{1a}$ and $R^{1b}$ are each, independently, H, lower alkyl, lower alkenyl, lower alkynyl, —$OR^a$, —$NR^aR^b$, carbocycle, carbocyclealkyl, heterocycle, or heterocyclealkyl, or $R^{1a}$ and $R^{1b}$ taken together with the nitrogen atom to which they are attached form heterocycle;

$R^{1c}$ is H, lower alkyl, carbocycle, heterocycle, carbocyclealkyl, or heterocyclealkyl;

wherein $R^{1a}$, $R^{1b}$, and $R^{1c}$ are each, independently, optionally substituted with one or more halo, cyano, —OR', —NR'R", =O, =S, —$S(O)_2R'$ or —$S(O)_2OR'$, wherein R' and R" are each, independently, H, lower alkyl, or lower haloalkyl.

In one embodiment, compounds are provided having the structure of Formula (II-A):

(II-A)

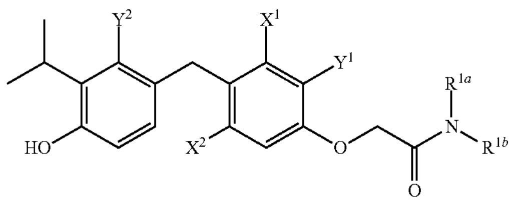

or a pharmaceutically acceptable isomer, racemate, hydrate, solvate, isotope, or salt thereof, wherein:

$X^1$ is lower alkyl, lower alkenyl, lower haloalkyl, or halo;

$X^2$ is lower alkyl, lower alkenyl, lower haloalkyl, or halo;

$Y^1$ and $Y^2$ are each, independently, H, cyano, halogen, lower alkyl, or lower alkoxy, wherein at least one of $Y^1$ and $Y^2$ is not H; and $R^{1a}$ and $R^{1b}$ are each, independently, H, lower alkyl, lower alkenyl, lower alkynyl, —$OR^a$, —$NR^aR^b$, carbocycle, carbocyclealkyl, heterocycle, or heterocyclealkyl, or $R^{1a}$ and $R^{1b}$ taken together with the nitrogen atom to which they are attached form heterocycle;

wherein $R^{1a}$ and $R^{1b}$ are each, independently, optionally substituted with one or more halo, cyano, —OR', —NR'R", =O, =S, —$S(O)_2R'$ or —$S(O)_2OR'$, wherein R' and R" are each, independently, H, lower alkyl, or lower haloalkyl.

In one embodiment, compounds are provided having the structure of Formula (II-B):

(II-B)

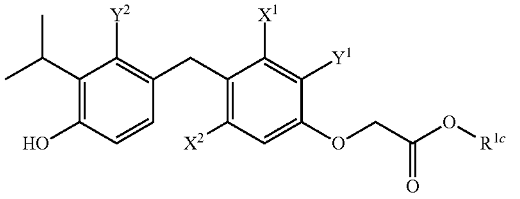

or a pharmaceutically acceptable isomer, racemate, hydrate, solvate, isotope, or salt thereof, wherein:

$X^1$ is lower alkyl, lower alkenyl, lower haloalkyl, or halo;

$X^2$ is lower alkyl, lower alkenyl, lower haloalkyl, or halo;

$Y^1$ and $Y^2$ are each, independently, H, cyano, halogen, lower alkyl, or lower alkoxy, wherein at least one of $Y^1$ and $Y^2$ is not H; and $R^{1c}$ is H, lower alkyl, carbocycle, heterocycle, carbocyclealkyl, or heterocyclealkyl;

wherein $R^{1c}$ is optionally substituted with one or more halo, cyano, —OR', —NR'R", =O, =S, —$S(O)_2R'$ or —$S(O)_2OR'$, wherein R' and R" are each, independently, H, lower alkyl, or lower haloalkyl.

In one embodiment, compounds are provided having the structure of Formula (III):

(III)

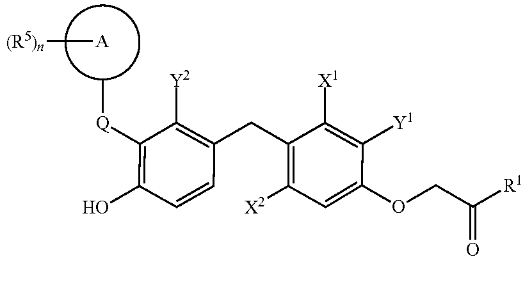

or a pharmaceutically acceptable isomer, racemate, hydrate, solvate, isotope, or salt thereof, wherein:

$X^1$ is lower alkyl, lower alkenyl, lower haloalkyl, or halo;

$X^2$ is lower alkyl, lower alkenyl, lower haloalkyl, or halo;

$Y^1$ and $Y^2$ are each, independently, H, cyano, halogen, lower alkyl, or lower alkoxy, wherein at least one of $Y^1$ and $Y^2$ is not H;

$R^1$ is —$NR^{1a}R^{1b}$ or —$OR^{1c}$;

$R^{1a}$ and $R^{1b}$ are each, independently, H, lower alkyl, lower alkenyl, lower alkynyl, —$OR^a$, —$NR^aR^b$, carbocycle, carbocyclealkyl, heterocycle, or heterocyclealkyl, or $R^{1a}$ and $R^{1b}$ taken together with the nitrogen atom to which they are attached form heterocycle;

$R^{1c}$ is H, lower alkyl, carbocycle, heterocycle, carbocyclealkyl, or heterocyclealkyl;

Q is —$C(R^3R^4)$— or —$\{C(R^3R^4)\}_2$—;

A is aryl or heteroaryl;

$R^3$ and $R^4$ are each, independently, H, halo, cyano, lower alkyl, lower alkenyl, lower alkynyl, lower haloalkyl, —$OR^a$, —$NR^aR^b$, carbocycle, heterocycle, carbocyclealkyl, or heterocyclealkyl, or $R^3$ and $R^4$, together, form =O or =S;

each $R^5$ is, independently, halo, cyano, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;

n is 0-5; and $R^a$ and $R^b$ are each, independently, H, lower alkyl, or lower haloalkyl;

wherein $R^{1a}$, $R^{1b}$, $R^{1c}$, $R^3$, $R^4$, $R^5$, $R^a$, and $R^b$ are each, independently, optionally substituted with one or more halo, cyano, —OR', —NR'R", =O, =S, —$S(O)_2R'$ or —$S(O)_2OR'$, wherein R' and R" are each, independently, H, lower alkyl, or lower haloalkyl.

In one embodiment, compounds are provided having the structure of Formula (III-A):

(III-A)

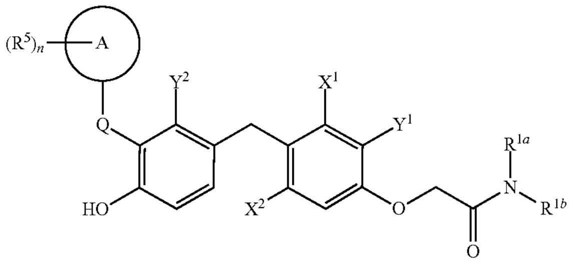

or a pharmaceutically acceptable isomer, racemate, hydrate, solvate, isotope, or salt thereof, wherein:

$X^1$ is lower alkyl, lower alkenyl, lower haloalkyl, or halo;

$X^2$ is lower alkyl, lower alkenyl, lower haloalkyl, or halo;

$Y^1$ and $Y^2$ are each, independently, H, cyano, halogen, lower alkyl, or lower alkoxy, wherein at least one of $Y^1$ and $Y^2$ is not H;

$R^{1a}$ and $R^{1b}$ are each, independently, H, lower alkyl, lower alkenyl, lower alkynyl, —$OR^a$, —$NR^aR^b$, carbocycle, carbocyclealkyl, heterocycle, or heterocyclealkyl, or $R^{1a}$ and $R^{1b}$ taken together with the nitrogen atom to which they are attached form heterocycle;

Q is —$C(R^3R^4)$— or —$\{C(R^3R^4)\}_2$—;

A is aryl or heteroaryl;

$R^3$ and $R^4$ are each, independently, H, halo, cyano, lower alkyl, lower alkenyl, lower alkynyl, lower haloalkyl, —$OR^a$, —$NR^aR^b$, carbocycle, heterocycle, carbocyclealkyl, or heterocyclealkyl, or $R^3$ and $R^4$, together, form =O or =S;

each $R^5$ is, independently, halo, cyano, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;

n is 0-5; and $R^a$ and $R^b$ are each, independently, H, lower alkyl, or lower haloalkyl;

wherein $R^{1a}$, $R^{1b}$, $R^3$, $R^4$, $R^5$, $R^a$, and $R^b$ are each, independently, optionally substituted with one or more halo, cyano, —OR', —NR'R", =O, =S, —$S(O)_2R'$ or —$S(O)_2OR'$, wherein R' and R" are each, independently, H, lower alkyl, or lower haloalkyl.

In one embodiment, compounds are provided having the structure of Formula (III-B):

(III-B)

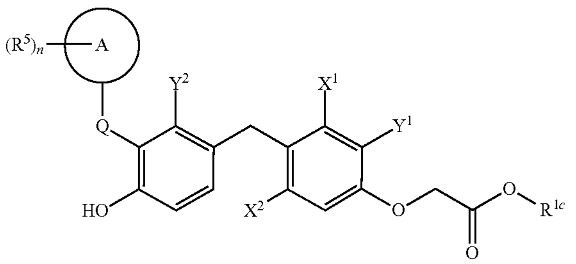

or a pharmaceutically acceptable isomer, racemate, hydrate, solvate, isotope, or salt thereof, wherein:

$X^1$ is lower alkyl, lower alkenyl, lower haloalkyl, or halo;

$X^2$ is lower alkyl, lower alkenyl, lower haloalkyl, or halo;

$Y^1$ and $Y^2$ are each, independently, H, cyano, halogen, lower alkyl, or lower alkoxy, wherein at least one of $Y^1$ and $Y^2$ is not H;

$R^{1c}$ is H, lower alkyl, carbocycle, heterocycle, carbocyclealkyl, or heterocyclealkyl;

Q is —$C(R^3R^4)$— or —$\{C(R^3R^4)\}_2$—;

A is aryl or heteroaryl;

$R^3$ and $R^4$ are each, independently, H, halo, cyano, lower alkyl, lower alkenyl, lower alkynyl, lower haloalkyl, —$OR^a$, —$NR^aR^b$, carbocycle, heterocycle, carbocyclealkyl, or heterocyclealkyl, or $R^3$ and $R^4$, together, form =O or =S;

each $R^5$ is, independently, halo, cyano, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;

n is 0-5; and $R^a$ and $R^b$ are each, independently, H, lower alkyl, or lower haloalkyl;

wherein $R^{1c}$, $R^3$, $R^4$, $R^5$, $R^a$, and $R^b$ are each, independently, optionally substituted with one or more halo, cyano, —OR', —NR'R", =O, =S, —$S(O)_2R'$ or —$S(O)_2OR'$, wherein R' and R" are each, independently, H, lower alkyl, or lower haloalkyl.

In one embodiment, compounds are provided having the structure of Formula (IV):

(IV)

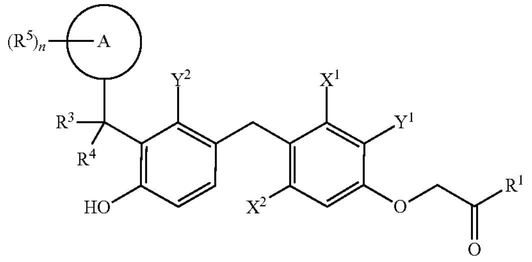

or a pharmaceutically acceptable isomer, racemate, hydrate, solvate, isotope, or salt thereof, wherein:

$X^1$ is lower alkyl, lower alkenyl, lower haloalkyl, or halo;

$X^2$ is lower alkyl, lower alkenyl, lower haloalkyl, or halo;

$Y^1$ and $Y^2$ are each, independently, H, cyano, halogen, lower alkyl, or lower alkoxy, wherein at least one of $Y^1$ and $Y^2$ is not H;

$R^1$ is —$NR^{1a}R^{1b}$ or —$OR^{1c}$;

$R^{1a}$ and $R^{1b}$ are each, independently, H, lower alkyl, lower alkenyl, lower alkynyl, —$OR^a$, —$NR^aR^b$, carbocycle, carbocyclealkyl, heterocycle, or heterocyclealkyl, or $R^{1a}$ and $R^{1b}$ taken together with the nitrogen atom to which they are attached form heterocycle;

$R^{1c}$ is H, lower alkyl, carbocycle, heterocycle, carbocyclealkyl, or heterocyclealkyl;

A is aryl or heteroaryl;

$R^3$ and $R^4$ are each, independently, H, halo, cyano, lower alkyl, lower alkenyl, lower alkynyl, lower haloalkyl, —$OR^a$, —$NR^aR^b$, carbocycle, heterocycle, carbocyclealkyl, or heterocyclealkyl, or $R^3$ and $R^4$, together, form =O or =S;

each $R^5$ is, independently, halo, cyano, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;

n is 0-5; and $R^a$ and $R^b$ are each, independently, H, lower alkyl, or lower haloalkyl;

wherein $R^{1a}$, $R^{1b}$, $R^{1c}$, $R^3$, $R^4$, $R^5$, $R^a$, and $R^b$ are each, independently, optionally substituted with one or more halo, cyano, —OR', —NR'R", =O, =S, —$S(O)_2R'$ or —$S(O)_2OR'$, wherein R' and R" are each, independently, H, lower alkyl, or lower haloalkyl.

In one embodiment, compounds are provided having the structure of Formula (IV-A):

(IV-A)

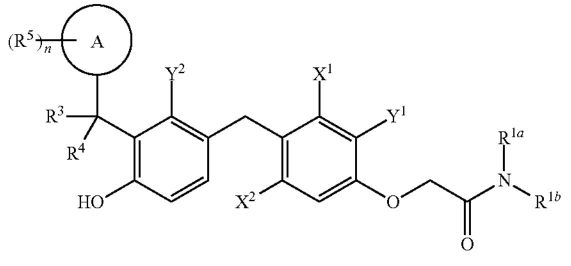

or a pharmaceutically acceptable isomer, racemate, hydrate, solvate, isotope, or salt thereof, wherein:

$X^1$ is lower alkyl, lower alkenyl, lower haloalkyl, or halo;

$X^2$ is lower alkyl, lower alkenyl, lower haloalkyl, or halo;

$Y^1$ and $Y^2$ are each, independently, H, cyano, halogen, lower alkyl, or lower alkoxy, wherein at least one of $Y^1$ and $Y^2$ is not H;

$R^{1a}$ and $R^{1b}$ are each, independently, H, lower alkyl, lower alkenyl, lower alkynyl, —$OR^a$, —$NR^aR^b$, carbocycle, carbocyclealkyl, heterocycle, or heterocyclealkyl, or $R^{1a}$ and $R^{1b}$ taken together with the nitrogen atom to which they are attached form heterocycle;

A is aryl or heteroaryl;

$R^3$ and $R^4$ are each, independently, H, halo, cyano, lower alkyl, lower alkenyl, lower alkynyl, lower haloalkyl, —$OR^a$, —$NR^aR^b$, carbocycle, heterocycle, carbocyclealkyl, or heterocyclealkyl, or $R^3$ and $R^4$, together, form =O or =S;

each $R^5$ is, independently, halo, cyano, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;

n is 0-5; and $R^a$ and $R^b$ are each, independently, H, lower alkyl, or lower haloalkyl;

wherein $R^{1a}$, $R^{1b}$, $R^3$, $R^4$, $R^5$, $R^a$, and $R^b$ are each, independently, optionally substituted with one or more halo, cyano, —OR', —NR'R", =O, =S, —$S(O)_2R'$ or —$S(O)_2OR'$, wherein R' and R" are each, independently, H, lower alkyl, or lower haloalkyl.

In one embodiment, compounds are provided having the structure of Formula (IV-B):

(IV-B)

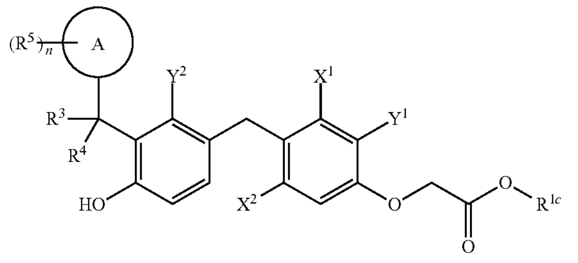

or a pharmaceutically acceptable isomer, racemate, hydrate, solvate, isotope, or salt thereof, wherein:

$X^1$ is lower alkyl, lower alkenyl, lower haloalkyl, or halo;

$X^2$ is lower alkyl, lower alkenyl, lower haloalkyl, or halo;

$Y^1$ and $Y^2$ are each, independently, H, cyano, halogen, lower alkyl, or lower alkoxy, wherein at least one of $Y^1$ and $Y^2$ is not H;

$R^{1c}$ is H, lower alkyl, carbocycle, heterocycle, carbocyclealkyl, or heterocyclealkyl;

A is aryl or heteroaryl;

$R^3$ and $R^4$ are each, independently, H, halo, cyano, lower alkyl, lower alkenyl, lower alkynyl, lower haloalkyl, —$OR^a$, —$NR^aR^b$, carbocycle, heterocycle, carbocyclealkyl, or heterocyclealkyl, or $R^3$ and $R^4$, together, form =O or =S;

each $R^5$ is, independently, halo, cyano, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;

n is 0-5; and $R^a$ and $R^b$ are each, independently, H, lower alkyl, or lower haloalkyl;

wherein $R^{1c}$, $R^3$, $R^4$, $R^5$, $R^a$, and $R^b$ are each, independently, optionally substituted with one or more halo, cyano, —OR', —NR'R", =O, =S, —$S(O)_2R'$ or —$S(O)_2OR'$, wherein R' and R" are each, independently, H, lower alkyl, or lower haloalkyl.

In one embodiment, compounds are provided having the structure of Formula (V):

(V)

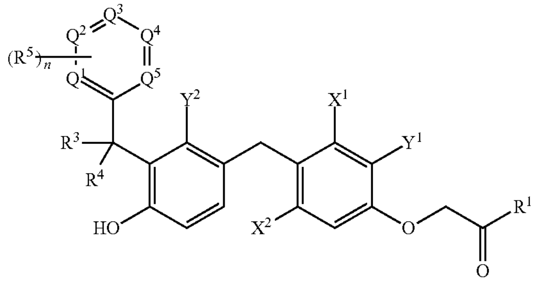

or a pharmaceutically acceptable isomer, racemate, hydrate, solvate, isotope, or salt thereof, wherein:

$Q^1$, $Q^2$, $Q^3$, $Q^4$, and $Q^5$ are each, independently, CH, $CR^5$, or N;

$X^1$ is lower alkyl, lower alkenyl, lower haloalkyl, or halo;

$X^2$ is lower alkyl, lower alkenyl, lower haloalkyl, or halo;

$Y^1$ and $Y^2$ are each, independently, H, cyano, halogen, lower alkyl, or lower alkoxy, wherein at least one of $Y^1$ and $Y^2$ is not H;

$R^1$ is —$NR^{1a}R^{1b}$ or —$OR^{1c}$;

$R^{1a}$ and $R^{1b}$ are each, independently, H, lower alkyl, lower alkenyl, lower alkynyl, —$OR^a$, —$NR^aR^b$, carbocycle, carbocyclealkyl, heterocycle, or heterocyclealkyl, or $R^{1a}$ and $R^{1b}$ taken together with the nitrogen atom to which they are attached form heterocycle;

$R^{1c}$ is H, lower alkyl, carbocycle, heterocycle, carbocyclealkyl, or heterocyclealkyl;

$R^3$ and $R^4$ are each, independently, H, halo, cyano, lower alkyl, lower alkenyl, lower alkynyl, lower haloalkyl, —$OR^a$, —$NR^aR^b$, carbocycle, heterocycle, carbocyclealkyl, or heterocyclealkyl, or $R^3$ and $R^4$, together, form =O or =S;

each $R^5$ is, independently, halo, cyano, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;

n is 0-5; and $R^a$ and $R^b$ are each, independently, H, lower alkyl, or lower haloalkyl;

wherein $R^{1a}$, $R^{1b}$, $R^{1c}$, $R^3$, $R^4$, $R^5$, $R^a$, and $R^b$ are each, independently, optionally substituted with one or more halo, cyano, —OR', —NR'R", =O, =S, —$S(O)_2R'$ or —$S(O)_2OR'$, wherein R' and R" are each, independently, H, lower alkyl, or lower haloalkyl.

In one embodiment, compounds are provided having the structure of Formula (V-A):

(V-A)

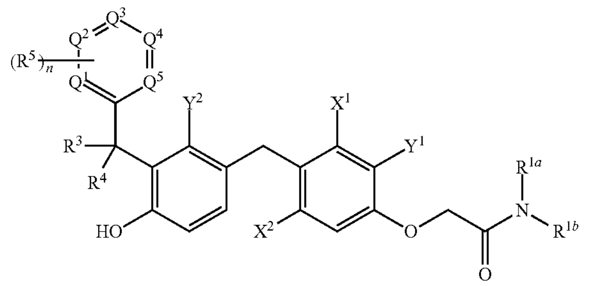

or a pharmaceutically acceptable isomer, racemate, hydrate, solvate, isotope, or salt thereof, wherein:

$Q^1$, $Q^2$, $Q^3$, $Q^4$, and $Q^5$ are each, independently, CH, $CR^5$, or N;

$X^1$ is lower alkyl, lower alkenyl, lower haloalkyl, or halo;

$X^2$ is lower alkyl, lower alkenyl, lower haloalkyl, or halo;

$Y^1$ and $Y^2$ are each, independently, H, cyano, halogen, lower alkyl, or lower alkoxy, wherein at least one of $Y^1$ and $Y^2$ is not H;

$R^{1a}$ and $R^{1b}$ are each, independently, H, lower alkyl, lower alkenyl, lower alkynyl, —$OR^a$, —$NR^aR^b$, carbocycle, carbocyclealkyl, heterocycle, or heterocyclealkyl, or $R^{1a}$ and $R^{1b}$ taken together with the nitrogen atom to which they are attached form heterocycle;

$R^3$ and $R^4$ are each, independently, H, halo, cyano, lower alkyl, lower alkenyl, lower alkynyl, lower haloalkyl, —$OR^a$, —$NR^aR^b$, carbocycle, heterocycle, carbocyclealkyl, or heterocyclealkyl, or $R^3$ and $R^4$, together, form ═O or ═S;

each $R^5$ is, independently, halo, cyano, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;

n is 0-5; and $R^a$ and $R^b$ are each, independently, H, lower alkyl, or lower haloalkyl;

wherein $R^{1a}$, $R^{1b}$, $R^3$, $R^4$, $R^5$, $R^a$, and $R^b$ are each, independently, optionally substituted with one or more halo, cyano, —OR', —NR'R", ═O, ═S, —$S(O)_2R'$ or —$S(O)_2OR'$, wherein R' and R" are each, independently, H, lower alkyl, or lower haloalkyl.

In one embodiment, compounds are provided having the structure of Formula (V-B):

(V-B)

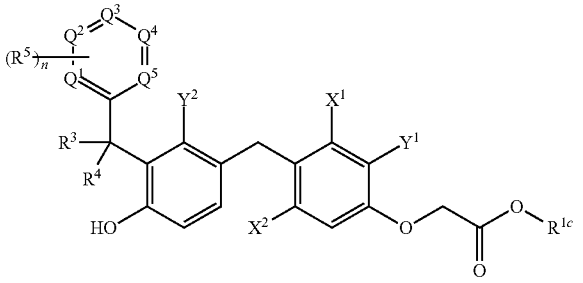

or a pharmaceutically acceptable isomer, racemate, hydrate, solvate, isotope, or salt thereof, wherein:

$Q^1$, $Q^2$, $Q^3$, $Q^4$, and $Q^5$ are each, independently, CH, $CR^5$, or N;

$X^1$ is lower alkyl, lower alkenyl, lower haloalkyl, or halo;

$X^2$ is lower alkyl, lower alkenyl, lower haloalkyl, or halo;

$Y^1$ and $Y^2$ are each, independently, H, cyano, halogen, lower alkyl, or lower alkoxy, wherein at least one of $Y^1$ and $Y^2$ is not H;

$R^{1c}$ is H, lower alkyl, carbocycle, heterocycle, carbocyclealkyl, or heterocyclealkyl;

$R^3$ and $R^4$ are each, independently, H, halo, cyano, lower alkyl, lower alkenyl, lower alkynyl, lower haloalkyl, —$OR^a$, —$NR^aR^b$, carbocycle, heterocycle, carbocyclealkyl, or heterocyclealkyl, or $R^3$ and $R^4$, together, form ═O or ═S;

each $R^5$ is, independently, halo, cyano, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;

n is 0-5; and $R^a$ and $R^b$ are each, independently, H, lower alkyl, or lower haloalkyl;

wherein $R^{1c}$, $R^3$, $R^4$, $R^5$, $R^a$, and $R^b$ are each, independently, optionally substituted with one or more halo, cyano, —OR', —NR'R", ═O, ═S, —$S(O)_2R'$ or —$S(O)_2OR'$, wherein R' and R" are each, independently, H, lower alkyl, or lower haloalkyl.

In one embodiment, compounds are provided having the structure of Formula (VI):

(VI)

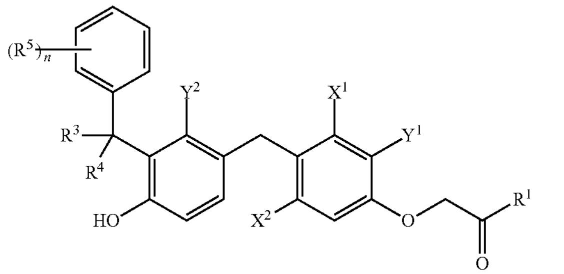

or a pharmaceutically acceptable isomer, racemate, hydrate, solvate, isotope, or salt thereof, wherein:

$X^1$ is lower alkyl, lower alkenyl, lower haloalkyl, or halo;

$X^2$ is lower alkyl, lower alkenyl, lower haloalkyl, or halo;

$Y^1$ and $Y^2$ are each, independently, H, cyano, halogen, lower alkyl, or lower alkoxy, wherein at least one of $Y^1$ and $Y^2$ is not H;

$R^1$ is —$NR^{1a}R^{1b}$ or —$OR^{1c}$;

$R^{1a}$ and $R^{1b}$ are each, independently, H, lower alkyl, lower alkenyl, lower alkynyl, —$OR^a$, —$NR^aR^b$, carbocycle, carbocyclealkyl, heterocycle, or heterocyclealkyl, or $R^{1a}$ and $R^{1b}$ taken together with the nitrogen atom to which they are attached form heterocycle;

$R^{1c}$ is H, lower alkyl, carbocycle, heterocycle, carbocyclealkyl, or heterocyclealkyl;

$R^3$ and $R^4$ are each, independently, H, halo, cyano, lower alkyl, lower alkenyl, lower alkynyl, lower haloalkyl, —$OR^a$, —$NR^aR^b$, carbocycle, heterocycle, carbocyclealkyl, or heterocyclealkyl, or $R^3$ and $R^4$, together, form =O or =S;

each $R^5$ is, independently, halo, cyano, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;

n is 0-5; and $R^a$ and $R^b$ are each, independently, H, lower alkyl, or lower haloalkyl;

wherein $R^{1a}$, $R^{1b}$, $R^{1c}$, $R^3$, $R^4$, $R^5$, $R^a$, and $R^b$ are each, independently, optionally substituted with one or more halo, cyano, —OR', —NR'R", =O, =S, —$S(O)_2$R' or —$S(O)_2$OR', wherein R' and R" are each, independently, H, lower alkyl, or lower haloalkyl.

In one embodiment, compounds are provided having the structure of Formula (VI-A):

(VI-A)

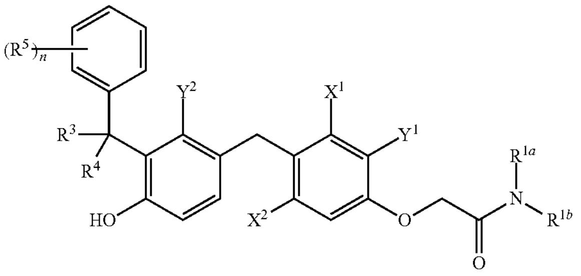

or a pharmaceutically acceptable isomer, racemate, hydrate, solvate, isotope, or salt thereof, wherein:

$X^1$ is lower alkyl, lower alkenyl, lower haloalkyl, or halo;

$X^2$ is lower alkyl, lower alkenyl, lower haloalkyl, or halo;

$Y^1$ and $Y^2$ are each, independently, H, cyano, halogen, lower alkyl, or lower alkoxy, wherein at least one of $Y^1$ and $Y^2$ is not H;

$R^{1a}$ and $R^{1b}$ are each, independently, H, lower alkyl, lower alkenyl, lower alkynyl, —$OR^a$, —$NR^aR^b$, carbocycle, carbocyclealkyl, heterocycle, or heterocyclealkyl, or $R^{1a}$ and $R^{1b}$ taken together with the nitrogen atom to which they are attached form heterocycle;

$R^3$ and $R^4$ are each, independently, H, halo, cyano, lower alkyl, lower alkenyl, lower alkynyl, lower haloalkyl, —$OR^a$, —$NR^aR^b$, carbocycle, heterocycle, carbocyclealkyl, or heterocyclealkyl, or $R^3$ and $R^4$, together, form =O or =S;

each $R^5$ is, independently, halo, cyano, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;

n is 0-5; and $R^a$ and $R^b$ are each, independently, H, lower alkyl, or lower haloalkyl;

wherein $R^{1a}$, $R^{1b}$, $R^3$, $R^4$, $R^5$, $R^a$, and $R^b$ are each, independently, optionally substituted with one or more halo, cyano, —OR', —NR'R", =O, =S, —$S(O)_2$R' or —$S(O)_2$OR', wherein R' and R" are each, independently, H, lower alkyl, or lower haloalkyl.

In one embodiment, compounds are provided having the structure of Formula (VI-B):

(VI-B)

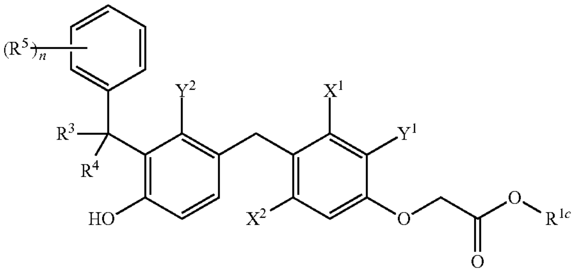

or a pharmaceutically acceptable isomer, racemate, hydrate, solvate, isotope, or salt thereof, wherein:

$X^1$ is lower alkyl, lower alkenyl, lower haloalkyl, or halo;

$X^2$ is lower alkyl, lower alkenyl, lower haloalkyl, or halo;

$Y^1$ and $Y^2$ are each, independently, H, cyano, halogen, lower alkyl, or lower alkoxy, wherein at least one of $Y^1$ and $Y^2$ is not H;

$R^{1c}$ is H, lower alkyl, carbocycle, heterocycle, carbocyclealkyl, or heterocyclealkyl;

$R^3$ and $R^4$ are each, independently, H, halo, cyano, lower alkyl, lower alkenyl, lower alkynyl, lower haloalkyl, —$OR^a$, —$NR^aR^b$, carbocycle, heterocycle, carbocyclealkyl, or heterocyclealkyl, or $R^3$ and $R^4$, together, form =O or =S;

each $R^5$ is, independently, halo, cyano, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;

n is 0-5; and $R^a$ and $R^b$ are each, independently, H, lower alkyl, or lower haloalkyl;

wherein $R^{1c}$, $R^3$, $R^4$, $R^5$, $R^a$, and $R^b$ are each, independently, optionally substituted with one or more halo, cyano, —OR', —NR'R", =O, =S, —$S(O)_2$R' or —$S(O)_2$OR', wherein R' and R" are each, independently, H, lower alkyl, or lower haloalkyl.

In one embodiment, compounds are provided having the structure of Formula (VII):

(VII)

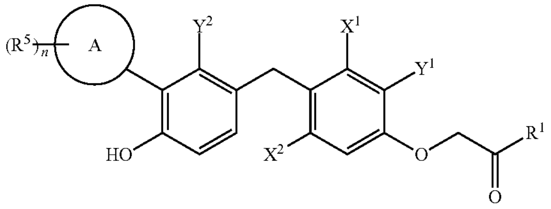

or a pharmaceutically acceptable isomer, racemate, hydrate, solvate, isotope, or salt thereof, wherein:

$X^1$ is lower alkyl, lower alkenyl, lower haloalkyl, or halo;
$X^2$ is lower alkyl, lower alkenyl, lower haloalkyl, or halo;
$Y^1$ and $Y^2$ are each, independently, H, cyano, halogen, lower alkyl, or lower alkoxy, wherein at least one of $Y^1$ and $Y^2$ is not H;
$R^1$ is —$NR^{1a}R^{1b}$ or —$OR^{1c}$;
$R^{1a}$ and $R^{1b}$ are each, independently, H, lower alkyl, lower alkenyl, lower alkynyl, —$OR^a$, —$NR^aR^b$, carbocycle, carbocyclealkyl, heterocycle, or heterocyclealkyl, or $R^{1a}$ and $R^{1b}$ taken together with the nitrogen atom to which they are attached form heterocycle;
$R^{1c}$ is H, lower alkyl, carbocycle, heterocycle, carbocyclealkyl, or heterocyclealkyl;
A is aryl or heteroaryl;
each $R^5$ is, independently, halo, cyano, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;
n is 0-5; and
$R^a$ and $R^b$ are each, independently, H, lower alkyl, or lower haloalkyl;
wherein $R^{1a}$, $R^{1b}$, $R^{1c}$, $R^5$, $R^a$, and $R^b$ are each, independently, optionally substituted with one or more halo, cyano, —OR', —NR'R", =O, =S, —$S(O)_2R'$ or —$S(O)_2OR'$, wherein R' and R" are each, independently, H, lower alkyl, or lower haloalkyl.

In one embodiment, compounds are provided having the structure of Formula (VII-A):

(VII-A)

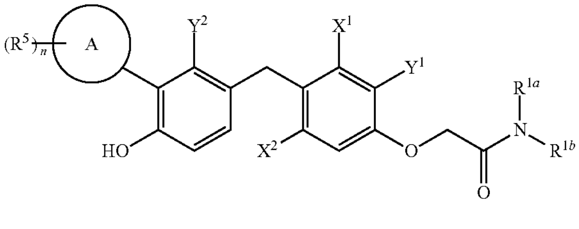

or a pharmaceutically acceptable isomer, racemate, hydrate, solvate, isotope, or salt thereof, wherein:

$X^1$ is lower alkyl, lower alkenyl, lower haloalkyl, or halo;
$X^2$ is lower alkyl, lower alkenyl, lower haloalkyl, or halo;
$Y^1$ and $Y^2$ are each, independently, H, cyano, halogen, lower alkyl, or lower alkoxy, wherein at least one of $Y^1$ and $Y^2$ is not H;
$R^{1a}$ and $R^{1b}$ are each, independently, H, lower alkyl, lower alkenyl, lower alkynyl, —$OR^a$, —$NR^aR^b$, carbocycle, carbocyclealkyl, heterocycle, or heterocyclealkyl, or $R^{1a}$ and $R^{1b}$ taken together with the nitrogen atom to which they are attached form heterocycle;
A is aryl or heteroaryl;
each $R^5$ is, independently, halo, cyano, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;
n is 0-5; and
$R^a$ and $R^b$ are each, independently, H, lower alkyl, or lower haloalkyl;
wherein $R^{1a}$, $R^{1b}$, $R^5$, $R^a$, and $R^b$ are each, independently, optionally substituted with one or more halo, cyano, —OR', —NR'R", =O, =S, —$S(O)_2R'$ or —$S(O)_2OR'$, wherein R' and R" are each, independently, H, lower alkyl, or lower haloalkyl.

In one embodiment, compounds are provided having the structure of Formula (VII-B):

(VII-B)

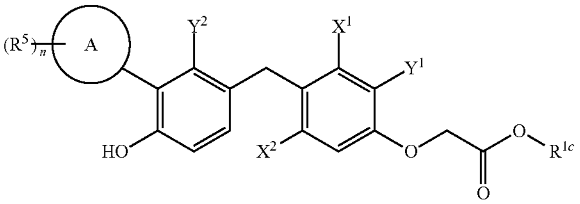

or a pharmaceutically acceptable isomer, racemate, hydrate, solvate, isotope, or salt thereof, wherein:

$X^1$ is lower alkyl, lower alkenyl, lower haloalkyl, or halo;
$X^2$ is lower alkyl, lower alkenyl, lower haloalkyl, or halo;
$Y^1$ and $Y^2$ are each, independently, H, cyano, halogen, lower alkyl, or lower alkoxy, wherein at least one of $Y^1$ and $Y^2$ is not H;
$R^{1c}$ is H, lower alkyl, carbocycle, heterocycle, carbocyclealkyl, or heterocyclealkyl;
A is aryl or heteroaryl;
each $R^5$ is, independently, halo, cyano, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;
n is 0-5; and
$R^a$ and $R^b$ are each, independently, H, lower alkyl, or lower haloalkyl;
wherein $R^{1a}$, $R^{1b}$, $R^{1c}$, $R^5$, $R^a$, and $R^b$ are each, independently, optionally substituted with one or more halo, cyano, —OR', —NR'R", =O, =S, —$S(O)_2R'$ or —$S(O)_2OR'$, wherein R' and R" are each, independently, H, lower alkyl, or lower haloalkyl.

In one embodiment, compounds are provided having the structure of Formula (VIII):

(VIII)

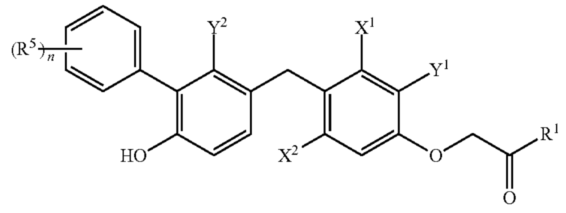

or a pharmaceutically acceptable isomer, racemate, hydrate, solvate, isotope, or salt thereof, wherein:

$X^1$ is lower alkyl, lower alkenyl, lower haloalkyl, or halo;

$X^2$ is lower alkyl, lower alkenyl, lower haloalkyl, or halo;

$Y^1$ and $Y^2$ are each, independently, H, cyano, halogen, lower alkyl, or lower alkoxy, wherein at least one of $Y^1$ and $Y^2$ is not H;

$R^1$ is —$NR^{1a}R^{1b}$ or —$OR^{1c}$;

$R^{1a}$ and $R^{1b}$ are each, independently, H, lower alkyl, lower alkenyl, lower alkynyl, —$OR^a$, —$NR^aR^b$, carbocycle, carbocyclealkyl, heterocycle, or heterocyclealkyl, or $R^{1a}$ and $R^{1b}$ taken together with the nitrogen atom to which they are attached form heterocycle;

$R^{1c}$ is H, lower alkyl, carbocycle, heterocycle, carbocyclealkyl, or heterocyclealkyl;

each $R^5$ is, independently, halo, cyano, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;

n is 0-5; and $R^a$ and $R^b$ are each, independently, H, lower alkyl, or lower haloalkyl;

wherein $R^{1a}$, $R^{1b}$, $R^{1c}$, $R^5$, $R^a$, and $R^b$ are each, independently, optionally substituted with one or more halo, cyano, —OR', —NR'R", =O, =S, —$S(O)_2R'$ or —$S(O)_2OR'$, wherein R' and R" are each, independently, H, lower alkyl, or lower haloalkyl.

In one embodiment, compounds are provided having the structure of Formula (VIII-A):

(VIII-A)

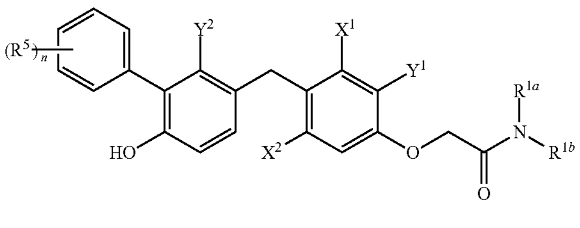

or a pharmaceutically acceptable isomer, racemate, hydrate, solvate, isotope, or salt thereof, wherein:

$X^1$ is lower alkyl, lower alkenyl, lower haloalkyl, or halo;

$X^2$ is lower alkyl, lower alkenyl, lower haloalkyl, or halo;

$Y^1$ and $Y^2$ are each, independently, H, cyano, halogen, lower alkyl, or lower alkoxy, wherein at least one of $Y^1$ and $Y^2$ is not H;

$R^{1a}$ and $R^{1b}$ are each, independently, H, lower alkyl, lower alkenyl, lower alkynyl, —$OR^a$, —$NR^aR^b$, carbocycle, carbocyclealkyl, heterocycle, or heterocyclealkyl, or $R^{1a}$ and $R^{1b}$ taken together with the nitrogen atom to which they are attached form heterocycle;

each $R^5$ is, independently, halo, cyano, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;

n is 0-5; and $R^a$ and $R^b$ are each, independently, H, lower alkyl, or lower haloalkyl;

wherein $R^{1a}$, $R^{1b}$, $R^5$, $R^a$, and $R^b$ are each, independently, optionally substituted with one or more halo, cyano, —OR', —NR'R", =O, =S, —$S(O)_2R'$ or —$S(O)_2OR'$, wherein R' and R" are each, independently, H, lower alkyl, or lower haloalkyl.

In one embodiment, compounds are provided having the structure of Formula (VIII-B):

(VIII-B)

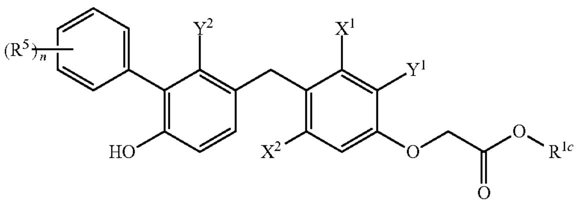

or a pharmaceutically acceptable isomer, racemate, hydrate, solvate, isotope, or salt thereof, wherein:

$X^1$ is lower alkyl, lower alkenyl, lower haloalkyl, or halo;

$X^2$ is lower alkyl, lower alkenyl, lower haloalkyl, or halo;

$Y^1$ and $Y^2$ are each, independently, H, cyano, halogen, lower alkyl, or lower alkoxy, wherein at least one of $Y^1$ and $Y^2$ is not H;

$R^{1c}$ is H, lower alkyl, carbocycle, heterocycle, carbocyclealkyl, or heterocyclealkyl;

each $R^5$ is, independently, halo, cyano, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;

n is 0-5; and $R^a$ and $R^b$ are each, independently, H, lower alkyl, or lower haloalkyl;

wherein $R^{1a}$, $R^{1b}$, $R^{1c}$, $R^5$, $R^a$, and $R^b$ are each, independently, optionally substituted with one or more halo, cyano, —OR', —NR'R", =O, =S, —$S(O)_2R'$ or —$S(O)_2OR'$, wherein R' and R" are each, independently, H, lower alkyl, or lower haloalkyl.

In one embodiment, compounds are provided having the structure of any one of Formula (III), Formula (III-A), Formula (III-B), Formula (IV), Formula (IV-A), Formula (IV-B), Formula (V), Formula (V-A), Formula (V-B), Formula (VI), Formula (VI-A), Formula (VI-B), or a pharmaceutically acceptable isomer, racemate, hydrate, solvate, isotope, or salt thereof, wherein $R^3$ is H.

In one embodiment, compounds are provided having the structure of Formula (III), Formula (III-A), Formula (III-B), Formula (IV), Formula (IV-A), Formula (IV-B), Formula (V), Formula (V-A), or a pharmaceutically acceptable isomer, racemate, hydrate, solvate, isotope, or salt thereof, wherein $R^3$ is carbocycle. In one embodiment, $R^3$ is cyclopropyl or cyclobutyl.

In one embodiment, compounds are provided having the structure of any one of Formula (III), Formula (III-A), Formula (III-B), Formula (IV), Formula (IV-A), Formula (IV-B), Formula (V), Formula (V-A), Formula (V-B), Formula (VI), Formula (VI-A), Formula (VI-B), or a pharmaceutically acceptable isomer, racemate, hydrate, solvate, isotope, or salt thereof, wherein $R^3$ is lower alkyl. In one embodiment, $R^3$ is methyl, ethyl, or propyl.

In one embodiment, compounds are provided having the structure of any one of Formula (III), Formula (III-A), Formula (III-B), Formula (IV), Formula (IV-A), Formula (IV-B), Formula (V), Formula (V-A), Formula (V-B), Formula (VI), Formula (VI-A), Formula (VI-B), or a pharmaceutically acceptable isomer, racemate, hydrate, solvate, isotope, or salt thereof, wherein $R^3$ is —$OR^a$. In one embodiment, $R^a$ is H. In one embodiment, $R^a$ is lower alkyl. In a more specific embodiment, $R^a$ is methyl.

In one embodiment, compounds are provided having the structure of any one of Formula (I), Formula (II), Formula (II-A), Formula (III), Formula (III-A), Formula (IV), Formula (IV-A), Formula (V), Formula (V-A), Formula (VI), Formula (VI-A), Formula (VII), Formula (VII-A), Formula (VIII), Formula (VIII-A), or a pharmaceutically acceptable isomer, racemate, hydrate, solvate, isotope, or salt thereof, wherein $R^1$ is —$NR^{1a}R^{1b}$ and $R^{1b}$ is H.

In one embodiment, compounds are provided having the structure of any one of Formula (I), Formula (II), Formula (II-A), Formula (III), Formula (III-A), Formula (IV), Formula (IV-A), Formula (V), Formula (V-A), Formula (VI), Formula (VI-A), Formula (VII), Formula (VII-A), Formula (VIII), Formula (VIII-A), or a pharmaceutically acceptable isomer, racemate, hydrate, solvate, isotope, or salt thereof, wherein $R^1$ is —$NR^{1a}R^{1b}$ and $R^{1a}$ is H.

In one embodiment, compounds are provided having the structure of any one of Formula (I), Formula (II), Formula (II-B), Formula (III), Formula (III-B), Formula (IV), Formula (IV-B), Formula (V), Formula (V-B), Formula (VI), Formula (VI-B), Formula (VII), Formula (VII-B), Formula (VIII), Formula (VIII-B), or a pharmaceutically acceptable isomer, racemate, hydrate, solvate, isotope, or salt thereof, wherein $R^1$ is —$OR^{1c}$ and $R^{1c}$ is H.

In one embodiment, compounds are provided having the structure of any one of Formula (I), Formula (II), Formula (II-B), Formula (III), Formula (III-B), Formula (IV), Formula (IV-B), Formula (V), Formula (V-B), Formula (VI), Formula (VI-B), Formula (VII), Formula (VII-B), Formula (VIII), Formula (VIII-B), or a pharmaceutically acceptable isomer, racemate, hydrate, solvate, isotope, or salt thereof, wherein $R^1$ is —$OR^{1c}$ and $R^{1c}$ is lower alkyl. In one embodiment, $R^{1c}$ is methyl or ethyl.

In one embodiment, compounds are provided having the structure of any one of Formula (I), Formula (II), Formula (II-A), Formula (II-B), Formula (III), Formula (III-A), Formula (III-B), Formula (IV), Formula (IV-A), Formula (IV-B), Formula (V), Formula (V-A), Formula (V-B), Formula (VI), Formula (VI-A), Formula (VI-B), Formula (VII), Formula (VII-A), Formula (VII-B), Formula (VIII), Formula (VIII-A), Formula (VIII-B), or a pharmaceutically acceptable isomer, racemate, hydrate, solvate, isotope, or salt thereof, wherein $X^1$ is lower alkyl. In one embodiment, $X^1$ is methyl.

In one embodiment, compounds are provided having the structure of any one of Formula (I), Formula (II), Formula (II-A), Formula (II-B), Formula (III), Formula (III-A), Formula (III-B), Formula (IV), Formula (IV-A), Formula (IV-B), Formula (V), Formula (V-A), Formula (V-B), Formula (VI), Formula (VI-A), Formula (VI-B), Formula (VII), Formula (VII-A), Formula (VII-B), Formula (VIII), Formula (VIII-A), Formula (VIII-B), or a pharmaceutically acceptable isomer, racemate, hydrate, solvate, isotope, or salt thereof, wherein $X^1$ is halo. In one embodiment, $X^1$ is Cl or Br. In one embodiment, $X^1$ is Cl. In one embodiment, $X^1$ is Br.

In one embodiment, compounds are provided having the structure of any one of Formula (I), Formula (II), Formula (II-A), Formula (II-B), Formula (III), Formula (III-A), Formula (III-B), Formula (IV), Formula (IV-A), Formula (IV-B), Formula (V), Formula (V-A), Formula (V-B), Formula (VI), Formula (VI-A), Formula (VI-B), Formula (VII), Formula (VII-A), Formula (VII-B), Formula (VIII), Formula (VIII-A), Formula (VIII-B), or a pharmaceutically acceptable isomer, racemate, hydrate, solvate, isotope, or salt thereof, wherein $X^1$ is lower haloalkyl. In one embodiment, $X^1$ is —$CF_3$.

In one embodiment, compounds are provided having the structure of any one of Formula (I), Formula (II), Formula (II-A), Formula (II-B), Formula (III), Formula (III-A), Formula (III-B), Formula (IV), Formula (IV-A), Formula (IV-B), Formula (V), Formula (V-A), Formula (V-B), Formula (VI), Formula (VI-A), Formula (VI-B), Formula (VII), Formula (VII-A), Formula (VII-B), Formula (VIII), Formula (VIII-A), Formula (VIII-B), or a pharmaceutically acceptable isomer, racemate, hydrate, solvate, isotope, or salt thereof, wherein $X^1$ is lower alkenyl. In one embodiment, $X^1$ is vinyl; in another embodiment, $X^1$ is isopropenyl.

In one embodiment, compounds are provided having the structure of any one of Formula (I), Formula (II), Formula (II-A), Formula (II-B), Formula (III), Formula (III-A), Formula (III-B), Formula (IV), Formula (IV-A), Formula (IV-B), Formula (V), Formula (V-A), Formula (V-B), Formula (VI), Formula (VI-A), Formula (VI-B), Formula (VII), Formula (VII-A), Formula (VII-B), Formula (VIII), Formula (VIII-A), Formula (VIII-B), or a pharmaceutically acceptable isomer, racemate, hydrate, solvate, isotope, or salt thereof, wherein $X^2$ is lower alkyl. In one embodiment, $X^2$ is methyl.

In one embodiment, compounds are provided having the structure of any one of Formula (I), Formula (II), Formula (II-A), Formula (II-B), Formula (III), Formula (III-A), Formula (III-B), Formula (IV), Formula (IV-A), Formula (IV-B), Formula (V), Formula (V-A), Formula (V-B), Formula (VI), Formula (VI-A), Formula (VI-B), Formula (VII), Formula (VII-A), Formula (VII-B), Formula (VIII), Formula (VIII-A), Formula (VIII-B), or a pharmaceutically acceptable isomer, racemate, hydrate, solvate, isotope, or salt thereof, wherein $X^2$ is halo. In one embodiment, $X^2$ is Cl or Br. In one embodiment, $X^2$ is Cl. In one embodiment, $X^2$ is Br.

In one embodiment, compounds are provided having the structure of any one of Formula (I), Formula (II), Formula (II-A), Formula (II-B), Formula (III), Formula (III-A), Formula (III-B), Formula (IV), Formula (IV-A), Formula (IV-B), Formula (V), Formula (V-A), Formula (V-B), Formula (VI), Formula (VI-A), Formula (VI-B), Formula (VII), Formula (VII-A), Formula (VII-B), Formula (VIII), Formula (VIII-A), Formula (VIII-B), or a pharmaceutically acceptable isomer, racemate, hydrate, solvate, isotope, or salt thereof, wherein $X^2$ is lower haloalkyl. In one embodiment, $X^2$ is —$CF_3$.

In one embodiment, compounds are provided having the structure of any one of Formula (I), Formula (II), Formula (II-A), Formula (II-B), Formula (III), Formula (III-A), Formula (III-B), Formula (IV), Formula (IV-A), Formula (IV-B), Formula (V), Formula (V-A), Formula (V-B), Formula (VI), Formula (VI-A), Formula (VI-B), Formula (VII), Formula (VII-A), Formula (VII-B), Formula (VIII), Formula (VIII-A), Formula (VIII-B), or a pharmaceutically acceptable isomer, racemate, hydrate, solvate, isotope, or salt thereof, wherein $X^2$ is lower alkenyl. In one embodiment, $X^2$ is vinyl; in another embodiment, $X^2$ is isopropenyl.

In one embodiment, compounds are provided having the structure of any one of Formula (III), Formula (III-A), Formula (III-B), Formula (IV), Formula (IV-A), Formula (IV-B), Formula (V), Formula (V-A), Formula (V-B), Formula (VI), Formula (VI-A), Formula (VI-B), Formula (VII), Formula (VII-A), Formula (VII-B), Formula (VIII), Formula (VIII-A), Formula (VIII-B), or a pharmaceutically acceptable isomer, racemate, hydrate, solvate, isotope, or salt thereof, wherein at least one $R^5$ is lower alkyl.

In one embodiment, compounds are provided having the structure of any one of Formula (III), Formula (III-A), Formula (III-B), Formula (IV), Formula (IV-A), Formula (IV-B), Formula (V), Formula (V-A), Formula (V-B), Formula (VI), Formula (VI-A), Formula (VI-B), Formula (VII), Formula (VII-A), Formula (VII-B), Formula (VIII), Formula (VIII-A), Formula (VIII-B), or a pharmaceutically acceptable isomer, racemate, hydrate, solvate, isotope, or salt thereof, wherein at least one $R^5$ is lower alkyl substituted with —OR'. In one embodiment, R' is H. In another embodiment, R' is lower alkyl.

In one embodiment, compounds are provided having the structure of any one of Formula (III), Formula (III-A), Formula (III-B), Formula (IV), Formula (IV-A), Formula (IV-B), Formula (V), Formula (V-A), Formula (V-B), Formula (VI), Formula (VI-A), Formula (VI-B), Formula (VII), Formula (VII-A), Formula (VII-B), Formula (VIII), Formula (VIII-A), Formula (VIII-B), or a pharmaceutically acceptable isomer, racemate, hydrate, solvate, isotope, or salt thereof, wherein at least one $R^5$ is lower haloalkyl.

In one embodiment, compounds are provided having the structure of any one of Formula (III), Formula (III-A), Formula (III-B), Formula (IV), Formula (IV-A), Formula (IV-B), Formula (V), Formula (V-A), Formula (V-B), Formula (VI), Formula (VI-A), Formula (VI-B), Formula (VII), Formula (VII-A), Formula (VII-B), Formula (VIII), Formula (VIII-A), Formula (VIII-B), or a pharmaceutically acceptable isomer, racemate, hydrate, solvate, isotope, or salt thereof, wherein at least one $R^5$ is —$OR^a$. In one embodiment, $R^a$ is lower alkyl. In one embodiment, $R^a$ is lower haloalkyl.

In one embodiment, compounds are provided having the structure of any one of Formula (III), Formula (III-A), Formula (III-B), Formula (IV), Formula (IV-A), Formula (IV-B), Formula (V), Formula (V-A), Formula (V-B), Formula (VI), Formula (VI-A), Formula (VI-B), Formula (VII), Formula (VII-A), Formula (VII-B), Formula (VIII), Formula (VIII-A), Formula (VIII-B), or a pharmaceutically acceptable isomer, racemate, hydrate, solvate, isotope, or salt thereof, wherein at least one $R^5$ is —$C(O)R^a$. In one embodiment, $R^a$ is lower alkyl.

In one embodiment, compounds are provided having the structure of any one of Formula (III), Formula (III-A), Formula (III-B), Formula (IV), Formula (IV-A), Formula (IV-B), Formula (V), Formula (V-A), Formula (V-B), Formula (VI), Formula (VI-A), Formula (VI-B), Formula (VII), Formula (VII-A), Formula (VII-B), Formula (VIII), Formula (VIII-A), Formula (VIII-B), or a pharmaceutically acceptable isomer, racemate, hydrate, solvate, isotope, or salt thereof, wherein at least one $R^5$ is —$NR^aC(O)R^b$. In one embodiment, $R^a$ is H and $R^b$ is lower alkyl. In one embodiment, $R^b$ is methyl.

In one embodiment, compounds are provided having the structure of any one of Formula (III), Formula (III-A), Formula (III-B), Formula (IV), Formula (IV-A), Formula (IV-B), Formula (V), Formula (V-A), Formula (V-B), Formula (VI), Formula (VI-A), Formula (VI-B), Formula (VII), Formula (VII-A), Formula (VII-B), Formula (VIII), Formula (VIII-A), Formula (VIII-B), or a pharmaceutically acceptable isomer, racemate, hydrate, solvate, isotope, or salt thereof, wherein at least one $R^5$ is —$C(O)OR^a$. In one embodiment, $R^a$ is lower alkyl. In one embodiment, $R^a$ is methyl or ethyl.

In one embodiment, compounds are provided having the structure of any one of Formula (III), Formula (III-A), Formula (III-B), Formula (IV), Formula (IV-A), Formula (IV-B), Formula (V), Formula (V-A), Formula (V-B), Formula (VI), Formula (VI-A), Formula (VI-B), Formula (VII), Formula (VII-A), Formula (VII-B), Formula (VIII), Formula (VIII-A), Formula (VIII-B), or a pharmaceutically acceptable isomer, racemate, hydrate, solvate, isotope, or salt thereof, wherein at least one $R^5$ is —$S(O)_2R^a$. In one embodiment, $R^a$ is lower alkyl. In one embodiment, $R^a$ is methyl.

In one embodiment, compounds are provided having the structure of any one of Formula (III), Formula (III-A), Formula (III-B), Formula (IV), Formula (IV-A), Formula (IV-B), Formula (V), Formula (V-A), Formula (V-B), Formula (VI), Formula (VI-A), Formula (VI-B), Formula (VII), Formula (VII-A), Formula (VII-B), Formula (VIII), Formula (VIII-A), Formula (VIII-B), or a pharmaceutically acceptable isomer, racemate, hydrate, solvate, isotope, or salt thereof, wherein at least one $R^5$ is halo. In one embodiment, at least one $R^5$ is F.

In one embodiment, compounds are provided having the structure of any one of Formula (III), Formula (III-A), Formula (III-B), Formula (IV), Formula (IV-A), Formula (IV-B), Formula (V), Formula (V-A), Formula (V-B), Formula (VI), Formula (VI-A), Formula (VI-B), Formula (VII), Formula (VII-A), Formula (VII-B), Formula (VIII), Formula (VIII-A), Formula (VIII-B), or a pharmaceutically acceptable isomer, racemate, hydrate, solvate, isotope, or salt thereof, wherein at least one $R^5$ is cyano.

In one embodiment, compounds are provided having the structure of any one of Formula (I), Formula (II), Formula (II-A), Formula (II-B), Formula (III), Formula (III-A), Formula (III-B), Formula (IV), Formula (IV-A), Formula (IV-B), Formula (V), Formula (V-A), Formula (V-B), Formula (VI), Formula (VI-A), Formula (VI-B), Formula (VII), Formula (VII-A), Formula (VII-B), Formula (VIII), Formula (VIII-A), Formula (VIII-B), or a pharmaceutically acceptable isomer, racemate, hydrate, solvate, isotope, or salt thereof, wherein $Y^1$ is halogen. In one embodiment, $Y^1$ is F. In one embodiment, $Y^1$ is Cl.

In one embodiment, compounds are provided having the structure of any one of Formula (I), Formula (II), Formula (II-A), Formula (II-B), Formula (III), Formula (III-A), Formula (III-B), Formula (IV), Formula (IV-A), Formula (IV-B), Formula (V), Formula (V-A), Formula (V-B), Formula (VI), Formula (VI-A), Formula (VI-B), Formula (VII), Formula (VII-A), Formula (VII-B), Formula (VIII), Formula (VIII-A), Formula (VIII-B), or a pharmaceutically acceptable isomer, racemate, hydrate, solvate, isotope, or salt thereof, wherein $Y^1$ is cyano.

In one embodiment, compounds are provided having the structure of any one of Formula (I), Formula (II), Formula (II-A), Formula (II-B), Formula (III), Formula (III-A), Formula (III-B), Formula (IV), Formula (IV-A), Formula (IV-B), Formula (V), Formula (V-A), Formula (V-B), Formula (VI), Formula (VI-A), Formula (VI-B), Formula (VII), Formula (VII-A), Formula (VII-B), Formula (VIII), Formula (VIII-A), Formula (VIII-B), or a pharmaceutically acceptable isomer, racemate, hydrate, solvate, isotope, or salt thereof, wherein $Y^1$ is lower alkyl.

In one embodiment, compounds are provided having the structure of any one of Formula (I), Formula (II), Formula (II-A), Formula (II-B), Formula (III), Formula (III-A), Formula (III-B), Formula (IV), Formula (IV-A), Formula (IV-B), Formula (V), Formula (V-A), Formula (V-B), Formula (VI), Formula (VI-A), Formula (VI-B), Formula (VII), Formula (VII-A), Formula (VII-B), Formula (VIII), Formula (VIII-A), Formula (VIII-B), or a pharmaceutically acceptable isomer, racemate, hydrate, solvate, isotope, or salt thereof, wherein $Y^1$ is lower alkoxy.

In one embodiment, compounds are provided having the structure of any one of Formula (I), Formula (II), Formula (II-A), Formula (II-B), Formula (III), Formula (III-A), Formula (III-B), Formula (IV), Formula (IV-A), Formula (IV-B), Formula (V), Formula (V-A), Formula (V-B), Formula (VI), Formula (VI-A), Formula (VI-B), Formula (VII), Formula (VII-A), Formula (VII-B), Formula (VIII), Formula (VIII-A), Formula (VIII-B), or a pharmaceutically acceptable isomer, racemate, hydrate, solvate, isotope, or salt thereof, wherein $Y^1$ is H.

In one embodiment, compounds are provided having the structure of any one of Formula (I), Formula (II), Formula (II-A), Formula (II-B), Formula (III), Formula (III-A), Formula (III-B), Formula (IV), Formula (IV-A), Formula (IV-B), Formula (V), Formula (V-A), Formula (V-B), Formula (VI), Formula (VI-A), Formula (VI-B), Formula (VII), Formula (VII-A), Formula (VII-B), Formula (VIII), Formula (VIII-A), Formula (VIII-B), or a pharmaceutically acceptable isomer, racemate, hydrate, solvate, isotope, or salt thereof, wherein $Y^2$ is halogen. In one embodiment, $Y^2$ is F. In one embodiment, $Y^2$ is Cl.

In one embodiment, compounds are provided having the structure of any one of Formula (I), Formula (II), Formula (II-A), Formula (II-B), Formula (III), Formula (III-A), Formula (III-B), Formula (IV), Formula (IV-A), Formula (IV-B), Formula (V), Formula (V-A), Formula (V-B), Formula (VI), Formula (VI-A), Formula (VI-B), Formula (VII), Formula (VII-A), Formula (VII-B), Formula (VIII), Formula (VIII-A), Formula (VIII-B), or a pharmaceutically acceptable isomer, racemate, hydrate, solvate, isotope, or salt thereof, wherein $Y^2$ is cyano.

In one embodiment, compounds are provided having the structure of any one of Formula (I), Formula (II), Formula (II-A), Formula (II-B), Formula (III), Formula (III-A), Formula (III-B), Formula (IV), Formula (IV-A), Formula (IV-B), Formula (V), Formula (V-A), Formula (V-B), Formula (VI), Formula (VI-A), Formula (VI-B), Formula (VII), Formula (VII-A), Formula (VII-B), Formula (VIII), Formula (VIII-A), Formula (VIII-B), or a pharmaceutically acceptable isomer, racemate, hydrate, solvate, isotope, or salt thereof, wherein $Y^2$ is lower alkyl.

In one embodiment, compounds are provided having the structure of any one of Formula (I), Formula (II), Formula (II-A), Formula (II-B), Formula (III), Formula (III-A), Formula (III-B), Formula (IV), Formula (IV-A), Formula (IV-B), Formula (V), Formula (V-A), Formula (V-B), Formula (VI), Formula (VI-A), Formula (VI-B), Formula (VII), Formula (VII-A), Formula (VII-B), Formula (VIII), Formula (VIII-A), Formula (VIII-B), or a pharmaceutically acceptable isomer, racemate, hydrate, solvate, isotope, or salt thereof, wherein $Y^2$ is lower alkoxy.

In one embodiment, compounds are provided having the structure of any one of Formula (I), Formula (II), Formula (II-A), Formula (II-B), Formula (III), Formula (III-A), Formula (III-B), Formula (IV), Formula (IV-A), Formula (IV-B), Formula (V), Formula (V-A), Formula (V-B), Formula (VI), Formula (VI-A), Formula (VI-B), Formula (VII), Formula (VII-A), Formula (VII-B), Formula (VIII), Formula (VIII-A), Formula (VIII-B), or a pharmaceutically acceptable isomer, racemate, hydrate, solvate, isotope, or salt thereof, wherein $Y^2$ is H.

In one embodiment, compounds are provided having the structure of any one of Formula (I), Formula (II), Formula (II-A), Formula (II-B), Formula (III), Formula (III-A), Formula (III-B), Formula (IV), Formula (IV-A), Formula (IV-B), Formula (V), Formula (V-A), Formula (V-B), Formula (VI), Formula (VI-A), Formula (VI-B), Formula (VII), Formula (VII-A), Formula (VII-B), Formula (VIII), Formula (VIII-A), Formula (VIII-B), or a pharmaceutically acceptable isomer, racemate, hydrate, solvate, isotope, or salt thereof, wherein $Y^1$ is F and $Y^2$ is H.

In one embodiment, compounds are provided having the structure of any one of Formula (I), Formula (II), Formula (II-A), Formula (II-B), Formula (III), Formula (III-A), Formula (III-B), Formula (IV), Formula (IV-A), Formula (IV-B), Formula (V), Formula (V-A), Formula (V-B), Formula (VI), Formula (VI-A), Formula (VI-B), Formula (VII), Formula (VII-A), Formula (VII-B), Formula (VIII), Formula (VIII-A), Formula (VIII-B), or a pharmaceutically acceptable isomer, racemate, hydrate, solvate, isotope, or salt thereof, wherein $Y^1$ is Cl and $Y^2$ is H.

In one embodiment, compounds are provided having the structure of any one of Formula (I), Formula (II), Formula (II-A), Formula (II-B), Formula (III), Formula (III-A), Formula (III-B), Formula (IV), Formula (IV-A), Formula (IV-B), Formula (V), Formula (V-A), Formula (V-B), Formula (VI), Formula (VI-A), Formula (VI-B), Formula (VII), Formula (VII-A), Formula (VII-B), Formula (VIII), Formula (VIII-A), Formula (VIII-B), or a pharmaceutically acceptable isomer, racemate, hydrate, solvate, isotope, or salt thereof, wherein $Y^1$ is cyano and $Y^2$ is H.

In one embodiment, compounds are provided having the structure of any one of Formula (I), Formula (II), Formula (II-A), Formula (II-B), Formula (III), Formula (III-A), Formula (III-B), Formula (IV), Formula (IV-A), Formula (IV-B), Formula (V), Formula (V-A), Formula (V-B), Formula (VI), Formula (VI-A), Formula (VI-B), Formula (VII), Formula (VII-A), Formula (VII-B), Formula (VIII), Formula (VIII-A), Formula (VIII-B), or a pharmaceutically acceptable isomer, racemate, hydrate, solvate, isotope, or salt thereof, wherein $Y^1$ is lower alkyl and $Y^2$ is H.

In one embodiment, compounds are provided having the structure of any one of Formula (I), Formula (II), Formula (II-A), Formula (II-B), Formula (III), Formula (III-A), Formula (III-B), Formula (IV), Formula (IV-A), Formula (IV-B), Formula (V), Formula (V-A), Formula (V-B), Formula (VI), Formula (VI-A), Formula (VI-B), Formula (VII), Formula (VII-A), Formula (VII-B), Formula (VIII), Formula (VIII-A), Formula (VIII-B), or a pharmaceutically acceptable isomer, racemate, hydrate, solvate, isotope, or salt thereof, wherein $Y^1$ is lower alkoxy and $Y^2$ is H.

In one embodiment, compounds are provided having the structure of any one of Formula (I), Formula (II), Formula (II-A), Formula (II-B), Formula (III), Formula (III-A), Formula (III-B), Formula (IV), Formula (IV-A), Formula (IV-B), Formula (V), Formula (V-A), Formula (V-B), Formula (VI), Formula (VI-A), Formula (VI-B), Formula (VII), Formula (VII-A), Formula (VII-B), Formula (VIII), Formula (VIII-A), Formula (VIII-B), or a pharmaceutically acceptable isomer, racemate, hydrate, solvate, isotope, or salt thereof, wherein $Y^1$ is H and $Y^2$ is F.

In one embodiment, compounds are provided having the structure of any one of Formula (I), Formula (II), Formula (II-A), Formula (II-B), Formula (III), Formula (III-A), Formula (III-B), Formula (IV), Formula (IV-A), Formula (IV-B), Formula (V), Formula (V-A), Formula (V-B), Formula (VI), Formula (VI-A), Formula (VI-B), Formula (VII), Formula (VII-A), Formula (VII-B), Formula (VIII), Formula (VIII-A), Formula (VIII-B), or a pharmaceutically acceptable isomer, racemate, hydrate, solvate, isotope, or salt thereof, wherein $Y^1$ is H and $Y^2$ is Cl.

In one embodiment, compounds are provided having the structure of any one of Formula (I), Formula (II), Formula (II-A), Formula (II-B), Formula (III), Formula (III-A), Formula (III-B), Formula (IV), Formula (IV-A), Formula (IV-B), Formula (V), Formula (V-A), Formula (V-B), Formula (VI), Formula (VI-A), Formula (VI-B), Formula (VII), Formula (VII-A), Formula (VII-B), Formula (VIII), Formula (VIII-A), Formula (VIII-B), or a pharmaceutically acceptable isomer, racemate, hydrate, solvate, isotope, or salt thereof, wherein $Y^1$ is H and $Y^2$ is cyano.

In one embodiment, compounds are provided having the structure of any one of Formula (I), Formula (II), Formula (II-A), Formula (II-B), Formula (III), Formula (III-A), Formula (III-B), Formula (IV), Formula (IV-A), Formula (IV-B), Formula (V), Formula (V-A), Formula (V-B), Formula (VI), Formula (VI-A), Formula (VI-B), Formula (VII), Formula (VII-A), Formula (VII-B), Formula (VIII), Formula (VIII-A), Formula (VIII-B), or a pharmaceutically acceptable isomer, racemate, hydrate, solvate, isotope, or salt thereof, wherein $Y^1$ is H and $Y^2$ is lower alkyl.

In one embodiment, compounds are provided having the structure of any one of Formula (I), Formula (II), Formula (II-A), Formula (II-B), Formula (III), Formula (III-A), Formula (III-B), Formula (IV), Formula (IV-A), Formula (IV-B), Formula (V), Formula (V-A), Formula (V-B), Formula (VI), Formula (VI-A), Formula (VI-B), Formula (VII), Formula (VII-A), Formula (VII-B), Formula (VIII), Formula (VIII-A), Formula (VIII-B), or a pharmaceutically acceptable isomer, racemate, hydrate, solvate, isotope, or salt thereof, wherein $Y^1$ is H and $Y^2$ is lower alkoxy.

In one embodiment, compounds are provided having the structure of any one of Formula (I), Formula (II), Formula (II-A), Formula (II-B), Formula (III), Formula (III-A), Formula (III-B), Formula (IV), Formula (IV-A), Formula (IV-B), Formula (V), Formula (V-A), Formula (V-B), Formula (VI), Formula (VI-A), Formula (VI-B), Formula (VII), Formula (VII-A), Formula (VII-B), Formula (VIII), Formula (VIII-A), Formula (VIII-B), or a pharmaceutically acceptable isomer, racemate, hydrate, solvate, isotope, or salt thereof, wherein $Y^1$ is F and $Y^2$ is F.

Representative compounds of Formula (I), and Formulas (II) through (VIII-B) as applicable, include the compounds listed in Table 1 below, as well as pharmaceutically acceptable salts thereof. To this end, representative compounds are identified herein by their respective "Compound Number", which is sometimes abbreviated as "Compound No.", "Cmpd. No." or "No."

TABLE 1

Representative Compounds

| CMPD NO | STRUCTURE | NAME |
|---|---|---|
| 1 | 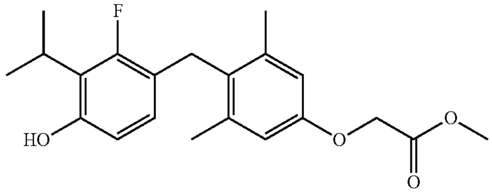 [SMILES: COC(=O)COc1cc(C)c(Cc2ccc(O)c(C(C)C)c2F)c(C)c1] | methyl 2-(4-(2-fluoro-4-hydroxy-3-isopropylbenzyl)-3,5-dimethylphenoxy)acetate |
| 2 | 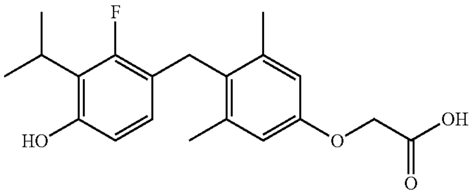 [SMILES: Cc1cc(OCC(=O)O)cc(C)c1Cc1ccc(O)c(C(C)C)c1F] | 2-(4-(2-fluoro-4-hydroxy-3-isopropylbenzyl)-3,5-dimethylphenoxy)acetic acid |
| 3 | 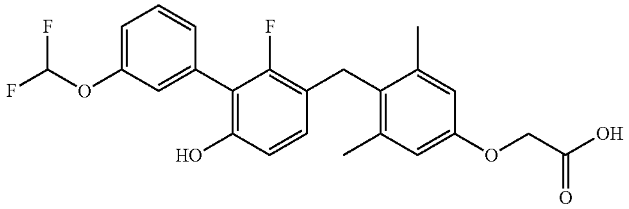 [SMILES: Cc1cc(OCC(=O)O)cc(C)c1Cc1ccc(O)c(-c2cccc(OC(F)F)c2)c1F] | 2-(4-((3'-(difluoromethoxy)-2-fluoro-6-hydroxy-[1,1'-biphenyl]-3-yl)methyl)-3,5-dimethylphenoxy)acetic acid |

TABLE 1-continued

| Representative Compounds | | |
|---|---|---|
| CMPD NO | STRUCTURE | NAME |
| 4 | 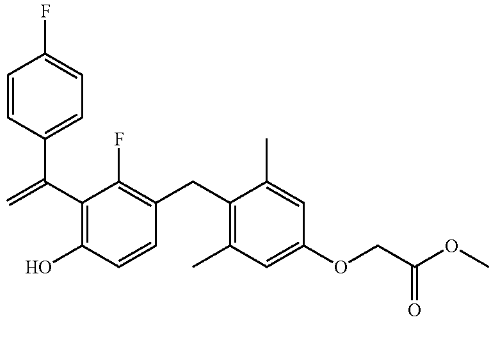 [SMILES: C=C(c1ccc(F)cc1)c1c(O)ccc(Cc2c(C)cc(OCC(=O)OC)cc2C)c1F] | methyl 2-(4-(2-fluoro-3-(1-(4-fluorophenyl)vinyl)-4-hydroxybenzyl)-3,5-dimethylphenoxy)acetate |
| 5 | 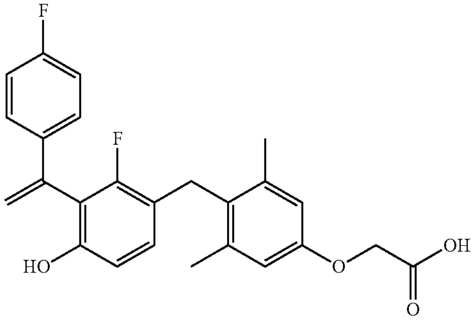 [SMILES: C=C(c1ccc(F)cc1)c1c(O)ccc(Cc2c(C)cc(OCC(=O)O)cc2C)c1F] | 2-(4-(2-fluoro-3-(1-(4-fluorophenyl)vinyl)-4-hydroxybenzyl)-3,5-dimethylphenoxy)acetic acid |
| 6 | 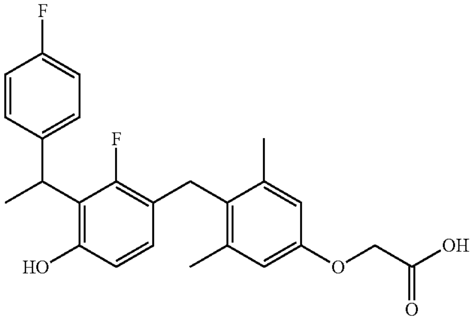 [SMILES: Cc1cc(OCC(=O)O)cc(C)c1Cc1ccc(O)c(C(C)c2ccc(F)cc2)c1F] | 2-(4-(2-fluoro-3-(1-(4-fluorophenyl)ethyl)-4-hydroxybenzyl)-3,5-dimethylphenoxy)acetic acid |
| 7 | 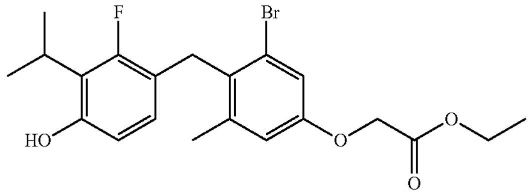 [SMILES: CCOC(=O)COc1cc(C)c(Cc2ccc(O)c(C(C)C)c2F)c(Br)c1] | ethyl 2-(3-bromo-4-(2-fluoro-4-hydroxy-3-isopropylbenzyl)-5-methylphenoxy)acetate |
| 8 | 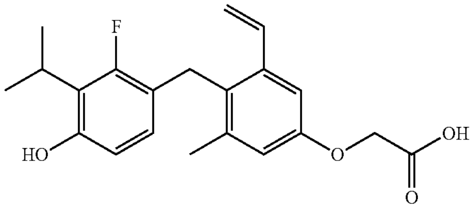 [SMILES: C=Cc1cc(OCC(=O)O)cc(C)c1Cc1ccc(O)c(C(C)C)c1F] | 2-(4-(2-fluoro-4-hydroxy-3-isopropylbenzyl)-3-methyl-5-vinylphenoxy)acetic acid |

TABLE 1-continued

| CMPD NO | Representative Compounds<br>STRUCTURE | NAME |
|---|---|---|
| 9 | 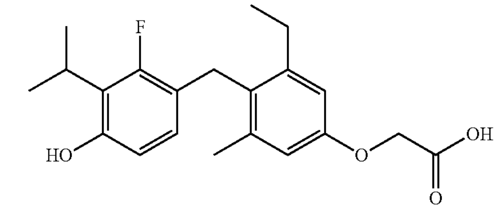 [SMILES: CCc1cc(OCC(=O)O)cc(C)c1Cc1ccc(O)c(C(C)C)c1F] | 2-(3-ethyl-4-(2-fluoro-4-hydroxy-3-isopropylbenzyl)-5-methylphenoxy) acetic acid |
| 10 | 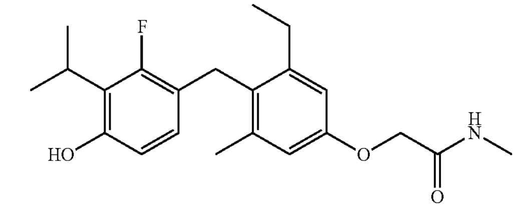 [SMILES: CCc1cc(OCC(=O)NC)cc(C)c1Cc1ccc(O)c(C(C)C)c1F] | 2-(3-ethyl-4-(2-fluoro-4-hydroxy-3-isopropylbenzyl)-5-methylphenoxy)-N-methylacetamide |
| 11 | 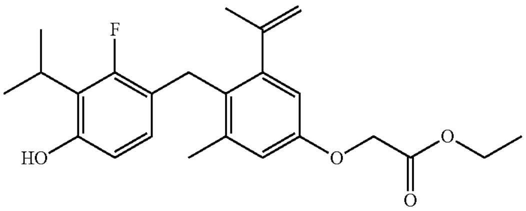 [SMILES: C=C(C)c1cc(OCC(=O)OCC)cc(C)c1Cc1ccc(O)c(C(C)C)c1F] | ethyl 2-(4-(2-fluoro-4-hydroxy-3-isopropylbenzyl)-3-methyl-5-(prop-l-en-2-yl)phenoxy)acetate |
| 12 | 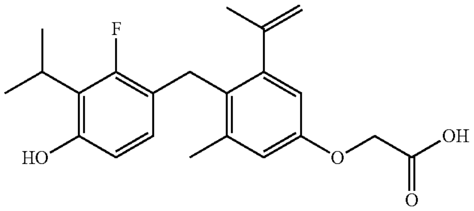 [SMILES: C=C(C)c1cc(OCC(=O)O)cc(C)c1Cc1ccc(O)c(C(C)C)c1F] | 2-(4-(2-fluoro-4-hydroxy-3-isopropylbenzyl)-3-methyl-5-(prop-1-en-2-yl)phenoxy)acetic acid |
| 13 | 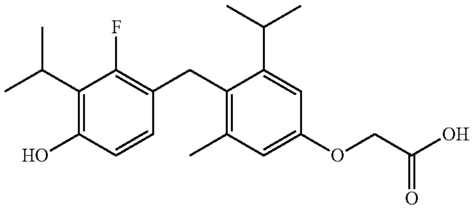 [SMILES: Cc1cc(OCC(=O)O)cc(C(C)C)c1Cc1ccc(O)c(C(C)C)c1F] | 2-(4-(2-fluoro-4-hydroxy-3-isopropylbenzyl)-3-isopropyl-5-methylphenoxy)acetic acid |
| 14 | 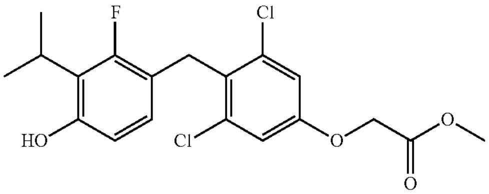 [SMILES: COC(=O)COc1cc(Cl)c(Cc2ccc(O)c(C(C)C)c2F)c(Cl)c1] | methyl 2-(3,5-dichloro-4-(2-fluoro-4-hydroxy-3-isopropylbenzyl)phenoxy)acetate |
| 15 | 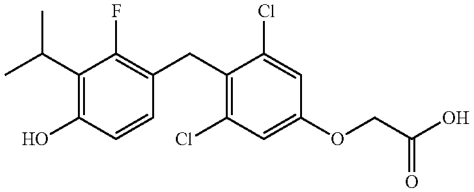 [SMILES: CC(C)c1c(O)ccc(Cc2c(Cl)cc(OCC(=O)O)cc2Cl)c1F] | 2-(3,5-dichloro-4-(2-fluoro-4-hydroxy-3-isopropylbenzyl)phenoxy)acetic acid |

TABLE 1-continued

Representative Compounds

| CMPD NO | STRUCTURE | NAME |
|---|---|---|
| 16 | 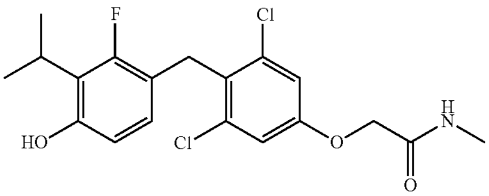 [SMILES: CNC(=O)COc1cc(Cl)c(Cc2ccc(O)c(C(C)C)c2F)c(Cl)c1] | 2-(3,5-dichloro-4-(2-fluoro-4-hydroxy-3-isopropylbenzyl)phenoxy)-N-methylacetamide |
| 17 | 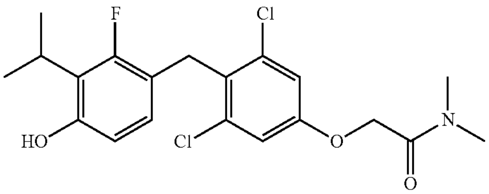 [SMILES: CC(C)c1c(O)ccc(Cc2c(Cl)cc(OCC(=O)N(C)C)cc2Cl)c1F] | 2-(3,5-dichloro-4-(2-fluoro-4-hydroxy-3-isopropylbenzyl)phenoxy)-N,N-dimethylacetamide |
| 18 | 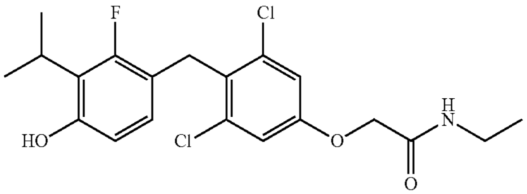 [SMILES: CCNC(=O)COc1cc(Cl)c(Cc2ccc(O)c(C(C)C)c2F)c(Cl)c1] | 2-(3,5-dichloro-4-(2-fluoro-4-hydroxy-3-isopropylbenzyl)phenoxy)-N-ethylacetamide |
| 19 | 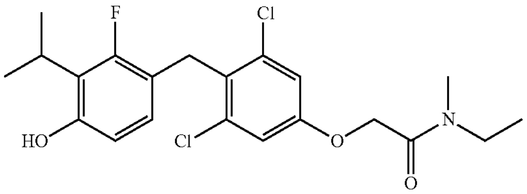 [SMILES: CCN(C)C(=O)COc1cc(Cl)c(Cc2ccc(O)c(C(C)C)c2F)c(Cl)c1] | 2-(3,5-dichloro-4-(2-fluoro-4-hydroxy-3-isopropylbenzyl)phenoxy)-N-ethyl-N-methylacetamide |
| 20 | 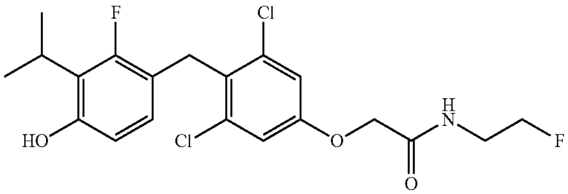 [SMILES: CC(C)c1c(O)ccc(Cc2c(Cl)cc(OCC(=O)NCCF)cc2Cl)c1F] | 2-(3,5-dichloro-4-(2-fluoro-4-hydroxy-3-isopropylbenzyl)phenoxy)-N-(2-fluoroethyl) acetamide |
| 21 | 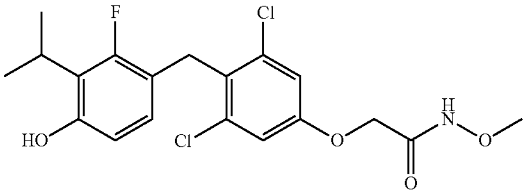 [SMILES: CONC(=O)COc1cc(Cl)c(Cc2ccc(O)c(C(C)C)c2F)c(Cl)c1] | 2-(3,5-dichloro-4-(2-fluoro-4-hydroxy-3-isopropylbenzyl)phenoxy)-N-methoxyacetamide |
| 22 | 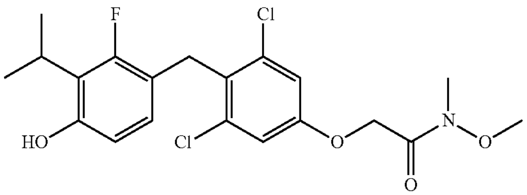 [SMILES: CON(C)C(=O)COc1cc(Cl)c(Cc2ccc(O)c(C(C)C)c2F)c(Cl)c1] | 2-(3,5-dichloro-4-(2-fluoro-4-hydroxy-3-isopropylbenzyl)phenoxy)-N-methoxy-N-methylacetamide |

TABLE 1-continued

| Representative Compounds | | |
|---|---|---|
| CMPD NO | STRUCTURE | NAME |
| 23 | 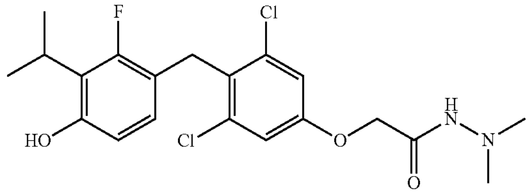 [SMILES: CC(C)c1c(O)ccc(Cc2c(Cl)cc(OCC(=O)NN(C)C)cc2Cl)c1F] | 2-(3,5-dichloro-4-(2-fluoro-4-hydroxy-3-isopropylbenzyl)phenoxy)-N',N'-dimethylacetohydrazide |
| 24 | 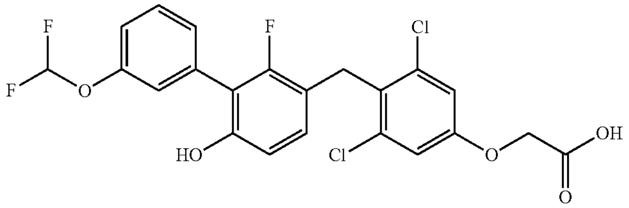 [SMILES: O=C(O)COc1cc(Cl)c(Cc2ccc(O)c(-c3cccc(OC(F)F)c3)c2F)c(Cl)c1] | 2-(3,5-dichloro-4-((3'-(difluoromethoxy)-2-fluoro-6-hydroxy-[1,1'-biphenyl]-3-yl)methyl)phenoxy) acetic acid |
| 25 | 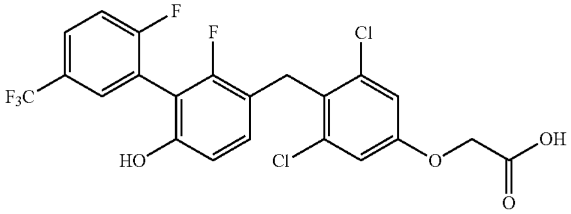 [SMILES: O=C(O)COc1cc(Cl)c(Cc2ccc(O)c(-c3cc(C(F)(F)F)ccc3F)c2F)c(Cl)c1] | 2-(3,5-dichloro-4-((2,2'-difluoro-6-hydroxy-5'-(trifluoromethyl)-[1,1'-biphenyl]-3-yl)methyl) phenoxy)acetic acid |
| 26 | 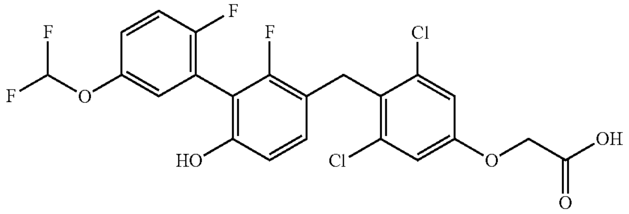 [SMILES: O=C(O)COc1cc(Cl)c(Cc2ccc(O)c(-c3cc(OC(F)F)ccc3F)c2F)c(Cl)c1] | 2-(3,5-dichloro-4-((5'-(difluoromethoxy)-2,2'-difluoro-6-hydroxy-[1,1'-biphenyl]-3-yl)methyl)phenoxy)acetic acid |
| 27 | 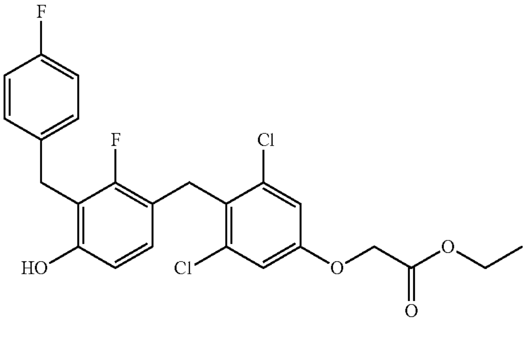 [SMILES: CCOC(=O)COc1cc(Cl)c(Cc2ccc(O)c(Cc3ccc(F)cc3)c2F)c(Cl)c1] | ethyl 2-(3,5-dichloro-4-(2-fluoro-3-(4-fluorobenzyl)-4-hydroxybenzyl)phenoxy) acetate |
| 28 | 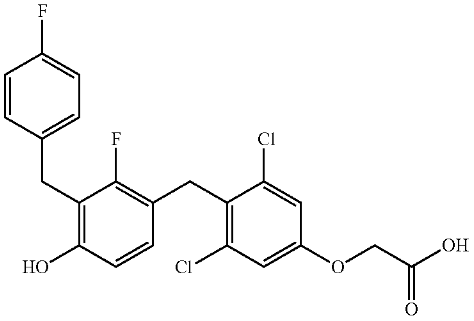 [SMILES: O=C(O)COc1cc(Cl)c(Cc2ccc(O)c(Cc3ccc(F)cc3)c2F)c(Cl)c1] | 2-(3,5-dichloro-4-(2-fluoro-3-(4-fluorobenzyl)-4-hydroxybenzyl)phenoxy) acetic acid |

TABLE 1-continued

| CMPD NO | STRUCTURE | NAME |
| --- | --- | --- |
| | Representative Compounds | |
| 29 | 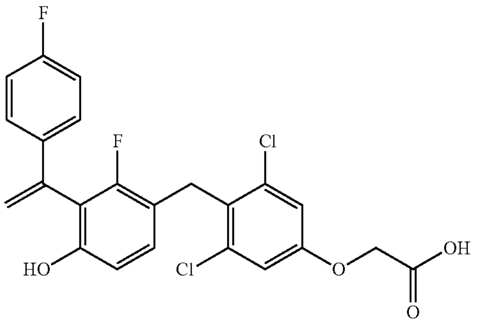 [SMILES: C=C(c1ccc(F)cc1)c1c(O)ccc(Cc2c(Cl)cc(OCC(=O)O)cc2Cl)c1F] | 2-(3,5-dichloro-4-(2-fluoro-3-(1-(4-fluorophenyl)vinyl)-4-hydroxybenzyl)phenoxy)acetic acid |
| 30 | 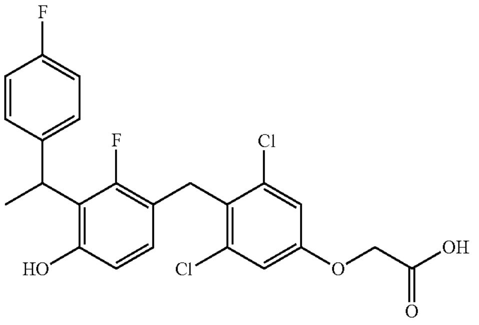 [SMILES: CC(c1ccc(F)cc1)c1c(O)ccc(Cc2c(Cl)cc(OCC(=O)O)cc2Cl)c1F] | 2-(3,5-dichloro-4-(2-fluoro-3-(1-(4-fluorophenyl)ethyl)-4-hydroxybenzyl)phenoxy)acetic acid |
| 31 | 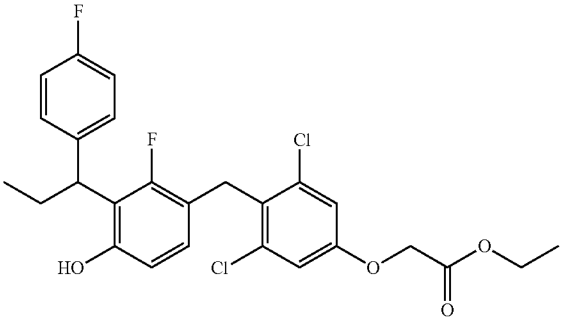 [SMILES: CCOC(=O)COc1cc(Cl)c(Cc2ccc(O)c(C(CC)c3ccc(F)cc3)c2F)c(Cl)c1] | ethyl 2-(3,5-dichloro-4-(2-fluoro-3-(1-(4-fluorophenyl)propyl)-4-hydroxybenzyl)phenoxy)acetate |
| 32 | 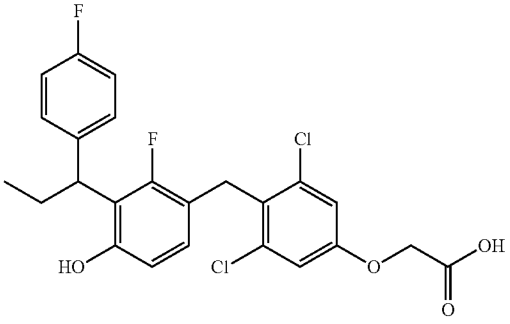 [SMILES: CCC(c1ccc(F)cc1)c1c(O)ccc(Cc2c(Cl)cc(OCC(=O)O)cc2Cl)c1F] | 2-(3,5-dichloro-4-(2-fluoro-3-(1-(4-fluorophenyl)propyl)-4-hydroxybenzyl)phenoxy)acetic acid |

TABLE 1-continued

| CMPD NO | STRUCTURE | NAME |
| --- | --- | --- |
| 33 | 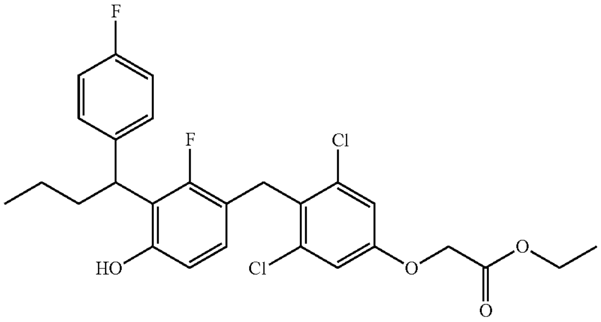 [SMILES: CCCC(c1ccc(F)cc1)c1c(O)ccc(Cc2c(Cl)cc(OCC(=O)OCC)cc2Cl)c1F] | ethyl 2-(3,5-dichloro-4-(2-fluoro-3-(1-(4-fluorophenyl)butyl)-4-hydroxybenzyl)phenoxy)acetate |
| 34 | 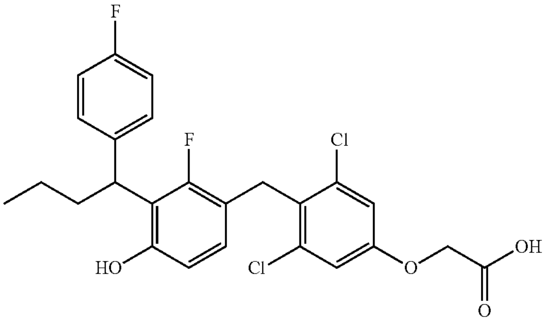 [SMILES: CCCC(c1ccc(F)cc1)c1c(O)ccc(Cc2c(Cl)cc(OCC(=O)O)cc2Cl)c1F] | 2-(3,5-dichloro-4-(2-fluoro-3-(1-(4-fluorophenyl)butyl)-4-hydroxybenzyl)phenoxy)acetic acid |
| 35 | 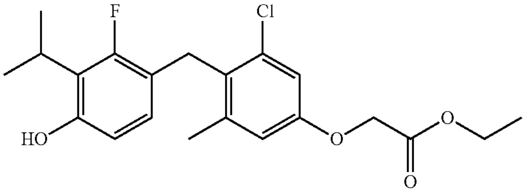 [SMILES: CCOC(=O)COc1cc(C)c(Cc2ccc(O)c(C(C)C)c2F)c(Cl)c1] | ethyl 2-(3-chloro-4-(2-fluoro-4-hydroxy-3-isopropylbenzyl)-5-methylphenoxy)acetate |
| 36 | 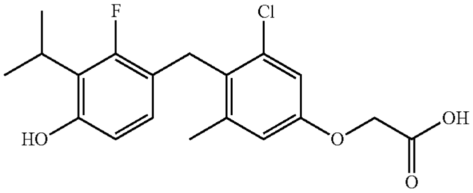 [SMILES: Cc1cc(OCC(=O)O)cc(Cl)c1Cc1ccc(O)c(C(C)C)c1F] | 2-(3-chloro-4-(2-fluoro-4-hydroxy-3-isopropylbenzyl)-5-methylphenoxy)acetic acid |
| 37 | 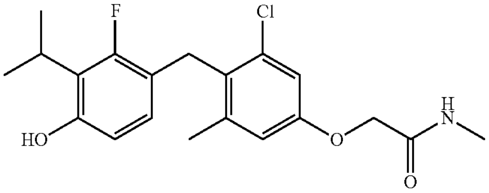 [SMILES: CNC(=O)COc1cc(C)c(Cc2ccc(O)c(C(C)C)c2F)c(Cl)c1] | 2-(3-chloro-4-(2-fluoro-4-hydroxy-3-isopropylbenzyl)-5-methylphenoxy)-N-methylacetamide |
| 38 | 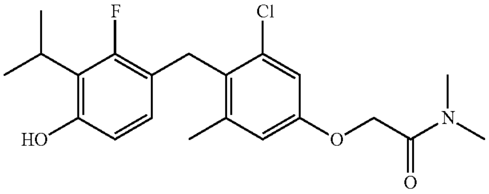 | 2-(3-chloro-4-(2-fluoro-4-hydroxy-3-isopropylbenzyl)-5-methylphenoxy)-N,N-dimethylacetamide |

Representative Compounds

TABLE 1-continued

Representative Compounds

| CMPD NO | STRUCTURE | NAME |
|---|---|---|
| 39 | 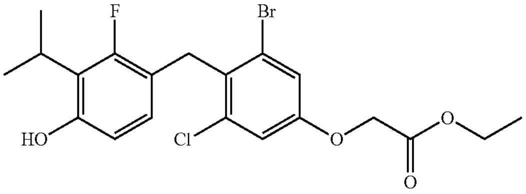 [SMILES: CCOC(=O)COc1cc(Cl)c(Cc2ccc(O)c(C(C)C)c2F)c(Br)c1] | ethyl 2-(3-bromo-5-chloro-4-(2-fluoro-4-hydroxy-3-isopropylbenzyl)phenoxy)acetate |
| 40 | 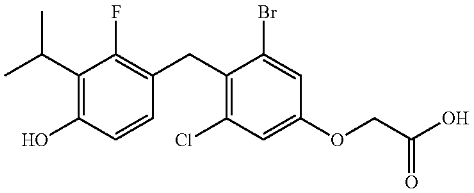 [SMILES: CC(C)c1c(O)ccc(Cc2c(Cl)cc(OCC(=O)O)cc2Br)c1F] | 2-(3-bromo-5-chloro-4-(2-fluoro-4-hydroxy-3-isopropylbenzyl)phenoxy)acetic acid |
| 41 | 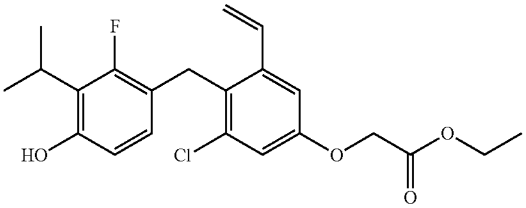 [SMILES: C=Cc1cc(OCC(=O)OCC)cc(Cl)c1Cc1ccc(O)c(C(C)C)c1F] | ethyl 2-(3-chloro-4-(2-fluoro-4-hydroxy-3-isopropylbenzyl)-5-vinylphenoxy)acetate |
| 42 | 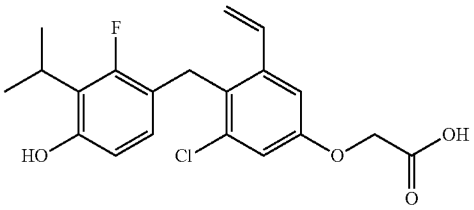 [SMILES: C=Cc1cc(OCC(=O)O)cc(Cl)c1Cc1ccc(O)c(C(C)C)c1F] | 2-(3-chloro-4-(2-fluoro-4-hydroxy-3-isopropylbenzyl)-5-vinylphenoxy)acetic acid |
| 43 | 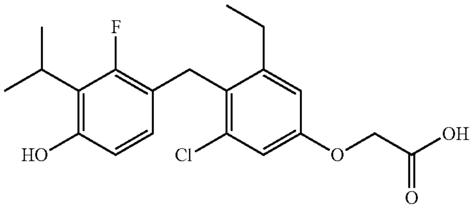 [SMILES: CCc1cc(OCC(=O)O)cc(Cl)c1Cc1ccc(O)c(C(C)C)c1F] | 2-(3-chloro-5-ethyl-4-(2-fluoro-4-hydroxy-3-isopropylbenzyl)phenoxy)acetic acid |
| 44 | 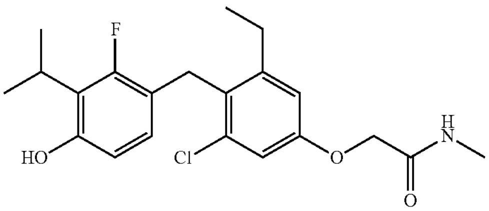 [SMILES: CCc1cc(OCC(=O)NC)cc(Cl)c1Cc1ccc(O)c(C(C)C)c1F] | 2-(3-chloro-5-ethyl-4-(2-fluoro-4-hydroxy-3-isopropylbenzyl)phenoxy)-N-methylacetamide |
| 45 | 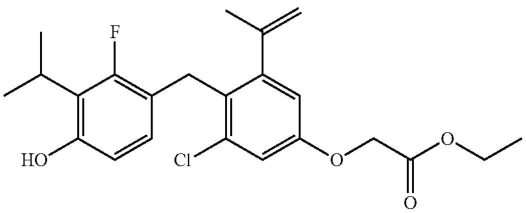 [SMILES: C=C(C)c1cc(OCC(=O)OCC)cc(Cl)c1Cc1ccc(O)c(C(C)C)c1F] | ethyl 2-(3-chloro-4-(2-fluoro-4-hydroxy-3-isopropylbenzyl)-5-(prop-1-en-2-yl)phenoxy) acetate |

TABLE 1-continued

| Representative Compounds | | |
| --- | --- | --- |
| CMPD NO | STRUCTURE | NAME |
| 46 | 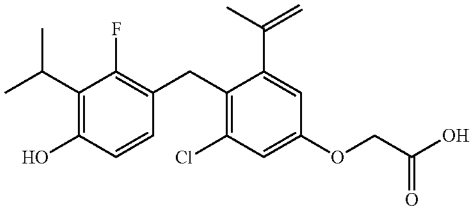 [SMILES: C=C(C)c1cc(OCC(=O)O)cc(Cl)c1Cc1ccc(O)c(C(C)C)c1F] | 2-(3-chloro-4-(2-fluoro-4-hydroxy-3-isopropylbenzyl)-5-(prop-1-en-2-yl)phenoxy)acetic acid |
| 47 | 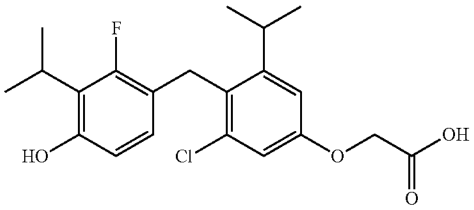 | 2-(3-chloro-4-(2-fluoro-4-hydroxy-3-isopropylbenzyl)-5-isopropylphenoxy)acetic acid |
| 48 | 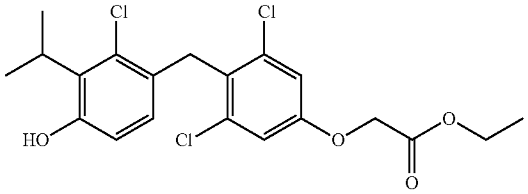 [SMILES: CCOC(=O)COc1cc(Cl)c(Cc2ccc(O)c(C(C)C)c2Cl)c(Cl)c1] | ethyl 2-(3,5-dichloro-4-(2-chloro-4-hydroxy-3-isopropylbenzyl)phenoxy)acetate |
| 49 | 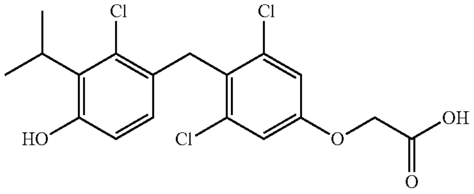 | 2-(3,5-dichloro-4-(2-chloro-4-hydroxy-3-isopropylbenzyl)phenoxy) acetic acid |
| 50 | 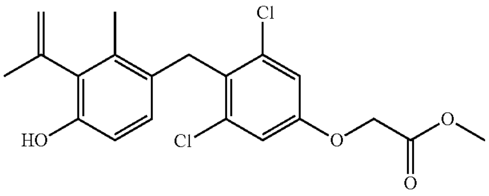 | methyl 2-(3,5-dichloro-4-(4-hydroxy-2-methyl-3-(prop-1-en-2-yl)benzyl)phenoxy) acetate |
| 51 | 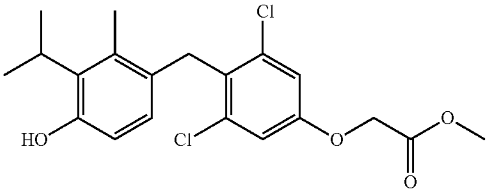 [SMILES: COC(=O)COc1cc(Cl)c(Cc2ccc(O)c(C(C)C)c2C)c(Cl)c1] | methyl 2-(3,5-dichloro-4-(4-hydroxy-3-isopropyl-2-methylbenzyl)phenoxy)acetate |
| 52 | 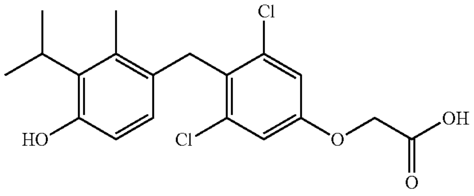 | 2-(3,5-dichloro-4-(4-hydroxy-3-isopropyl-2-methylbenzyl)phenoxy)acetic acid |

TABLE 1-continued

Representative Compounds

| CMPD NO | STRUCTURE | NAME |
| --- | --- | --- |
| 53 | 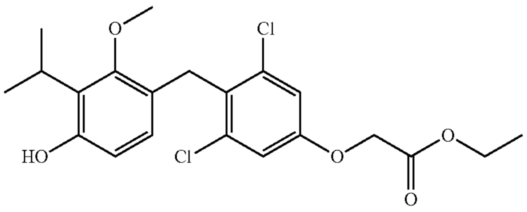 [SMILES: CCOC(=O)COc1cc(Cl)c(Cc2ccc(O)c(C(C)C)c2OC)c(Cl)c1] | ethyl 2-(3,5-dichloro-4-(4-hydroxy-3-isopropyl-2-methoxybenzyl)phenoxy)acetate |
| 54 | 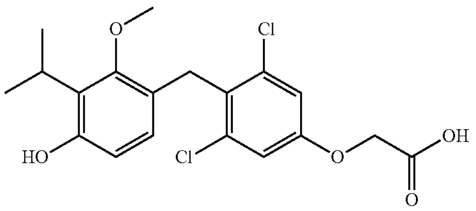 [SMILES: COc1c(Cc2c(Cl)cc(OCC(=O)O)cc2Cl)ccc(O)c1C(C)C] | 2-(3,5-dichloro-4-(4-hydroxy-3-isopropyl-2-methoxybenzyl) phenoxy)acetic acid |
| 55 | 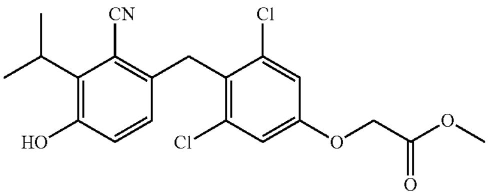 [SMILES: COC(=O)COc1cc(Cl)c(Cc2ccc(O)c(C(C)C)c2C#N)c(Cl)c1] | methyl 2-(3,5-dichloro-4-(2-cyano-4-hydroxy-3-isopropylbenzyl)phenoxy)acetate |
| 56 | 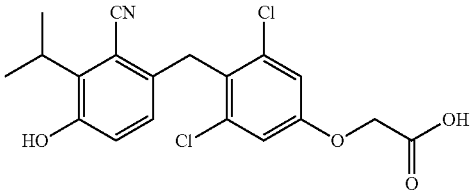 [SMILES: CC(C)c1c(O)ccc(Cc2c(Cl)cc(OCC(=O)O)cc2Cl)c1C#N] | 2-(3,5-dichloro-4-(2-cyano-4-hydroxy-3-isopropylbenzyl)phenoxy)acetic acid |
| 57 | 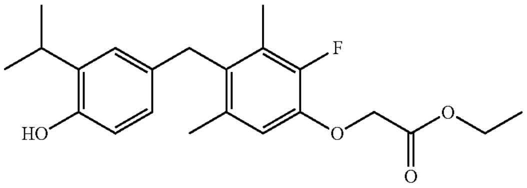 [SMILES: CCOC(=O)COc1cc(C)c(Cc2ccc(O)c(C(C)C)c2)c(C)c1F] | ethyl 2-(2-fluoro-4-(4-hydroxy-3-isopropylbenzyl)-3,5-dimethylphenoxy)acetate |
| 58 | 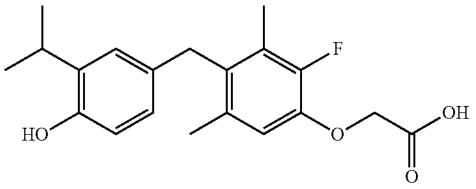 [SMILES: Cc1cc(OCC(=O)O)c(F)c(C)c1Cc1ccc(O)c(C(C)C)c1] | 2-(2-fluoro-4-(4-hydroxy-3-isopropylbenzyl)-3,5-dimethylphenoxy)acetic acid |
| 59 | 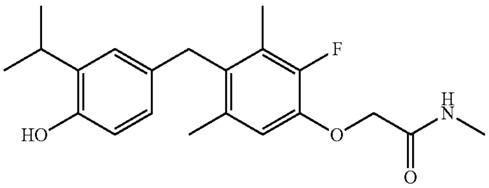 [SMILES: CNC(=O)COc1cc(C)c(Cc2ccc(O)c(C(C)C)c2)c(C)c1F] | 2-(2-fluoro-4-(4-hydroxy-3-isopropylbenzyl)-3,5-dimethylphenoxy)-N-methylacetamide |

TABLE 1-continued

| CMPD NO | STRUCTURE | NAME |
|---|---|---|
| 60 | 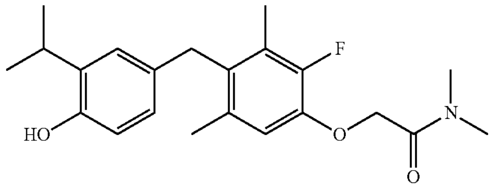 [SMILES: Cc1cc(OCC(=O)N(C)C)c(F)c(C)c1Cc1ccc(O)c(C(C)C)c1] | 2-(2-fluoro-4-(4-hydroxy-3-isopropylbenzyl)-3,5-dimethylphenoxy)-N,N-dimethylacetamide |
| 61 | 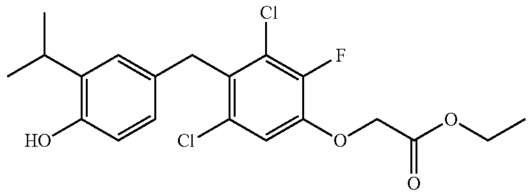 | ethyl 2-(3,5-dichloro-2-fluoro-4-(4-hydroxy-3-isopropylbenzyl)phenoxy)acetate |
| 62 | 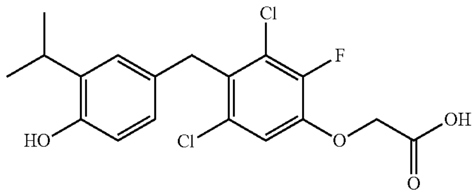 [SMILES: CC(C)c1cc(Cc2c(Cl)cc(OCC(=O)O)c(F)c2Cl)ccc1O] | 2-(3,5-dichloro-2-fluoro-4-(4-hydroxy-3-isopropylbenzyl)phenoxy)acetic acid |
| 63 | 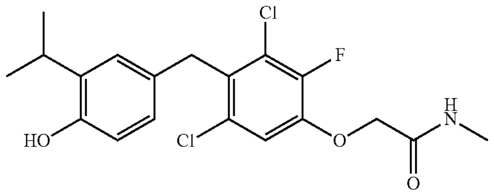 [SMILES: CNC(=O)COc1cc(Cl)c(Cc2ccc(O)c(C(C)C)c2)c(Cl)c1F] | 2-(3,5-dichloro-2-fluoro-4-(4-hydroxy-3-isopropylbenzyl)phenoxy)-N-methylacetamide |
| 64 | 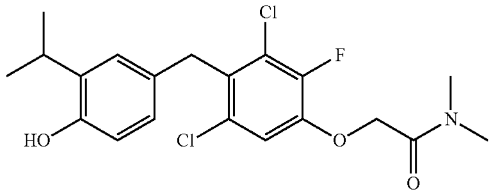 [SMILES: CC(C)c1cc(Cc2c(Cl)cc(OCC(=O)N(C)C)c(F)c2Cl)ccc1O] | 2-(3,5-dichloro-2-fluoro-4-(4-hydroxy-3-isopropylbenzyl)phenoxy)-N,N-dimethylacetamide |
| 65 | 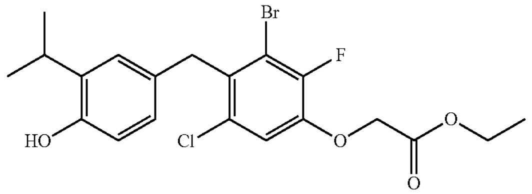 | ethyl 2-(3-bromo-5-chloro-2-fluoro-4-(4-hydroxy-3-isopropylbenzyl)phenoxy) acetate |
| 66 | 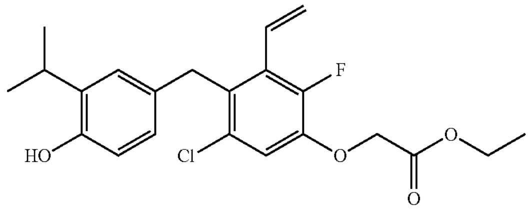 [SMILES: C=Cc1c(F)c(OCC(=O)OCC)cc(Cl)c1Cc1ccc(O)c(C(C)C)c1] | ethyl 2-(5-chloro-2-fluoro-4-(4-hydroxy-3-isopropylbenzyl)-3-vinylphenoxy)acetate |

Representative Compounds

TABLE 1-continued

| CMPD NO | STRUCTURE | NAME |
|---|---|---|
| 67 | 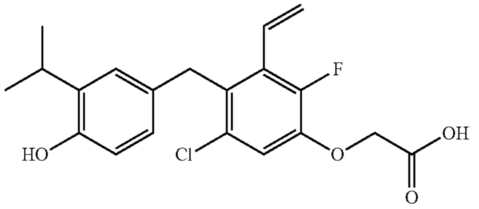 [SMILES: C=Cc1c(F)c(OCC(=O)O)cc(Cl)c1Cc1ccc(O)c(C(C)C)c1] | 2-(5-chloro-2-fluoro-4-(4-hydroxy-3-isopropylbenzyl)-3-vinylphenoxy)acetic acid |
| 68 | 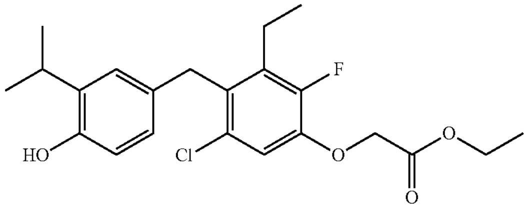 [SMILES: CCOC(=O)COc1cc(Cl)c(Cc2ccc(O)c(C(C)C)c2)c(CC)c1F] | ethyl 2-(5-chloro-3-ethyl-2-fluoro-4-(4-hydroxy-3-isopropylbenzyl)phenoxy)acetate |
| 69 | 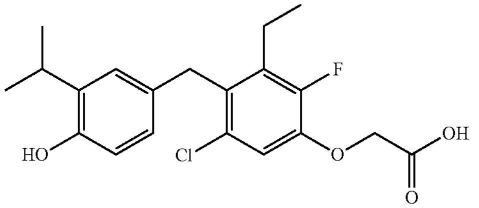 [SMILES: CCc1c(F)c(OCC(=O)O)cc(Cl)c1Cc1ccc(O)c(C(C)C)c1] | 2-(5-chloro-3-ethyl-2-fluoro-4-(4-hydroxy-3-isopropylbenzyl)phenoxy)acetic acid |
| 70 | 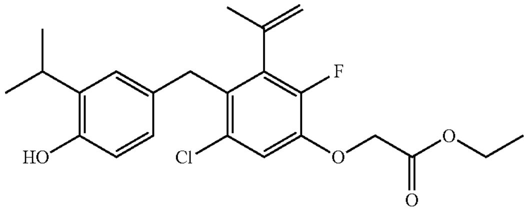 [SMILES: C=C(C)c1c(F)c(OCC(=O)OCC)cc(Cl)c1Cc1ccc(O)c(C(C)C)c1] | ethyl 2-(5-chloro-2-fluoro-4-(4-hydroxy-3-isopropylbenzyl)-3-(prop-1-en-2-yl)phenoxy) acetate |
| 71 | 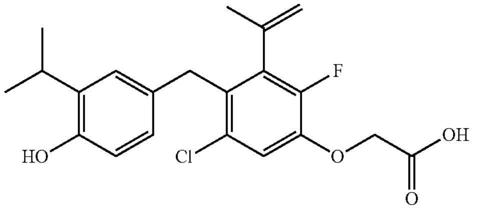 [SMILES: C=C(C)c1c(F)c(OCC(=O)O)cc(Cl)c1Cc1ccc(O)c(C(C)C)c1] | 2-(5-chloro-2-fluoro-4-(4-hydroxy-3-isopropylbenzyl)-3-(prop-1-en-2-yl)phenoxy) acetic acid |
| 72 | 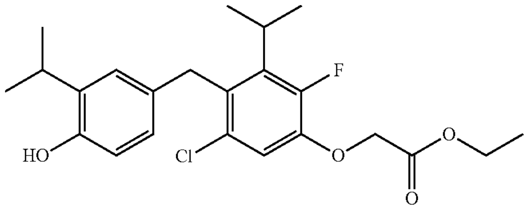 [SMILES: CCOC(=O)COc1cc(Cl)c(Cc2ccc(O)c(C(C)C)c2)c(C(C)C)c1F] | ethyl 2-(5-chloro-2-fluoro-4-(4-hydroxy-3-isopropylbenzyl)-3-isopropylphenoxy)acetate |
| 73 | 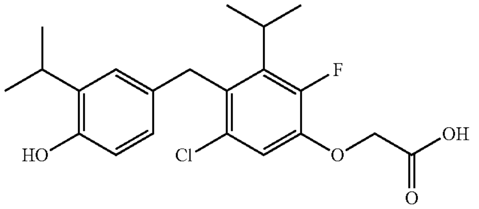 [SMILES: CC(C)c1cc(Cc2c(Cl)cc(OCC(=O)O)c(F)c2C(C)C)ccc1O] | 2-(5-chloro-2-fluoro-4-(4-hydroxy-3-isopropylbenzyl)-3-isopropylphenoxy)acetic acid |

TABLE 1-continued

| Representative Compounds | | |
|---|---|---|
| CMPD NO | STRUCTURE | NAME |
| 74 | 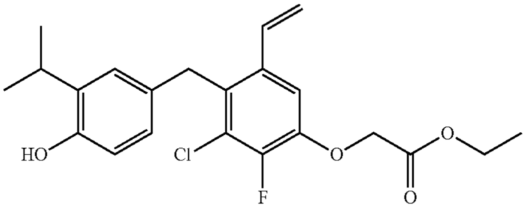 [SMILES: C=Cc1cc(OCC(=O)OCC)c(F)c(Cl)c1Cc1ccc(O)c(C(C)C)c1] | ethyl 2-(3-chloro-2-fluoro-4-(4-hydroxy-3-isopropylbenzyl)-5-vinylphenoxy)acetate |
| 75 | 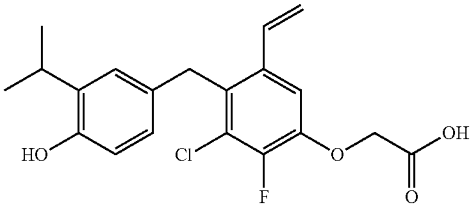 [SMILES: C=Cc1cc(OCC(=O)O)c(F)c(Cl)c1Cc1ccc(O)c(C(C)C)c1] | 2-(3-chloro-2-fluoro-4-(4-hydroxy-3-isopropylbenzyl)-5-vinylphenoxy)acetic acid |
| 76 | 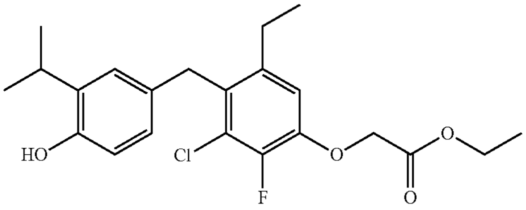 [SMILES: CCOC(=O)COc1cc(CC)c(Cc2ccc(O)c(C(C)C)c2)c(Cl)c1F] | ethyl 2-(3-chloro-5-ethyl-2-fluoro-4-(4-hydroxy-3-isopropylbenzyl)phenoxy)acetate |
| 77 | 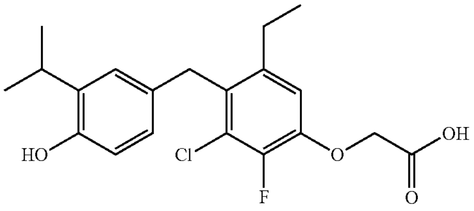 [SMILES: CCc1cc(OCC(=O)O)c(F)c(Cl)c1Cc1ccc(O)c(C(C)C)c1] | 2-(3-chloro-5-ethyl-2-fluoro-4-(4-hydroxy-3-isopropylbenzyl)phenoxy)acetic acid |
| 78 | 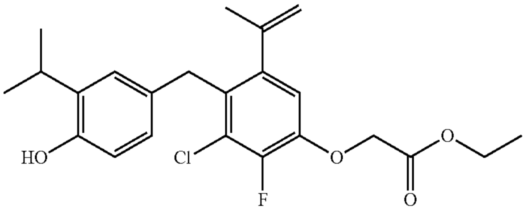 [SMILES: C=C(C)c1cc(OCC(=O)OCC)c(F)c(Cl)c1Cc1ccc(O)c(C(C)C)c1] | ethyl 2-(3-chloro-2-fluoro-4-(4-hydroxy-3-isopropylbenzyl)-5-(prop-1-en-2-yl)phenoxy)acetate |
| 79 | 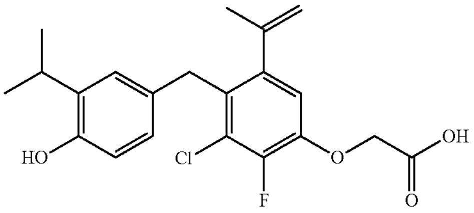 [SMILES: C=C(C)c1cc(OCC(=O)O)c(F)c(Cl)c1Cc1ccc(O)c(C(C)C)c1] | 2-(3-chloro-2-fluoro-4-(4-hydroxy-3-isopropylbenzyl)-5-(prop-1-en-2-yl)phenoxy)acetic acid |
| 80 | 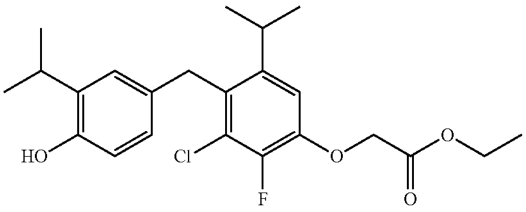 [SMILES: CCOC(=O)COc1cc(C(C)C)c(Cc2ccc(O)c(C(C)C)c2)c(Cl)c1F] | ethyl 2-(3-chloro-2-fluoro-4-(4-hydroxy-3-isopropylbenzyl)-5-isopropylphenoxy)acetate |

TABLE 1-continued

| Representative Compounds | | |
|---|---|---|
| CMPD NO | STRUCTURE | NAME |
| 81 | 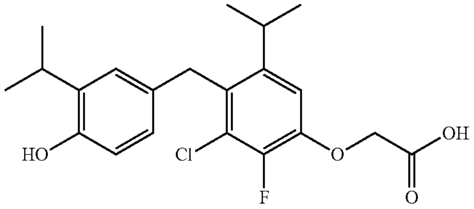 [SMILES: CC(C)c1cc(Cc2c(C(C)C)cc(OCC(=O)O)c(F)c2Cl)ccc1O] | 2-(3-chloro-2-fluoro-4-(4-hydroxy-3-isopropylbenzyl)-5-isopropylphenoxy)acetic acid |
| 82 | 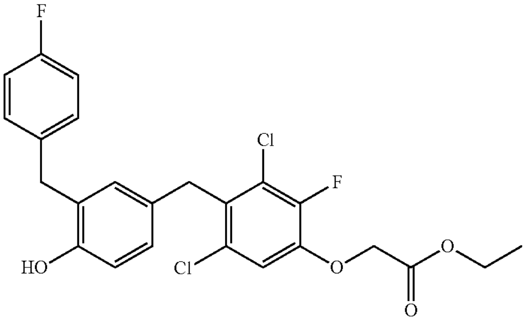 [SMILES: CCOC(=O)COc1cc(Cl)c(Cc2ccc(O)c(Cc3ccc(F)cc3)c2)c(Cl)c1F] | ethyl 2-(3,5-dichloro-2-fluoro-4-(3-(4-fluorobenzyl)-4-hydroxybenzyl)phenoxy)acetate |
| 83 | 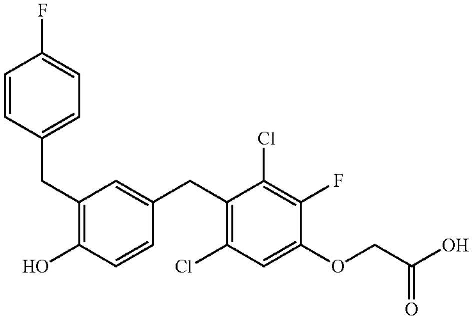 [SMILES: O=C(O)COc1cc(Cl)c(Cc2ccc(O)c(Cc3ccc(F)cc3)c2)c(Cl)c1F] | 2-(3,5-dichloro-2-fluoro-4-(3-(4-fluorobenzyl)-4-hydroxybenzyl)phenoxy)acetic acid |
| 84 | 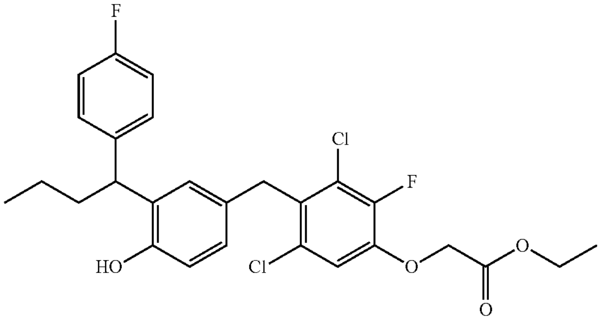 [SMILES: CCCC(c1ccc(F)cc1)c1cc(Cc2c(Cl)cc(OCC(=O)OCC)c(F)c2Cl)ccc1O] | ethyl 2-(3,5-dichloro-2-fluoro-4-(3-(1-(4-fluorophenyl)butyl)-4-hydroxybenzyl)phenoxy)acetate |
| 85 | 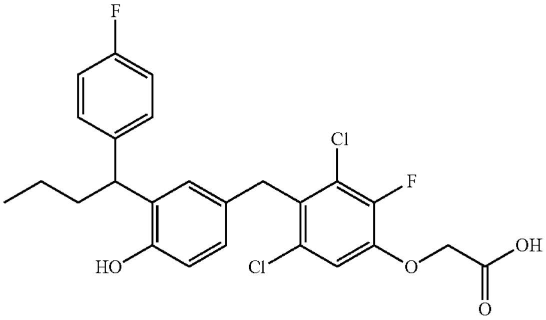 [SMILES: CCCC(c1ccc(F)cc1)c1cc(Cc2c(Cl)cc(OCC(=O)O)c(F)c2Cl)ccc1O] | 2-(3,5-dichloro-2-fluoro-4-(3-(l-(4-fluorophenyl)butyl)-4-hydroxybenzyl)phenoxy)acetic acid |

TABLE 1-continued

Representative Compounds

| CMPD NO | STRUCTURE | NAME |
| --- | --- | --- |
| 86 | 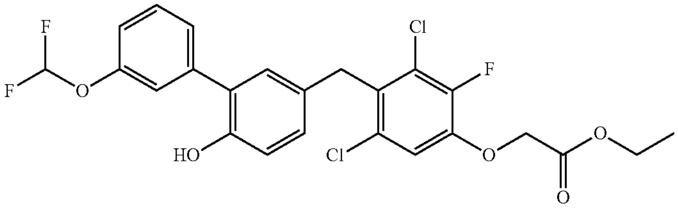 [SMILES: CCOC(=O)COc1cc(Cl)c(Cc2ccc(O)c(-c3cccc(OC(F)F)c3)c2)c(Cl)c1F] | ethyl 2-(3,5-dichloro-4-((3'-(difluoromethoxy)-6-hydroxy-[1,1'-biphenyl]-3-yl)methyl)-2-fluorophenoxy)acetate |
| 87 | 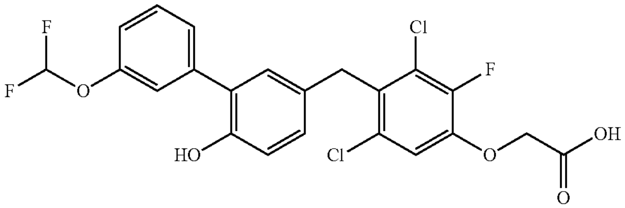 [SMILES: O=C(O)COc1cc(Cl)c(Cc2ccc(O)c(-c3cccc(OC(F)F)c3)c2)c(Cl)c1F] | 2-(3,5-dichloro-4-((3'-(difluoromethoxy)-6-hydroxy-[1,1'-biphenyl]-3-yl)methyl)-2-fluorophenoxy)acetic acid |
| 88 | 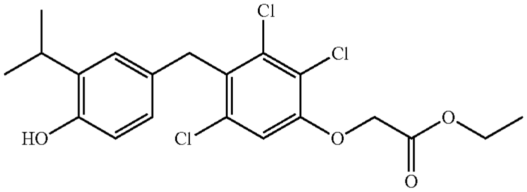 [SMILES: CCOC(=O)COc1cc(Cl)c(Cc2ccc(O)c(C(C)C)c2)c(Cl)c1Cl] | ethyl 2-(2,3,5-trichloro-4-(4-hydroxy-3-isopropylbenzyl)phenoxy)acetate |
| 89 | 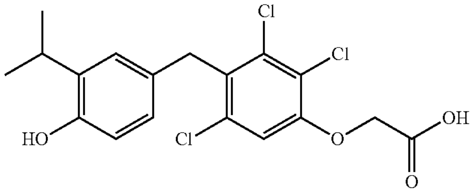 [SMILES: CC(C)c1cc(Cc2c(Cl)cc(OCC(=O)O)c(Cl)c2Cl)ccc1O] | 2-(2,3,5-trichloro-4-(4-hydroxy-3-isopropylbenzyl)phenoxy)acetic acid |
| 90 | 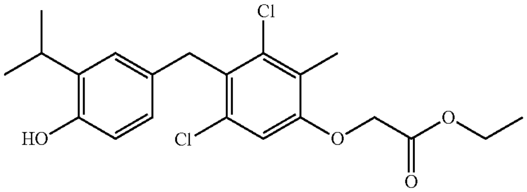 | ethyl 2-(3,5-dichloro-4-(4-hydroxy-3-isopropylbenzyl)-2-methylphenoxy)acetate |
| 91 | 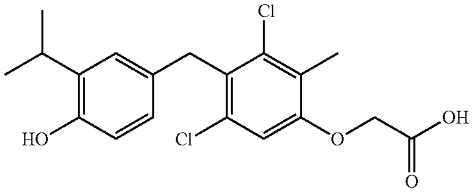 [SMILES: Cc1c(OCC(=O)O)cc(Cl)c(Cc2ccc(O)c(C(C)C)c2)c1Cl] | 2-(3,5-dichloro-4-(4-hydroxy-3-isopropylbenzyl)-2-methylphenoxy)acetic acid |
| 92 | 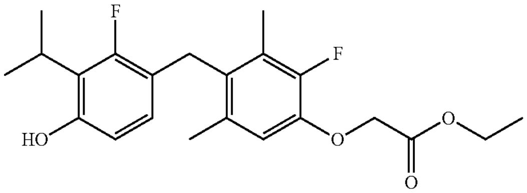 [SMILES: CCOC(=O)COc1cc(C)c(Cc2ccc(O)c(C(C)C)c2F)c(C)c1F] | ethyl 2-(2-fluoro-4-(2-fluoro-4-hydroxy-3-isopropylbenzyl)-3,5-dimethylphenoxy)acetate |

TABLE 1-continued

| Representative Compounds | | |
| --- | --- | --- |
| CMPD NO | STRUCTURE | NAME |
| 93 | 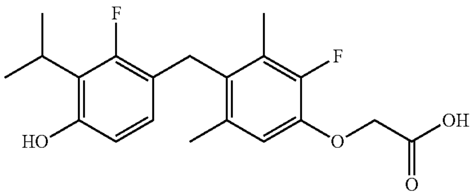 [SMILES: Cc1cc(OCC(=O)O)c(F)c(C)c1Cc1ccc(O)c(C(C)C)c1F] | 2-(2-fluoro-4-(2-fluoro-4-hydroxy-3-isopropylbenzyl)-3,5-dimethylphenoxy)acetic acid |
| 94 | 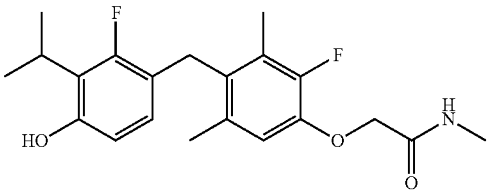 [SMILES: CNC(=O)COc1cc(C)c(Cc2ccc(O)c(C(C)C)c2F)c(C)c1F] | 2-(2-fluoro-4-(2-fluoro-4-hydroxy-3-isopropylbenzyl)-3,5-dimethylphenoxy)-N-methylacetamide |
| 95 | 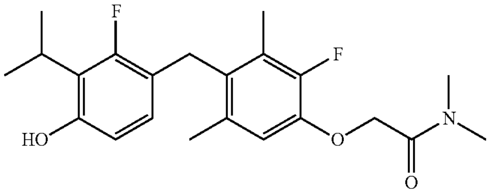 [SMILES: Cc1cc(OCC(=O)N(C)C)c(F)c(C)c1Cc1ccc(O)c(C(C)C)c1F] | 2-(2-fluoro-4-(2-fluoro-4-hydroxy-3-isopropylbenzyl)-3,5-dimethylphenoxy)-N,N-dimethylacetamide |
| 96 | 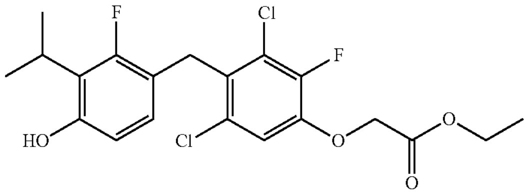 [SMILES: CCOC(=O)COc1cc(Cl)c(Cc2ccc(O)c(C(C)C)c2F)c(Cl)c1F] | ethyl 2-(3,5-dichloro-2-fluoro-4-(2-fluoro-4-hydroxy-3-isopropylbenzyl)phenoxy) acetate |
| 97 | 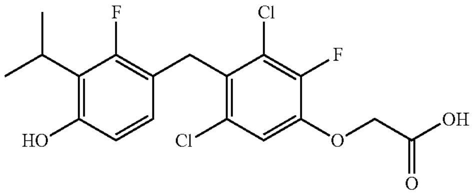 | 2-(3,5-dichloro-2-fluoro-4-(2-fluoro-4-hydroxy-3-isopropylbenzyl)phenoxy) acetic acid |
| 98 | 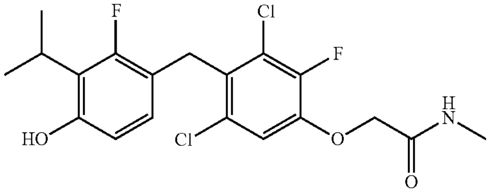 [SMILES: CNC(=O)COc1cc(Cl)c(Cc2ccc(O)c(C(C)C)c2F)c(Cl)c1F] | 2-(3,5-dichloro-2-fluoro-4-(2-fluoro-4-hydroxy-3-isopropylbenzyl)phenoxy)-N-methylacetamide |
| 99 | 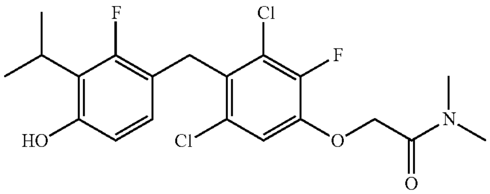 | 2-(3,5-dichloro-2-fluoro-4-(2-fluoro-4-hydroxy-3-isopropylbenzyl)phenoxy)-N,N-dimethylacetamide |

TABLE 1-continued

| Representative Compounds | | |
|---|---|---|
| CMPD NO | STRUCTURE | NAME |
| 100 | 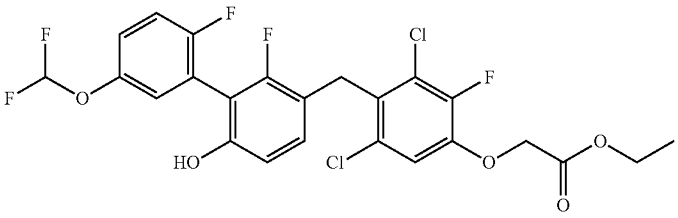 [SMILES: CCOC(=O)COc1cc(Cl)c(Cc2ccc(O)c(-c3cc(OC(F)F)ccc3F)c2F)c(Cl)c1F] | ethyl 2-(3,5-dichloro-4-((5'-(difluoromethoxy)-2,2'-difluoro-6-hydroxy-[1,1'-biphenyl]-3-yl) methyl)-2-fluorophenoxy)acetate |
| 101 | 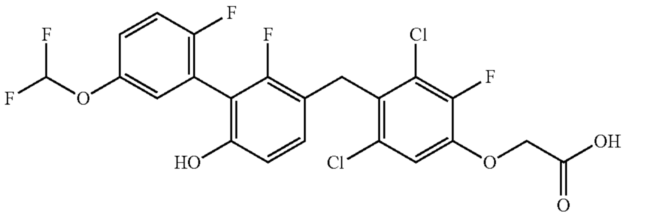 [SMILES: O=C(O)COc1cc(Cl)c(Cc2ccc(O)c(-c3cc(OC(F)F)ccc3F)c2F)c(Cl)c1F] | 2-(3,5-dichloro-4-((5'-(difluoromethoxy)-2,2'-difluoro-6-hydroxy-[1,1'-biphenyl]-3-yl)methyl)-2-fluorophenoxy) acetic acid |
| 102 | 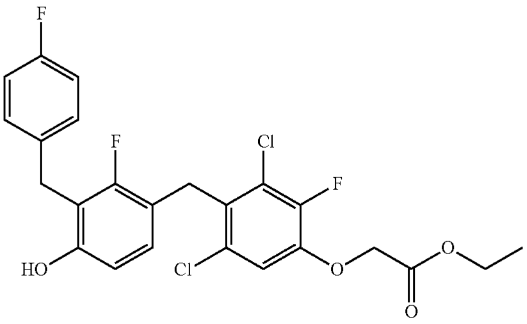 [SMILES: CCOC(=O)COc1cc(Cl)c(Cc2ccc(O)c(Cc3ccc(F)cc3)c2F)c(Cl)c1F] | ethyl 2-(3,5-dichloro-2-fluoro-4-(2-fluoro-3-(4-fluorobenzyl)-4-hydroxybenzyl) phenoxy)acetate |
| 103 | 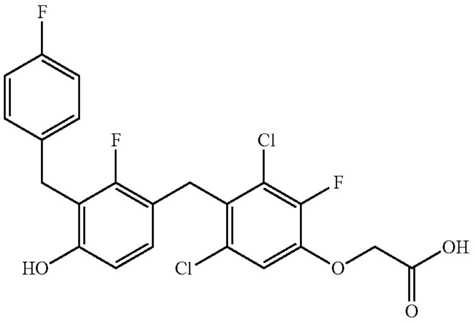 [SMILES: O=C(O)COc1cc(Cl)c(Cc2ccc(O)c(Cc3ccc(F)cc3)c2F)c(Cl)c1F] | 2-(3,5-dichloro-2-fluoro-4-(2-fluoro-3-(4-fluorobenzyl)-4-hydroxybenzyl) phenoxy)acetic acid |
| 104 | 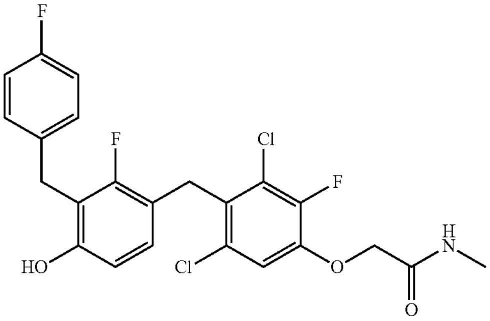 [SMILES: CNC(=O)COc1cc(Cl)c(Cc2ccc(O)c(Cc3ccc(F)cc3)c2F)c(Cl)c1F] | 2-(3,5-dichloro-2-fluoro-4-(2-fluoro-3-(4-fluorobenzyl)-4-hydroxybenzyl) phenoxy)-N-methylacetamide |

TABLE 1-continued

| CMPD NO | STRUCTURE | NAME |
|---|---|---|
| | Representative Compounds | |
| 105 | 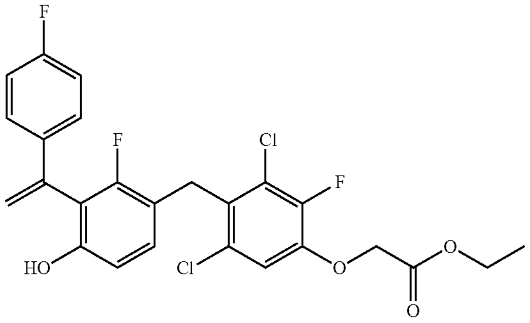 [SMILES: C=C(c1ccc(F)cc1)c1c(O)ccc(Cc2c(Cl)cc(OCC(=O)OCC)c(F)c2Cl)c1F] | ethyl 2-(3,5-dichloro-2-fluoro-4-(2-fluoro-3-(1-(4-fluorophenyl)vinyl)-4-hydroxybenzyl)phenoxy)acetate |
| 106 | 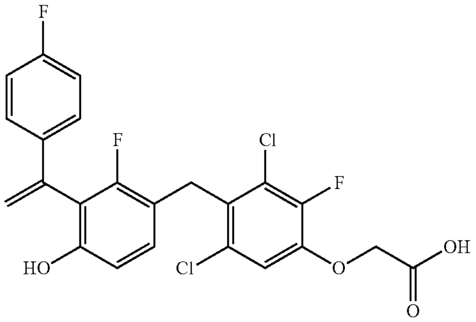 [SMILES: C=C(c1ccc(F)cc1)c1c(O)ccc(Cc2c(Cl)cc(OCC(=O)O)c(F)c2Cl)c1F] | 2-(3,5-dichloro-2-fluoro-4-(2-fluoro-3-(1-(4-fluorophenyl)vinyl)-4-hydroxybenzyl)phenoxy)acetic acid |
| 107 | 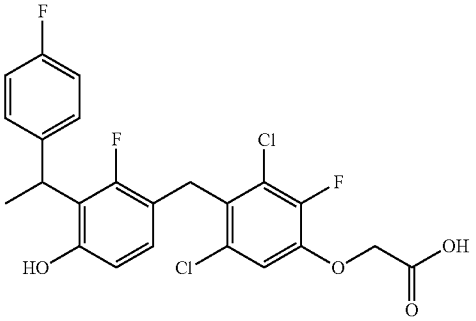 [SMILES: CC(c1ccc(F)cc1)c1c(O)ccc(Cc2c(Cl)cc(OCC(=O)O)c(F)c2Cl)c1F] | 2-(3,5-dichloro-2-fluoro-4-(2-fluoro-3-(1-(4-fluorophenyl)ethyl)-4-hydroxybenzyl)phenoxy)acetic acid |
| 108 | 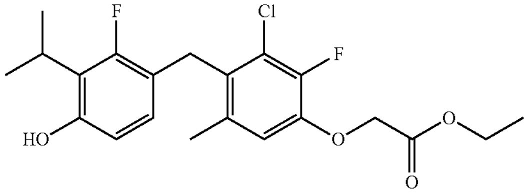 | ethyl 2-(3-chloro-2-fluoro-4-(2-fluoro-4-hydroxy-3-isopropylbenzyl)-5-methylphenoxy)acetate |
| 109 | 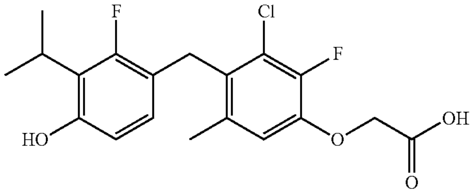 | 2-(3-chloro-2-fluoro-4-(2-fluoro-4-hydroxy-3-isopropylbenzyl)-5-methylphenoxy)acetic acid |

TABLE 1-continued

| Representative Compounds | | |
|---|---|---|
| CMPD NO | STRUCTURE | NAME |
| 110 | 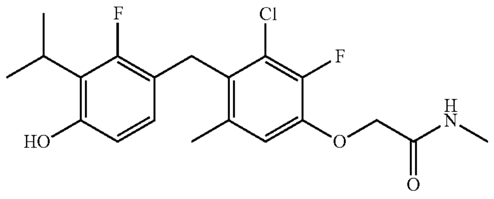 | 2-(3-chloro-2-fluoro-4-(2-fluoro-4-hydroxy-3-isopropylbenzyl)-5-methylphenoxy)-N-methylacetamide |
| 111 | 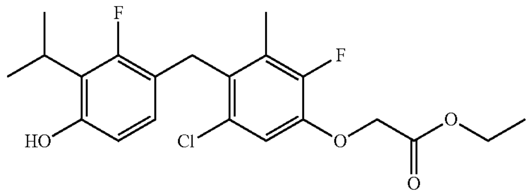 [SMILES: CCOC(=O)COc1cc(Cl)c(Cc2ccc(O)c(C(C)C)c2F)c(C)c1F] | ethyl 2-(5-chloro-2-fluoro-4-(2-fluoro-4-hydroxy-3-isopropylbenzyl)-3-methylphenoxy)acetate |
| 112 | 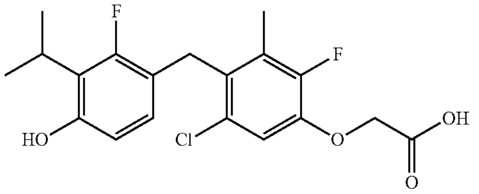 [SMILES: Cc1c(F)c(OCC(=O)O)cc(Cl)c1Cc1ccc(O)c(C(C)C)c1F] | 2-(5-chloro-2-fluoro-4-(2-fluoro-4-hydroxy-3-isopropylbenzyl)-3-methylphenoxy)acetic acid |
| 113 | 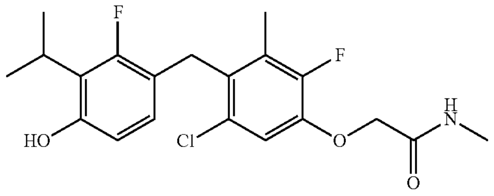 [SMILES: CNC(=O)COc1cc(Cl)c(Cc2ccc(O)c(C(C)C)c2F)c(C)c1F] | 2-(5-chloro-2-fluoro-4-(2-fluoro-4-hydroxy-3-isopropylbenzyl)-3-methylphenoxy)-N-methylacetamide |
| 114 | 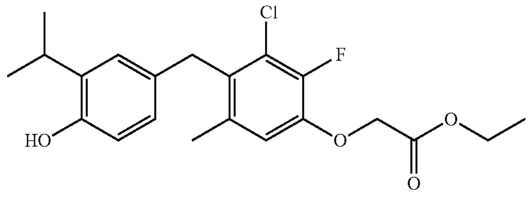 | ethyl 2-(3-chloro-2-fluoro-4-(4-hydroxy-3-isopropylbenzyl)-5-methylphenoxy)acetate |
| 115 | 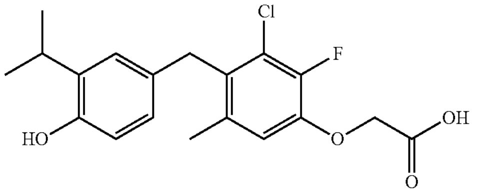 [SMILES: Cc1cc(OCC(=O)O)c(F)c(Cl)c1Cc1ccc(O)c(C(C)C)c1] | 2-(3-chloro-2-fluoro-4-(4-hydroxy-3-isopropylbenzyl)-5-methylphenoxy)acetic acid |
| 116 | 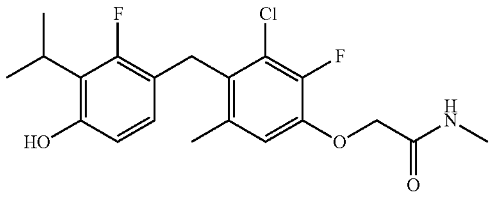 | 2-(3-chloro-2-fluoro-4-(2-fluoro-4-hydroxy-3-isopropylbenzyl)-5-methylphenoxy)-N-methyl-acetamide |

TABLE 1-continued

| Representative Compounds | | |
|---|---|---|
| CMPD NO | STRUCTURE | NAME |
| 117 | 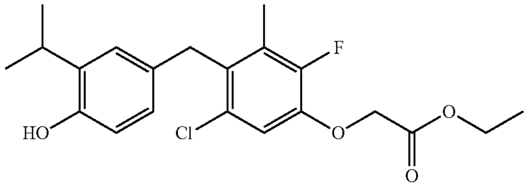 [SMILES: CCOC(=O)COc1cc(Cl)c(Cc2ccc(O)c(C(C)C)c2)c(C)c1F] | ethyl 2-(5-chloro-2-fluoro-4-(4-hydroxy-3-isopropylbenzyl)-3-methylphenoxy)acetate |
| 118 | 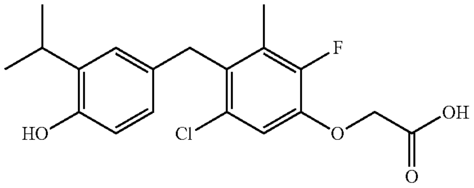 [SMILES: Cc1c(F)c(OCC(=O)O)cc(Cl)c1Cc1ccc(O)c(C(C)C)c1] | 2-(5-chloro-2-fluoro-4-(4-hydroxy-3-isopropylbenzyl)-3-methylphenoxy)acetic acid |
| 119 | 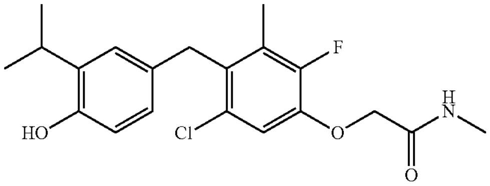 [SMILES: CNC(=O)COc1cc(Cl)c(Cc2ccc(O)c(C(C)C)c2)c(C)c1F] | 2-(5-chloro-2-fluoro-4-(4-hydroxy-3-isopropylbenzyl)-3-methylphenoxy)-N-methyl-acetamide |
| 120 | 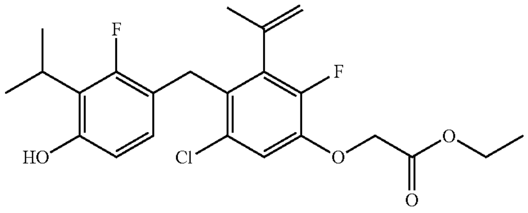 [SMILES: C=C(C)c1c(F)c(OCC(=O)OCC)cc(Cl)c1Cc1ccc(O)c(C(C)C)c1F] | ethyl 2-(5-chloro-2-fluoro-4-(2-fluoro-4-hydroxy-3-isopropylbenzyl)-3-(prop-1-en-2-yl)phenoxy)acetate |
| 121 | 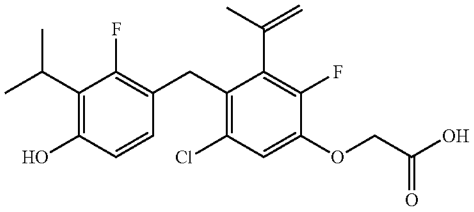 [SMILES: C=C(C)c1c(F)c(OCC(=O)O)cc(Cl)c1Cc1ccc(O)c(C(C)C)c1F] | 2-(5-chloro-2-fluoro-4-(2-fluoro-4-hydroxy-3-isopropylbenzyl)-3-(prop-1-en-2-yl)phenoxy)acetic acid |
| 122 | 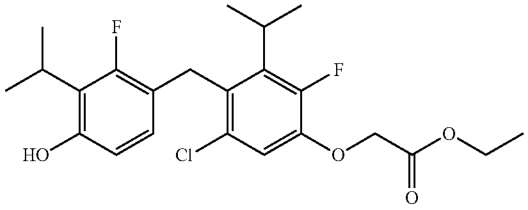 [SMILES: CCOC(=O)COc1cc(Cl)c(Cc2ccc(O)c(C(C)C)c2F)c(C(C)C)c1F] | ethyl 2-(5-chloro-2-fluoro-4-(2-fluoro-4-hydroxy-3-isopropylbenzyl)-3-isopropylphenoxy)acetate |
| 123 | 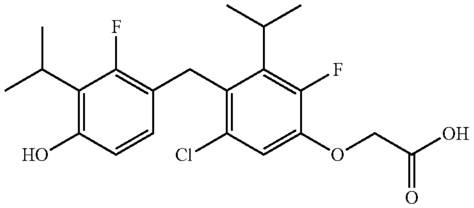 [SMILES: CC(C)c1c(O)ccc(Cc2c(Cl)cc(OCC(=O)O)c(F)c2C(C)C)c1F] | 2-(5-chloro-2-fluoro-4-(2-fluoro-4-hydroxy-3-isopropylbenzyl)-3-isopropylphenoxy)acetic acid |

TABLE 1-continued

Representative Compounds

| CMPD NO | STRUCTURE | NAME |
| --- | --- | --- |
| 124 | 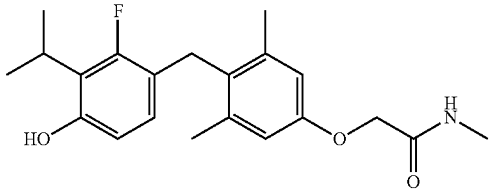 [SMILES: CNC(=O)COc1cc(C)c(Cc2ccc(O)c(C(C)C)c2F)c(C)c1] | 2-(4-(2-fluoro-4-hydroxy-3-isopropylbenzyl)-3,5-dimethylphenoxy)-N-methylacetamide |
| 125 | 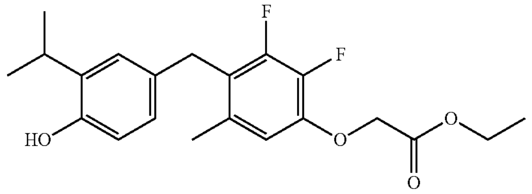 [SMILES: CCOC(=O)COc1cc(C)c(Cc2ccc(O)c(C(C)C)c2)c(F)c1F] | ethyl 2-(2,3-difluoro-4-(4-hydroxy-3-isopropylbenzyl)-5-methylphenoxy)acetate |
| 126 | 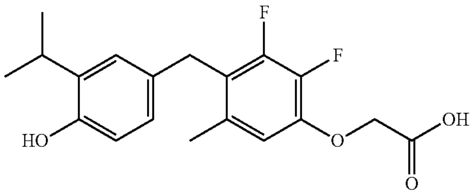 [SMILES: Cc1cc(OCC(=O)O)c(F)c(F)c1Cc1ccc(O)c(C(C)C)c1] | 2-(2,3-difluoro-4-(4-hydroxy-3-isopropylbenzyl)-5-methylphenoxy)acetic acid |
| 127 | 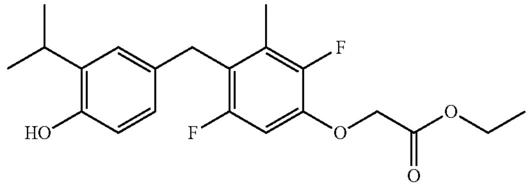 [SMILES: CCOC(=O)COc1cc(F)c(Cc2ccc(O)c(C(C)C)c2)c(C)c1F] | ethyl 2-(2,5-difluoro-4-(4-hydroxy-3-isopropylbenzyl)-3-methylphenoxy)acetate |
| 128 | 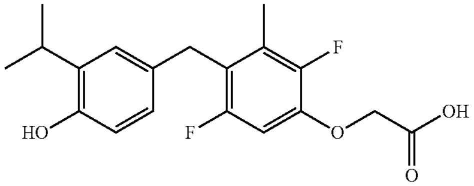 [SMILES: Cc1c(F)c(OCC(=O)O)cc(F)c1Cc1ccc(O)c(C(C)C)c1] | 2-(2,5-difluoro-4-(4-hydroxy-3-isopropylbenzyl)-3-methylphenoxy)acetic acid |
| 129 | 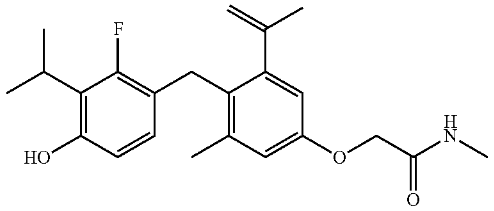 [SMILES: C=C(C)c1cc(OCC(=O)NC)cc(C)c1Cc1ccc(O)c(C(C)C)c1F] | 2-(4-(2-fluoro-4-hydroxy-3-isopropylbenzyl)-3-methyl-5-(prop-1-en-2-yl)phenoxy)-N-methylacetamide |
| 130 | 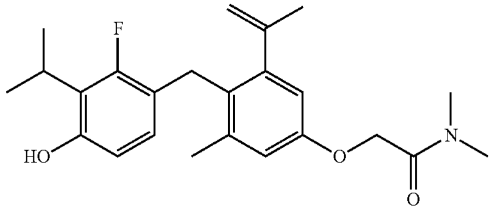 [SMILES: C=C(C)c1cc(OCC(=O)N(C)C)cc(C)c1Cc1ccc(O)c(C(C)C)c1F] | 2-(4-(2-fluoro-4-hydroxy-3-isopropylbenzyl)-3-methyl-5-(prop-1-en-2-yl)phenoxy)-N,N-dimethylacetamide |

TABLE 1-continued

| Representative Compounds | | |
|---|---|---|
| CMPD NO | STRUCTURE | NAME |
| 131 | 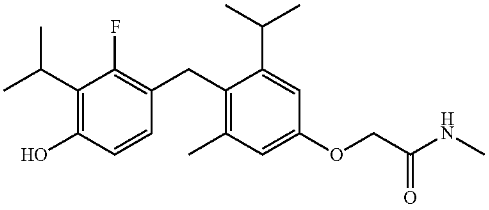 [SMILES: CNC(=O)COc1cc(C)c(Cc2ccc(O)c(C(C)C)c2F)c(C(C)C)c1] | 2-(4-(2-fluoro-4-hydroxy-3-isopropylbenzyl)-3-isopropyl-5-methylphenoxy)-N-methylacetamide |
| 132 | 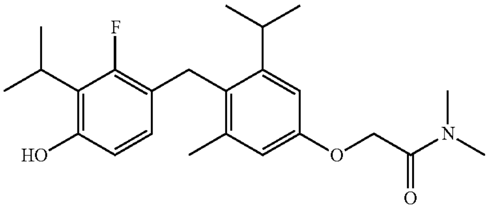 [SMILES: Cc1cc(OCC(=O)N(C)C)cc(C(C)C)c1Cc1ccc(O)c(C(C)C)c1F] | 2-(2,3-difluoro-4-(4-hydroxy-3-isopropylbenzyl)-5-methylphenoxy)-N-methylacetamide |
| 133 | 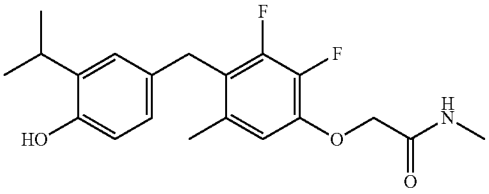 [SMILES: CNC(=O)COc1cc(C)c(Cc2ccc(O)c(C(C)C)c2)c(F)c1F] | 2-(2,3-difluoro-4-(4-hydroxy-3-isopropylbenzyl)-5-methylphenoxy)-N-methylacetamide |
| 134 | 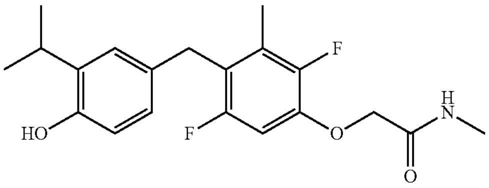 [SMILES: CNC(=O)COc1cc(F)c(Cc2ccc(O)c(C(C)C)c2)c(C)c1F] | 2-(2,5-difluoro-4-(4-hydroxy-3-isopropylbenzyl)-3-methylphenoxy)-N-methylacetamide |
| 135 | 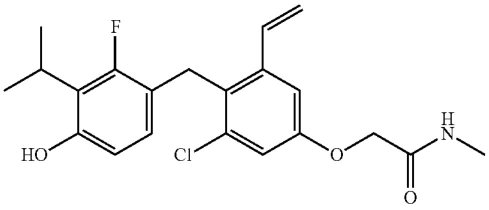 [SMILES: C=Cc1cc(OCC(=O)NC)cc(Cl)c1Cc1ccc(O)c(C(C)C)c1F] | 2-(3-chloro-4-(2-fluoro-4-hydroxy-3-isopropylbenzyl)-5-vinylphenoxy)-N-methylacetamide |
| 136 | 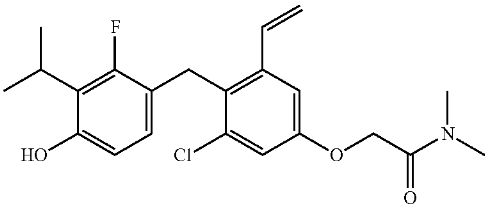 [SMILES: C=Cc1cc(OCC(=O)N(C)C)cc(Cl)c1Cc1ccc(O)c(C(C)C)c1F] | 2-(3-chloro-4-(2-fluoro-4-hydroxy-3-isopropylbenzyl)-5-vinylphenoxy)-N,N-dimethylacetamide |
| 137 | 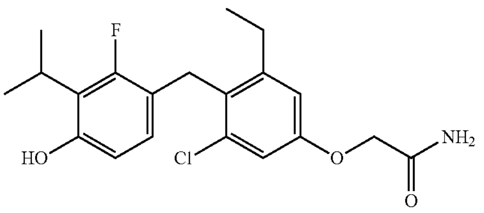 [SMILES: CCc1cc(OCC(N)=O)cc(Cl)c1Cc1ccc(O)c(C(C)C)c1F] | 2-(3-chloro-5-ethyl-4-(2-fluoro-4-hydroxy-3-isopropylbenzyl)phenoxy)acetamide |

TABLE 1-continued

| CMPD NO | Representative Compounds STRUCTURE | NAME |
|---|---|---|
| 138 | 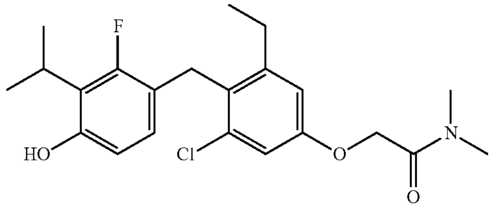 [SMILES: CCc1cc(OCC(=O)N(C)C)cc(Cl)c1Cc1ccc(O)c(C(C)C)c1F] | 2-(3-chloro-5-ethyl-4-(2-fluoro-4-hydroxy-3-isopropylbenzyl)phenoxy)-N,N-dimethylacetamide |
| 139 | 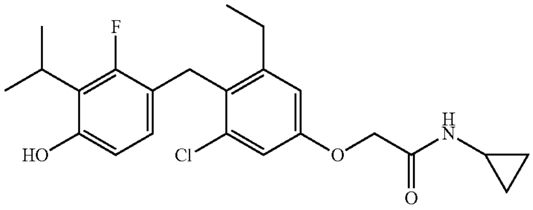 [SMILES: CCc1cc(OCC(=O)NC2CC2)cc(Cl)c1Cc1ccc(O)c(C(C)C)c1F] | 2-(3-chloro-5-ethyl-4-(2-fluoro-4-hydroxy-3-isopropylbenzyl)phenoxy)-N-cyclopropylacetamide |
| 140 | 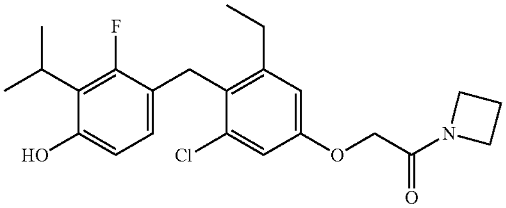 [SMILES: CCc1cc(OCC(=O)N2CCC2)cc(Cl)c1Cc1ccc(O)c(C(C)C)c1F] | 1-(azetidin-1-yl)-2-(3-chloro-5-ethyl -4-(2-fluoro-4-hydroxy-3-isopropylbenzyl)phenoxy) ethan-1-one |
| 141 | 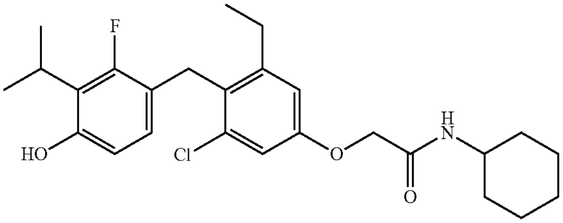 [SMILES: CCc1cc(OCC(=O)NC2CCCCC2)cc(Cl)c1Cc1ccc(O)c(C(C)C)c1F] | 2-(3-chloro-5-ethyl-4-(2-fluoro-4-hydroxy-3-isopropylbenzyl)phenoxy)-N-cyclohexylacetamide |
| 142 | 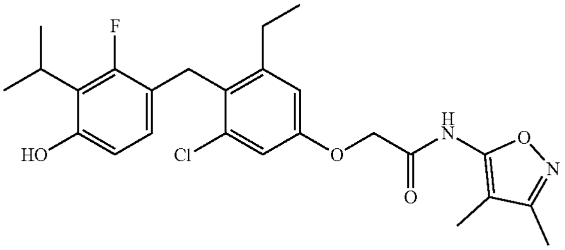 [SMILES: CCc1cc(OCC(=O)Nc2onc(C)c2C)cc(Cl)c1Cc1ccc(O)c(C(C)C)c1F] | 2-(3-chloro-5-ethyl-4-(2-fluoro-4-hydroxy-3-isopropylbenzyl)phenoxy)-N-(3,4-dimethylisoxazol-5-yl)acetamide |
| 143 | 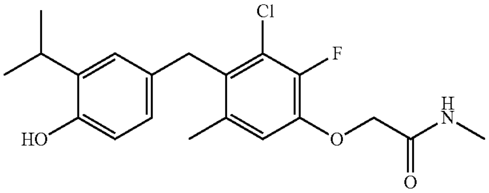 | 2-(3-chloro-2-fluoro-4-(4-hydroxy-3-isopropylbenzyl)-5-methylphenoxy)-N-methylacetamide |
| 144 | 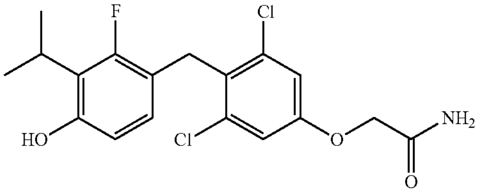 [SMILES: CC(C)c1c(O)ccc(Cc2c(Cl)cc(OCC(N)=O)cc2Cl)c1F] | 2-(3,5-dichloro-4-(2-fluoro-4-hydroxy-3-isopropylbenzyl)phenoxy)acetamide |

TABLE 1-continued

Representative Compounds

| CMPD NO | STRUCTURE | NAME |
|---|---|---|
| 145 | 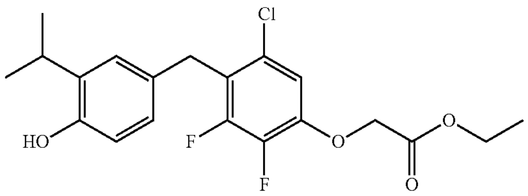 [SMILES: CCOC(=O)COc1cc(Cl)c(Cc2ccc(O)c(C(C)C)c2)c(F)c1F] | ethyl 2-(5-chloro-2,3-difluoro-4-(4-hydroxy-3-isopropylbenzyl)phenoxy)acetate |
| 146 | 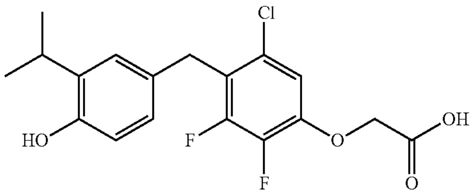 [SMILES: CC(C)c1cc(Cc2c(Cl)cc(OCC(=O)O)c(F)c2F)ccc1O] | 2-(5-chloro-2,3-difluoro-4-(4-hydroxy-3-isopropylbenzyl)phenoxy)acetic acid |
| 147 | 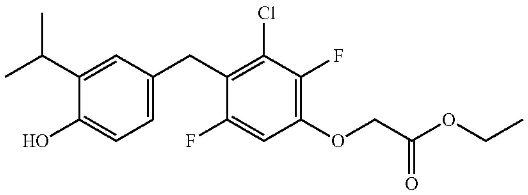 | ethyl 2-(3-chloro-2,5-difluoro-4-(4-hydroxy-3-isopropylbenzyl)phenoxy)acetate |
| 148 | 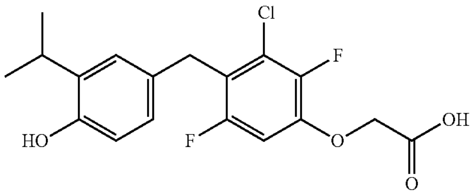 | 2-(3-chloro-2,5-difluoro-4-(4-hydroxy-3-isopropylbenzyl)phenoxy)acetic acid |
| 149 | 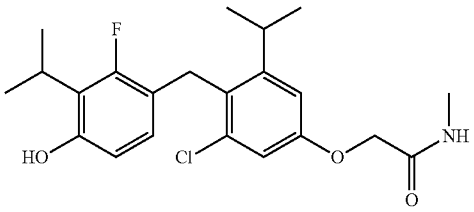 [SMILES: CNC(=O)COc1cc(Cl)c(Cc2ccc(O)c(C(C)C)c2F)c(C(C)C)c1] | 2-(3-chloro-4-(2-fluoro-4-hydroxy-3-isopropylbenzyl)-5-isopropylphenoxy)-N-methylacetamide |
| 150 | 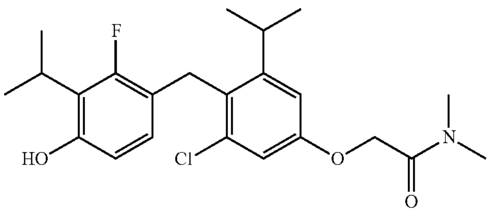 [SMILES: CC(C)c1cc(OCC(=O)N(C)C)cc(Cl)c1Cc1ccc(O)c(C(C)C)c1F] | 2-(3-chloro-4-(2-fluoro-4-hydroxy-3-isopropylbenzyl)-5-isopropylphenoxy)-N,N-dimethylacetamide |
| 151 | 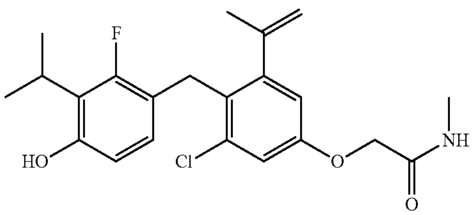 [SMILES: C=C(C)c1cc(OCC(=O)NC)cc(Cl)c1Cc1ccc(O)c(C(C)C)c1F] | 2-(3-chloro-4-(2-fluoro-4-hydroxy-3-isopropylbenzyl)-5-(prop-1-en-2-yl)phenoxy)-N-methylacetamide |

TABLE 1-continued

| Representative Compounds | | |
|---|---|---|
| CMPD NO | STRUCTURE | NAME |
| 152 | 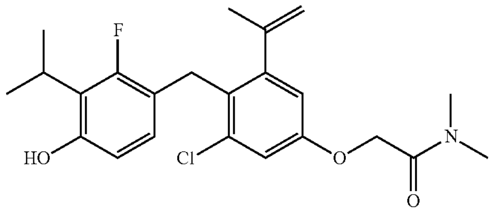 [SMILES: C=C(C)c1cc(OCC(=O)N(C)C)cc(Cl)c1Cc1ccc(O)c(C(C)C)c1F] | 2-(3-chloro-4-(2-fluoro-4-hydroxy-3-isopropylbenzyl)-5-(prop-1-en-2-yl)phenoxy)-N,N-dimethylacetamide |
| 153 | 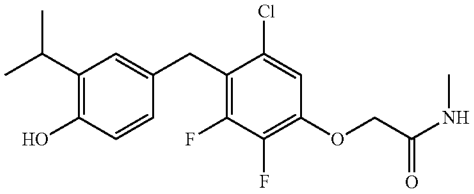 [SMILES: CNC(=O)COc1cc(Cl)c(Cc2ccc(O)c(C(C)C)c2)c(F)c1F] | 2-(5-chloro-2,3-difluoro-4-(4-hydroxy-3-isopropylbenzyl)phenoxy)-N-methylacetamide |
| 154 | 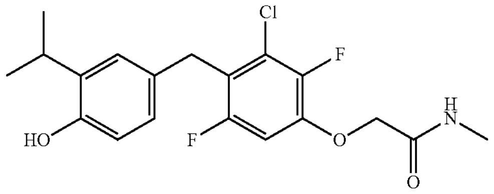 | 2-(3-chloro-2,5-difluoro-4-(4-hydroxy-3-isopropylbenzyl)phenoxy)-N-methylacetamide |
| 155 | 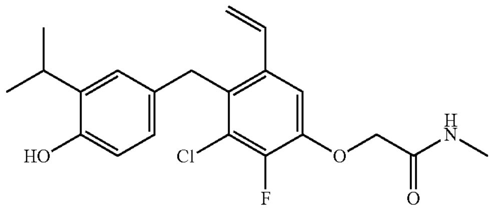 [SMILES: C=Cc1cc(OCC(=O)NC)c(F)c(Cl)c1Cc1ccc(O)c(C(C)C)c1] | 2-(3-chloro-2-fluoro-4-(4-hydroxy-3-isopropylbenzyl)-5-vinylphenoxy)-N-methylacetamide |
| 156 | 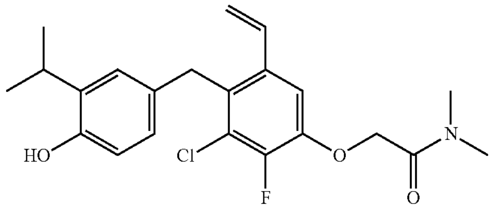 [SMILES: C=Cc1cc(OCC(=O)N(C)C)c(F)c(Cl)c1Cc1ccc(O)c(C(C)C)c1] | 2-(3-chloro-2-fluoro-4-(4-hydroxy-3-isopropylbenzyl)-5-vinylphenoxy)-N,N-dimethylacetamide |
| 157 | 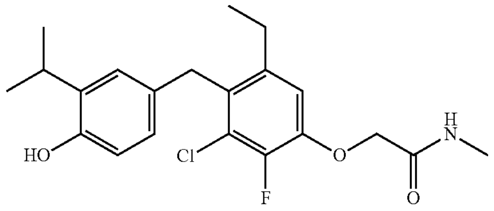 [SMILES: CCc1cc(OCC(=O)NC)c(F)c(Cl)c1Cc1ccc(O)c(C(C)C)c1] | 2-(3-chloro-5-ethyl-2-fluoro-4-(4-hydroxy-3-isopropylbenzyl)phenoxy)-N-methylacetamide |
| 158 | 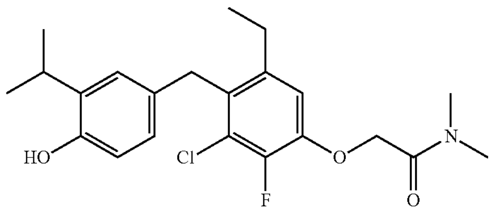 [SMILES: CCc1cc(OCC(=O)N(C)C)c(F)c(Cl)c1Cc1ccc(O)c(C(C)C)c1] | 2-(3-chloro-5-ethyl-2-fluoro-4-(4-hydroxy-3-isopropylbenzyl)phenoxy)-N,N-dimethylacetamide |

TABLE 1-continued

| Representative Compounds | | |
|---|---|---|
| CMPD NO | STRUCTURE | NAME |
| 159 | 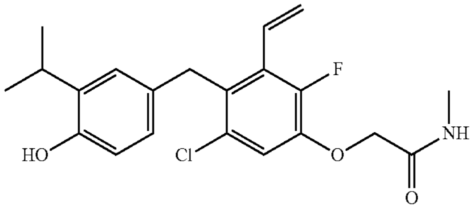 [SMILES: C=Cc1c(F)c(OCC(=O)NC)cc(Cl)c1Cc1ccc(O)c(C(C)C)c1] | 2-(5-chloro-2-fluoro-4-(4-hydroxy-3-isopropylbenzyl)-3-vinylphenoxy)-N-methylacetamide |
| 160 | 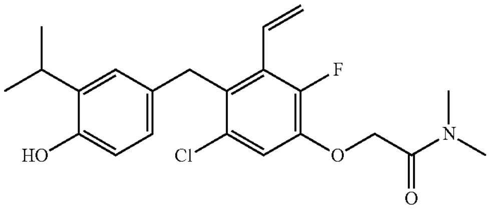 [SMILES: C=Cc1c(F)c(OCC(=O)N(C)C)cc(Cl)c1Cc1ccc(O)c(C(C)C)c1] | 2-(5-chloro-2-fluoro-4-(4-hydroxy-3-isopropylbenzyl)-3-vinylphenoxy)-N,N-dimethylacetamide |
| 161 | 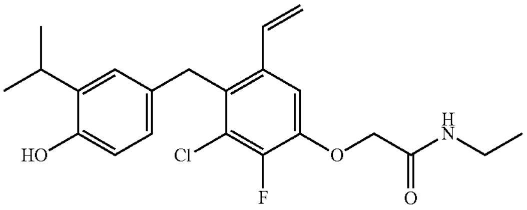 [SMILES: C=Cc1cc(OCC(=O)NCC)c(F)c(Cl)c1Cc1ccc(O)c(C(C)C)c1] | 2-(3-chloro-2-fluoro-4-(4-hydroxy-3-isopropylbenzyl)-5-vinylphenoxy)-N-ethylacetamide |
| 162 | 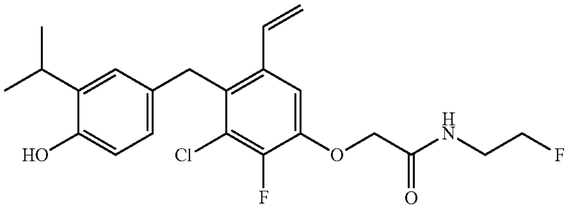 [SMILES: C=Cc1cc(OCC(=O)NCCF)c(F)c(Cl)c1Cc1ccc(O)c(C(C)C)c1] | 2-(3-chloro-2-fluoro-4-(4-hydroxy-3-isopropylbenzyl)-5-vinylphenoxy)-N-(2-fluoroethyl)acetamide |
| 163 | 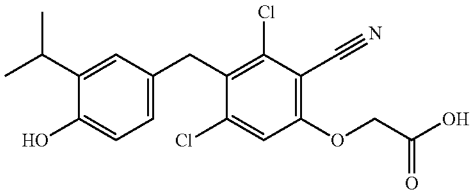 [SMILES: CC(C)c1cc(Cc2c(Cl)cc(OCC(=O)O)c(C#N)c2Cl)ccc1O] | 2-(3,5-dichloro-2-cyano-4-(4-hydroxy-3-isopropylbenzyl)phenoxy)acetic acid |
| 164 | 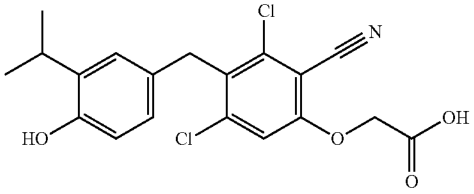 [SMILES: CC(C)c1cc(Cc2c(Cl)cc(OCC(=O)O)c(C#N)c2Cl)ccc1O] | 2-(3,5-dichloro-2-cyano-4-(4-hydroxy-3-isopropylbenzyl)phenoxy)acetic acid |
| 165 | 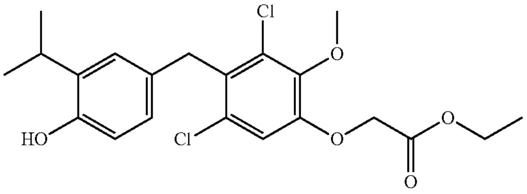 [SMILES: CCOC(=O)COc1cc(Cl)c(Cc2ccc(O)c(C(C)C)c2)c(Cl)c1OC] | ethyl 2-(3,5-dichloro-4-(4-hydroxy-3-isopropylbenzyl)-2-methoxyphenoxy)acetate |

TABLE 1-continued

| Representative Compounds | | |
|---|---|---|
| CMPD NO | STRUCTURE | NAME |
| 166 | 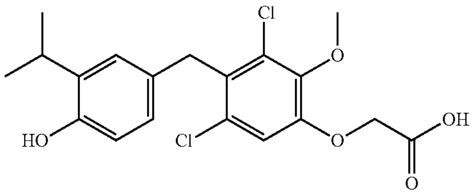 [SMILES: COc1c(OCC(=O)O)cc(Cl)c(Cc2ccc(O)c(C(C)C)c2)c1Cl] | 2-(3,5-dichloro-4-(4-hydroxy-3-isopropylbenzyl)-2-methoxyphenoxy)acetic acid |
| 167 | 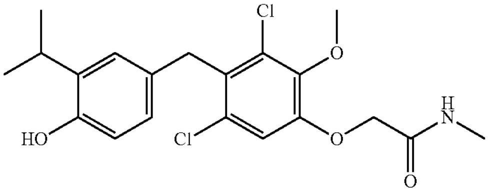 [SMILES: CNC(=O)COc1cc(Cl)c(Cc2ccc(O)c(C(C)C)c2)c(Cl)c1OC] | 2-(3,5-dichloro-4-(4-hydroxy-3-isopropylbenzyl)-2-methoxyphenoxy)-N-methylacetamide |

"Isomer" is used herein to encompass all chiral, diastereomeric or racemic forms of a structure, unless a particular stereochemistry or isomeric form is specifically indicated. Such compounds can be enriched or resolved optical isomers at any or all asymmetric atoms as are apparent from the depictions, at any degree of enrichment. Both racemic and diastereomeric mixtures, as well as the individual optical isomers can be synthesized so as to be substantially free of their enantiomeric or diastereomeric partners, and these are all within the scope of certain embodiments of the invention. The isomers resulting from the presence of a chiral center comprise a pair of nonsuperimposable-isomers that are called "enantiomers." Single enantiomers of a pure compound are optically active (i.e., they are capable of rotating the plane of plane polarized light and designated R or S).

"Isolated optical isomer" means a compound which has been substantially purified from the corresponding optical isomer(s) of the same formula. For example, the isolated isomer may be at least about 80%, at least 80% or at least 85% pure by weight. In other embodiments, the isolated isomer is at least 90% pure or at least 98% pure, or at least 99% pure by weight.

"Substantially enantiomerically or diastereomerically" pure means a level of enantiomeric or diastereomeric enrichment of one enantiomer with respect to the other enantiomer or diastereomer of at least about 80%, and more specifically in excess of 80%, 85%, 90%, 95%, 98%, 99%, 99.5% or 99.9%.

The terms "racemate" and "racemic mixture" refer to an equal mixture of two enantiomers. A racemate is labeled "(±)" because it is not optically active (i.e., will not rotate plane-polarized light in either direction since its constituent enantiomers cancel each other out). All compounds with an asterisk (*) adjacent to a tertiary or quaternary carbon are optically active isomers, which may be purified from the respective racemate and/or synthesized by appropriate chiral synthesis.

A "hydrate" is a compound that exists in combination with water molecules. The combination can include water in stoichiometric quantities, such as a monohydrate or a dihydrate, or can include water in random amounts. As the term is used herein a "hydrate" refers to a solid form; that is, a compound in a water solution, while it may be hydrated, is not a hydrate as the term is used herein.

A "solvate" is similar to a hydrate except that a solvent other that water is present. For example, methanol or ethanol can form an "alcoholate", which can again be stoichiometric or non-stoichiometric. As the term is used herein a "solvate" refers to a solid form; that is, a compound in a solvent solution, while it may be solvated, is not a solvate as the term is used herein.

"Isotope" refers to atoms with the same number of protons but a different number of neutrons, and an isotope of a compound of Formula (I) includes any such compound wherein one or more atoms are replaced by an isotope of that atom. For example, carbon 12, the most common form of carbon, has six protons and six neutrons, whereas carbon 13 has six protons and seven neutrons, and carbon 14 has six protons and eight neutrons. Hydrogen has two stable isotopes, deuterium (one proton and one neutron) and tritium (one proton and two neutrons). While fluorine has a number of isotopes, fluorine 19 is longest-lived. Thus, an isotope of a compound having the structure of Formula (I) includes, but not limited to, compounds of Formula (I) wherein one or more carbon 12 atoms are replaced by carbon-13 and/or carbon-14 atoms, wherein one or more hydrogen atoms are replaced with deuterium and/or tritium, and/or wherein one or more fluorine atoms are replaced by fluorine-19.

"Salt" generally refers to an organic compound, such as a carboxylic acid or an amine, in ionic form, in combination with a counter ion. For example, salts formed between acids in their anionic form and cations are referred to as "acid addition salts". Conversely, salts formed between bases in the cationic form and anions are referred to as "base addition salts."

The term "pharmaceutically acceptable" refers an agent that has been approved for human consumption and is generally non-toxic. For example, the term "pharmaceutically acceptable salt" refers to nontoxic inorganic or organic acid and/or base addition salts (see, e.g., Lit et al., Salt Selection for Basic Drugs, *Int. J. Pharm.,* 33, 201-217, 1986) (incorporated by reference herein).

Pharmaceutically acceptable base addition salts of compounds of the invention include, for example, metallic salts including alkali metal, alkaline earth metal, and transition metal salts such as, for example, calcium, magnesium, potassium, sodium, and zinc salts. Pharmaceutically acceptable base addition salts also include organic salts made from basic amines such as, for example, N,N'dibenzylethylenediamine, chloroprocaine, choline, diethanolamine, ethylenediamine, meglumine (N-methylglucamine), tromethamine (tris-hydroxymethyl methylamine), and procaine.

Pharmaceutically acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, aromatic aliphatic, heterocyclic, carboxylic, and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, hippuric, malonic, oxalic, embonic (pamoic), methanesulfonic, ethanesulfonic, benzenesulfonic, panthothenic, trifluoromethanesulfonic, 2-hydroxyethanesulfonic, p-toluenesulfonic, sulfanilic, cyclohexylaminosulfonic, stearic, alginic, βhydroxybutyric, salicylic, -galactaric, and galacturonic acid.

Although pharmaceutically unacceptable salts are not generally useful as medicaments, such salts may be useful, for example as intermediates in the synthesis of compounds having the structure of Formula I, for example in their purification by recrystallization.

In certain embodiments, the invention provides a pharmaceutical composition comprising a compound of the invention together with at least one pharmaceutically acceptable carrier, diluent, or excipient. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid, or lower alkyl ethers of cellulose, silicic acid, fatty acids, fatty acid amines, fatty acid monoglycerides and diglycerides, pentaerythritol fatty acid esters, polyoxyethylene, hydroxymethylcellulose, and polyvinylpyrrolidone. Similarly, the carrier or diluent can include any sustained release material known in the art, such as glyceryl monostearate or glyceryl distearate, alone or mixed with a wax.

As used herein, the term "pharmaceutical composition" refers to a composition containing one or more of the compounds described herein, or a pharmaceutically acceptable isomer, racemate, hydrate, solvate, isotope or salt thereof, formulated with a pharmaceutically acceptable carrier, which can also include other additives, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein. Conventional procedures and ingredients for the selection and preparation of suitable formulations are described, for example, in *Remington: The Science and Practice of Pharmacy,* 21$^{st}$ Ed., Gennaro, Ed., Lippencott Williams & Wilkins (2005) and in The United States Pharmacopeia: The National Formulary (USP 36 NF31), published in 2013.

As used herein, the term "pharmaceutically acceptable carrier" refers to any ingredient other than the disclosed compounds, or a pharmaceutically acceptable isomer, racemate, hydrate, solvate, isotope or salt thereof (e.g., a carrier capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The formulations can be mixed with auxiliary agents which do not deleteriously react with the active compounds. Such additives can include wetting agents, emulsifying and suspending agents, salt for influencing osmotic pressure, buffers and/or coloring substances, preserving agents, sweetening agents, or flavoring agents. The compositions can also be sterilized if desired.

The route of administration can be any route which effectively transports the active compound of the invention to the appropriate or desired site of action, such as oral, nasal, pulmonary, buccal, subdermal, intradermal, transdermal, or parenteral, including intravenous, subcutaneous and/or intramuscular. In one embodiment, the route of administration is oral.

Dosage forms can be administered once a day, or more than once a day, such as twice or thrice daily. Alternatively, dosage forms can be administered less frequently than daily, such as every other day, or weekly, if found to be advisable by a prescribing physician or drug's prescribing information. Dosing regimens include, for example, dose titration to the extent necessary or useful for the indication to be treated, thus allowing the patient's body to adapt to the treatment, to minimize or avoid unwanted side effects associated with the treatment, and/or to maximize the therapeutic effect of the present compounds. Other dosage forms include delayed or controlled-release forms. Suitable dosage regimens and/or forms include those set out, for example, in the latest edition of the *Physicians' Desk Reference*, incorporated herein by reference.

In another embodiment, there are provided methods of making a composition of a compound described herein including formulating a compound of the invention with a pharmaceutically acceptable carrier or diluent. In some embodiments, the pharmaceutically acceptable carrier or diluent is suitable for oral administration. In some such embodiments, the methods can further include the step of formulating the composition into a tablet or capsule. In other embodiments, the pharmaceutically acceptable carrier or diluent is suitable for parenteral administration. In some such embodiments, the methods further include the step of lyophilizing the composition to form a lyophilized preparation.

In another embodiment, a method of treating a subject having a neurodegenerative disease is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof. In one embodiment, the neurodegenerative disease is a demyelinating disease. In another embodiment, the demyelinating disease is a chronic demyelinating disease. In yet another embodiment, the demyelinating disease is or is associated with a X-linked genetic disorder, leukodystrophy, dementia, tauopathy, or ischaemic stroke. In another embodiment, the demyelinating disease is or is associated with adult Refsum disease, Alexander disease, Alzheimer's disease, Balo concentric sclerosis, Canavan disease, central pontine myelinolysis (CPM), cerebral palsy, cerebrotendineous xanthomatosis, chronic inflammatory demyelinating polyneuropathy (CIDP), Devic's syndrome, diffuse myelinoclastic sclerosis, encephalomyelitis, idiopathic inflammatory demyelinating disease (IIDD), infantile Refsum disease, Krabbe disease, Leber hereditary optic neuropathy, Marburg multiple sclerosis, Marchiafava-Bignami disease, metachromatic leukodystrophy, multifocal motor neuropathy, paraproteinemic demyelinating polyneuropathy, Pelizaeus-Merzbacher disease, peroneal muscular atrophy, progressive multifocal leukoencephalopathy, transverse myelitis, tropical spastic paraparesis, van der Knaap disease, or Zellweger syndrome. In one embodiment, the demyelinating disease is or is associated with multiple sclerosis, MCT8 deficiency, X-linked adrenoleukodystrophy (ALD), amyotrophic lateral sclerosis (ALS), Alzheimer's disease, frontotemporal dementia, or lacunar stroke.

As used herein, the term "neurodegenerative disease" refers to any type of disease that is characterized by the progressive deterioration of the nervous system.

As used herein, the term "demyelinating disease" refers to any disease or medical condition of the nervous system in which myelin is damaged or lost, or in which the growth or development of the myelin sheath is impaired. Demyelination inhibits the conduction of signals in the affected nerves, causing impairment in sensation, movement, cognition, or other functions for which nerves are involved. Demyelinating diseases have a number of different causes and can be hereditary or acquired. In some cases, a demyelinating disease is caused by an infectious agent, an autoimmune response, a toxic agent or traumatic injury. In other cases, the cause of the demyelinating disease is unknown ("idiopathic") or develops from a combination of factors.

As used herein, the term "leukodystrophy" refers to a group of diseases that affects the growth or development of the myelin sheath.

As used herein, the term "leukoencephalopathy" refers to any of a group of diseases affecting the white substance of the brain; can refer specifically to several diseases including, for example, "leukoencephalopathy with vanishing white matter" and "toxic leukoencephalopathy." Leukoencephalopathies are leukodystrophy-like diseases.

As used herein, the term "tauopathy" refers to tau-related disorders or conditions, e.g., Alzheimer's Disease (AD), Progressive Supranuclear Palsy (PSP), Corticobasal Degeneration (CBD), Pick's Disease (PiD), Argyrophilic grain disease (AGD), Frontotemporal dementia and Parkinsonism associated with chromosome 17 (FTDP-17), Parkinson's disease, stroke, traumatic brain injury, mild cognitive impairment and the like.

As used herein, the terms "multiple sclerosis" and "MS" refer to a slowly progressive CNS disease characterized by disseminated patches of demyelination in the brain and spinal cord, resulting in multiple and varied neurological symptoms and signs, usually with remissions and exacerbation. The cause of MS is unknown but an immunological abnormality is suspected. An increased family incidence suggests genetic susceptibility, and women are somewhat more often affected than men. The symptoms of MS include weakness, lack of coordination, paresthesias, speech disturbances, and visual disturbances, most commonly double vision. More specific signs and symptoms depend on the location of the lesions and the severity and destructiveness of the inflammatory and sclerotic processes. Relapsing-remitting multiple sclerosis (RRMS) is a clinical course of MS that is characterized by clearly defined, acute attacks with full or partial recovery and no disease progression between attacks. Secondary-progressive multiple sclerosis (SPMS) is a clinical course of MS that initially is relapsing-remitting, and then becomes progressive at a variable rate, possibly with an occasional relapse and minor remission. Primary-progressive multiple sclerosis (PPMS) presents initially in the progressive form. A clinically isolated syndrome is the first neurologic episode, which is caused by inflammation/demyelination at one or more sites in the CNS. Progressive-relapsing multiple sclerosis (PRMS) is a rare form of MS (~5%) characterized by a steadily worsening disease state from onset, with acute relapses but no remissions.

In yet another embodiment, a method of treating a subject having a X-linked genetic disorder is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof. In one embodiment, the X-linked genetic disorder is MCT8 deficiency or X-linked adrenoleukodystrophy (ALD).

In another embodiment, a method of treating a subject having a leukodystrophy is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof. In one embodiment, the leukodystrophy is adrenoleukodystrophy (ALD), adrenomyeloneuropathy (AMN), cerebral form of adrenoleukodystrophy (cALD), metachromatic leukodystrophy (MLD), Canavan's disease, or Krabbe disease (globoid leukodystrophy). As used herein, the term "adrenomyeloneuropathy" or "AMN" refers to an adult variant of X-linked adrenoleukodystrophy, characterized by ABCD1 gene mutation, that results in impaired peroxisome function with accumulation of very long chain fatty acids (VLCFA) and demyelination.

In one embodiment, a method of treating a subject having a tauopathy is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof. In one embodiment, the tauopathy is Alzheimer's disease, frontotemporal dementia, primary age-related tauopathy (PART), Pick's disease, or frontotemporal dementia and parkinsonism linked to chromosome 17 (FTDP-17).

In yet another embodiment, a method of treating a subject having an ischaemic stroke is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof. In one embodiment, the ischaemic stroke is lacunar stroke (also called "lacunar infarct"). In another embodiment, the present method is used to treat a subject suffering from a lacunar stroke syndrome (LACS).

In another embodiment, a method of treating a subject having adult Refsum disease, infantile Refsum disease, Alexander disease, Alzheimer's disease, balo concentric sclerosis, Canavan disease, central pontine myelinolysis (CPM), cerebral palsy, cerebrotendineous xanthomatosis, chronic inflammatory demyelinating polyneuropathy (CIDP), Devic's syndrome, diffuse myelinoclastic sclerosis, encephalomyelitis, idiopathic inflammatory demyelinating disease (IIDD), Krabbe disease, Leber hereditary optic neuropathy, leukodystrophy, Marburg multiple sclerosis, Marchiafava-Bignami disease, metachromatic leukodystrophy (MLD), multifocal motor neuropathy (MMN), multiple sclerosis (MS), paraproteinemic demyelinating polyneuropathy, Pelizaeus-Merzbacher disease (PMD), progressive multifocal leukoencephaalopathy (PML), tropical spastic paraparesis (TSP), X-linked adrenoleukodystrophy (X-ALD, ALO, or X-linked ALO), or Zellweger syndrome is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof.

In one embodiment, the demyelinating disease is multiple sclerosis. In another embodiment, the demyelinating disease is X-linked adrenoleukodystrophy (ALD).

In another embodiment, a method of treating a subject having an amyotrophic lateral sclerosis (ALS) disease is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof. In one embodiment, the ALS is sporadic or familial ALS, or ALS with Superoxide dismutase-1 mutation.

In one embodiment, a method of treating a subject having a medical condition associated with increased activity of TGF-β is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof. In one embodiment, the medical condition associated with increased activity of TGF-β is a fibrotic disease. In another embodiment, the fibrotic disease is or is associated with nonalcoholic steatohepatitis (NASH), idiopathic pulmonary fibrosis (IPF), systemic scleroderma, or Alport syndrome. As used herein, the term "Alport syndrome" refers to a hereditary disorder caused by mutations in the a3a4a5(IV) collagen network genes resulting in structural defects in the glomerular basement membrane (GBM) early during development leading subsequently to the breakdown of the filtration barrier, development of renal fibrosis and kidney failure.

As used herein, the term "fibrotic disease" refers to a condition, disease or disorder that is amenable to treatment by administration of a compound having anti-fibrotic activity. Fibrotic diseases include, but are not limited to, pulmonary fibrosis, including idiopathic pulmonary fibrosis (IPF) and pulmonary fibrosis from a known etiology, liver fibrosis, and renal-fibrosis. Other exemplary fibrotic diseases include musculoskeletal fibrosis, cardiac fibrosis, post-surgical adhesions, scleroderma, glaucoma, and skin lesions such as keloids.

In another embodiment, a method of treating a subject having NASH, NAFLD, NAFLD with hyperlipidemia, alcoholic liver disease/alcoholic steatohepatitis, liver fibrosis associated with viral infection (HBV, HCV), fibrosis associated with cholestatic diseases (primary biliary cholangitis, primary sclerosing cholangitis), (familial) hypercholesterolemia, dyslipidemia, genetic lipid disorders, cirrhosis, alcohol-induced fibrosis, hemochromatosis, glycogen storage diseases, alpha-1 antitrypsin deficiency, autoimmune hepatitis, Wilson's disease, Crigler-Najjar Syndrome, lysosomal acid lipase deficiency, liver disease in cystic fibrosis is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof.

In another embodiment, a method of treating a subject having Alport syndrome, diabetic nephropathy, FSGS, fibrosis associated with IgA nephropathy, chronic kidney diseases (CKD), post AKI, HIV associated CKD, chemotherapy induced CKD, CKD associated with nephrotoxic agents, nephrogenic systemic fibrosis, tubulointerstitial fibrosis, glomerulosclerosis, or polycystic kidney disease (PKD) is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof.

In another embodiment, a method of treating a subject having IPF, ILD, pulmonary fibrosis, pulmonary fibrosis associated with autoimmune diseases like rheumatoid arthritis, scleroderma or Sjogren's syndrome, asthma-related pulmonary fibrosis, COPD, asbestos or silica induced PF, silicosis, respiratory bronchiolitis, Idiopathic interstitial pneumonias (IIP), Idiopathic nonspecific interstitial pneumonia, Respiratory bronchiolitis-interstitial lung disease, desquamative interstitial pneumonia, acute interstitial pneumonia, Rare IIPs: Idiopathic lymphoid interstitial pneumonia, idiopathic pleuroparenchymal fibroelastosis, unclassifiable idiopathic interstitial pneumonias, hypersensitivity pneumonitis, radiation-induced lung injury, progressive massive fibrosis—pneumoconiosis, bronchiectasis, byssinosis, chronic respiratory disease, chronic obstructive pulmonary disease (COPD), emphysema, pulmonary arterial hypertension (PAH), or Cystic fibrosis is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof.

In another embodiment, a method of treating a subject having scleroderma/systemic sclerosis, graft versus host disease, hypertrophic scars, keloids, nephrogenic systemic fibrosis, porphyria cutanea tarda, restrictive dermopathy, Dupuytren's contracture, dermal fibrosis, nephrogenic systemic fibrosis/nephrogenic fibrosing dermopathy, mixed connective tissue disease, scleromyxedema, eosinophilic fasciitis, fibrosis caused by exposure to chemicals or physical agents. GvHD induced fibrosis, Scleredema adultorum, Lipodermatosclerosis, or Progeroid disorders (progeria, acrogeria, Werner's syndrome) is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof.

In another embodiment, a method of treating a subject having atrial fibrosis, endomyocardial fibrosis, cardiac fibrosis, atherosclerosis, restenosis, or arthrofibrosis is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof.

In another embodiment, a method of treating a subject having mediastinal fibrosis, myelofibrosis, post-polycythemia vera myelofibrosis, or post essential thrombocythemia is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof.

In another embodiment, a method of treating a subject having Crohn's disease, retroperitoneal fibrosis, intestinal fibrosis, fibrosis in inflammatory bowel disease, ulcerative colitis, GI fibrosis due to cystic fibrosis, or pancreatic fibrosis due to pancreatitis is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof.

In another embodiment, a method of treating a subject having endometrial fibrosis, uterine fibroids, or Peyronie's disease is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof.

In another embodiment, a method of treating a subject having macular degeneration, diabetic retinopathy, retinal fibrovascular diseases, or vitreal retinopathy is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof.

In another embodiment, a method of treating a subject having scarring associated with trauma (surgical complications, chemotherapeutics drug-induced fibrosis, radiation induced fibrosis) is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof.

As used herein, the term "administration" refers to providing a compound, a prodrug of a compound, or a pharmaceutical composition comprising the compound or prodrug as described herein. The compound or composition can be administered by another person to the subject or it can be self-administered by the subject. Non-limiting examples of routes of administration are oral, parenteral (e.g., intravenous), or topical.

As used herein, the term "treatment" refers to an intervention that ameliorates a sign or symptom of a disease or pathological condition. As used herein, the terms "treatment", "treat" and "treating," with reference to a disease, pathological condition or symptom, also refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease. A prophylactic treatment is a treatment administered to a subject who does not exhibit signs of a disease or exhibits only early signs, for the purpose of decreasing the risk of developing pathology. A therapeutic treatment is a treatment administered to a subject after signs and symptoms of the disease have developed.

As used herein, the term "subject" refers to an animal (e.g., a mammal, such as a human). A subject to be treated according to the methods described herein may be one who has been diagnosed with a neurodegenerative disease involving demyelination, insufficient myelination, or underdevelopment of a myelin sheath, e.g., a subject diagnosed with multiple sclerosis or cerebral palsy, or one at risk of developing the condition. Diagnosis may be performed by any method or technique known in the art. One skilled in the art will understand that a subject to be treated according to the present disclosure may have been subjected to standard tests or may have been identified, without examination, as one at risk due to the presence of one or more risk factors associated with the disease or condition.

As used herein, the term "effective amount" refers to a quantity of a specified agent sufficient to achieve a desired effect in a subject being treated with that agent. Ideally, an effective amount of an agent is an amount sufficient to inhibit or treat the disease without causing substantial toxicity in the subject. The effective amount of an agent will be dependent on the subject being treated, the severity of the affliction, and the manner of administration of the pharmaceutical composition. Methods of determining an effective amount of the disclosed compound sufficient to achieve a desired effect in a subject will be understood by those of skill in the art in light of this disclosure.

As used herein, the terms "chronic" refers to a medical disorder or condition that persists over time or is frequently recurring.

Compounds having the structure of Formulas (I), (II), (III), (IV), (V), (VI), (VII) and (VIII) can be synthesized using standard synthetic techniques known to those skilled in the art. For example, compounds of the present invention can be synthesized using appropriately modified synthetic procedures set forth in WO 2014/178892, WO 2014/178931, WO 2016/134292, WO 2017/201320, WO 2018/032012, and Schemes 1-7 below.

To this end, the reactions, processes, and synthetic methods described herein are not limited to the specific conditions described in the following experimental section, but rather are intended as a guide to one with suitable skill in this field. For example, reactions may be carried out in any suitable solvent, or other reagents to perform the transformation[s] necessary. Generally, suitable solvents are protic or aprotic solvents which are substantially non-reactive with the reactants, the intermediates or products at the temperatures at which the reactions are carried out (i.e., temperatures which may range from the freezing to boiling temperatures, or higher if reactions are run in sealed vessels). A given reaction may be carried out in one solvent or a mixture of more than one solvent. Depending on the particular reaction, suitable solvents for a particular work-up following the reaction may be employed.

Scheme 1

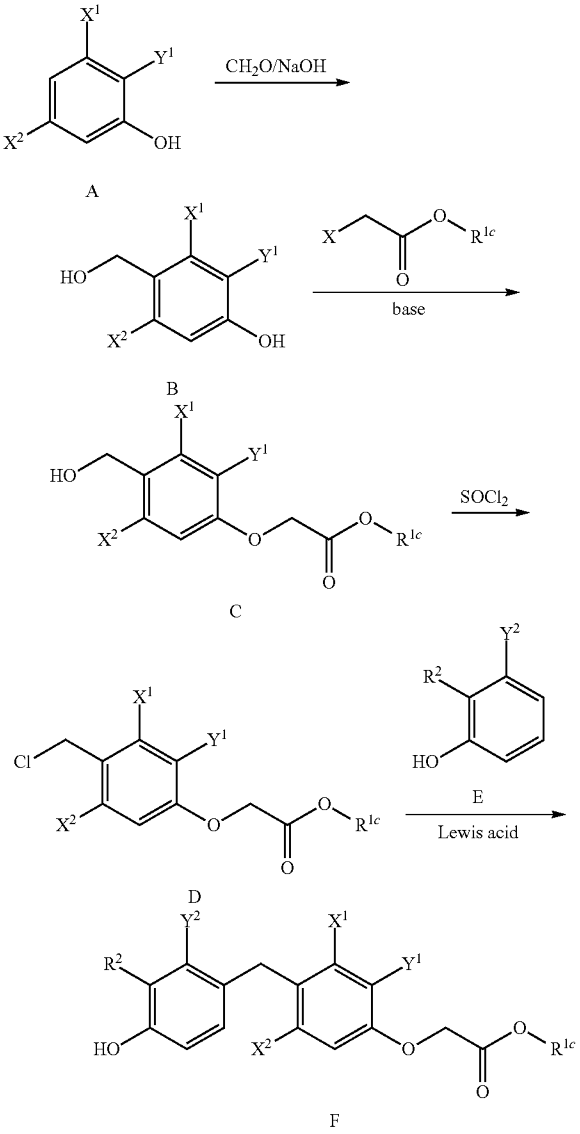

Compounds of the present invention can be prepared according to Scheme 1. Referring to Scheme 1, a di- or tri-substituted phenol (A) (for example, 3,5-dichlorophenol or 3-methyl-5-chlorophenol or 3,5-dichloro-2-fluoro-phenol, or the like) is reacted with a formaldehyde equivalent (for example, aqueous formaldehyde or paraformaldehyde or dimethoxymethane or the like) to give a hydroxymethyl derivative (B), which is subsequently reacted with an activated acetate moiety (for example ethyl chloroacetate or methyl bromoacetate or the like) in the presence of base, selectively at the phenolic oxygen, to provide intermediate (C). The hydroxymethyl group is activated (for example, through reaction with thionyl chloride or oxalyl chloride or p-toluenesulfonylchloride or the like) to give a chloromethyl derivative (D) (or the corresponding tosylate, or mesylate, or bromomethyl analog, or the like), which is condensed with a 2-substituted phenol (E) in the presence of a Lewis acid (like zinc chloride, or aluminum chloride, or the like) to give an ester (F). Alternatively intermediate alcohol (C) can be reacted directly with phenol (E) in the presence of a protic acid like sulfuric acid or the like, or a Lewis acid like boron trifluoride etherate or the like.

Scheme 2.

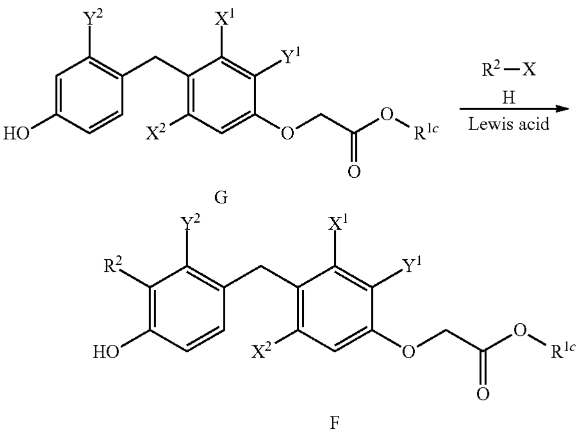

Compounds of the present invention can be prepared according to Scheme 2. Referring to Scheme 2, phenol G (=F, $R^2$=H; prepared according to Scheme 1) is then reacted with a reactive halide H, for example p-fluorobenzyl chloride or 1-(1-chloroethyl)-4-fluorobenzene or 2,4-difluorobenzyl alcohol or the like, in the presence of a Lewis acid like Zinc chloride or Aluminum chloride or boron trifluoride etherate or the like, to give a 3'-alkylated product like ester F.

Scheme 3.

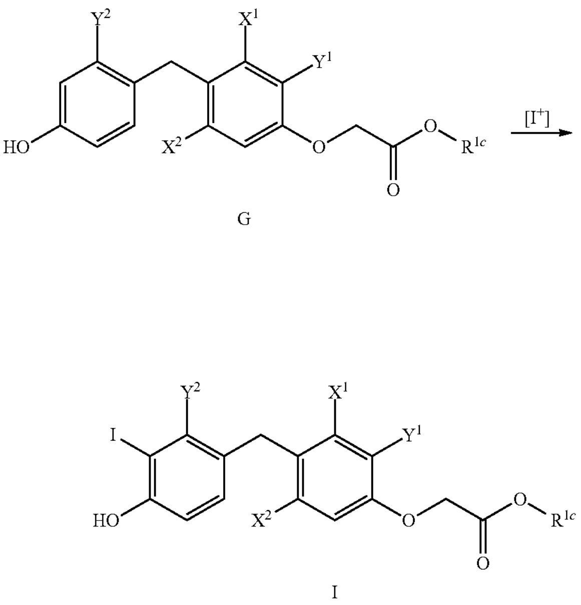

-continued

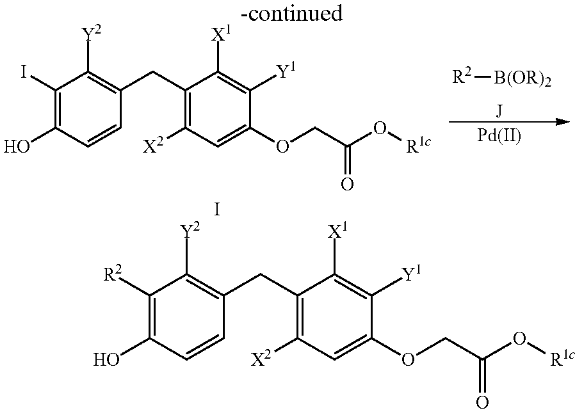

I

K

Compounds of the present invention can be prepared according to Scheme 3. Referring to Scheme 3, ortho-iodination of phenol G, for example using N-iodosuccinimide or solid iodine or the like, provides key intermediate I. To prepare compounds of the present invention, I is reacted with a boronic acid (or boronate) J under various Suzuki conditions to provide esters K of the present invention.

Scheme 4.

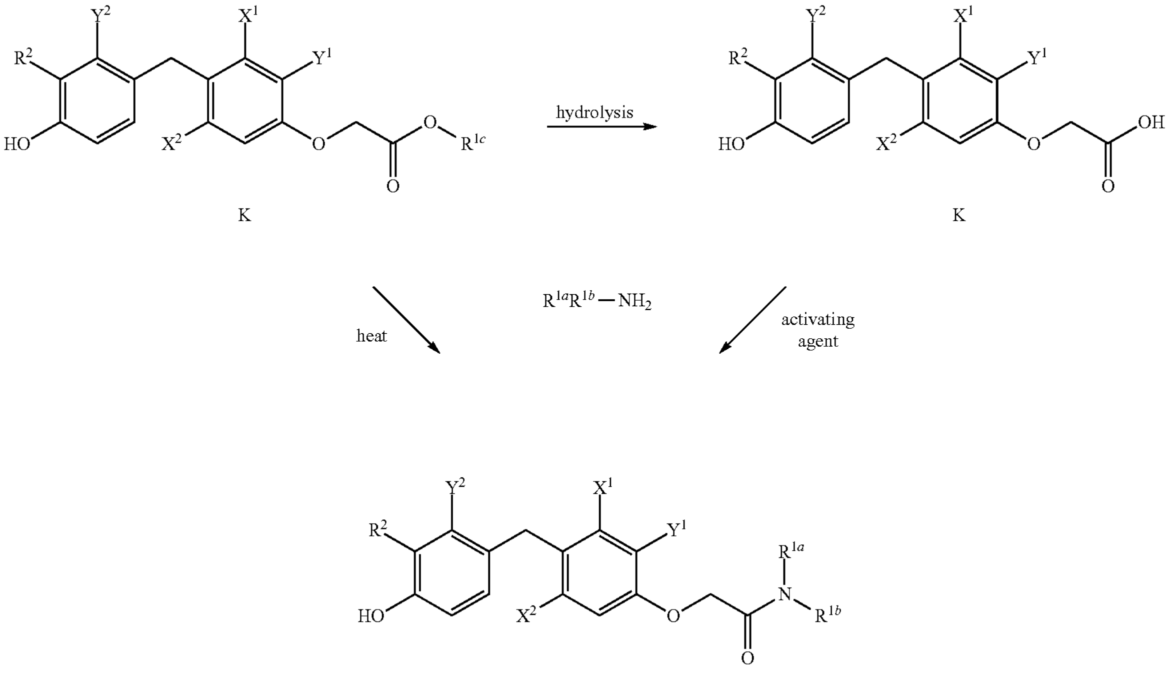

K

K

M

As shown in Scheme 4, hydrolysis of the ester group of (K), for example using aqueous sodium hydroxide (if R' is methyl) or TFA (if R' is t-butyl) provides acids (L) of the present invention. If desired, acid (L) can be converted to an amide (M) by condensing with the corresponding amine (for example methylamine or propylamine or 2-sulfonylethylamine or the like) in the presence of a coupling agent like DDC or EDCl or the like, or by forming an activated intermediate (for example the corresponding acid chloride) using thionyl chloride or the like. Alternatively, if desired, either esters (K), or acids (L) may be heated with an amine $R^{1b}R^{1c}NH$, for example methylamine or propylamine or 2-sulfonylethylamine or the like, to give amides (M) of the present invention.

Scheme 5.

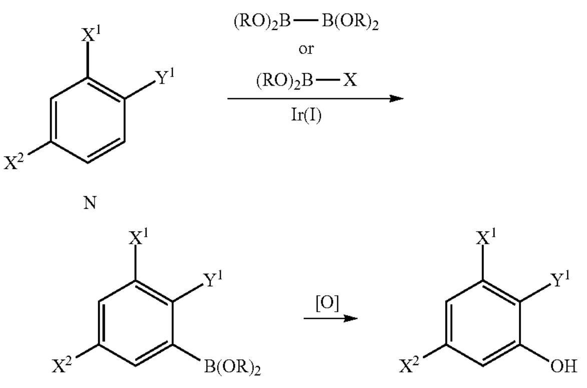

N

O

A

Phenols (A) of the present invention may be commercially available, or may be prepared according to Scheme 5. Referring to Scheme 5, di- or -tri-substituted arenes (N) may be oxidatively borolated using an activated borylating agent like (bis-pinacolato)diboron or the like, in the presence of an active metal catalyst like (1,5-cyclooctadiene)(methoxy) iridium(I) dimer or the like, to give the corresponding boronate (O). Oxidative deborylation of 0, for example using hydrogen peroxide solution, provides the corresponding phenol (A).

Scheme 6.

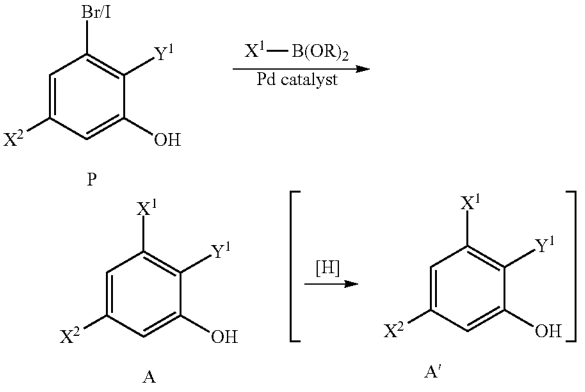

An alternative approach to the preparation of key intermediate phenols (A) is described in Scheme 6. Referring to Scheme 6, di- or tri-substituted phenols (P) having one substituent as bromine or iodine may be reacted under Suzuki coupling conditions, for example using a boronic acid or boronate reagent or the like, in the presence of a Palladium catalyst like $Pd(OAc)_2$ or $Pd(dppf)Cl_2$ or the like, to produce alkyl, alkenyl, or alkynyl products (A). In the case where $X^1$ is an alkene or alkyne, subsequent hydrogenation, for example using Pd—C catalyst under a hydrogen atmosphere, can provide the corresponding alkyl-substituted (A').

Scheme 7.

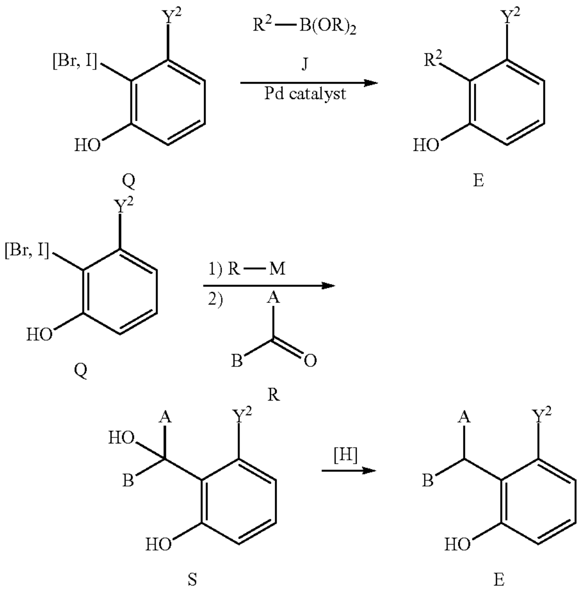

Substituted phenols (E) as employed in Scheme 3 may be prepared as indicated in Scheme 7. Referring to Scheme 7, a 2-halophenol (Q) like 2-bromophenol or 2-bromo-3-fluorophenol or the like may be condensed with a boronic acid or ester (J) under Suzuki conditions in the presence of a palladium catalyst or the like, to give 2-substituted phenol (E). In the case where the $R^2$ group is an alkene or alkyne, subsequent hydrogenation, for example using Pd—C catalyst under a hydrogen atmosphere, can provide the corresponding alkyl-substituted phenyl (E). Alternatively a 2-halophenol (Q) like 2-bromophenol or 2-bromo-3-fluorophenol or the like may be metallated using isopropylmagnesium bromide or n-butyllithium or the like, then condensed with an aldehyde or ketone (R), to give an intermediate like (S). Deoxygenation of (S) under hydrogenolysis conditions, using hydrogen gas in the presence of a palladium or platinum catalyst or the like, or under reductive-deoxygenation conditions in the presence of a reducing agent triethylsilane or the like, in the presence of an acid like TFA or the like, produces substituted phenol (E).

Scheme 8.

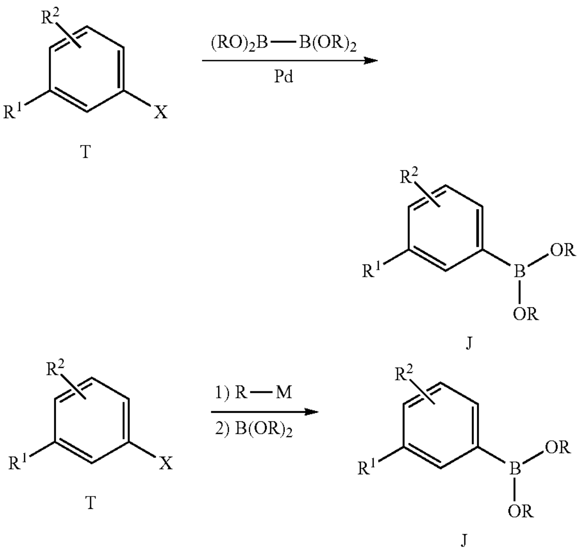

Arylboronic acids or esters (J) as employed in Scheme 3 may be sourced commercially, or may be prepared as described in Scheme 8. Referring to Scheme 8, aryl halides (T) may be reacted with di(pinacolato)diboron or a similar reagent, using a palladium catalyst or the like, to give (J). Alternatively (T) may be metallated using isopropylmagnesium bromide or n-butyllithium or the like, then reacted with a trialkoxyborate or the like, to provide (J).

EXAMPLES

The invention is further illustrated by the following examples. The examples below are non-limiting are merely representative of various aspects of the invention. Solid and dotted wedges within the structures herein disclosed illustrate relative stereochemistry, with absolute stereochemistry depicted only when specifically stated or delineated.

General Methods

All reagents, for which the synthesis is not described in the experimental part, are either commercially available, or are known compounds or may be formed from known compounds by known methods by a person skilled in the art.

The compounds and intermediates produced according to the methods of the invention may require purification. Purification of organic compounds is well known to a person skilled in the art and there may be several ways of purifying the same compound. In some cases, no purification may be necessary. In some cases, the compounds may be purified by crystallization. In some cases, impurities may be stirred out using a suitable solvent.

In some cases, the compounds may be purified by chromatography, particularly flash column chromatography, using purpose-made or prepacked silica gel cartridges and eluents such as gradients of solvents such as heptane, ether, ethyl acetate, acetonitrile, ethanol and the like. In some cases, the compounds may be purified by preparative HPLC (normal-phase or reversed-phase) using methods as described. Preparative HPLC purification by reverse phase HPLC was performed using gradients of acetonitrile in aqueous TFA or an equivalent HPLC system such as Methanol in aqueous ammonium acetate.

Purification methods as described herein may provide compounds of the present invention which possess a sufficiently basic or acidic functionality in the form of a salt, such as, in the case of a compound of the present invention which is sufficiently basic, a trifluoroacetate or formate salt, or, in the case of a compound of the present invention which is sufficiently acidic, an ammonium salt. A salt of this type can either be transformed into its free base or free acid form, respectively, by various methods known to a person skilled in the art, or be used as salts in subsequent biological assays. It is to be understood that the specific form of a compound of the present invention as isolated and as described herein is not necessarily the only form in which said compound can be applied to a biological assay in order to quantify the specific biological activity.

All the starting materials and reagents are commercially available and were used as is. $^{1}$H Nuclear magnetic resonance (NMR) spectroscopy was carried out using a Bruker instrument operating at 400 MHz using the stated solvent at around room temperature unless otherwise stated. In all cases, NMR data were consistent with the proposed structures.

Characteristic chemical shifts (5) are given in parts-per-million using conventional abbreviations for designation of major peaks: e.g. s, singlet; d, doublet; t, triplet; q, quartet; dd, doublet of doublets; dt, doublet of triplets; m, multiplet; br, broad.

Chemical names were generated using the ChemDraw naming software (Version 17.0.0.206) by PerkinElmer Informatics, Inc. In some cases, generally accepted names and generally accepted acronyms for commercially available reagents were used in place of names generated by the naming software.

Intermediate A1

Synthesis of methyl 2-(4-formyl-3,5-dimethylphenoxy)acetate (Intermediate A1)

A1

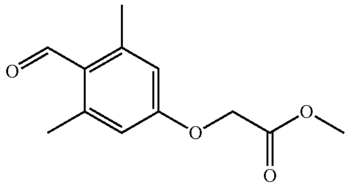

To a solution of 2,6-dimethyl-4-hydroxybenzaldehyde (5.0 g, 33.3 mmol) in acetone (50 mL) were added methyl chloroacetate (3.9 g, 36.6 mmol), NaI (1.1 g, 6.66 mmol) and $Cs_2CO_3$ (11.0 g, 33.3 mmol). The mixture was stirred at 55° C. for 5 h. Water (200 mL) was added and the mixture was extracted with EtOAc (50 mL*3). The combined organic layer was washed with brine (100 mL), dried over $Na_2SO_4$ and concentrated in vacuo. The crude product was purified by silica gel column chromatography (pet. ether/EtOAc=4:1) to afford Intermediate A1 (7.1 g, 96.0% yield) as a yellow solid.

TLC: Pet. ether/EtOAc=3/1 (v/v), Rf=0.5

LCMS: RT=3.177 min, [M+1]=223.0

$^{1}$H NMR: (400 MHz, DMSO-d6) δ 10.34 (s, 1H), 6.70 (s, 2H), 4.85 (s, 2H), 3.67 (s, 3H).

Intermediate A2

Synthesis of methyl 2-(4-(hydroxymethyl)-3,5-dimethylphenoxy)acetate (Intermediate A2)

A2

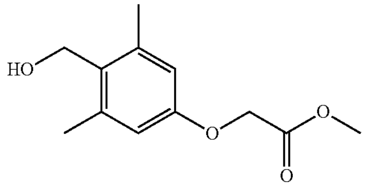

To a mixture of Intermediate A1 (6.9 g, 31.1 mmol) in MeOH (50 mL) at 0° C. was added $NaBH_4$ (1.2 g, 31.1 mmol). The mixture was stirred at rt for 2 h. Water (50 mL) was added, and the mixture was extracted with EtOAc (20 mL*2). The organic layer was washed with brine (20 mL), dried over $Na_2SO_4$ and concentrated in vacuo. The residue was purified by silica gel column chromatography (Pet. ether/EtOAc=3:1) to afford Intermediate A2 (5.8 g) as a white solid.

TLC: Pet. ether/EtOAc=3/1 (v/v), Rf=0.3

$^{1}$H NMR: (400 MHz, DMSO-d6) δ 6.56 (s, 2H), 4.73 (s, 2H), 4.59 (t, J=8.0, 1H), 4.39 (d, J=7.6 Hz, 2H), 3.68 (s, 3H), 2.30 (s, 6H).

Intermediate A3

Synthesis of methyl 2-(4-(chloromethyl)-3,5-dimethylphenoxy)acetate (Intermediate A3)

A3

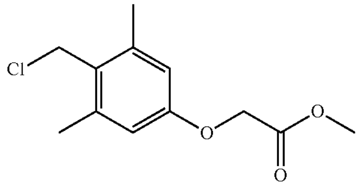

To a solution of Intermediate A2 (5.8 g, 25.9 mmol) in DCM (50 mL) at 0° C. was added $SOCl_2$ (9.2 g, 77.6 mmol) dropwise. The mixture was stirred at rt for 2 h. The mixture was concentrated in vacuo and the product was washed with n-hexane (50 mL) to afford Intermediate A3 (5.3 g, 84.4% yield) as a white solid.

TLC: Pet. ether/EtOAc=3/1 (v/v), Rf=0.6

$^1$H NMR: (400 MHz, DMSO-d6) δ 6.65 (s, 2H), 4.77 (s, 2H), 4.75 (s, 2H), 3.69 (s, 3H), 2.33 (s, 6H),

Intermediate A4

Synthesis of 3-bromo-4-(hydroxymethyl)-5-methylphenol (Intermediate A4)

A4

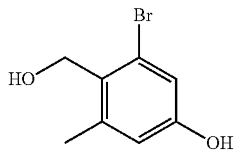

To a solution of sodium hydroxide (1.76 g, 44.1 mmol) in water (30 mL) was added 3-bromo-5-methyl-phenol (7.5 g, 40.1 mmol). The solution was heated to 45° C., and formaldehyde (3.25 g, 40.1 mmol, 37%/w in water) was added dropwise. The mixture was stirred at 45° C. for 2 h. The mixture was cooled, and water (10 mL) was added. The mixture was acidified with HCl (3N) to pH~3. The mixture was extracted with EtOAc (20 mL*2). The combined organic phase was washed with brine (30 mL), dried over $Na_2SO_4$ and concentrated in vacuo. The residue was purified by silica gel column chromatography (pet. ether: EtOAc=30:1 to 4:1) to afford Intermediate A4 (1.0 g, 4.6 mmol, 11.5% yield) as a white solid.

TLC: Pet. ether/EtOAc=1/1 (v/v), Rf=0.8

$^1$H NMR: (400 MHz, DMSO-$d_6$) δ 9.67 (s, 1H), 6.80 (d, J=2.4 Hz, 1H), 6.60 (d, J=2.5 Hz, 1H), 4.73 (t, J=5.1 Hz, 1H), 4.51 (d, J=5.1 Hz, 2H), 2.33 (s, 3H).

Intermediate A5

Synthesis of ethyl 2-(3-bromo-4-(hydroxymethyl)-5-methylphenoxy)acetate (Intermediate A5)

A5

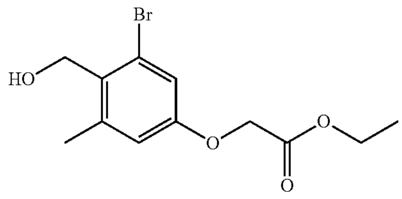

To a solution of Intermediate A4 (1.0 g, 4.6 mmol) and sodium bicarbonate (657 mg, 7.8 mmol) in DMF (10 mL) at rt was added ethyl 2-bromoacetate (1.0 g, 6.0 mmol). The mixture was stirred at rt overnight. Water (20 mL) was added, and the mixture was extracted with EtOAc (20 mL*2). The combined organic phase was washed with brine (30 mL), dried over $Na_2SO_4$, and concentrated in vacuo. The residue was purified by silica gel column chromatography (pet. ether:EtOAc=100:1 to 5:1) to afford Intermediate A5 (600 mg, 42% yield) as a white solid.

TLC: Pet. ether/EtOAc=2/1 (v/v), Rf=0.7

$^1$H NMR: (400 MHz, DMSO-$d_6$) δ 6.99 (d, J=2.8 Hz, 1H), 6.83-6.80 (m, 1H), 4.85 (t, J=5.2 Hz, 1H), 4.79 (s, 2H), 4.55 (d, J=5.2 Hz, 2H), 4.17 (q, J=7.2 Hz, 2H), 2.38 (s, 3H), 1.21 (t, J=7.2 Hz, 3H).

Intermediate A6

Synthesis of ethyl 2-(3-bromo-4-(chloromethyl)-5-methylphenoxy)acetate (Intermediate A6)

A6

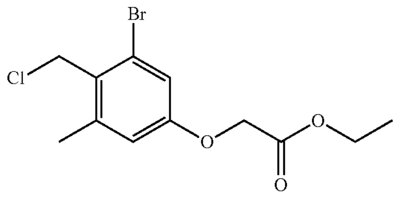

To a solution of Intermediate A5 (600 mg, 1.98 mmol) in dichloromethane (10 mL) at rt was added thionyl chloride (471 mg, 3.96 mmol). The mixture was stirred at rt for 1 h, then concentrated in vacuo to afford Intermediate A6 (600 mg, 94% yield) as a white solid.

TLC: Pet. ether/EtOAc=2/1 (v/v), Rf=0.8

$^1$H NMR: (400 MHz, DMSO-$d_6$) δ 7.10 (d, J=2.8 Hz, 1H), 6.92-6.89 (m, 1H), 4.84 (s, 4H), 4.17 (q, J=7.2 Hz, 2H), 2.42 (s, 3H), 1.21 (t, J=7.2 Hz, 3H).

Intermediate A7

Synthesis of 3,5-dichloro-4-(hydroxymethyl)phenol (Intermediate A7)

A7

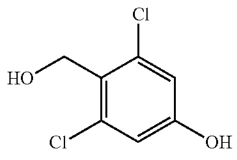

To a solution of NaOH (6.7 g, 169 mmol) in water (20 mL) was added 3,5-dichlorophenol (25.0 g, 153 mmol). The mixture was heated to 45° C. and 36% aqueous formaldehyde (12.4 g, 153 mmol) was added dropwise slowly. The mixture was stirred at 45° C. for 2 h, then cooled to rt. The pH was adjusted to 3-4 with 1N HCl, and the mixture was stirred at rt for 20 min. The solid was filtered, washed with water (50 mL) and dried to afford Intermediate A7 (11.5 g, 59.6 mmol, 39% yield) as an off-white solid.

TLC: EtOAc/pet. ether 1/3, $R^f$ 0.36

$^1$H NMR: (400 MHz, DMSO-$d_6$) δ 10.02 (s, 1H), 6.82 (s, 2H), 4.98 (s, 1H), 4.57 (d, J=2.1 Hz, 2H)

Intermediate A8

Synthesis of methyl 2-(3,5-dichloro-4-(hydroxymethyl)phenoxy)acetate (Intermediate A8)

A8

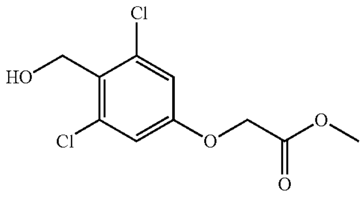

To a solution of Intermediate A7 (3.0 g, 15.5 mmol) in acetone (40 mL) were added potassium carbonate (3.22 g, 23.3 mmol) and methyl 2-chloroacetate (2.02 g, 18.6 mmol). The mixture was refluxed for 2 h. The mixture was cooled to rt, diluted with water (120 mL), and extracted with EtOAc (80 mL*3). The combined organic phase was washed with brine (200 mL), dried over $Na_2SO_4$, and concentrated in vacuo. The residue was purified by silica gel column chromatography (pet. ether/EtOAc=20/1 to 5/1) to afford Intermediate A8 (2.0 g, 7.54 mmol, 48.5% yield) as a white solid.

TLC: EtOAc/pet. ether 1/5, $R^f$ 0.28

$^1$H NMR: (400 MHz, DMSO-$d_6$) δ 7.10 (s, 2H), 5.08 (t, J=5.3 Hz, 1H), 4.91 (s, 2H), 4.61 (d, J=5.3 Hz, 2H), 3.70 (s, 3H).

Intermediate A9

Synthesis of ethyl 2-(3,5-dichloro-4-(hydroxymethyl)phenoxy)acetate (Intermediate A9)

A9

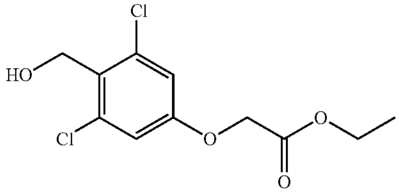

To a solution of Intermediate A7 (13.0 g, 67.4 mmol) in DMF (120 mL) at rt were added ethyl 2-bromoacetate (11.25 g, 67.4 mmol) and $K_2CO_3$ (11.2 g, 80.8 mmol). The mixture was stirred at rt for 2 h, diluted with water (200 mL), and extracted with EtOAc (100 mL*3). The combined organic phase was washed with water (100 mL*3) and brine (200 mL), dried over $Na_2SO_4$, and concentrated in vacuo. The crude product was purified by silica gel column chromatography (pet. ether/EtOAc=5/1) to afford Intermediate A9 (15 g, 79% yield) as an off-white solid.

TLC: EtOAc/pet. ether=1/5 (v/v), Rf=0.42

$^1$H NMR: (400 MHz, DMSO-$d_6$) δ 7.09 (s, 2H), 5.09 (t, J=5.2 Hz, 1H), 4.88 (s, 2H), 4.60 (d, J=5.2 Hz, 2H), 4.17 (q, J=7.1 Hz, 2H), 1.21 (t, J=7.1 Hz, 3H).

Intermediate A10

Synthesis of methyl 2-(3,5-dichloro-4-(chloromethyl)phenoxy)acetate (Intermediate A10)

A10

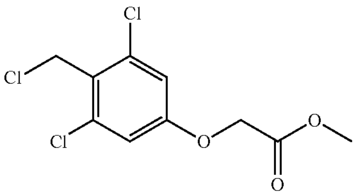

To a mixture of Intermediate A8 (1.0 g, 3.77 mmol) in DCM (10 mL) was added thionyl chloride (0.67 g, 5.66 mmol). The mixture was stirred at rt for 1 h, then was concentrated in vacuo to afford crude Intermediate A10 (1.0 g, 3.53 mmol, 93.5% yield) as a light yellow solid.

TLC: EtOAc/pet. ether 1/5, $R^f$ 0.72

$^1$H NMR: (400 MHz, DMSO-$d_6$) δ 7.21 (s, 2H), 4.94 (s, 2H), 4.85 (s, 2H), 3.71 (s, 3H).

Intermediate A11

Synthesis of ethyl 2-(3,5-dichloro-4-(chloromethyl)phenoxy)acetate (Intermediate A11)

A11

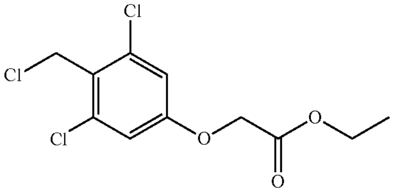

To a reaction mixture of Intermediate A9 (15.0 g, 3.77 mmol) in DCM (150 mL) at 0° C. was added dropwise thionyl chloride (9.59 g, 80.6 mmol). The mixture was stirred at rt for 1 h, diluted with DCM (100 mL), and concentrated in vacuo to afford Intermediate A11 (15.0 g, 93.5% yield) as a light yellow solid.

TLC: EtOAc/pet. ether=1/5 (v/v), Rf=0.72

$^1$H NMR: (400 MHz, DMSO-$d_6$) δ 7.20 (s, 2H), 4.92 (s, 2H), 4.86 (s, 2H), 4.17 (q, J=7.2 Hz, 2H), 1.21 (t, J=7.1 Hz, 3H).

Intermediate A12

Synthesis of 3-chloro-4-(hydroxymethyl)-5-methylphenol (Intermediate A12)

A12

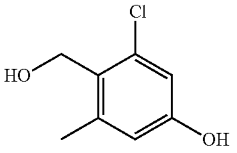

To a mixture of 3-chloro-5-methyl-phenol (3.55 g, 24.9 mmol) in water (10 mL) at rt was added NaOH (1.10 g, 27.42 mmol). The mixture was heated to 45° C., and formaldehyde (0.75 g, 24.93 mmol, 37%/w in water) was added dropwise. The mixture was stirred at 45° C. for 2 h. The mixture was cooled to rt, then acidified with HCl (3N) to pH~3, and extracted with EtOAc (10 mL*3). The combined organic phase was washed with brine (15 mL), dried over $Na_2SO_4$, and concentrated in vacuo. The crude product was purified by silica gel column chromatography (pet. ether/EtOAc=50/1 to 5/1) to afford Intermediate A12 (0.76 g, 4.40 mmol, 17.7% yield) as an off-white solid.

TLC: EtOAc/pet. ether=1/1 (v/v), Rf=0.8

$^1$H NMR: (400 MHz, DMSO-$d_6$) δ 9.68 (s, 1H), 6.62 (d, J=2.4 Hz, 1H), 6.56 (d, J=2.4 Hz, 1H), 4.73 (t, J=5.2 Hz, 1H), 4.49 (d, J=5.2 Hz, 2H), 2.31 (s, 3H).

Intermediate A13

Synthesis of ethyl 2-(3-chloro-4-(hydroxymethyl)-5-methylphenoxy)acetate (Intermediate A13)

A13

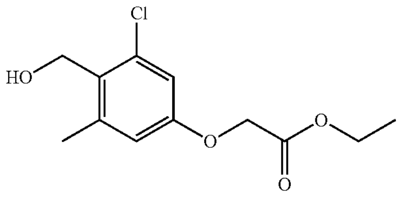

To a solution of Intermediate A12 (1.00 g, 5.79 mmol) in DMF (10 mL) at rt were added $K_2CO_3$ (0.97 g, 6.95 mmol), and ethyl bromoacetate (0.98 g, 5.79 mmol). The mixture was stirred at rt for 4 h, then diluted with water (30 mL) and extracted with EtOAc (10 mL*3). The combined organic phase was washed with brine (20 mL), dried over $Na_2SO_4$, and concentrated in vacuo to afford Intermediate A13 (1.2 g, 75.9% yield).

TLC: EtOAc/pet. ether=1/2 (v/v), Rf=0.54

Intermediate A14

Synthesis of ethyl 2-(3-chloro-4-(chloromethyl)-5-methylphenoxy)acetate (Intermediate A14)

A14

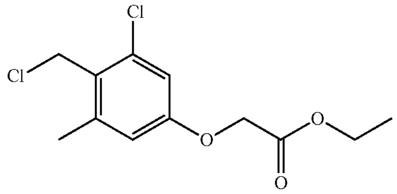

To a solution of Intermediate A13 (1.00 g, 3.87 mmol) in DCM (10 mL) at rt was added $SOCl_2$ (0.55 g, 4.64 mmol). The mixture was stirred at rt for 2 h, then concentrated in vacuo to afford Intermediate A14 (1.0 g, 93.4% yield) as a white solid.

TLC: EtOAc/pet. ether=1/10 (v/v), Rf=0.67

$^1$H NMR: (400 MHz, DMSO-$d_6$) δ 6.95 (d, J=2.6 Hz, 1H), 6.86 (d, J=2.6 Hz, 1H), 4.82 (d, J=5.3 Hz, 4H), 4.16 (q, J=7.0 Hz, 2H), 2.39 (s, 2H), 1.20 (t, J=7.2 Hz, 3H).

Intermediate A15

Synthesis of 3-bromo-5-chloro-4-(hydroxymethyl)phenol (Intermediate A15)

A15

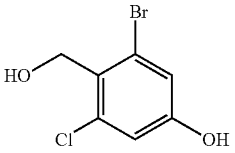

To a solution of NaOH (463 mg, 11.6 mmol) in water (20 mL) at rt was added 3-chloro-5-bromophenol (2.4 g, 11.6 mmol). The mixture was heated to 45° C., and formaldehyde (347 mg, 11.6 mmol) was added dropwise. The mixture was stirred overnight at 45° C., then diluted with water (20 mL), acidified with 1N HCl to pH~6-7, and extracted with EtOAc (20 mL*2). The combined organic phase was washed with brine (30 mL), dried over $Na_2SO_4$, and concentrated in vacuo. The crude product was purified by silica gel column chromatography (pet. ether/EtOAc=100/1 to 5/1) to afford Intermediate A15 (850 mg, 31% yield) as a white solid.

TLC: Pet. ether/EtOAc=3/1 (v/v), Rf=0.35.

LCMS: RT=1.619 min, [M−1]=234.9.

Intermediate A16

Synthesis of ethyl 2-(3-bromo-5-chloro-4-(hydroxymethyl)phenoxy)acetate (Intermediate A16)

A16

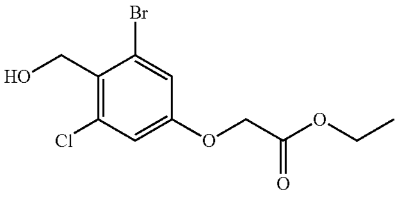

To a solution of Intermediate A15 (850 mg, 3.58 mmol) in DMF (10 mL) at rt were added $K_2CO_3$ (742 mg, 5.37 mmol) and ethyl bromoacetate (717 mg, 4.30 mmol); the mixture was stirred at rt for 2 h. Water (30 mL) was added and the resultant mixture was extracted with EtOAc (30 mL*2). The combined organic phase was washed with water (20 mL*3) and brine (30 mL*3), dried over $Na_2SO_4$ and concentrated in vacuo to afford Intermediate A16 (920 mg, 79% yield) as a white solid.

TLC: Pet. ether/EtOAc=3/1 (v/v), Rf=0.51

$^1$H NMR: (400 MHz, DMSO-$d_6$) δ 7.23 (d, J=2.8 Hz, 1H), 7.13 (d, J=2.4 Hz, 1H), 5.07 (t, J=5.2 Hz, 1H), 4.88 (s, 2H), 4.63 (d, J=5.2 Hz, 2H), 4.17 (q, J=7.2 Hz, 2H), 1.21 (t, J=7.2 Hz, 3H).

Intermediate A17

Synthesis of ethyl 2-(3-bromo-5-chloro-4-(chloromethyl)phenoxy)acetate (Intermediate A17)

A17

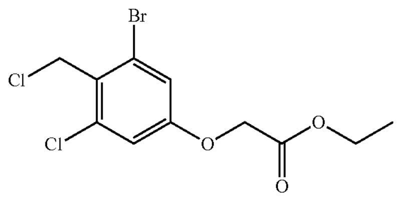

To a solution of Intermediate A16 (500 mg, 1.55 mmol) in DCM (7 mL) at 0° C. was added $SOCl_2$ (276 mg, 2.32 mmol). The mixture was stirred at rt for 2 h, then concentrated in vacuo to afford crude Intermediate A17 (500 mg, 94.6% yield) as a white solid.

TLC: Pet. ether/EtOAc=3/1 (v/v), Rf=0.79

$^1$H NMR: (400 MHz, DMSO-$d_6$) δ 7.34 (d, J=2.4 Hz, 1H), 7.24 (d, J=2.4 Hz, 1H), 4.92 (s, 2H), 4.88 (s, 2H), 4.17 (q, J=7.2 Hz, 2H), 1.21 (t, J=7.2 Hz, 3H).

Intermediate A18

Synthesis of 4-bromo-2-fluoro-3,5-dimethylphenol (Intermediate A18)

A18

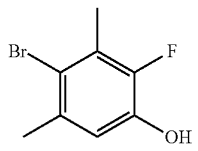

To a solution of 4-bromo-3,5-dimethylphenol (20 g, 99.5 mmol) in DCE (200 mL) at rt was added N-Fluoropyridinium triflate (24.6 g, 99.5 mmol); the resultant solution was heated to 80° C. overnight. The reaction was cooled to rt, diluted with EtOAc (1000 mL), and filtered. The filtrate was washed with water (400 mL*3), and brine (400 mL*2), dried over $Na_2SO_4$, and concentrated in vacuo. The crude product was purified by silica gel column chromatography (EtOAc/pet. ether=1/50) to afford Intermediate A18 (6.0 g, 27.5% yield) as a yellow solid.

TLC: EtOAc/pet. ether=1/10, Rf=0.45

$^1$H NMR: (400 MHz, DMSO-$d_6$) δ 9.88 (d, J=1.2 Hz, 1H), 6.81 (d, J=9.2 Hz, 1H), 2.24 (d, J=3.2 Hz, 6H).

$^{19}$F NMR: (376 MHz, DMSO-$d_6$) δ −137.26.

Intermediate A19

Synthesis of 1-(benzyloxy)-4-bromo-2-fluoro-3,5-dimethylbenzene (Intermediate A19)

A19

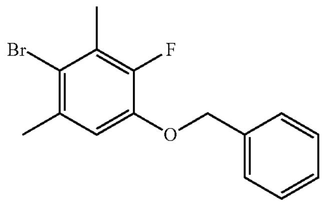

To a solution of Intermediate A18 (6.0 g, 27.4 mmol) in DMF (35 mL) at rt were added benzyl bromide (5.2 g, 30.1 mmol) and $Cs_2CO_3$ (17.9 g, 54.8 mmol); the resultant mixture was stirred overnight at rt. The reaction mixture was diluted with EtOAc (300 mL) and filtered. The filtrate was washed with water (100 mL*2), then brine (100 mL*2), dried over $Na_2SO_4$, and concentrated in vacuo. The crude product was purified by silica gel column chromatography (EtOAc/pet. ether=1/100) to afford Intermediate A19 (6.6 g, 77.9% yield) as a white solid.

TLC: EtOAc/pet. ether=1/10, Rf=0.78

$^1$H NMR: (400 MHz, DMSO-$d_6$) δ 7.57-7.30 (m, 5H), 7.20 (d, J=8.9 Hz, 1H), 5.16 (s, 2H), 2.31 (s, 3H), 2.27 (d, J=2.8 Hz, 3H).

$^{19}$F NMR: (376 MHz, DMSO-$d_6$) δ −135.63.

Intermediate A20

Synthesis of 4-(benzyloxy)-3-fluoro-2,6-dimethylbenzaldehyde (Intermediate A20)

A20

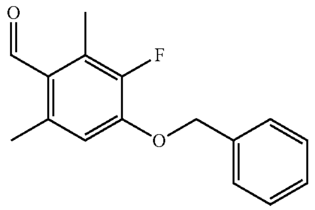

To a solution of Intermediate A19 (6.6 g, 21.3 mmol) in THF (70 mL) at −60° C. was added dropwise n-BuLi (23.5 mmol, 9.4 mL of 2.5M). The resultant mixture was stirred for 1 h at −60° C., then DMF (3.1 g, 42.7 mmol) was added. The reaction was stirred at −60° C. for 1 h, then quenched with water (100 mL) and extracted with EtOAc (100 mL*2). The combined organic phase was washed with brine (100 mL*2), dried over $Na_2SO_4$, and concentrated in vacuo. The crude product was purified by silica gel column chromatography (EtOAc/pet. ether=1/10) to afford Intermediate A20 (4.1 g, 74.3% yield) as a white solid.

TLC: EtOAc/pet. ether=1/10, Rf=0.65

$^1$H NMR: (400 MHz, DMSO-$d_6$) δ 10.34 (d, J=1.2 Hz, 1H), 7.60-7.28 (m, 5H), 7.10 (d, J=8.0 Hz, 1H), 5.26 (s, 2H), 2.54 (s, 3H), 2.45 (d, J=2.4 Hz, 3H).

$^{19}$F NMR: (376 MHz, DMSO-$d_6$) δ −142.02.

Intermediate A21

Synthesis of 3-fluoro-4-hydroxy-2,6-dimethylbenzaldehyde (Intermediate A21)

A21

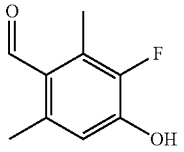

To a solution of Intermediate A20 (4.1 g, 15.9 mmol) in THF (60 mL) at rt was added Pd/C (600 mg (5% w/w), 0.28 mmol). The flask was degassed and flushed three times with $H_2$ (g), then stirred for 1.5 h. The reaction mixture was filtered; the filtrate was concentrated in vacuo. The crude product was recrystallized from hexane (5 mL) to afford Intermediate A21 (2.4 g, 89.9% yield) as a white solid.

TLC: EtOAc/pet. ether=1/10, Rf=0.35

$^1H$ NMR: (400 MHz, DMSO-$d_6$) δ 10.78 (s, 1H), 10.29 (d, J=0.8 Hz, 1H), 6.69 (d, J=8.4 Hz, 1H), 2.47 (s, 3H), 2.44 (d, J=2.4 Hz, 3H).

$^{19}F$ NMR: (376 MHz, DMSO-$d_6$) δ −143.64.

Intermediate A22

Synthesis of 2-fluoro-4-(hydroxymethyl)-3,5-dimethylphenol (Intermediate A22)

A22

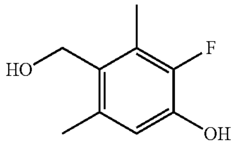

To a solution of Intermediate A21 (2.4 g, 14.3 mmol) in ethanol (30 mL) at 0° C. was added $NaBH_4$ (540 mg, 14.3 mmol) portionwise. The reaction was warmed to rt with stirring for 1.5 h. The reaction was quenched with water (50 mL), acidified to pH~2 with HCl (1N), and extracted with EtOAc (100 mL*2). The combined organic phase was dried over $Na_2SO_4$ and concentrated in vacuo to afford Intermediate A22 (2.4 g, 98.8% yield) as a yellow solid.

TLC: EtOAc/pet. ether=1/10, Rf=0.23

$^1H$ NMR: (400 MHz, DMSO-$d_6$) δ 9.45 (d, J=0.8 Hz, 1H), 6.56 (d, J=9.2 Hz, 1H), 4.60 (brs, 1H), 4.37 (s, 2H), 2.22 (s, 3H), 2.20 (d, J=2.4 Hz, 3H).

$^{19}F$ NMR: (376 MHz, DMSO-$d_6$) δ −143.28.

Intermediate A23

Synthesis of ethyl 2-(2-fluoro-4-(hydroxymethyl)-3,5-dimethylphenoxy)acetate (Intermediate A23)

A23

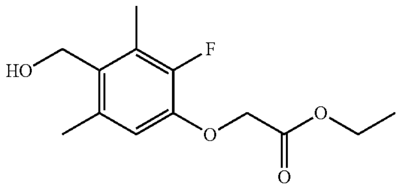

To a solution of Intermediate A22 (2.0 g, 11.7 mmol) and ethyl 2-bromoacetate (2.0 g, 11.7 mmol) in DMF (20 mL) at rt was added $Cs_2CO_3$ (4.6 g, 14.1 mmol); the resultant mixture was stirred at rt for 3 h. The reaction was diluted with EtOAc (80 mL), and filtered. The filtrate was washed with water (30 mL*2), dried over $Na_2SO_4$, and concentrated in vacuo. The crude product was purified by silica gel column chromatography (EtOAc/pet. ether=1/5) to afford Intermediate A23 (1.6 g, 53% yield) as a white solid.

TLC: EtOAc/pet. ether=1/10, Rf=0.57

$^1H$ NMR: (400 MHz, DMSO-$d_6$) δ 6.72 (d, J=8.4 Hz, 1H), 4.81 (s, 2H), 4.72 (t, J=5.2 Hz, 1H), 4.40 (dd, J=5.2, 0.8 Hz, 2H), 4.16 (q, J=6.8 Hz, 2H), 2.28 (s, 3H), 2.23 (d, J=2.4 Hz, 3H), 1.21 (t, J=6.8 Hz, 3H).

Intermediate A24

Synthesis of ethyl 2-(4-(chloromethyl)-2-fluoro-3,5-dimethylphenoxy)acetate (Intermediate A24)

A24

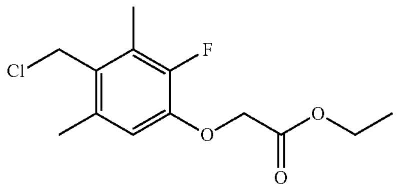

To a solution of Intermediate A23 (1.9 g, 7.4 mmol) in DCM (10 mL) at rt were added $SOCl_2$ (0.9 g, 7.4 mmol) and a catalytic amount of DMF (0.05 mL); the resultant solution was stirred at rt for 2 h. The reaction was concentrated in vacuo to afford Intermediate A24 (2.0 g, 98.5% yield) as a white solid.

TLC: EtOAc/pet. ether=1/10, Rf=0.88

$^1H$ NMR: (400 MHz, DMSO-$d_6$) δ 6.82 (d, J=8.2 Hz, 1H), 4.85 (s, 2H), 4.76 (d, J=0.8 Hz, 2H), 4.17 (q, J=7.2 Hz, 2H), 2.31 (s, 3H), 2.26 (d, J=2.4 Hz, 3H), 1.21 (t, J=7.2 Hz, 3H).

$^{19}F$ NMR: (376 MHz, DMSO-$d_6$) δ −140.27.

Intermediate A25

Synthesis of 2-(3,5-dichloro-2-fluorophenyl)-4,4,5,5-tetramethyl-1,3,2-dioxaborolane (Intermediate A25)

A25

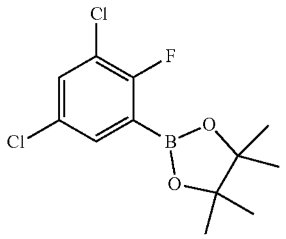

A mixture of 2,4-dichloro-1-fluorobenzene (30 g, 182 mmol), 4,4'-di-tert-butyl-2,2'-bipyridine (1.2 g, 4.5 mmol), bis(pinacolato)diboron (46.2 g, 182 mmol) and (1,5-cyclooctadiene)(methoxy)iridium(I) dimer (2.4 g, 3.6 mmol) in THF (300 mL) was stirred at 80° C. for 6 h under $N_2$ atmosphere. The reaction was concentrated in vacuo; the residue was purified by silica gel column chromatography (pet. ether/EtOAc=20/1, v/v) to afford Intermediate A25 (50 g, 94% yield) as a white solid.

TLC: EtOAc/pet. ether=1/10 (v/v), Rf=0.35

$^{1}$H NMR: (400 MHz, DMSO) δ 7.94 (m, 1H), 7.51 (m, 1H), 1.30 (s, 14H).

Intermediate A26

Synthesis of 3,5-dichloro-2-fluorophenol (Intermediate A26)

A26

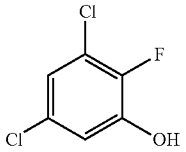

To a solution of Intermediate A25 (50.0 g, 172 mmol) in THF (1 L) at rt was added $H_2O_2$ (100 mL of 30% in water); the resultant mixture was stirred at rt for 3 h. The reaction was extracted with EtOAc (50 mL*3); the combined organic phase was washed with brine (200 mL), dried over $Na_2SO_4$, and concentrated in vacuo to afford Intermediate A26 (50 g, 99.7% yield, 62% purity) as a white solid.

TLC: EtOAc/pet. ether=1/10 (v/v), Rf=0.2

$^{1}$H NMR: (400 MHz, DMSO) δ 10.93 (s, 1H), 7.12 (m, 1H), 6.96 (m, 1H).

Intermediate A27

Synthesis of 3,5-dichloro-2-fluoro-4-(hydroxymethyl)phenol (Intermediate A27)

A27

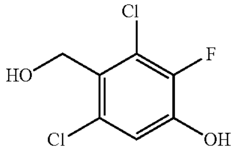

To a solution of Intermediate A26 (45.0 g, 157 mmol) in water (200 mL) at rt were added formaldehyde (4.7 g, 157 mmol) and NaOH (6.2 g, 157 mmol); the resultant mixture was stirred at 50° C. for 32 h. The reaction mixture was extracted with EtOAc (100 mL*3); the combined organic phase was washed with brine (200 mL), dried over $Na_2SO_4$, concentrated in vacuo and purified by silica gel column chromatography (pet. ether/EtOAc=5:1) to afford Intermediate A27 (22 g, 66% yield) as a white solid.

TLC: EtOAc/pet. ether=1/5 (v/v), Rf=0.41

$^{1}$H NMR: (400 MHz, DMSO) δ 10.85 (s, 1H), 7.01 (d, J=7.7 Hz, 1H), 5.12 (s, 1H), 4.58 (d, J=5.0 Hz, 2H).

Intermediate A28

Synthesis of ethyl 2-(3,5-dichloro-2-fluoro-4-(hydroxymethyl)phenoxy)acetate (Intermediate A28)

A28

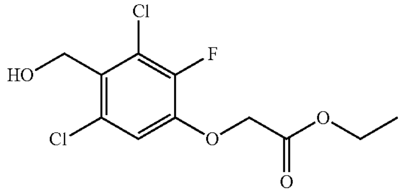

To a solution of Intermediate A27 (10.3 g, 49.1 mmol) in DMF (50 mL) at rt were added $K_2CO_3$ (8.1 g, 58.9 mmol) and ethyl 2-bromoacetate (9.0 g, 54 mmol); the resultant mixture was stirred at rt for 16 h. The reaction was poured into water (50 mL), and extracted with EtOAc (50 mL*3); the combined organic phase was washed with brine (200 mL), dried over $Na_2SO_4$, and concentrated in vacuo to afford Intermediate A28 (14.0 g, 49.1 mmol, 96% yield) as a white solid.

TLC: EtOAc/pet. ether=1/5 (v/v), Rf=0.44

$^{1}$H NMR: (400 MHz, DMSO) δ 7.36 (d, J=7.6 Hz, 1H), 5.22 (t, J=5.4 Hz, 1H), 5.00 (s, 2H), 4.62 (d, J=5.3 Hz, 2H), 4.18 (d, J=7.1 Hz, 2H), 1.21-1.14 (m, 3H).

Intermediate A29

Synthesis of ethyl 2-(3,5-dichloro-4-(chloromethyl)-2-fluorophenoxy)acetate (Intermediate A29)

A29

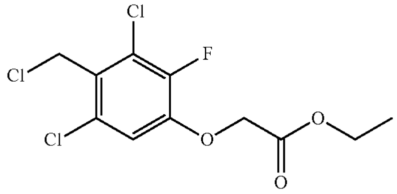

To a solution of Intermediate A28 (14.5 g, 48.8 mmol) in DCM (50 mL) was added thionyl chloride (8.71 g, 73.6 mmol). After stirring at rt for 3 h, the reaction mixture was concentrated in vacuo to afford Intermediate A29 (14 g, 90% yield) as a white solid.

TLC: EtOAc/pet. ether=1/5 (v/v), Rf=0.6

$^{1}$H NMR: (400 MHz, DMSO) δ 7.49 (d, J=7.6 Hz, 1H), 5.04 (s, 2H), 4.87 (s, 2H), 4.18 (m, 2H), 1.21 (t, J=7.1 Hz, 3H).

Intermediate A30

Synthesis of 2-(3-bromo-5-chloro-2-fluorophenyl)-4,4,5,5-tetramethyl-1,3,2-dioxaborolane (Intermediate A30)

A30

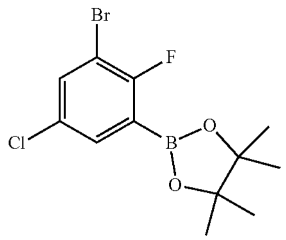

A mixture of 1-fluoro-2-bromo-4-chlorobenzene (10.0 g, 47.8 mmol), bis(pinacolato)diboron (12.1 g, 47.8 mmol), (1, 5-cyclooctadiene)(methoxy)iridium(I) dimer (633 mg, 955 umol) and 4,4'-di-tert-butyl-2,2'-bipyridine (320 mg, 1.2 mmol) in THF (100 mL) was stirred at 80° C. overnight under $N_2$ atmosphere. Water (60 mL) was added and the resultant mixture was extracted with EtOAc (30 mL*3). The combined organic phase was washed with brine (50 mL), dried over $Na_2SO_4$ and concentrated in vacuo. The crude product was purified by silica gel column chromatography (EtOAc/pet. ether=1/100 to 1/30) to afford Intermediate A30 (14.0 g, 87.4% yield) as a white solid.

TLC: EtOAc/pet. ether=1/10 (v/v), Rf=0.75

$^1H$ NMR: (400 MHz, DMSO-$d_6$) δ 7.99 (dd, J=6.0, 2.8 Hz, 1H), 7.54 (dd, J=4.4, 2.8 Hz, 1H), 1.30 (s, 12H).

Intermediate A31

Synthesis of 3-bromo-5-chloro-2-fluorophenol (Intermediate A31)

A31

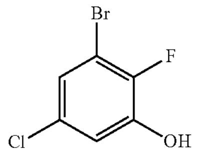

To a solution of Intermediate A30 (14.0 g, 41.7 mmol) in THF (100 mL) at rt was added $H_2O_2$ (23.7 mL of 30% aqueous solution, 209 mmol); the mixture was stirred at rt for 2 h. The reaction was quenched with $Na_2S_2O_3$ (8.0 g) and extracted with EtOAc (50 mL*3).

The combined organic phase was washed with brine (100 mL), dried over $Na_2SO_4$ and concentrated in vacuo to afford Intermediate A31 (9.0 g, 95.6% yield) as a yellow liquid.

TLC: EtOAc/pet. ether=1/10 (v/v), Rf=0.5

$^1H$ NMR: (400 MHz, DMSO-$d_6$) δ 10.90 (s, 1H), 7.20 (dd, J=4.8, 2.4 Hz, 1H), 7.00 (dd, J=7.2, 2.4 Hz, 1H).

Intermediate A32

Synthesis of 3-bromo-5-chloro-2-fluoro-4-(hydroxymethyl)phenol (Intermediate A32)

A32

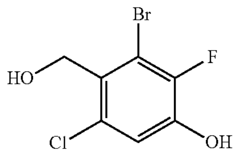

To a solution of NaOH (6.2 g, 156.6 mmol) in $H_2O$ (100 mL) at rt was added Intermediate A31 (9.1 g, 40.4 mmol). The mixture was heated to 45° C. and HCHO (4.7 mL of 37% aqueous, 40.4 mmol) was added dropwise. The mixture was stirred at 45° C. overnight. The reaction was cooled to rt and diluted with water (50 mL), then acidified to pH~5-6 with 1N HCl and extracted with EtOAc (30 mL*3). The combined organic phase was washed with brine (100 mL), dried over $Na_2SO_4$ and concentrated in vacuo. The crude product was purified by silica gel column chromatography (pet. ether/EtOAc=50/1 to 5/1) to afford Intermediate A32 (4.1 g, 39.7% yield) as a white solid.

TLC: EtOAc/pet. ether=1/5 (v/v), Rf=0.20

$^1H$ NMR: (400 MHz, DMSO-$d_6$) δ 10.83 (s, 1H), 7.05 (d, J=7.8 Hz, 1H), 5.10 (t, J=5.2 Hz, 1H), 4.62 (d, J=5.1 Hz, 2H).

Intermediate A33

Synthesis of ethyl 2-(3-bromo-5-chloro-2-fluoro-4-(hydroxymethyl)phenoxy)acetate (Intermediate A33)

A33

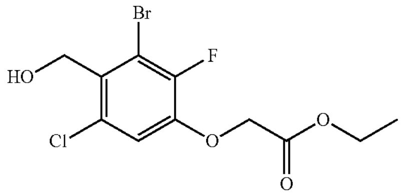

To a solution of Intermediate A32 (4.0 g, 15.7 mmol) in DMF (5 mL) at rt were added $K_2CO_3$ (2.6 g, 18.8 mmol) and ethyl 2-bromoacetate (2.6 g, 15.7 mmol); the mixture was stirred at rt for 1 h. The reaction was poured into water (50 mL); the mixture was extracted with EtOAc (20 mL*3). The combined organic phase was washed with brine (50 mL), dried over $Na_2SO_4$, and concentrated in vacuo to afford Intermediate A33 (5.0 g, 93.5% yield) as a white solid.

TLC: EtOAc/pet. ether=1/5 (v/v), Rf=0.25

Intermediate A34

Synthesis of ethyl 2-(3-bromo-5-chloro-4-(chloromethyl)-2-fluorophenoxy)acetate (Intermediate A34)

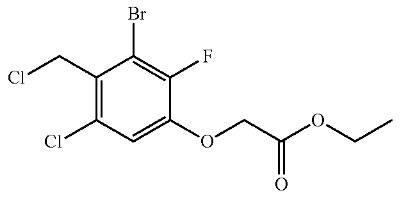

A34

To a solution of Intermediate A33 (5.0 g, 14.6 mmol) in DCM (50 mL) was added $SOCl_2$ (2.6 g, 21.9 mmol). The mixture was stirred at rt for 1 h. Water (50 mL) was added and the resultant mixture was extracted with DCM (20 mL*3). The combined organic phase was washed with brine (50 mL), dried over $Na_2SO_4$ and concentrated in vacuo to afford Intermediate A34 (5.0 g, 94.9% yield) as a white solid.

TLC: EtOAc/pet. ether=1/5 (v/v), Rf=0.5

Intermediate A35

Synthesis of 2-(5-bromo-3-chloro-2-fluorophenyl)-4,4,5,5-tetramethyl-1,3,2-dioxaborolane (Intermediate A35)

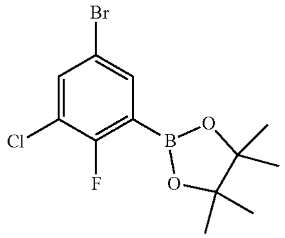

A35

A mixture of 1-fluoro-2-chloro-4-bromobenzene (10.0 g, 47.8 mmol), bis(pinacolato)diboron (12.1 g, 47.8 mmol), (1,5-cyclooctadiene)(methoxy)iridium(I) dimer (633 mg, 955 umol) and 4,4'-di-tert-butyl-2,2'-bipyridine (320 mg, 1.2 mmol) in THF (100 mL) was stirred at 80° C. overnight under $N_2$ atmosphere. Water (60 mL) was added and the mixture was extracted with EtOAc (30 mL*3). The combined organic phase was washed with brine (50 mL), dried over $Na_2SO_4$, and concentrated in vacuo. The crude product was purified by silica gel column chromatography (EtOAc/pet. ether=1/100 to 1/30) to afford Intermediate A35 (14.5 g, 90.6% yield) as a white solid.

TLC: EtOAc/pet. ether=1/10 (v/v), Rf=0.75

$^1$H NMR: (400 MHz, DMSO-$d_6$) δ 8.03 (dd, J=6.4, 2.4 Hz, 1H), 7.64 (dd, J=4.4, 2.8 Hz, 1H), 1.31 (s, 12H).

Intermediate A36

Synthesis of 5-bromo-3-chloro-2-fluorophenol (Intermediate A36)

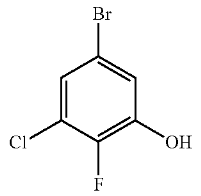

A36

To a solution of Intermediate A35 (14.5 g, 43.2 mmol) in THF (100 mL) at rt was added aqueous $H_2O_2$ (24.5 mL of 37% aqueous solution, 216 mmol); the mixture was stirred at rt for 2 h. $Na_2S_2O_3$ (8.0 g) was added; the mixture was stirred for 20 min, then extracted with EtOAc (50 mL*3). The combined organic phase was washed with brine (100 mL), dried over $Na_2SO_4$ and concentrated in vacuo to afford Intermediate A36 (9.7 g, 99.5% yield) as a yellow liquid.

TLC: EtOAc/pet. ether=1/10 (v/v), Rf=0.5

Intermediate A37

Synthesis of 5-bromo-3-chloro-2-fluoro-4-(hydroxymethyl)phenol (Intermediate A37)

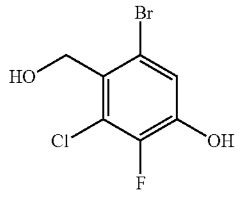

A37

To a solution of NaOH (2.0 g, 49.1 mmol) in $H_2O$ (100 mL) at rt was added Intermediate A36 (10.0 g, 40.6 mmol). The mixture was heated to 45° C. and formaldehyde (3.3 mL of 37% aqueous, 40.6 mmol) was added dropwise. The mixture was stirred at 45° C. overnight. The reaction was cooled to rt and diluted with water (50 mL), then acidified with 1N HCl to pH~5-6 and extracted with EtOAc (30 mL*3). The combined organic phase was washed with brine (100 mL), dried over $Na_2SO_4$ and concentrated in vacuo. The crude product was purified by silica gel column chromatography (EtOAc/pet. ether=1/50 to 1/5) to afford Intermediate A37 (7.6 g, 73.1% yield) as a white solid.

TLC: EtOAc/pet. ether=1/5 (v/v), Rf=0.20

$^1$H NMR: (400 MHz, DMSO-$d_6$) δ 10.87 (s, 1H), 7.18 (d, J=8.0 Hz, 1H), 5.12 (t, J=5.2 Hz, 1H), 4.62-4.58 (m, 2H).

Intermediate A38

Synthesis of ethyl 2-(5-bromo-3-chloro-2-fluoro-4-(hydroxymethyl)phenoxy)acetate (Intermediate A38)

A38

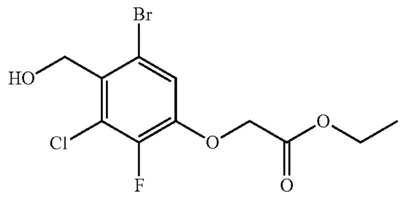

To a solution of Intermediate A37 (7.6 g, 29.7 mmol) in DMF (70 mL) at rt were added $K_2CO_3$ (4.9 g, 29.7 mmol) and ethyl 2-bromoacetate (5.0 g, 29.7 mmol); the mixture was stirred at rt for 1 h. The reaction was poured into water (50 mL) and extracted with EtOAc (20 mL*3); the combined organic phase was washed with brine (50 mL), dried over $Na_2SO_4$, and concentrated in vacuo to afford Intermediate A38 (10.0 g, 99.0% yield) as a white solid.

TLC: EtOAc/pet. ether=1/5 (v/v), Rf=0.25

Intermediate A39

Synthesis of ethyl 2-(5-bromo-3-chloro-4-(chloromethyl)-2-fluorophenoxy)acetate (Intermediate A39)

A39

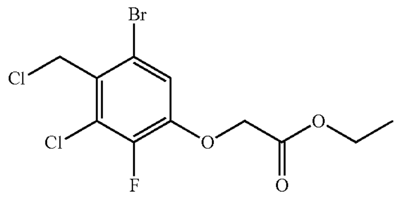

To a solution of Intermediate A38 (10.0 g, 29.3 mmol) in DCM (100 mL) was added $SOCl_2$ (5.3 g, 43.9 mmol). The mixture was stirred at rt for 1 h. Water (50 mL) was added and the mixture was extracted with DCM (20 mL*3). The combined organic phase was washed with brine (50 mL), dried over $Na_2SO_4$, and concentrated in vacuo to afford Intermediate A39 (10.0 g, 95.2% yield) as a white solid.

TLC: EtOAc/pet. ether=1/5 (v/v), Rf=0.5

Intermediate A40

Synthesis of 2,3,5-trichloro-4-(hydroxymethyl)phenol (Intermediate A40)

A40

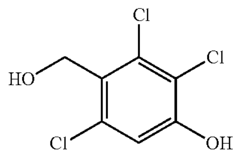

To a solution of NaOH (41 mg, 1.01 mmol) in water (10 mL) at rt was added 2,3,5-trichlorophenol (200 mg, 1.01 mmol). The mixture was heated to 45° C., and formaldehyde (82 mg of 37% aqueous solution, 1.01 mmol) was added dropwise. The mixture was stirred at 45° C. overnight; the resultant solution was diluted with water (20 mL), acidified with 1N HCl to pH~5-6, and extracted with EtOAc (20 mL*2). The combined organic phase was washed with brine (30 mL), dried over $Na_2SO_4$, and concentrated in vacuo. The crude product was purified by Prep-TLC (pet. ether/EtOAc=3/1) to afford Intermediate A40 (100 mg, 43.4% yield) as a white solid.

TLC: Pet. ether/EtOAc=3/1 (v/v), Rf=0.30.

LCMS: RT=1.467 min, [M−1]=226.8.

$^1$H NMR: (400 MHz, DMSO-$d_6$) δ 11.11 (s, 1H), 7.02 (s, 1H), 5.10 (t, J=5.2 Hz, 1H), 4.62 (d, J=4.8 Hz, 2H).

Intermediate A41

Synthesis of ethyl 2-(2,3,5-trichloro-4-(hydroxymethyl)phenoxy)acetate (Intermediate A41)

A41

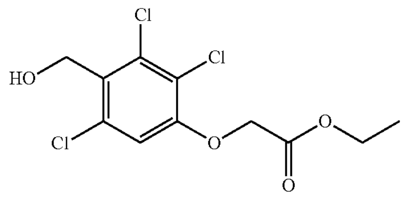

To a solution of Intermediate A40 (100 mg, 0.44 mmol) in DMF (5 mL) at rt were added $K_2CO_3$ (91 mg, 0.66 mmol) and ethyl bromoacetate (88 mg, 0.53 mmol); the mixture was stirred at rt for 2 h. Water (10 mL) was added and the mixture was extracted with EtOAc (20 mL*2). The combined organic phase was washed with water (20 mL*3) and brine (20 mL*2), dried over $Na_2SO_4$ and concentrated in vacuo to afford Intermediate A41 (130 mg, 94.3% yield) as a white solid.

TLC: Pet. ether/EtOAc=3/1 (v/v), Rf=0.42.

$^1$H NMR: (400 MHz, DMSO-$d_6$) δ 7.31 (s, 1H), 5.21 (t, J=5.4 Hz, 1H), 5.04 (s, 2H), 4.66 (d, J=5.2 Hz, 2H), 4.18 (q, J=7.2 Hz, 2H), 1.21 (t, J=7.2 Hz, 3H).

Intermediate A42

Synthesis of ethyl 2-(2,3,5-trichloro-4-(chloromethyl)phenoxy)acetate (Intermediate A42)

A42

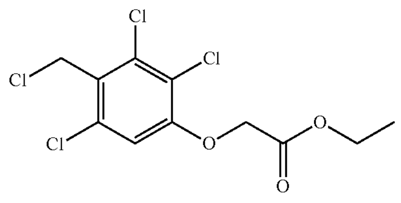

To a solution of Intermediate A41 (130 mg, 0.41 mmol) in DCM (3 mL) at 0° C. was added $SOCl_2$ (74 mg, 0.62 mmol); the resultant mixture was stirred at rt for 3 h. The mixture was concentrated in vacuo to afford Intermediate A42 (115 mg, 83.5% yield) as a white solid.

TLC: Pet. ether/EtOAc=3/1 (v/v), Rf=0.72.

$^1$H NMR: (400 MHz, DMSO-$d_6$) δ 7.44 (s, 1H), 5.08 (s, 2H), 4.91 (s, 2H), 4.18 (q, J=7.2 Hz, 2H), 1.21 (t, J=7.2 Hz, 3H).

Intermediate A43

Synthesis of 3,5-dichloro-2-(hydroxymethyl)phenol (Intermediate A43)

A43

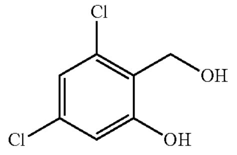

To a solution of 4,6-dichlorosalicylaldehyde (2.5 g, 13.09 mmol) in THF (5 mL) at 0° C. was added $NaBH_4$ (594.19 mg, 15.71 mmol). The mixture was stirred at rt for 2 h, then diluted with water (20 mL). The mixture was acidified to pH~4-5 with 2N HCl and extracted with EtOAc (20 mL*2); the combined organic extracts were washed with brine (30 mL), dried over $Na_2SO_4$ and concentrated in vacuo to afford Intermediate A43 (2.3 g, 93% yield) as white solid.

TLC: Pet. ether/EtOAc=3/1 (v/v), Rf=0.24.

LCMS: RT=1.403 min, [M−1]=190.9.

$^1$H NMR: (400 MHz, DMSO-$d_6$) δ 10.44 (s, 1H), 6.98 (d, J=2.0 Hz, 1H), 6.83 (d, J=2.0 Hz, 1H), 4.51 (s, 2H).

Intermediate A44

Synthesis of 3,5-dichloro-2-methylphenol (Intermediate A44)

A44

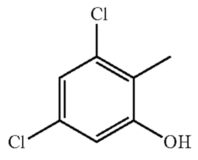

A mixture of Intermediate A43 (2.1 g, 10.9 mmol), $Et_3SiH$ (5.1 g, 43.5 mmol) and TFA (12.4 g, 109 mmol) in DCM (20 mL) was stirred at rt for 2 days. The reaction mixture was diluted with EtOAc (30 mL), washed with brine (10 mL*2), and dried over $Na_2SO_4$. The crude product was concentrated in vacuo and purified by silica gel column chromatography (pet. ether/EtOAc=50/1 to 20/1) to afford Intermediate A44 (890 mg, 46.2% yield) as a yellow solid.

TLC: Pet. ether/EtOAc=3/1 (v/v), Rf=0.65.

LCMS: RT=1.505 min, [M−1]=175.0.

$^1$H NMR: (400 MHz, DMSO-$d_6$) δ 10.36 (d, J=1.2 Hz, 1H), 6.97 (d, J=2.0 Hz, 1H), 6.80 (d, J=2.0 Hz, 1H), 2.12 (s, 3H).

Intermediate A45

Synthesis of 3,5-dichloro-4-(hydroxymethyl)-2-methylphenol (Intermediate A45)

A45

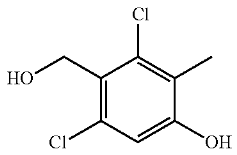

To a solution of NaOH (201 mg, 5.03 mmol) in water (20 mL) at rt was added Intermediate A44 (890 mg, 5.03 mmol). The mixture was heated to 45° C., and formaldehyde (408 mg of 37% aqueous solution, 5.03 mmol) was added dropwise. The mixture was stirred at 45° C. overnight, then diluted with water (20 mL) acidified with 1N HCl to pH~5-6, and extracted with EtOAc (20 mL*2). The combined organic phase was washed with brine (30 mL), dried over $Na_2SO_4$, and concentrated in vacuo. The crude product was purified by silica gel column chromatography (pet. ether/EtOAc=20/1 to 5/1) to afford Intermediate A45 (400 mg, 38.4% yield) as a white solid.

TLC: Pet. ether/EtOAc=3/1 (v/v), Rf=0.31.

LCMS: RT=0.637 min, [M−1]=205.0.

$^1$H NMR: (400 MHz, DMSO-$d_6$) δ 10.28 (s, 1H), 6.84 (s, 1H), 4.94 (t, J=5.2 Hz, 1H), 4.59 (d, J=4.8 Hz, 2H), 2.15 (s, 3H).

Intermediate A46

Synthesis of ethyl 2-(3,5-dichloro-4-(hydroxymethyl)-2-methylphenoxy)acetate (Intermediate A46)

A46

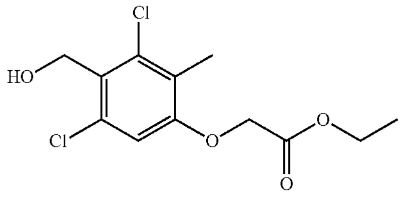

To a solution of Intermediate A45 (400 mg, 1.93 mmol) in DMF (5 mL) at rt were added $K_2CO_3$ (400 mg, 2.90 mmol) and ethyl bromoacetate (387 mg, 2.32 mmol). The mixture was stirred at rt for 2 h. The reaction mixture was diluted with EtOAc (30 mL), washed with brine (10 mL*2), dried over $Na_2SO_4$ and concentrated in vacuo to afford Intermediate A46 (520 mg, 91.8% yield) as a white solid.

TLC: Pet. ether/EtOAc=3/1 (v/v), Rf=0.53.

$^1$H NMR: (400 MHz, DMSO-$d_6$) δ 7.07 (s, 1H), 5.06 (t, J=5.2 Hz, 1H), 4.92 (s, 2H), 4.64 (d, J=5.2 Hz, 2H), 4.17 (q, J=7.2 Hz, 2H), 2.24 (s, 3H), 1.21 (t, J=7.2 Hz, 3H).

Intermediate A47

Synthesis of ethyl 2-(3,5-dichloro-4-(chloromethyl)-2-methylphenoxy)acetate (Intermediate A47)

A47

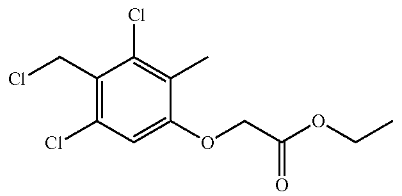

To a solution of Intermediate A46 (520 mg, 1.77 mmol) in DCM (5 mL) at 0° C. was added $SOCl_2$ (316 mg, 2.66 mmol). The mixture was stirred at rt for 2 h. The mixture was concentrated in vacuo to afford Intermediate A47 (530 mg, 95.8% yield) as a white solid.

TLC: Pet. ether/EtOAc=3/1 (v/v), Rf=0.67.

$^1H$ NMR: (400 MHz, DMSO-$d_6$) δ 7.18 (s, 1H), 4.96 (s, 2H), 4.89 (s, 2H), 4.17 (q, J=7.2 Hz, 2H), 2.26 (s, 3H), 1.21 (t, J=7.2 Hz, 3H).

Intermediate A48

Synthesis of 2-(3-chloro-2-fluoro-5-methylphenyl)-4,4,5,5-tetramethyl-1,3,2-dioxaborolane (Intermediate A48)

A48

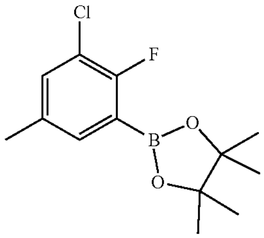

To a mixture of 3-chloro-4-fluorotoluene (10.0 g, 69.2 mmol), 4,4'-di-tert-butyl-2,2'-bipyridine (464 mg, 1.73 mmol) and (1,5-cyclooctadiene)(methoxy)iridium(I) dimer (917 mg, 1.38 mmol) in THF (100 mL) was added bis (pinacolato)diboron (17.6 g, 69.2 mmol). The mixture was heated to 80° C. overnight. The mixture was cooled to rt; water (20 mL) was added and the resultant mixture was extracted with EtOAc (20 mL*3). The combined organic phase was washed with brine (20 mL), dried over $Na_2SO_4$ and concentrated in vacuo. The crude product was purified by silica gel column chromatography (pet. ether/EtOAc=100/1 to 30/1) to afford Intermediate A48 (17.5 g, 93.5% yield) as a white solid.

TLC: Pet. ether/EtOAc=3/1 (v/v), Rf=0.40.

$^1H$ NMR: (400 MHz, DMSO-$d_6$) δ 7.52 (ddd, J=7.2, 2.4, 0.8 Hz, 1H), 7.37 (ddd, J=5.2, 2.4, 0.8 Hz, 1H), 2.28 (s, 3H), 1.29 (s, 12H).

Intermediate A49

Synthesis of 3-chloro-2-fluoro-5-methylphenol (Intermediate A49)

A49

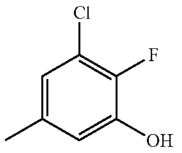

To a mixture of Intermediate A48 (2.8 g, 10.35 mmol) in THF (30 mL) was added aqueous $H_2O_2$ (1.8 g of 30% w/w, 52 mmol). The mixture stirred at rt for 2 h. $Na_2S_2O_3$ (8.0 g) was added; the mixture was stirred for 20 min, then extracted with EtOAc (20 mL*3). The combined organic phase was washed with brine (50 mL), dried over $Na_2SO_4$, concentrated in vacuo and purified by silica gel column chromatography (pet. ether/EtOAc=100/1 to 10/1) to afford Intermediate A49 (1.6 g, 96.2% yield) as a yellow oil.

TLC: Pet. ether/EtOAc=5/1 (v/v), Rf=0.41.

$^1H$ NMR: (400 MHz, DMSO-$d_6$) δ 10.19 (d, J=4.8 Hz, 1H), 6.74 (ddd, J=6.0, 2.0, 0.8 Hz, 1H), 6.71 (ddd, J=8.0, 2.4, 0.8 Hz, 1H), 2.18 (s, 3H).

Intermediate A50

Synthesis of 3-chloro-2-fluoro-4-(hydroxymethyl)-5-methylphenol (Intermediate A50)

A50

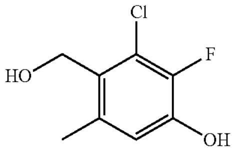

To a solution of NaOH (398 mg, 9.96 mmol) in water (20 mL) at rt was added Intermediate A49 (1.6 g, 10 mmol). The mixture was heated to 45° C. and aqueous HCHO (889 mg of 37% w/w, 11 mmol) was added dropwise. The mixture was stirred at 45° C. overnight, then diluted with water (20 mL), acidified with 1N HCl to pH~5-6, and extracted with EtOAc (20 mL*2). The combined organic phase was washed with brine (30 mL), dried over $Na_2SO_4$, and concentrated in vacuo. The crude product was purified by silica gel column chromatography (pet. ether/EtOAc=100/1 to 5/1) to afford Intermediate A50 (1.0 g, 52.6% yield) as a white solid.

TLC: Pet. ether/EtOAc=3/1 (v/v), Rf=0.37.

$^1H$ NMR: (400 MHz, DMSO-$d_6$) δ 10.15 (s, 1H), 6.82-6.63 (m, 1H), 4.87 (t, J=5.2 Hz, 1H), 4.52-4.47 (m, 2H), 2.29 (s, 3H).

Intermediate A51

Synthesis of ethyl 2-(3-chloro-2-fluoro-4-(hydroxymethyl)-5-methylphenoxy)acetate (Intermediate A51)

A51

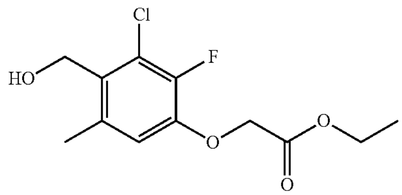

To a solution of Intermediate A50 (900 mg, 4.72 mmol) in DMF (10 mL) at rt were added $K_2CO_3$ (783 mg, 5.67 mmol) and ethyl bromoacetate (788 mg, 4.72 mmol). The mixture was stirred at rt for 1 h. Water (30 mL) was added and the resultant mixture was extracted with EtOAc (10 mL*2). The combined organic phase was washed with brine (30 mL), dried over $Na_2SO_4$ and concentrated in vacuo to afford Intermediate A51 (1.3 g, 99.9% yield) as a white solid.

TLC: pet. ether/EtOAc=3/1 (v/v), Rf=0.45.

$^1H$ NMR: (400 MHz, DMSO-$d_6$) δ 6.98 (d, J=8.0 Hz, 1H), 4.96 (s, 1H), 4.90 (s, 2H), 4.53 (s, 2H), 4.21-4.13 (m, 2H), 2.36-2.33 (m, 3H), 1.21 (t, J=7.2 Hz, 3H).

Intermediate A52

Synthesis of ethyl 2-(3-chloro-2-fluoro-4-(hydroxymethyl)-5-methylphenoxy)acetate (Intermediate A52)

A52

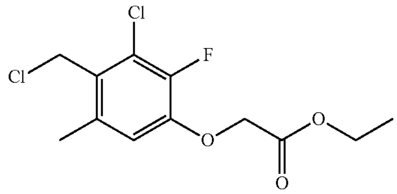

To a solution of Intermediate A51 (1.3 g, 4.7 mmol) in DCM (20 mL) at rt was added $SOCl_2$ (1.1 g, 9.4 mmol). The resultant mixture was stirred at rt for 1 h. The mixture was concentrated in vacuo to afford crude Intermediate A52 (1.3 g, 92.8% yield) as a white solid.

TLC: pet. ether/EtOAc=3/1 (v/v), Rf=0.57.

$^1H$ NMR: (400 MHz, DMSO-$d_6$) δ 7.09 (d, J=8.4 Hz, 1H), 4.94 (s, 2H), 4.83 (d, J=0.8 Hz, 2H), 4.18 (q, J=7.2 Hz, 2H), 2.39-2.36 (m, 3H), 1.21 (t, J=7.2 Hz, 3H).

Intermediate A53

Synthesis of 2-(5-chloro-2-fluoro-3-methylphenyl)-4,4,5,5-tetramethyl-1,3,2-dioxaborolane (Intermediate A53)

A53

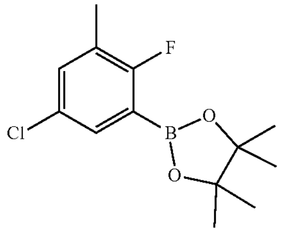

A mixture of 2-fluoro-5-chlorotoluene (6.0 g, 41.5 mmol), bis(pinacolato)diboron (10.5 g, 41.5 mmol), (1, 5-cyclooctadiene) (methoxy)iridium(I) dimer (550 mg, 830 umol) and 4,4'-di-tert-butyl-2,2'-bipyridine (268 mg, 1.0 mmol) in THF (60 mL) was stirred at 80° C. overnight under an $N_2$ atmosphere. Water (60 mL) was added and the resultant mixture was extracted with EtOAc (30 mL*3). The combined organic phase was washed with brine (50 mL), dried over $Na_2SO_4$ and concentrated in vacuo. The crude product was purified by silica gel column chromatography (EtOAc/pet. ether=1/100 to 1/30) to afford Intermediate A53 (9.4 g, 83.9% yield) as a white solid.

TLC: EtOAc/pet. ether=1/10 (v/v), Rf=0.75

$^1H$ NMR: (400 MHz, DMSO-$d_6$) δ 7.50 (dd, J=6.0, 2.8 Hz, 1H), 7.37-7.34 (m, 1H), 2.20 (d, J=2.4 Hz, 3H), 1.28 (s, 12H).

Intermediate A54

Synthesis of 5-chloro-2-fluoro-3-methylphenol (Intermediate A54)

A54

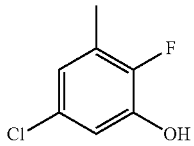

To a solution of Intermediate A53 (9.4 g, 34.7 mmol) in THF (100 mL) at rt was added aqueous $H_2O_2$ (30% w/w) (19.7 g, 174 mmol); the resultant mixture was stirred at rt for 2 h. The reaction was cooled to 0° C. and $Na_2S_2O_3$ (15.0 g) was added. Water (100 mL) was added; the mixture was stirred for 20 min, then extracted with EtOAc (50 mL*3). The combined organic phase was washed with brine (100 mL), dried over $Na_2SO_4$ and concentrated in vacuo to afford Intermediate A54 (5.0 g, 89.3% yield) as a white solid.

TLC: EtOAc/pet. ether=1/10 (v/v), Rf=0.5

LCMS: RT=1.246 min, [M−1]=159.0

Intermediate A55

Synthesis of 5-chloro-2-fluoro-4-(hydroxymethyl)-3-methylphenol (Intermediate A55)

A55

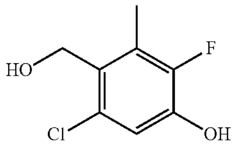

To a solution of NaOH (1.4 g, 34.3 mmol) in $H_2O$ (50 mL) at rt was added Intermediate A54 (50.0 g, 31.3 mmol). The mixture was heated to 45° C. and aqueous HCHO (2.5 g of 37% w/w, 31.3 mmol) was added dropwise. The mixture was stirred at 45° C. overnight. The reaction was cooled to rt and diluted with water (60 mL), acidified with 1N HCl to pH~5-6 and extracted with EtOAc (30 mL*3). The combined organic phase was washed with brine (100 mL), dried over $Na_2SO_4$ and concentrated in vacuo. The crude product was purified by silica gel column chromatography (EtOAc/pet. ether=1/50 to 1/5) to afford Intermediate 55 (2.0 g, 33.9% yield) as a white solid.

TLC: EtOAc/pet. ether=1/5 (v/v), Rf=0.20

$^1$H NMR: (400 MHz, DMSO-$d_6$) δ 10.20 (s, 1H), 6.82 (d, J=8.0 Hz, 1H), 4.92 (t, J=5.2 Hz, 1H), 4.51 (d, J=3.2 Hz, 2H), 2.27 (d, J=2.8 Hz, 3H).

Intermediate A56

Synthesis of ethyl 2-(5-chloro-2-fluoro-4-(hydroxymethyl)-3-methylphenoxy)acetate (Intermediate A56)

A56

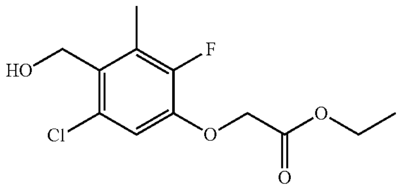

To a solution of Intermediate A55 (2.0 g, 10.5 mmol) in DMF (20 mL) at rt were added $K_2CO_3$ (1.7 g, 12.6 mmol) and ethyl bromoacetate (1.8 g, 10.5 mmol). The mixture was stirred at rt for 1 h. The reaction was poured into water (50 mL) and extracted with EtOAc (20 mL*3). The combined organic phase was washed with brine (50 mL), dried over $Na_2SO_4$, and concentrated in vacuo to afford Intermediate A56 (2.8 g, 96.6% yield) as a white solid.

TLC: EtOAc/pet. ether=1/5 (v/v), Rf=0.25

Intermediate A57

Synthesis of ethyl 2-(5-chloro-4-(chloromethyl)-2-fluoro-3-methylphenoxy)acetate (Intermediate A57)

A57

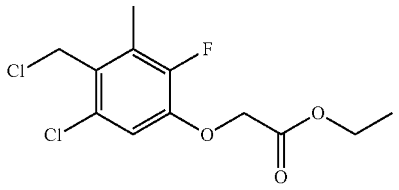

To a solution of Intermediate A56 (2.8 g, 10.1 mmol) in DCM (100 mL) was added $SOCl_2$ (1.8 g, 15.2 mmol). The mixture was stirred at rt for 1 h. Water (50 mL) was added and the resultant mixture was extracted with DCM (20 mL*3). The combined organic phase was washed with brine (50 mL), dried over $Na_2SO_4$ and concentrated in vacuo to afford Intermediate A57 (2.8 g, 93.3% yield) as a white solid.

TLC: EtOAc/pet. ether=1/5 (v/v), Rf=0.5

Intermediate A58

Synthesis of 2-(2,3-difluoro-5-methylphenyl)-4,4,5,5-tetramethyl-1,3,2-dioxaborolane (Intermediate A58)

A58

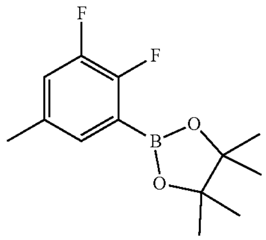

To 1,2-difluoro-4-methylbenzene (8.0 g, 62 mmol), 4,4'-Di-tert-butyl-2,2'-bipyridine (419 mg, 1.56 mmol) and [Ir(OMe)(1,5-cod)]2 (828 mg, 1.25 mmol) in THF (80 mL) was added B2Pin2 (15.9 g, 62.4 mmol). The mixture was heated to 80° C. overnight and was cooled down to rt. Water (100 mL) was added, and the mixture was extracted with EtOAc (50 mL*3). The combined organic layer was washed with brine (100 mL), dried over $Na_2SO_4$ and concentrated in vacuum. The crude product was purified by silica gel column (EtOAc/pet. ether=1/100) to afford Intermediate A58 (11.0 g, 69% yield) as a white solid.

$^1$H NMR: (400 MHz, DMSO-$d_6$) δ 7.42-7.33 (m, 1H), 7.22 (ddt, J=4.5, 2.2, 1.1 Hz, 1H), 2.29 (s, 3H), 1.30 (s, 12H).

Intermediate A59

Synthesis of 2,3-difluoro-5-methylphenol (Intermediate A59)

A59

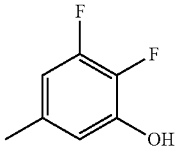

To Intermediate A58 (11 g, 43 mmol) in THF (100 mL) was added hydrogen peroxide (24.5 g, 216 mmol, 22 mL, 30% wt/wt). The mixture was stirred at rt for 2 h. $Na_2S_2O_3$ (4.0 g) was added and the mixture was extracted with EtOAc (50 mL*3). The combined organic phase was washed by brine (100 mL), dried over $Na_2SO_4$, concentrated in vacuum and purified by silica gel column (pet. ether/EtOAc=100/1 to 5/1) to afford Intermediate A59 (6 g, 96% yield) as yellow oil.

LCMS: T=0.98 min, [M−1]=143.1

Intermediate A60

Synthesis of 2,3-difluoro-4-(hydroxymethyl)-5-methylphenol (Intermediate A60)

A60

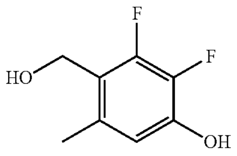

To a solution of NaOH (916 mg, 22.90 mmol) in water (30 mL) at rt was added Intermediate A59 (3 g, 21 mmol). The mixture was heated to 45° C., 37% formaldehyde (1.7 g, 20.8 mmol, 2 mL, 37% wt/wt) was added dropwise. The mixture was stirred at 45° C. overnight and cooled down. The mixture was diluted with water (20 mL), acidified to pH=6-7 with 1M HCl and extracted with EtOAc (50 mL*3). The organic phase was washed by brine (50 mL), dried over $Na_2SO_4$ and concentrated in vacuum. The crude product was purified with silica gel column (Pet. ether/EtOAc=20/1 to 5/1) to afford Intermediate A60 (1.2 g, 33%) as a white solid.

$^1$H NMR (400 MHz, DMSO-$d_6$) δ 10.15 (s, 1H), 6.59 (dd, J=8.1, 1.9 Hz, 1H), 4.89 (t, J=5.4 Hz, 1H), 4.42-4.38 (m, 2H), 2.25 (s, 3H).

Intermediate A61

Synthesis of ethyl 2-(2,3-difluoro-4-(hydroxymethyl)-5-methylphenoxy)acetate (Intermediate A61)

A61

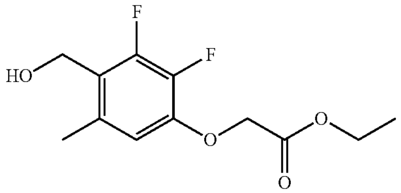

To a solution of intermediate A60 (800 mg, 4.6 mmol) in DMF (10 mL) at rt was added $K_2CO_3$ (762 mg, 5.51 mmol) and ethyl 2-bromoacetate (767 mg, 4.59 mmol). The mixture was stirred at rt overnight, diluted with water (30 mL) and was extracted with EtOAc (20 mL*3). The combined organic phase was washed by brine (10 mL), dried over $Na_2SO_4$, concentrated under reduce pressure to afford compound 5 (1.0 g, 83.7% yield) as a white solid.

Intermediate A62

Synthesis of 2-(2,5-difluoro-3-methylphenyl)-4,4,5,5-tetramethyl-1,3,2-dioxaborolane (Intermediate A62)

A62

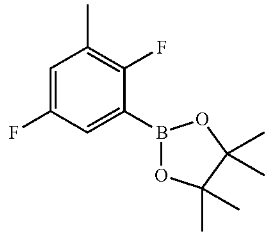

To a solution of 1-bromo-2,5-difluoro-3-methylbenzene (500 mg, 2.42 mmol) and Bis(pinacolato)diboron (920 mg, 3.62 mmol) in 1,4-dioxane (19 mL) was added KOAc (948 mg, 9.66 mmol) and Pd(dppf)$Cl_2$ (197 mg, 0.24 mmol). The mixture was stirred at 85° C. overnight and was cooled down to rt. The mixture was diluted with water (100 mL) and was extracted with EtOAc (100 mL). The organic phase was dried over $Na_2SO_4$, concentrated under vacuum and purified by silica gel chromatography (EtOAc/pet. ether=1/5) to afford the Intermediate A62 (350 mg, 57% yield) as a white solid.

$^1$H NMR (400 MHz, DMSO-$d_6$) δ 7.34-7.26 (m, 1H), 7.10 (dt, J=7.9, 3.7 Hz, 1H), 2.21 (d, J=2.3 Hz, 3H), 1.29 (s, 12H).

Intermediate A63

Synthesis of ethyl 2-(2,5-difluoro-4-(hydroxymethyl)-3-methylphenoxy)acetate (Intermediate A63)

A63

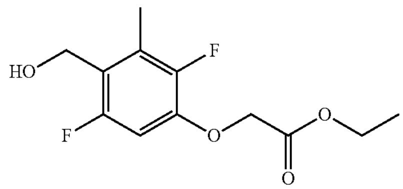

To a solution of Intermediate A62 (350 mg, 1.38 mmol) in THF (5 mL) was added $H_2O_2$ (234 mg, 6.89 mmol). The mixture was stirred at rt 2 h and was diluted with water (30 mL) and DCM (30 mL). The organic phase was washed with brine (30 mL), dried over $Na_2SO_4$, concentrated under vacuum. The resulting yellow solid (177 mg, 1.23 mmol), along with NaOH (54 mg, 1.35 mmol) was dissolved in water (5 mL) and was heated to 45° C. Formaldehyde (40 mg, 1.35 mmol) was added and the mixture was stirred at 45° C. overnight. After cooling to rt, the mixture was acidified with 1N HCl to pH~7, diluted with water (30 mL) and was extracted with EtOAc (30 mL). The organic phase was dried over $Na_2SO_4$, concentrated under reduce pressure. The resulting solid was dissolved in DMF (3 mL) and ethyl 2-bromoacetate (253 mg, 1.52 mmol) and $K_2CO_3$ (261 mg, 1.89 mmol) were added. The mixture was stirred at rt for 2 h and was partitioned between water (30 mL) and EtOAc (30 mL). The organic phase was washed with water (30 mL*3) and brine (30 mL), dried over $Na_2SO_4$, concentrated under vacuum to afford the product Intermediate A63 (328 mg, 91% yield) as white solid.

$^1$H NMR (400 MHz, DMSO-$d_6$) δ 7.95 (s, 4H), 6.89 (dd, J=11.2, 7.2 Hz, 1H), 4.88 (s, 2H), 4.43 (s, 2H), 4.16 (s, 3H), 4.11 (s, 1H), 2.27 (d, J=2.6 Hz, 3H), 1.21 (s, 5H).

Intermediate A64

Synthesis of ethyl 2-(4-(chloromethyl)-2,5-difluoro-3-methylphenoxy)acetate (Intermediate A64)

A64

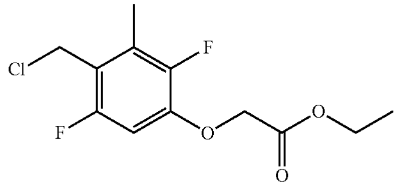

To a solution of Intermediate A63 (328 mg, 1.26 mmol) in DCM (4 mL) was added thionyl chloride (225 mg, 1.89 mmol). The mixture was stirred at rt 1 h. The mixture was concentrated under vacuum to afford the Intermediate A64 (276 mg, 79% yield) as yellow solid.

1H NMR (400 MHz, DMSO-$d_6$) δ 7.01 (dd, J=11.4, 7.2 Hz, 1H), 4.92 (s, 2H), 4.77 (d, J=1.7 Hz, 2H), 4.17 (q, J=7.1 Hz, 2H), 2.30 (d, J=2.6 Hz, 3H), 1.21 (t, J=7.1 Hz, 3H).

Intermediate A65

Synthesis of (6-chloro-2,3-difluorophenyl)methanol (Intermediate A65)

A65

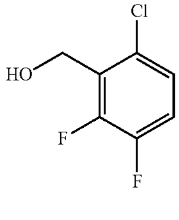

To a solution of 6-chloro-2,3-difluorobenzaldehyde (3.0 g, 16 mmol) in THF (30 mL) at rt was added NaBH4 (707 mg, 18.7 mmol). The mixture was heated to 50° C. and stirred overnight and was cooled down to rt. H2O (50 mL) was added. The mixture was extracted with EtOAc (25 mL*2). The combined organic layer was washed with water (25 mL*2), brine (50 mL), dried over Na2SO4 and was concentrated to dryness to afford Intermediate A65 (2.8 g, 92% yield) as a white solid. 1H NMR: (400 MHz, DMSO-d6) δ 7.45 (dt, J=10.1, 8.8 Hz, 1H), 7.35 (ddd, J=9.0, 4.5, 1.9 Hz, 1H), 5.36 (s, 1H), 4.59 (d, J=2.5 Hz, 2H).

Intermediate A66

Synthesis of tert-butyl((6-chloro-2,3-difluorobenzyl)oxy)dimethylsilane (Intermediate A66)

A66

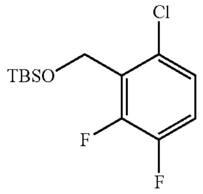

To intermediate A65 (2.8 g, 16 mmol), imidazole (2.1 g, 31 mmol) in DCM (30 mL) at rt was added TBSCl (2.6 g, 17 mmol). The mixture was stirred at rt for 1 h. The mixture was diluted with H2O (30 mL), extracted with DCM (25 mL*2). The combined organic layer was washed with water (25 mL*2), brine (50 mL), dried over $Na_2SO_4$, concentrated to dryness to afford Intermediate A66 (4.5 g, 98% yield) as a colorless oil. 1H NMR: (400 MHz, DMSO-$d_6$) δ 7.49 (dt, J=10.0, 8.8 Hz, 1H), 7.38 (ddd, J=9.0, 4.2, 1.7 Hz, 1H), 4.81-4.76 (m, 2H), 0.85 (s, 9H), 0.08 (s, 6H).

Intermediate A67

Synthesis of ethyl 2-(5-chloro-2,3-difluoro-4-(hydroxymethyl)phenoxy)acetate (Intermediate A67)

A67

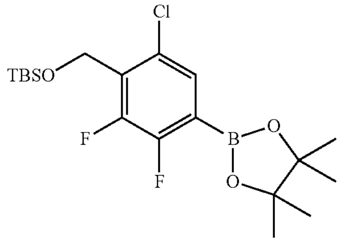

Intermediate A66 (5.8 g, 19.81 mmol), Bis(pinacolato) diboron (5.0 g, 20 mmol), $[Ir(OMe)(1,5\text{-cod})]_2$ (263 mg, 0.400 mmol) and 4,4'-Di-tert-butyl-2,2'-bipyridine (133 mg, 0.501 mmol) in THF (40 mL) was stirred at 80° C. for 4 h. The mixture was cooled down to rt. The mixture was diluted with $H_2O$ (30 mL), extracted with EtOAc (10 mL*2). The combined organic layer was washed with water (20 mL*2), brine (20 mL), dried over $Na_2SO_4$, purified with silica gel column (Pet. ether to Pet. ether/EtOAc=10/1) to afford Intermediate A67 (7.0 g, 84% yield) as a colorless oil.

$^1$H NMR: (400 MHz, DMSO-$d_6$) δ 7.42 (dd, J=4.4, 2.0 Hz, 1H), 4.79 (d, J=2.2 Hz, 2H), 1.31 (s, 12H), 0.85 (s, 9H), 0.08 (s, 6H).

Intermediate A68

Synthesis of 4-(((tert-butyldimethylsilyl)oxy) methyl)-5-chloro-2,3-difluorophenol (Intermediate A68)

A68

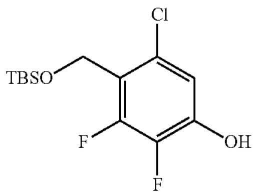

To Intermediate A67 (7.8 g, 19 mmol) in THF (80 mL) was added hydrogen peroxide (3.2 g, 93 mmol). The mixture was stirred at rt overnight. The mixture was diluted with $H_2O$ (100 mL) and was extracted with EtOAc (50 mL*2). The combined organic layer was washed with water (50 mL*2), brine (50 mL), dried over $Na_2SO_4$, purified by silica column (Pet. ether/EtOAc=10/1) to afford Intermediate A68 (4.7 g, 82% yield) as a white solid.

$^1$H NMR: (400 MHz, DMSO-$d_6$) δ 10.98 (s, 1H), 6.88 (dd, J=7.3, 2.1 Hz, 1H), 4.68 (d, J=2.2 Hz, 2H), 0.85 (d, J=1.3 Hz, 9H), 0.06 (d, J=1.4 Hz, 6H).

Intermediate A69

Synthesis of ethyl 2-(4-(((tert-butyldimethylsilyl) oxy)methyl)-5-chloro-2,3-difluorophenoxy)acetate (Intermediate A69)

A69

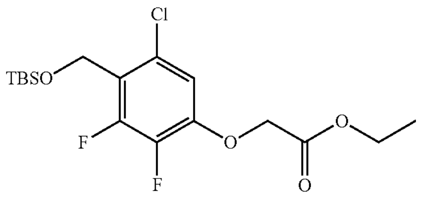

Intermediate A68 (3.0 g, 9.7 mmol), $K_2CO_3$ (2.0 g, 15 mmol) and ethyl 2-bromoacetate (2.0 g, 11.66 mmol) in DMF (30 mL) was stirred at rt for 3 h. The mixture was diluted with $H_2O$ (100 mL), extracted with EtOAc (25 mL). The combined organic layer was washed with water (25 mL*5), brine (50 mL), dried over $Na_2SO_4$, concentrated to dryness to afford product Intermediate A69 (3.5 g, 91% yield) as a yellow solid.

$^1$H NMR: (400 MHz, DMSO-$d_6$) δ 7.24 (dd, J=7.1, 2.1 Hz, 1H), 5.00 (s, 2H), 4.72 (d, J=2.2 Hz, 2H), 4.21-4.15 (m, 2H), 1.21 (dd, J=7.4, 6.8 Hz, 3H), 0.85 (s, 9H), 0.08 (s, 6H).

Intermediate A70

Synthesis of ethyl 2-(5-chloro-4-(chloromethyl)-2,3-difluorophenoxy)acetate (Intermediate A70)

A70

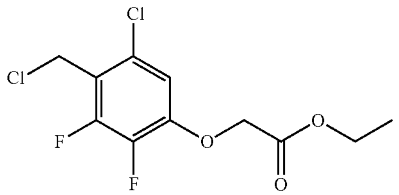

To a solution of Intermediate A69 (3.5 g, 8.9 mmol) in DCM (20 mL) was added TBAF (1 M in THF, 9.8 mL). The mixture was stirred at rt for 1 h. The mixture was diluted with $H_2O$ (50 mL) and was extracted with DCM (25 mL). The combined organic layer was washed with water (25 mL*2), brine (50 mL), dried over $Na_2SO_4$ and was concentrated to dryness to afford compound 7 (2.4 g, 97% yield) as a colorless oil. To a solution of compound 7 (2.4 g, 8.6 mmol) in DCM (20 mL) was added $SOCl_2$ (1.5 g, 12.8 mmol). The mixture was stirred at rt for 2 h. The mixture was concentrated to dryness to afford Intermediate A70 (2.5 g, 94% yield) as a white solid.

$^1$H NMR: (400 MHz, DMSO-$d_6$) δ 7.35 (dd, J=7.2, 2.2 Hz, 1H), 5.04 (s, 2H), 4.80 (d, J=1.9 Hz, 2H), 4.18 (q, J=7.1 Hz, 2H), 1.21 (t, J=7.1 Hz, 3H).

Intermediate A71

Synthesis of 3-chloro-2,5-difluoro-4-(hydroxymethyl)phenol (Intermediate A71)

A71

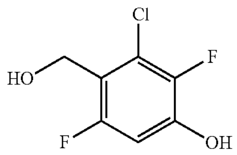

To 2-chloro-1,4-difluorobenzene (19.8 g, 133 mmol), 4,4'-Di-tert-butyl-2,2'-bipyridine (894 mg, 3.33 mmol) and $[Ir(OMe)(1,5\text{-cod})]_2$ (1.7 g, 2.67 mmol) in THF (100 mL) was added 4,4'-Di-tert-butyl-2,2'-bipyridine (33.8 g, 133.30 mmol). The mixture was heated to 80° C. overnight and was cooled down to rt. Water (80 mL) was added and the mixture was extracted with EtOAc (50 mL*3). The combined organic phase was washed with brine (80 mL), dried over $Na_2SO_4$ and concentrated in vacuum. The resulting solid was dissolved in THF (100 mL) and hydrogen peroxide (22.6 g, 664.85 mmol, 68.5 mL) was added at 0° C. The mixture was stirred at rt 4 h. The reaction was quenched with $Na_2S_2O_3$ aqueous saturated (10 mL) and was extracted with EtOAc (100 mL*3). The combined organic phase was washed with brine (100 mL), dried over $Na_2SO_4$ and concentrated in vacuum. The resulting solid was dissolved in water (30 mL) at rt and NaOH (1.8 g, 45.58 mmol) was added. The mixture was heated to 45° C., $CH_2O$ (3.7 g, 45.58 mmol) was added dropwise. The mixture was stirred at 45° C. overnight and cooled down to rt. The mixture was diluted with water (20 mL), acidified to pH=5-6 with 1 N HCl and was extracted with EtOAc (50 mL*2). The combined organic phase was washed by brine (60 mL), dried over $Na_2SO_4$, concentrated under reduce pressure. The crude product was purified with silica gel column (Pet. ether/EtOAc=20/1 to 5/1) to afford Intermediate A71 (1.5 g, 6% yield) as a white solid.

LCMS: T=0.36 min, [M−1]=193.0

Intermediate A72

Synthesis of ethyl 2-(3-chloro-2,5-difluoro-4-(hydroxymethyl)phenoxy)acetate (Intermediate A72)

A72

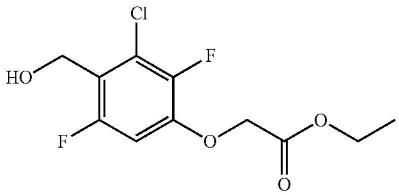

To a solution of Intermediate A71 (500 mg, 2.57 mmol) in DMF (6 mL) at rt was added $K_2CO_3$ (533 mg, 3.85 mmol) and ethyl 2-bromoacetate (515 mg, 3.08 mmol). The mixture was stirred at rt 2 h. The reaction mixture was diluted with EtOAc (30 mL), washed with brine (10 mL*2), dried over $Na_2SO_4$ and was concentrated in vacuum to afford Intermediate A72 (710 mg, 98% yield) as a white solid.

$^1$H NMR: (400 MHz, DMSO-$d_6$) δ 7.20 (dd, J=11.2, 7.0 Hz, 1H), 5.21 (s, 1H), 4.97 (s, 2H), 4.51 (s, 2H), 4.18 (t, J=7.2 Hz, 2H), 1.21 (t, J=7.2 Hz, 3H).

Intermediate A73

Synthesis of ethyl 2-(3-chloro-4-(chloromethyl)-2,5-difluorophenoxy)acetate (Intermediate A73)

A73

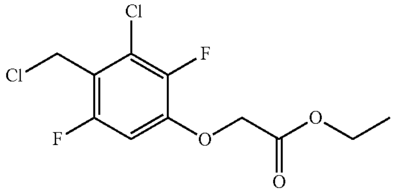

To a solution of Intermediate A72 (710 mg, 2.53 mmol) in DCM (5 mL) at 0° C. was added thionyl chloride (451 mg, 3.79 mmol). The mixture was stirred at rt 2 h. The mixture was concentrated in vacuum to afford crude Intermediate A73 (688 mg, 91% yield) as yellow solid.

HNMR: $^1$H NMR (400 MHz, DMSO-$d_6$) δ 7.34 (dd, J=11.5, 7.0 Hz, 1H), 5.00 (s, 2H), 4.79 (d, J=1.6 Hz, 2H), 4.18 (q, J=7.1 Hz, 2H), 1.21 (t, J=7.1 Hz, 3H).

Intermediate A74

Synthesis of 4-(benzyloxy)-2,6-dichlorobenzaldehyde (Intermediate A74)

A74

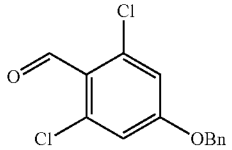

To a solution of 2,6-dichloro-4-hydroxybenzaldehyde (6.5 g, 34 mmol) in DMF (50 mL) was added $K_2CO_3$ (5.6 g, 41 mmol) and BnBr (5.8 g, 34 mmol). The mixture was stirred at rt for 2 h, diluted with water (50 mL), was extracted with EtOAc (30 mL*3). The combined organic phase was washed by brine (50 mL), dried over $Na_2SO_4$, concentrated in vacuum and washed by n-hexane to afford intermediate A74 (8.6 g, 90% yield) as a white solid.

$^1$H NMR: (400 MHz, DMSO-$d_6$) δ 10.28 (s, 1H), 7.49-7.35 (m, 5H), 7.30 (s, 2H), 5.27 (s, 2H).

Intermediate A75

Synthesis of 2,4-dichloro-6-iodophenol (Intermediate A75)

A75

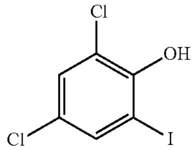

To a solution of 2,4-dichlorophenol (5.0 g, 30.67 mmol) in DCM (30 mL) was added NIS (8.3 g, 36.81 mmol) and TsOH (1.2 g, 6.13 mmol). The mixture was stirred at rt overnight. The mixture was diluted with $H_2O$ (50 mL) and was extracted DCM (50 mL). The organic phase was washed by brine (20 mL), dried over $Na_2SO_4$ and was concentrated in vacuum to afford Intermediate A75 (2.0 g, 23% yield) as a white solid.

LCMS: T=2.376 min, [M−1]=286.7

Intermediate A76

Synthesis of 1,5-dichloro-3-iodo-2-methoxybenzene (Intermediate A76)

A76

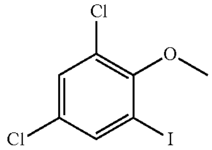

To a solution of Intermediate A75 (1.5 g, 5.33 mmol) in DMF (10 mL) was added $K_2CO_3$ (1.1 g, 8.00 mmol) and MeI (1.1 g, 8.00 mmol). The reaction was stirred at rt 3 h. The mixture was diluted with $H_2O$ (50 mL) and was extracted EtOAc (20 mL*2). The combined organic phase was washed by brine (50 mL*2), dried over $Na_2SO_4$ and was concentrated in vacuum to afford Intermediate A76 (1.5 g, 97% yield) as a brown solid.

$^1$H NMR: (400 MHz, DMSO-$d_6$) δ 7.89 (d, J=2.5 Hz, 1H), 7.71 (d, J=2.5 Hz, 1H), 3.77 (s, 3H).

Intermediate A77

Synthesis of 3,5-dichloro-2-methoxyphenol (Intermediate A77)

A77

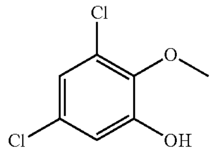

To a solution of Intermediate A76 (1.7 g, 5.8 mmol) in water (1 mL) at rt was added KOH (1.3 g, 23 mmol), $Pd_2(dba)_3$ (532 mg, 0.58 mmol) and tBuXPhos (247 mg, 0.58 mmol). The reaction was heated to 100° C. overnight and was cooled down to rt. The reaction mixture was diluted with $H_2O$ (50 mL), extracted EtOAc (20 mL*2). The combined organic phase was washed with brine (20 mL*2), dried over $Na_2SO_4$, concentrated under reduce pressure. The crude product was purified with silica gel column (Pet. ether/EtOAc=50/1) to afford Intermediate A77 (560 mg, 50% yield) as a brown solid.

LCMS: T=1.256 min, [M−1]=190.9

Intermediate A78

Synthesis of 3,5-dichloro-4-(hydroxymethyl)-2-methoxyphenol (Intermediate A78)

A78

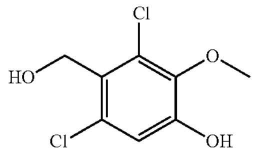

To a solution of NaOH (113 mg, 2.83 mmol) in water (20 mL) at rt was added Intermediate A77 (546 mg, 2.83 mmol). The mixture was heated to 45° C., $CH_2O$ (230 mg, 2.83 mmol) was added dropwise. The mixture was stirred at 45° C. overnight and cooled down to rt. The mixture was diluted with water (20 mL), acidified to pH=5-6 by 1 N HCl and was extracted with EtOAc (20 mL*2). The combined organic phase was washed by brine (30 mL), dried over $Na_2SO_4$, and was concentrated under reduce pressure. The crude product was purified with silica gel column (Pet. ether/EtOAc=20/1 to 5/1) to afford Intermediate A78 (280 mg, 44% yield) as a white solid.

LCMS: T=1.052 min, [M−1]=220.9

Intermediate A79

Synthesis of ethyl 2-(3,5-dichloro-4-(hydroxymethyl)-2-methoxyphenoxy)acetate (Intermediate A79)

A79

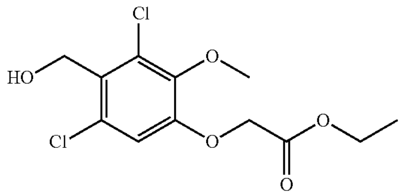

To a solution of Intermediate A78 (280 mg, 1.26 mmol) in DMF (5 mL) at rt was added $K_2CO_3$ (260 mg, 1.88 mmol) and ethyl 2-bromoacetate (251 mg, 1.51 mmol). The mixture was stirred at rt 2 h. The reaction mixture was diluted with EtOAc (30 mL), washed with brine (20 mL*2), dried over $Na_2SO_4$ and concentrated in vacuum to afford Intermediate A79 (380 mg, 98% yield) as a white solid.

$^1$H NMR; (400 MHz, DMSO-$d_6$) δ 7.17 (s, 1H), 5.12 (t, J=5.2 Hz, 1H), 4.96 (s, 2H), 4.60 (d, J=5.2 Hz, 2H), 4.18 (t, J=7.2 Hz, 2H), 3.79 (s, 3H), 1.21 (t, J=7.2 Hz, 3H).

Intermediate A80

Synthesis of ethyl 2-(3,5-dichloro-4-(chloromethyl)-2-methoxyphenoxy)acetate (Intermediate A80)

A80

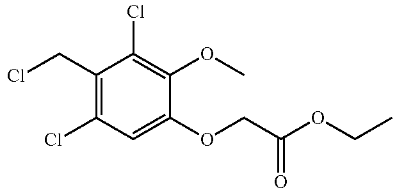

To a solution of Intermediate A79 (380 mg, 1.23 mmol) in DCM (5 mL) at 0° C. was added $SOCl_2$ (219 mg, 1.84 mmol). The mixture was stirred at rt 2 h. The mixture was concentrated in vacuum to afford Intermediate A80 (378 mg, 94% yield) as a white solid.

$^1$H NMR; (400 MHz, DMSO-$d_6$) δ 7.29 (s, 1H), 5.00 (s, 2H), 4.86 (s, 2H), 4.18 (q, J=7.2 Hz, 2H), 3.82 (s, 3H), 1.21 (t, J=7.2 Hz, 3H).

Intermediate B1

Synthesis of 3-fluoro-2-(prop-1-en-2-yl)phenol (Intermediate B1)

B1

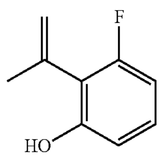

To a mixture of 2-bromo-3-fluorophenol (38.0 g, 200 mmol), isopropenyl-2-boron(pinacolate) (50.4 g, 300 mmol) and $Pd(dppf)Cl_2 \cdot CH_2Cl_2$ (16.3 g, 20 mmol) in 1,4-dioxane (300 mL) and water (30 mL) at rt was added $K_2CO_3$ (55.3 g, 400 mmol). The mixture was heated to 70° C. and stirred overnight. The reaction mixture was cooled to rt, quenched with water (100 mL) and extracted with EtOAc (100 mL*3). The combined organic phase was washed with brine (200 mL), dried over $Na_2SO_4$, concentrated in vacuo and purified by silica gel column chromatography (EtOAc/pet. ether=1/100 to 1/20) to afford Intermediate B1 (23.0 g, 76% yield) as white solid.

TLC: EtOAc/pet. ether=1/10 (v/v), Rf=0.55

$^1$H NMR: (400 MHz, DMSO-$d_6$) δ 9.72 (s, 1H), 7.06 (td, J=8.4, 6.8 Hz, 1H), 6.66 (td, J=8.4, 1.2 Hz, 1H), 6.59 (m, 1.0 Hz, 1H), 5.28 (m, 1H), 4.89 (m, 1H), 1.98 (s, 3H).

Intermediate B2

Synthesis of 3-fluoro-2-isopropylphenol (Intermediate B2)

B2

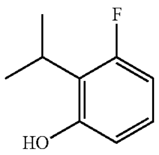

To a solution of Intermediate B1 (23.0 g, 151 mmol) in MeOH (300 mL) was added Pd/C (10%) (6.0 g). The reaction mixture was stirred at 60° C. overnight. The mixture was cooled to 0° C., filtered, and concentrated in vacuo to afford Intermediate B2 (21.0 g, 90% yield) as a yellow oil.

TLC: EtOAc/pet. ether=1/50 (v/v), $R_f$=0.25

$^1$H NMR: (400 MHz, DMSO-$d_6$) δ 9.69 (s, 1H), 7.00-6.93 (m, 1H), 6.65-6.60 (m, 1H), 6.52 (ddd, J=10.8, 8.0, 1.2 Hz, 1H), 3.40 (m, 1H), 1.25 (dd, J=7.2, 1.2 Hz, 6H).

Intermediate B3

Synthesis of 2-(3-(difluoromethoxy)phenyl)-4,4,5,5-tetramethyl-1,3,2-dioxaborolane (Intermediate B3)

B3

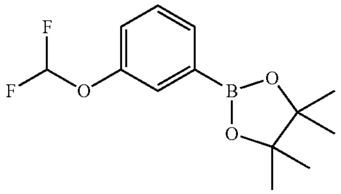

A mixture of 3-bromophenyl difluoromethyl ether (250 mg, 1.12 mmol), bis(pinacolato)diboron (311 mg, 1.23 mmol), $Pd(dppf)Cl_2$ (73 mg, 0.10 mmol) and KOAc (323 mg, 3.36 mmol) in 1,4-dioxane (5 mL) was stirred at 80° C. overnight. The mixture was filtered and concentrated in vacuo to afford Intermediate B3 (270 mg, 89.4% yield) as a black oil which was used without further purification.

TLC: Pet. ether/EtOAc=10/1 (v/v), Rf=0.8

Intermediate B4

Synthesis of 1-(1-bromovinyl)-4-fluorobenzene (Intermediate B4)

B4

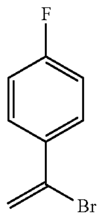

To a solution of 4-fluoroacetophenone (10.0 g, 72.4 mmol), $P(OPh)_3$ (35.4 g, 109 mmol) and triethylamine (11.7 g, 116 mmol) in DCM (100 mL) at −15° C. was added $Br_2$ (17.4 g, 109 mmol) dropwise. The mixture was stirred at rt for 1 h. The mixture was concentrated to dryness and purified by silica gel column chromatography (pet. ether eluant) to afford Intermediate B4 (8.0 g, 54.9% yield) as a colorless oil that is best stored at 0° C.

TLC: Pet. ether, $R_f$=0.91

$^1$H NMR: (400 MHz, Chloroform-d) δ 7.63-7.50 (m, 2H), 7.03 (t, J=8.7 Hz, 2H), 6.05 (d, J=2.1 Hz, 1H), 5.76 (d, J=2.0 Hz, 1H).

Intermediate B5

Synthesis of 2-(1-(4-fluorophenyl)vinyl)-4,4,5,5-tetramethyl-1,3,2-dioxaborolane (Intermediate B5)

B5

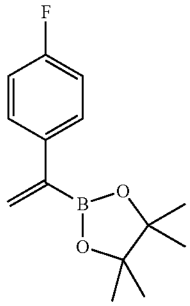

A solution of Intermediate B4 (3.0 g, 14.9 mmol), bis(pinacolato)diboron (5.7 g, 22.4 mmol), $Pd(PPh_3)_2Cl_2$ (1.1 g, 1.49 mmol), KOAc (4.4 g, 44.8 mmol) and $PPh_3$ (1.2 g, 4.48 mmol) in toluene (50 mL) was stirred at 100° C. overnight. The mixture was concentrated in vacuo. Water (30 mL) was added, and the mixture was extracted with EtOAc (25 mL*2). The combined organic phase was washed with brine (50 mL), dried over $Na_2SO_4$, concentrated in vacuo, and purified by silica gel column chromatography (pet. ether/EtOAc=20/1) to afford Intermediate B5 (1.5 g, 40.5% yield) as a yellow oil.

TLC: Pet. ether, $R_f$=0.69

$^1H$ NMR: (400 MHz, Chloroform-d) δ 7.45 (dd, J=8.7, 5.6 Hz, 2H), 7.00 (t, J=8.8 Hz, 2H), 6.04 (s, 2H), 1.32 (s, 12H).

Intermediate B6

Synthesis of 3-fluoro-2-(4-fluorobenzyl)phenol (Intermediate B6)

B6

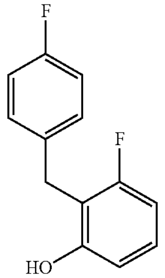

To a solution of 4-fluorobenzyl bromide (1.0 g, 5.29 mmol) and 6-fluoro-2-hydroxyphenylboronic acid (1.2 g, 7.94 mmol) in toluene (10 mL) at rt were added $Pd(dppf)Cl_2$ (387 mg, 0.53 mmol) and $K_3PO_4$ (3.4 g, 15.87 mmol). The reaction was heated to 100° C. overnight under $N_2$(g). Water (20 mL) was added, and the resultant mixture was extracted with EtOAc (10 mL*2). The combined organic phase was washed with brine (30 mL), dried over $Na_2SO_4$, and concentrated in vacuo. The crude product was purified by silica gel column chromatography (pet. ether/EtOAc=100/1-20/1) followed by reversed-phase column chromatography to afford Intermediate B6 (180 mg, 15.4% yield) as a light yellow oil.

TLC: Pet. ether/EtOAc=5/1 (v/v), Rf=0.29.

Intermediate B7

Synthesis of 3-fluoro-2-(1-(4-fluorophenyl)-1-hydroxypropyl)phenol (Intermediate B7)

B7

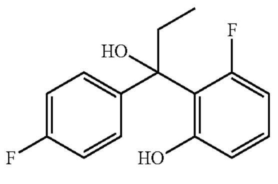

To a solution of 2-bromo-3-fluorophenol (1.00 g, 5.24 mmol) in THF (10 mL) at −30° C. was added dropwise n-BuLi (2.5 M, 4.00 mL, 10.0 mmol). The reaction mixture was stirred at −30° C. for 30 min and then cooled to −50° C.; (4-fluorophenyl) ethyl ketone (0.73 g, 4.36 mmol) in THF (3 mL) was added dropwise. The mixture was stirred at −50° C. for 2 h, quenched with aqueous $NH_4Cl$ solution (30 mL) and acidified with HCl (1N) to pH~6, then extracted with EtOAc (20 mL*3). The combined organic phase was washed with brine (30 mL), dried over $Na_2SO_4$, and concentrated in vacuo. The crude product was purified by reversed-phase column chromatography to afford Intermediate B7 (230 mg, 20% yield) as a yellow oil.

TLC: EtOAc/pet. ether=1/5 (v/v), Rf=0.36

$^1H$ NMR: (400 MHz, DMSO-$d_6$) δ 11.07 (s, 1H), 7.47-7.40 (m, 2H), 7.36 (s, 1H), 7.18-7.04 (m, 3H), 6.58 (dt, J=8.3, 1.1 Hz, 1H), 6.49 (ddd, J=12.0, 8.2, 1.3 Hz, 1H), 2.49-2.42 (m, 2H), 2.22-2.15 (m, 1H), 0.89 (t, J=7.2 Hz, 3H).

Intermediate B8

Synthesis of 3-fluoro-2-(1-(4-fluorophenyl)propyl)phenol (Intermediate B8)

B8

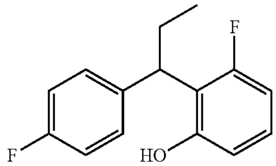

To a solution of Intermediate B7 (230 mg, 1.14 mmol) in DCM (5 mL) at rt was added $Et_3SiH$ (528 mg, 4.54 mmol); the mixture was cooled to 0° C., and TFA (3.88 g, 34.1 mmol) was added dropwise. The mixture was stirred at rt for 3 h, then concentrated in vacuo. The crude product was purified by silica gel column chromatography (pet. ether/EtOAc=50/1 to 10/1) to afford Intermediate B8 (80 mg, 37% yield) as a yellow oil.

TLC: EtOAc/pet. ether=1/5 (v/v), $R_f$=0.60

Intermediate B9

Synthesis of 3-fluoro-2-(1-(4-fluorophenyl)-1-hydroxybutyl)phenol (Intermediate B9)

B9

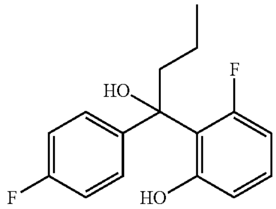

To a solution of 2-bromo-3-fluorophenol (1.00 g, 5.24 mmol) in THF (10 mL) at −30° C. was added dropwise n-BuLi (2.5 M, 4.0 mL, 10.0 mmol). The reaction mixture was stirred at −30° C. for 30 min, then cooled to −50° C.; (4-fluorophenyl) propyl ketone (0.73 g, 4.36 mmol) in THF (3 mL) was added dropwise. The mixture was stirred at −50° C. for 2 h, quenched with aqueous $NH_4Cl$ solution (30 mL) and acidified with HCl (1N) to pH~6, then extracted with EtOAc (10 mL*3). The combined organic phase was washed with brine (20 mL), dried over $Na_2SO_4$, and concentrated in vacuo. The crude product was purified by reversed-phase column chromatography to afford Intermediate B9 (250 mg, 20% yield) as a yellow oil.

TLC: EtOAc/pet. ether=1/5 (v/v), Rf=0.36

$^1H$ NMR: (400 MHz, DMSO-$d_6$) δ 11.06 (s, 1H), 7.46-7.40 (m, 2H), 7.40 (s, 1H), 7.17-7.06 (m, 3H), 6.57 (dt, J=8.2, 1.1 Hz, 1H), 6.49 (ddd, J=12.0, 8.2, 1.3 Hz, 1H), 2.47-2.37 (m, 1H), 2.19-2.07 (m, 1H), 2.03-1.96 (m, 1H), 1.62-1.44 (m, 1H), 0.90 (t, J=7.4 Hz, 3H).

Intermediate B10

Synthesis of 3-fluoro-2-(1-(4-fluorophenyl)butyl) phenol (Intermediate B10)

B10

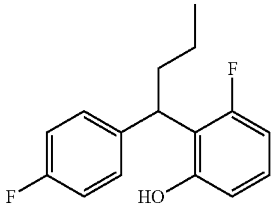

To a solution of Intermediate B9 (230 mg, 826 umol) in DCM (5 mL) at rt was added $Et_3SiH$ (384 mg, 3.31 mmol). The mixture was cooled to 0° C., and TFA (2.83 g, 24.8 mmol) was added dropwise. The mixture was stirred at rt for 3 h, then concentrated in vacuo. The crude product was purified by silica gel column chromatography (pet. ether/EtOAc=50/1 to 10/1) to afford Intermediate B10 (130 mg, 60% yield) as a yellow oil.

TLC: EtOAc/pet. ether=1/5 (v/v), $R_f$=0.60

$^1$H NMR: (400 MHz, DMSO-$d_6$) δ 9.88 (d, J=1.6 Hz, 1H), 7.33-7.27 (m, 2H), 7.10-7.04 (m, 2H), 7.03-6.97 (m, 1H), 6.66-6.61 (m, 1H), 6.54 (ddd, J=10.9, 8.3, 1.1 Hz, 1H), 4.48-4.39 (m, 1H), 2.23-2.08 (m, 1H), 2.06-1.96 (m, 1H), 1.18 (d, J=7.4 Hz, 1H), 0.88 (t, J=7.3 Hz, 3H).

Intermediate B11

Synthesis of 3-chloro-2-(prop-1-en-2-yl)phenol (Intermediate B11)

B11

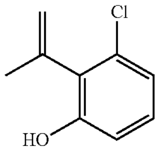

To a mixture of 2-bromo-3-chlorophenol (1.0 g, 4.8 mmol), isopropenyl-2-boron(pinacolate) (1.2 g, 7.2 mmol) and Pd(dppf)$Cl_2$·$CH_2Cl_2$ (170 mg, 0.24 mmol) in 1,4-dioxane (10 mL) and $H_2O$ (2 mL) at rt was added $K_2CO_3$ (1.3 g, 9.6 mmol). The mixture was heated to 75° C. overnight. The reaction mixture was cooled to rt, quenched with water (30 mL) and extracted with EtOAc (30 mL*3). The combined organic phase was washed with brine (20 mL), dried over $Na_2SO_4$, concentrated in vacuo and purified by silica gel column chromatography (EtOAc/pet. ether=1/20) to afford Intermediate B11 (800 mg, 98% yield) as a white solid.

TLC: EtOAc/pet. ether=1/10 (v/v), Rf=0.55

$^1$H NMR: (400 MHz, DMSO) δ 9.65 (s, 1H), 7.06 (t, J=8.1 Hz, 1H), 6.86 (d, J=8.0 Hz, 1H), 6.79 (d, J=8.2 Hz, 1H), 5.27 (s, 1H), 4.78 (s, 1H), 1.93 (s, 3H).

Intermediate B12

Synthesis of 3-chloro-2-isopropylphenol (Intermediate B12)

B12

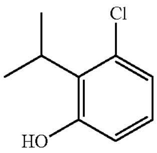

To a solution of Intermediate B11 (800 mg, 4.7 mmol) in THF (20 mL) was added Raney-Ni (40 mg). The reaction mixture was stirred at 60° C. overnight under $H_2$ gas (1 atm). The mixture was cooled to 0° C. and filtered, then concentrated in vacuo to afford Intermediate B12 (800 mg, 98% yield) as a yellow oil.

TLC: EtOAc/pet. ether=1/50 (v/v), $R_f$=0.25

$^1$H NMR: (400 MHz, DMSO) δ 9.69 (s, 1H), 6.96 (m, 1H), 6.82-6.71 (m, 2H), 3.61-3.48 (m, 1H), 1.29 (d, J=7.1 Hz, 6H).

Intermediate B13

Synthesis of 3-methoxy-2-(prop-1-en-2-yl)phenol (Intermediate B13)

B13

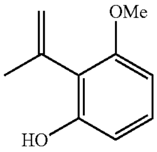

To a solution of 2-bromo-3-methoxyphenol (500 mg, 2.46 mmol) and propenyl-2-boron(pinacolate) (621 mg, 3.69 mmol) in 1.4-dioxane (10 mL) at rt under $N_2$ (g) were added Pd(dppf)$Cl_2$ (360 mg, 0.49 mmol) and $K_2CO_3$ (681 mg, 4.93 mmol). The mixture was heated to 80° C. overnight. The mixture was diluted with EtOAc (20 mL), washed with brine (10 mL*2), dried over $Na_2SO_4$, filtered and concentrated in vacuo. The crude product was purified by silica gel column chromatography (EtOAc/pet. ether=1/100-1/10) to afford Intermediate B13 (200 mg, 49.4% yield) as a light yellow liquid.

TLC: Pet. ether/EtOAc=10/1 (v/v), Rf=0.75.

$^1$H NMR: (400 MHz, DMSO-$d_6$) δ 9.02 (s, 1H), 6.98 (t, J=8.0 Hz, 1H), 6.43 (ddd, J=9.2, 8.4, 0.8 Hz, 2H), 5.15 (dt, J=3.2, 1.6 Hz, 1H), 4.71 (dd, J=2.4, 1.2 Hz, 1H), 3.67 (s, 3H), 1.89 (t, J=1.2 Hz, 3H).

Intermediate B14

Synthesis of 2-isopropyl-3-methoxyphenol (Intermediate B14)

B14

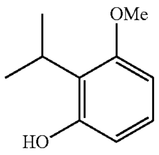

To a solution of Intermediate B13 (400 mg, 2.44 mmol) in THF (10 mL) at rt was added Pd/C (100 mg, 2.44 mmol). The mixture was degassed several times in vacuo, then placed under a $H_2$ atmosphere. The mixture was stirred at 60° C. overnight. The reaction was filtered and concentrated to afford Intermediate B14 (400 mg, 98.7% yield) as a white solid.

TLC: Pet. ether/EtOAc=10/1 (v/v), Rf=0.76.

$^1$H NMR: (400 MHz, DMSO-$d_6$) δ 9.11 (s, 1H), 6.89 (t, J=8.0 Hz, 1H), 6.42-6.35 (m, 2H), 3.70 (s, 3H), 3.50-3.46 (m, 1H), 1.21 (d, J=7.2 Hz, 6H).

Intermediate B15

Synthesis of 3-hydroxy-2-(prop-1-en-2-yl)benzonitrile (Intermediate B15)

B15

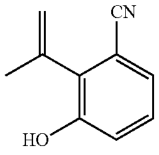

To a mixture of 2-bromo-3-hydroxybenzonitrile (800 mg, 4.04 mmol), isopropenyl-2-boron(pinacolate) (1.36 g, 8.08 mmol) and Pd(dppf)$Cl_2$·$CH_2Cl_2$ (260 mg, 0.40 mmol) in 1,4-dioxane (10 mL) and $H_2O$ (2 mL) at rt was added $K_2CO_3$ (1.68 g, 12.12 mmol). The mixture was heated to 75° C. overnight. The reaction mixture was cooled to rt, quenched with water (30 mL) and extracted with EtOAc (30 mL*3). The combined organic phase was washed with brine (20 mL), dried over $Na_2SO_4$, concentrated in vacuo and purified by silica gel column chromatography (EtOAc/pet. ether=1/20) to afford Intermediate B15 (400 mg, 62.2% yield) as a white solid.

TLC: EtOAc/pet. ether=1/5 (v/v), Rf=0.55

$^1$H NMR: (400 MHz, DMSO-$d_6$) δ 10.13 (s, 1H), 7.30-7.20 (m, 2H), 7.12 (dd, J=7.9, 1.5 Hz, 1H), 5.34 (q, J=1.6 Hz, 1H), 4.98-4.95 (m, 1H), 2.03 (s, 3H).

Intermediate B16

Synthesis of 3-hydroxy-2-isopropylbenzonitrile (Intermediate B16)

B16

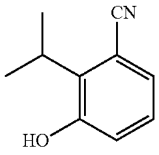

To a solution of Intermediate B15 (400 mg, 4.7 mmol) in THF (20 mL) was added Pd/C (5%) (40 mg). The reaction mixture was stirred at rt overnight under $H_2$ atmosphere. The mixture was filtered, concentrated to dryness, and purified by Prep-TLC (pet. ether/EtOAc=5/1) to afford Intermediate B16 (150 mg, 37.1% yield) as a white solid.

TLC: EtOAc/pet. ether=1/5 (v/v), $R_f$=0.61

$^1$H NMR: (400 MHz, DMSO-$d_6$) δ 10.06 (s, 1H), 7.22-7.14 (m, 2H), 7.08 (dd, J=7.0, 2.4 Hz, 1H), 3.41 (p, J=7.1 Hz, 1H), 1.34 (d, J=7.1 Hz, 6H).

Intermediate B17

Synthesis of 2-(1-(4-fluorophenyl)-1-hydroxybutyl)phenol (Intermediate B17)

B17

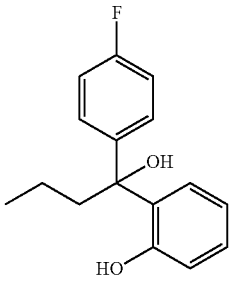

To a solution of 2-bromophenol (1.25 g, 7.22 mmol) in dry THF (15 mL) at −50° C. was added dropwise n-BuLi (15.0 mmol, 6.02 mL of 2.5M). The mixture was warmed to room temperature and stirred for 1 h. The resultant solution was cooled to 0° C.; 4-fluorophenyl-n-propyl ketone (1.00 g, 6.02 mmol) in THF (5 mL) was added dropwise. The mixture was stirred at room temperature for 2 h. $NH_4Cl$ (aq) (15 mL) was added. The mixture was acidified to pH~4-5 with 1N HCl, then extracted with DCM (15 mL*2). The combined organic phase was dried with $Na_2SO_4$, concentrated in vacuo, and purified by reversed-phase column chromatography to afford Intermediate B17 (1.0 g, 63.9% yield) as a colorless oil.

TLC: EtOAc/pet. ether=1/5 (v/v), Rf=0.48

$^1$H NMR: (400 MHz, DMSO-$d_6$) δ 9.57 (s, 1H), 7.40-7.32 (m, 3H), 7.10-7.02 (m, 3H), 6.79 (td, J=7.6, 1.3 Hz, 1H), 6.66 (dd, J=8.0, 1.3 Hz, 1H), 6.21 (s, 1H), 2.42-2.31 (m, 1H), 2.14-2.02 (m, 1H), 1.27-1.20 (m, 2H), 0.85 (t, J=7.4 Hz, 3H).

Intermediate B18

Synthesis of 2-(1-(4-fluorophenyl)butyl)phenol (Intermediate B18)

B18

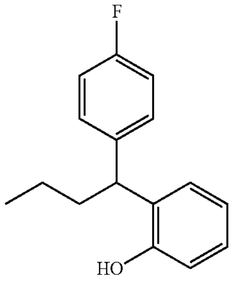

A mixture of Intermediate B17 (1.0 g, 3.84 mmol), $Et_3SiH$ (1.79 g, 15.4 mmol) and TFA (4.38 g, 38.4 mmol) in DCM (10 mL) was stirred at rt for 3 h. The mixture was concentrated in vacuo and purified by silica gel column chromatography to afford product Intermediate B18 (800 mg, 85.2% yield) as a white solid.

TLC: EtOAc/pet. ether=1/5 (v/v), Rf=0.66

$^1$H NMR: (400 MHz, DMSO-$d_6$) δ 9.30 (s, 1H), 7.31-7.24 (m, 2H), 7.17 (dd, J=8.1, 1.6 Hz, 1H), 7.04 (t, J=8.9 Hz, 2H), 7.00-6.94 (m, 1H), 6.75 (d, J=7.7 Hz, 2H), 4.29 (t, J=7.9 Hz, 1H), 1.96-1.86 (m, 2H), 1.17 (t, J=7.1 Hz, 2H), 0.86 (d, J=7.4 Hz, 3H).

Intermediate B19

Synthesis of 3'-(difluoromethoxy)-[1,1'-biphenyl]-2-ol (Intermediate B19)

B19

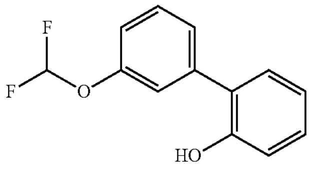

A mixture of Intermediate B3 (3.5 g, 13 mmol), 2-bromophenol (1.5 g, 8.67 mmol), Pd(dppf)$Cl_2$ (634 mg, 0.87 mmol) and $K_2CO_3$ (3.6 g, 26 mmol) in 1,4-dioxane (30 mL) and water (3 mL) was stirred at 90° C. overnight. Water (50 mL) was added, and the mixture was extracted with EtOAc (30 mL*2). The combined organic phase was washed with brine (50 mL), dried over $Na_2SO_4$, and concentrated in vacuo. The residue was purified by silica gel column chromatography (pet. ether/EtOAc=20/1 to 5/1, v/v) to afford Intermediate B19 (700 mg, 34% yield) as a yellow oil.

TLC: EtOAc/pet. ether=1/5 (v/v), Rf=0.54

LCMS: RT=2.551 min; [M−1]=235.0

Intermediate B19

Synthesis of 4-iodo-2-isopropyl-1-(methoxymethoxy)benzene (Intermediate B20)

B20

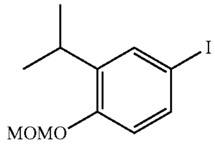

To a solution of 4-iodo-2-isopropylphenol (20.0 g, 76.3 mmol) in DCM (200 mL) was added DIEA (29.6 g, 229 mmol) and MOMCl (9.2 g, 114 mmol). The mixture was stirred at rt for 3 h. Water (500 mL) was added, and the mixture was extracted with EtOAc (200 mL*3). The combined organic layer was washed by brine (500 mL), dried over $Na_2SO_4$ and concentrated in vacuum to dryness. The residue was purified by silica gel column (Petroleum ether) to afford Intermediate B20 (14 g, 60% yield) as a yellow oil.

$^1$H NMR: (400 MHz, DMSO-$d_6$) δ 7.45 (d, J=8.0 Hz, 2H), 6.87 (d, J=8.2 Hz, 1H), 5.20 (s, 2H), 3.37 (d, J=0.6 Hz, 3H), 1.15 (d, J=6.9 Hz, 6H).

Intermediate C1

Synthesis of methyl 2-(4-(3-bromo-2-fluoro-4-hydroxybenzyl)-3,5-dimethylphenoxy)acetate (Intermediate C1)

C1

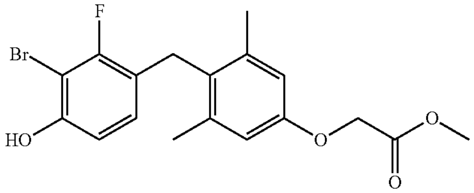

A solution of Intermediate A3 (1 g, 4.12 mmol), 2-bromo-3-fluorophenol (2.3 g, 12.4 mmol) and $ZnCl_2$ (1M in THF, 10.3 mL) in DCE (5 mL) was stirred at 95° C. overnight. The mixture was concentrated in vacuo and purified by silica gel column chromatography (pet. ether/EtOAc=5:1) and Prep-TLC (pet. ether/EtOAc=3:1) to afford Intermediate C1 (100 mg, 6.1% yield) as a colorless oil.

TLC: Pet. ether/EtOAc=5/1 (v/v), Rf=0.4

$^1$H NMR: (400 MHz, DMSO-d6) δ 10.44 (s, 1H), 6.66 (s, 2H), 6.64 (d, J=8.8 Hz, 1H), 6.37 (t, J=8.4 Hz, 1H), 4.75 (s, 2H), 3.82 (s, 2H), 3.71 (s, 3H), 2.13 (s, 6H).

Intermediate C2

Synthesis of ethyl 2-(3-bromo-4-(2-fluoro-4-hydroxy-3-isopropylbenzyl)-5-methylphenoxy)acetate (Intermediate C2)

C2

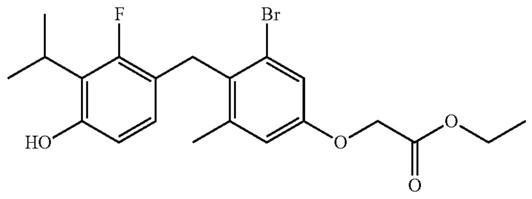

To a solution of Intermediate A6 (1.06 g, 3.3 mmol) in DCE (20 mL) at rt were added Intermediate B2 (1.52 g, 9.9 mmol) and $ZnCl_2$/THF (1M) (8.2 mL, 8.25 mmol). The reaction was heated to 85° C. and stirred for 2 h. The reaction mixture was diluted with DCM (20 mL), washed with brine (2*10 mL), dried over $Na_2SO_4$, and concentrated in vacuo. The crude product was purified by silica gel column chromatography (EtOAc/pet. ether=1/5) to afford Intermediate C7 (530 mg, 38.8% yield) as a solid.

TLC: EtOAc/pet. ether=1/5 (v/v), Rf=0.35

$^1$H NMR: (400 MHz, DMSO) δ 9.48 (d, J=1.5 Hz, 1H), 7.08 (d, J=2.7 Hz, 1H), 6.88 (d, J=2.7 Hz, 1H), 6.49-6.43 (m, 1H), 6.17 (t, J=8.6 Hz, 1H), 4.80 (s, 2H), 4.18 (d, J=7.1 Hz, 2H), 3.93 (s, 2H), 2.16 (s, 2H), 1.26 (m, 6H), 1.17 (t, J=7.1 Hz, 3H).

Intermediate C3

Synthesis of ethyl 2-(4-(3-bromo-2-fluoro-4-hydroxybenzyl)-3,5-dichlorophenoxy)acetate (Intermediate C3)

C3

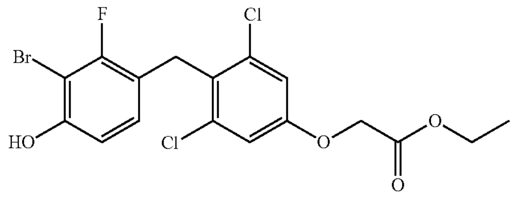

A solution of 2-bromo-3-fluorophenol (1.54 g, 8.07 mmol), Intermediate A11 (800 mg, 2.69 mmol) and $ZnCl_2$ (916 mg, 6.72 mmol) in DCE (20 mL) was stirred at 90° C. overnight. The mixture was cooled to rt and concentrated in vacuo. Water (30 mL) was added, and the mixture was extracted with EtOAc (25 mL*2). The combined organic phase was washed with brine (50 mL), dried over $Na_2SO_4$, concentrated in vacuo and purified by silica gel column chromatography (pet. ether/EtOAc=5/1) to afford Intermediate C3 (600 mg, 49.4% yield) as a white solid.

TLC: EtOAc/pet. ether=1/5 (v/v), Rf=0.4

LCMS: RT=2.795 min, [M−1]=448.9

$^1$H NMR: (400 MHz, DMSO-$d_6$) δ 10.55 (s, 1H), 7.18 (s, 2H), 6.68 (dd, J=8.5, 1.4 Hz, 1H), 6.57 (t, J=8.6 Hz, 1H), 4.89 (s, 2H), 4.18 (q, J=7.1 Hz, 2H), 4.09 (s, 2H), 1.21 (t, J=7.1 Hz, 3H).

Intermediate C4

Synthesis of methyl 2-(4-(3-bromo-4-hydroxy-2-methylbenzyl)-3,5-dichlorophenoxy)acetate (Intermediate C4)

C4

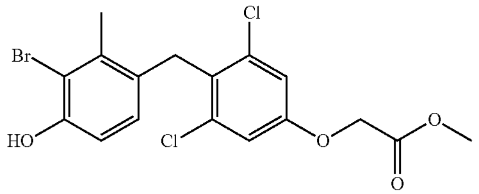

To a solution of 2-bromo-3-methylphenol (1.0 g, 5.4 mmol) and Intermediate A10 (758 mg, 2.7 mmol) in DCE (10.0 mL) was added $ZnCl_2$ (1M/THF) (6.7 mmol, 6.7 mL). The mixture was stirred at 85° C. overnight. The mixture was cooled to rt; water (20 mL) was added and the resultant mixture was extracted with DCM (10 mL*3). The combined organic phase was washed with brine (20 mL), dried over $Na_2SO_4$, concentrated in vacuo and purified by silica gel column chromatography (EtOAc/pet. ether=1/30 to 1/10) to afford Intermediate C4 (400 mg, 34% yield) as a white solid.

TLC: EtOAc/pet. ether=1/5 (v/v), $R_f$=0.30

$^1$H NMR: (400 MHz, DMSO-$d_6$) δ 9.94 (s, 1H), 7.20 (s, 2H), 6.65 (d, J=8.4 Hz, 1H), 6.19 (d, J=8.4 Hz, 1H), 4.93 (s, 2H), 4.05 (s, 2H), 3.72 (s, 3H), 2.45 (s, 3H).

Intermediate C5

Synthesis of ethyl 2-(3-bromo-5-chloro-2-fluoro-4-(4-hydroxy-3-isopropylbenzyl)phenoxy)acetate (Intermediate C5)

C5

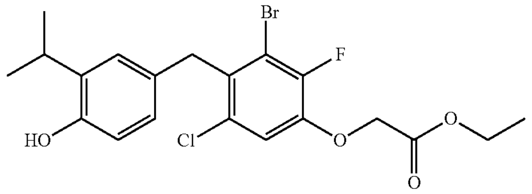

To a solution of Intermediate A34 (1.0 g, 2.9 mmol) in DCE (10 mL) at rt were added 2-isopropylphenol (1.1 g, 8.3 mmol) and $ZnCl_2$ (6.9 mmol, 6.9 mL). The reaction was heated to 85° C. and stirred overnight. The reaction mixture was cooled to rt; water (30 mL) was added and the resultant mixture was extracted with DCM (20 mL*3). The combined organic phase was washed with brine (40 mL), dried over $Na_2SO_4$ and concentrated in vacuo. The crude product was purified by silica gel column chromatography (EtOAc/pet. ether=1/100 to 1/10) to afford Intermediate C5 (550 mg, 43.1% yield) as a white solid.

TLC: Pet. ether/EtOAc=5/1 (v/v), Rf=0.20

$^1$H NMR: (400 MHz, DMSO-$d_6$) δ 9.11 (s, 1H), 7.44 (d, J=7.6 Hz, 1H), 6.97 (s, 1H), 6.65 (d, J=1.2 Hz, 2H), 4.99 (s, 2H), 4.18 (q, J=6.8 Hz, 2H), 4.11 (s, 2H), 3.13 (p, J=6.8 Hz, 1H), 1.19-1.15 (m, 3H), 1.11 (d, J=6.8 Hz, 6H).

Intermediate C6

Synthesis of ethyl 2-(5-bromo-3-chloro-2-fluoro-4-(4-hydroxy-3-isopropylbenzyl)phenoxy)acetate (Intermediate C6)

C6

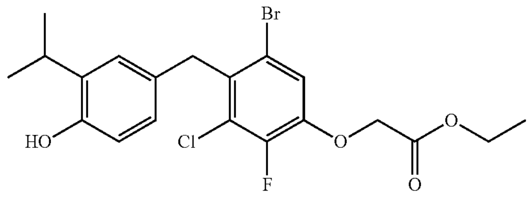

To a solution of Intermediate A39 (6.0 g, 16.7 mmol) in DCE (100 mL) at rt were added 2-isopropylphenol (6.8 g, 50.0 mmol) and $ZnCl_2$ (41.7 mmol, 42 mL). The reaction was heated to 85° C. and stirred overnight. The reaction mixture was cooled to rt; water (60 mL) was added and the mixture was extracted with DCM (30 mL*3). The combined organic phase was washed with brine (100 mL), dried over $Na_2SO_4$ and concentrated in vacuo. The crude product was purified by silica gel column chromatography (EtOAc/pet. ether=1/100 to 1/10) to afford Intermediate C6 (2.6 g, 33.9% yield) as a white solid.

TLC: Pet. ether/EtOAc=5/1 (v/v), Rf=0.20

$^1$H NMR: (400 MHz, DMSO-$d_6$) δ 9.13 (s, 1H), 7.54 (d, J=7.6 Hz, 1H), 6.97 (s, 1H), 6.67-6.63 (m, 2H), 5.00 (s, 2H), 4.18 (q, J=7.2 Hz, 2H), 4.10 (s, 2H), 3.13 (p, J=6.8 Hz, 1H), 1.21 (t, J=7.2 Hz, 3H), 1.11 (d, J=6.8 Hz, 6H).

Intermediate C7

Synthesis of ethyl 2-(4-(3-bromo-2-fluoro-4-hydroxybenzyl)-3,5-dichloro-2-fluorophenoxy)acetate (Intermediate C7)

C7

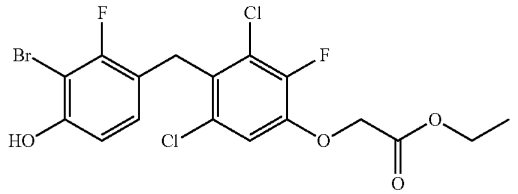

To a solution of 2-bromo-3-fluorophenol (1.8 g, 9.3 mmol) and Intermediate A29 (1.0 g, 3.1 mmol) in chlorobenzene (20 mL) was added $ZnCl_2$ (1.0 g, 3.1 mmol). The mixture was stirred at 160° C. in a microwave for 2 h. The mixture was cooled to rt. Water (150 mL) was added and the resultant mixture was extracted with DCM (100 mL*3). The combined organic phase was washed with brine (100 mL), dried over $Na_2SO_4$, concentrated in vacuo and purified by silica gel column chromatography (EtOAc/pet. ether=1/5) to afford Intermediate C7 (950 mg, 67.7% yield) as a solid.

TLC: EtOAc/pet. ether=1/5 (v/v), $R_f$=0.25

$^1$H NMR: (400 MHz, DMSO) δ 10.58 (s, 1H), 7.45 (d, J=7.6 Hz, 1H), 6.69 (d, J=8.7 Hz, 1H), 6.61 (d, J=8.5 Hz, 1H), 5.02 (d, J=6.8 Hz, 2H), 4.18 (d, J=7.1 Hz, 2H), 4.11 (s, 2H), 1.21 (s, 3H).

Intermediate C8

Synthesis of 3,5-dichloro-4-(3-isopropyl-4-(methoxymethoxy)benzyl)phenol (Intermediate C8)

C8

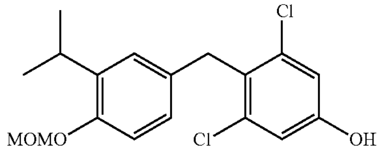

A solution of Intermediate B20 (8.2 g, 27 mmol) in THF (80 mL) was cooled down to −20° C. i-PrMgCl (1 M in THF, 32 mL) was added dropwise. The mixture was stirred at rt for 2 h and then cooled down to −70° C. A solution of Intermediate A74 (5.0 g, 18 mmol) in THF (10 mL) was added dropwise. The solution was stirred at −70° C. for 2 h. Saturated $NH_4Cl$ aqueous (50 mL) was added and the mixture was extracted with EtOAc (50 mL*3). The combined organic phase was washed by brine (200 mL), dried over $Na_2SO_4$, concentrated in vacuum. The resulting brown oil was filtered through a plug of silica and the filtrate was concentrated. Half of the resulting yellow solid was dissolved in THF (30 mL) and Pd/C (750 mg, 6.18 mmol) was added. The mixture was stirred at 50° C. under $H_2$ atmosphere overnight. The reaction was cooled to rt and filtered. Water (30 mL) was added and the mixture was extracted with EtOAc (20 mL*3). The combined organic phase was washed by brine (50 mL), dried over $Na_2SO_4$ and concentrated in vacuum. The resulting yellow oil was dissolved in DCM (20 mL), cooled to 0° C. and $Et_3SiH$ (3.60 g, 30.98 mmol) was added dropwise. TFA (1.4 g, 12.39 mmol) was then added dropwise. The mixture was stirred at rt for 0.5 h. The mixture was acidified to pH=7 with saturated aqueous $NaHCO_3$. The mixture was extracted with EtOAc (30 mL*2). The combined organic layer was washed with brine (50 mL), dried over $Na_2SO_4$ and concentrated in vacuum and purified by silica gel column (pet. ether/EtOAc=30/1 to 10/1) to afford Intermediate C8 (1.7 g, 80% yield) as yellow solid.

$^1$H NMR: (400 MHz, DMSO-$d_6$) δ 10.24 (s, 1H), 7.06 (d, J=2.2 Hz, 1H), 6.90 (d, J=8.4 Hz, 1H), 6.88 (s, 2H), 6.79 (dd, J=8.4, 2.3 Hz, 1H), 5.15 (s, 2H), 4.05 (s, 2H), 3.36 (s, 3H), 3.22 (p, J=7.0 Hz, 1H), 1.13 (d, J=6.9 Hz, 6H).

Intermediate C9

Synthesis of 3,5-dichloro-2-iodo-4-(3-isopropyl-4-(methoxymethoxy)benzyl)phenol (Intermediate C9)

C9

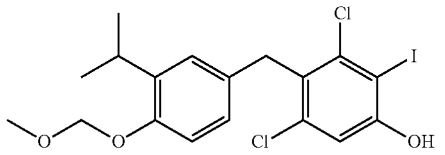

A solution of Intermediate C8 (1.6 g, 4.50 mmol) in DCM (30 mL) was cooled down to 0° C. NIS (912 mg, 4.05 mmol) was added in portion. The mixture was stirred at 0° C. for 4 h. Water (30 mL) was added and the mixture was extracted with DCM (20 mL*3). The combined organic phase was washed by brine (50 mL), dried over $Na_2SO_4$, concentrated in vacuum and purified by silica gel column (pet. ether/EtOAc=50/1 to 5/1) to afford Intermediate C9 (200 mg, 9% yield) as a white solid.

$^1$H NMR (400 MHz, DMSO-$d_6$) δ 11.12 (s, 1H), 7.06 (d, J=2.3 Hz, 1H), 6.98 (s, 1H), 6.90 (d, J=8.4 Hz, 1H), 6.75 (dd, J=8.5, 2.3 Hz, 1H), 5.15 (s, 2H), 4.19 (s, 2H), 3.36 (s, 3H), 3.25-3.18 (m, 1H), 1.13 (d, J=6.9 Hz, 6H).

Intermediate C10

Synthesis of 2,4-dichloro-6-hydroxy-3-(3-isopropyl-4-(methoxymethoxy)benzyl)benzonitrile (Intermediate C10)

C10

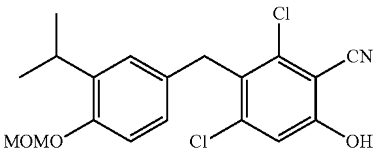

To a mixture of Intermediate C9 (50 mg, 88 μmol), $Pd_2(dba)_3$ (10 mg, 18 μmol) and dppf (8 mg, 8 μmol) in NMP (1 mL) was added $Zn(CN)_2$ (21 mg, 176 μmol). The mixture was heated to 150° C. and stirred for 1 h under microwave condition. The mixture was cooled down to rt. Water (20 mL) was added and the mixture was extracted with EtOAc (15 mL*3). The combined organic phase was washed by brine (30 mL), dried over $Na_2SO_4$ and purified by Prep-TLC (pet. ether/EtOAc=2/1) to afford Intermediate C10 (30 mg, 90% yield) as a white solid.

$^1$H NMR (400 MHz, DMSO-$d_6$) δ 12.01 (s, 1H), 7.10 (s, 1H), 7.06 (d, J=2.3 Hz, 1H), 6.91 (d, J=8.4 Hz, 1H), 6.77 (dd, J=8.4, 2.3 Hz, 1H), 5.16 (s, 2H), 4.11 (s, 2H), 3.36 (s, 3H), 3.26-3.18 (m, 1H), 1.14 (d, J=7.0 Hz, 6H).

Intermediate D1

Synthesis of 2-bromo-4-(difluoromethoxy)-1-fluorobenzene (Intermediate D1)

D1

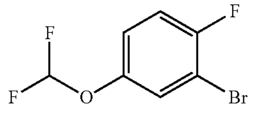

A mixture of sodium chlorodifluoroacetate (1.0 g, 5.2 mmol), 3-bromo-4-fluorophenol (1.60 g, 10.5 mmol) and $K_2CO_3$ (868 mg, 6.3 mmol) in DMF (10 mL) was stirred at 100° C. for 2 h. The mixture was cooled to rt. Concentrated HCl (1.5 ml) and water (3 mL) were added and the mixture was stirred at rt for 1 h. The mixture was cooled to 0° C. NaOH (4M, 5 mL) and water (25 mL) were added, and the mixture was extracted with $Et_2O$ (5 mL*3). The organic layer was washed with brine (15 ml), dried over $Na_2SO_4$ and purified by silica gel column chromatography (pet. ether/EtOAc=200/1 to 100/1) to afford Intermediate D1 (150 mg, 11% yield) as a colorless oil.

TLC: Pet. ether/EtOAc=100/1 (v/v), Rf=0.55

$^1$H NMR: (400 MHz, DMSO-$d_6$) δ 7.62 (dd, J=6.0, 3.2 Hz, 1H), 7.46 (t, J=8.8 Hz, 1H), 7.28 (dt, J=9.2, 3.6 Hz, 1H), 7.24 (t, J=73.6 Hz, 1H).

$^{19}$F NMR: (376 MHz, DMSO-$d_6$) δ −82.81, −112.84.

Intermediate D2

Synthesis of 2-(5-(difluoromethoxy)-2-fluorophenyl)-4,4,5,5-tetramethyl-1,3,2-dioxaborolane (Intermediate D2)

D2

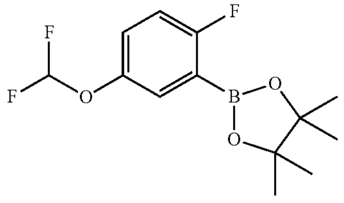

To a mixture of Intermediate D1 (150 mg, 622 umol), bis(pinacolato)diboron (175 mg, 684 umol) and Pd(dppf)$Cl_2$·$CH_2Cl_2$ (25 mg, 31 umol) in 1,4-dioxane (5.0 mL) at rt was added potassium acetate (183 mg, 1.8 mmol). The mixture was heated to 110° C. for 3 h. The mixture was cooled to rt and filtered. The filtrate was concentrated in vacuo to afford crude Intermediate D2 (175 mg, 97% yield) which was used without further purification.

TLC: EtOAc/pet. ether=1/10 (v/v), Rf=0.65

Example 1

Synthesis of methyl 2-(4-(2-fluoro-4-hydroxy-3-isopropylbenzyl)-3,5-dimethylphenoxy)acetate (Compound 1)

1

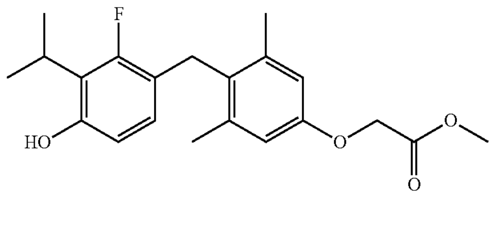

To a solution of Intermediate B2 (381 mg, 2.3 mmol) and Intermediate A3 (200 mg, 0.78 mmol) in DCE (5.0 mL) was added $ZnCl_2$ (1M/THF) (1.9 mmol, 1.9 mL). The mixture was stirred at 85° C. overnight. The mixture was cooled to rt; water (20 mL) was added and the resultant mixture was extracted with DCM (10 mL*3). The combined organic phase was washed with brine (20 mL), dried over $Na_2SO_4$, concentrated in vacuo and purified by Prep-TLC (EtOAc/pet. ether=1/5) to afford Compound 1 (35 mg, 12% yield) as a light yellow oil.

TLC: EtOAc/pet. ether=1/5 (v/v), $R_f$=0.30

Example 2

Synthesis of 2-(4-(2-fluoro-4-hydroxy-3-isopropylbenzyl)-3,5-dimethylphenoxy)acetic acid (Compound 2)

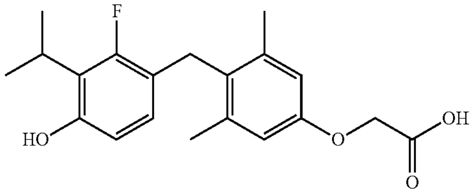

2

To a solution of Compound 1 (35 mg, 94 umol) in THF/$H_2O$ (2.0 mL/0.5 mL) at rt was added LiOH·$H_2O$ (12 mg, 280 umol). The mixture was stirred at rt for 1 h. The mixture was diluted with water (30 mL), acidified with 1N HCl to pH~3-4, and extracted with EtOAc (15 mL*3). The combined organic phase was washed with brine (30 mL), dried over $Na_2SO_4$ and concentrated in vacuo. The crude product was purified by Prep-HPLC to afford Compound 2 (10 mg, 30% yield) as a white solid.

TLC: MeOH/DCM=1/10 (v/v), Rf=0.30

LCMS: RT=4.025 min, [M−1]=345.1

$^1$H NMR: (400 MHz, DMSO-$d_6$) δ 9.43 (s, 1H), 6.62 (s, 2H), 6.43 (d, J=8.4 Hz, 1H), 6.14 (d, J=8.8 Hz, 1H), 4.62 (s, 2H), 3.74 (s, 2H), 2.11 (s, 6H), 1.26 (d, J=7.0 Hz, 6H).

Example 3

Synthesis of 2-(4-((3'-(difluoromethoxy)-2-fluoro-6-hydroxy-[1,1'-biphenyl]-3-yl)methyl)-3,5-dimethylphenoxy)acetic acid (Compound 3)

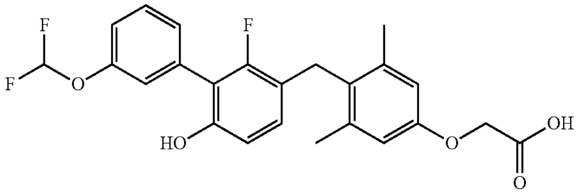

3

To a solution of Intermediate C1 (136 mg, 0.50 mmol) and Intermediate B3 (100 mg, 0.25 mmol) in 1,4-dioxane (4 mL) at rt were added Pd(dppf)$Cl_2$ (18 mg, 0.03 mmol) and $NaHCO_3$ (2N) (0.75 mmol, 0.4 mL). The reaction was heated under $N_2$ to 80° C. overnight. LiOH·$H_2O$ (32 mg, 0.75 mmol) was added, and the mixture was stirred at rt for 30 min. The reaction mixture was diluted with EtOAc (10 mL), and the pH was adjusted to pH~4 with 1N HCl. The aqueous layer was extracted with EtOAc (20 mL*2). The combined organic layer was washed with brine (20 mL), dried over $Na_2SO_4$ and concentrated in vacuo. The crude product was purified by Prep-HPLC to afford Compound 3 (20 mg, 17.8% yield) as a white solid.

TLC: DCM/MeOH=10/1 (v/v), Rf=0.2

LCMS: RT=3.752 min, [M−1]=445.1

1H NMR: (400 MHz, DMSO-d6) δ 9.96 (s, 1H), 7.46 (d, J=7.2 Hz, 1H), 7.27 (d, J=0.4 Hz, 1H), 7.26 (t, J=92.8, 1H), 7.19 (s, 1H), 7.16 (d, J=8.0 Hz, 1H), 6.65 (d, J=80 Hz, 1H), 6.57 (s, 2H), 6.37 (t, J=8.8 Hz, 1H), 4.25 (s, 2H), 3.79 (s, 2H), 2.13 (s, 6H).

Example 4

Synthesis of methyl 2-(4-(2-fluoro-3-(1-(4-fluorophenyl)vinyl)-4-hydroxybenzyl)-3,5-dimethylphenoxy)acetate (Compound 4)

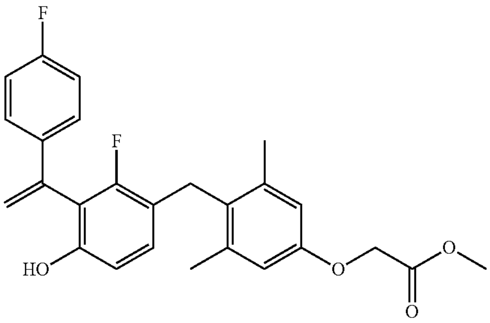

4

A solution of Intermediate B5 (234 mg, 944 umol), Intermediate C1 (250 mg, 629 umol), Pd(dppf)$Cl_2$ (46 mg, 63 umol) and $NaHCO_3$(aq) (2M, 1 mL) in 1,4-dioxane (5 mL) was stirred at 80° C. overnight. The mixture was cooled to rt, and concentrated in vacuo. Water (30 mL) was added, and the mixture was extracted with EtOAc (25 mL*2). The combined organic phase was washed with brine (50 mL), dried over $Na_2SO_4$, concentrated in vacuo and purified by Prep-TLC (DCM/MeOH=10/1) to afford Compound 4 (100 mg, 36.2% yield) as a yellow solid.

TLC: EtOAc/pet. ether=1/5 (v/v), Rf=0.55

Example 5

Synthesis of 2-(4-(2-fluoro-3-(1-(4-fluorophenyl)vinyl)-4-hydroxybenzyl)-3,5-dimethylphenoxy)acetic acid (Compound 5)

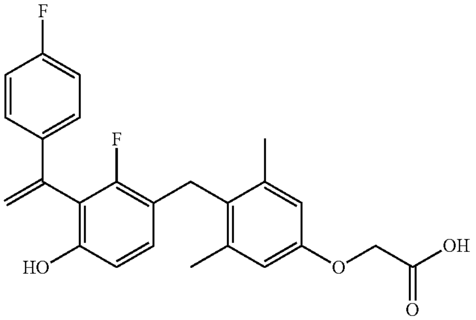

5

A solution of Compound 4 (100 mg, 228 umol) and LiOH·$H_2O$ (48 mg, 1.14 mmol) in water (1 mL) and methanol (3 mL) was stirred at rt for 1 h. The mixture was acidified to pH~5 with 1N HCl, water (30 mL) was added, and the mixture was extracted with EtOAc (25 mL*2). The combined organic phase was washed with brine (50 mL), dried over $Na_2SO_4$, concentrated in vacuo and purified by Prep-TLC (DCM/MeOH=10/1) to afford Compound 5 (50 mg, 51.6% yield) as a white solid.

TLC: EtOAc/pet. ether=1/5 (v/v), $R_f$=0

$^1$H NMR: (400 MHz, DMSO-$d_6$) δ 9.48 (s, 1H), 7.60-7.45 (m, 3H), 7.32 (dd, J=8.4, 5.5 Hz, 2H), 7.15 (t, J=8.7 Hz, 2H), 6.62 (s, 2H), 6.56 (d, J=8.6 Hz, 1H), 6.37 (t, J=8.6 Hz, 1H), 5.97 (s, 1H), 5.23 (s, 1H), 4.57 (s, 2H), 3.77 (s, 2H), 2.15 (s, 6H).

Example 6

Synthesis of 2-(4-(2-fluoro-3-(1-(4-fluorophenyl)ethyl)-4-hydroxybenzyl)-3,5-dimethylphenoxy)acetic acid (Compound 6)

6

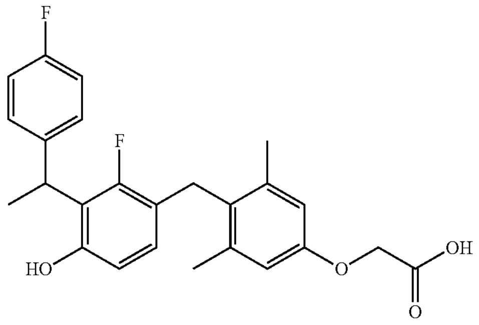

A solution of Compound 5 (50 mg, 118 umol), and Pd/C (5%) (50 mg) in MeOH (5 mL) was stirred at 50° C. under $H_2$ atmosphere overnight. The mixture was cooled to rt, filtered and concentrated in vacuo, then purified by Prep-HPLC to afford Compound 6 (20 mg, 39.8% yield) as a white solid.

TLC: MeOH/DCM=1/10 (v/v), Rf=0.30

LCMS: RT=2.264 min, [M−1]=425.1

$^1$H NMR: (400 MHz, DMSO-$d_6$) δ 12.91 (s, 1H), 9.62 (s, 1H), 7.32-7.25 (m, 2H), 7.12-7.04 (m, 2H), 6.61 (s, 2H), 6.49 (d, J=8.4 Hz, 1H), 6.20 (t, J=8.6 Hz, 1H), 4.60 (s, 3H), 3.71 (d, J=4.6 Hz, 2H), 2.09 (s, 6H), 1.64 (dd, J=7.4, 1.2 Hz, 3H).

Example 7

Synthesis of ethyl 2-(3-bromo-4-(2-fluoro-4-hydroxy-3-isopropylbenzyl)-5-methylphenoxy)acetate (Compound 7)

7

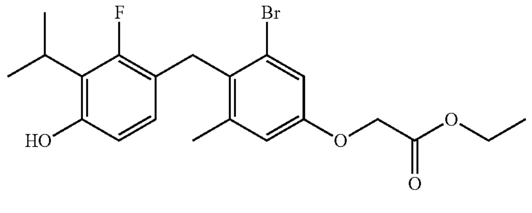

To a solution of Intermediate B2 (720 mg, 4.66 mmol) in DCE (5 mL) at rt were added Intermediate A6 (500 mg, 1.55 mmol) and $ZnCl_2$ in THF (3.11 mL of 1.0M, 3.11 mmol). The reaction was heated to 90° C. overnight. The reaction mixture was diluted with DCM (20 mL), washed with brine (10 mL*2), dried over $Na_2SO_4$, and concentrated in vacuo. The crude product was purified by silica gel column chromatography (pet. ether/EtOAc=10/1) to afford Compound 7 (250 mg, 36.6% yield) as a colorless oil.

TLC: Pet. ether/EtOAc=5/1 (v/v), Rf=0.21

$^1$H NMR: (400 MHz, DMSO-$d_6$) δ 9.48 (s, 1H), 7.08 (d, J=2.7 Hz, 1H), 6.88 (d, J=2.7 Hz, 1H), 6.45 (d, J=8.3 Hz, 1H), 6.17 (t, J=8.6 Hz, 1H), 4.80 (s, 2H), 4.18 (q, J=7.1 Hz, 2H), 3.93 (s, 2H), 3.38 (p, J=7.1 Hz, 1H), 2.17 (s, 3H), 1.26 (d, J=7.1 Hz, 6H), 1.24-1.18 (m, 3H).

Example 8

Synthesis of 2-(4-(2-fluoro-4-hydroxy-3-isopropylbenzyl)-3-methyl-5-vinylphenoxy)acetic acid (Compound 8)

8

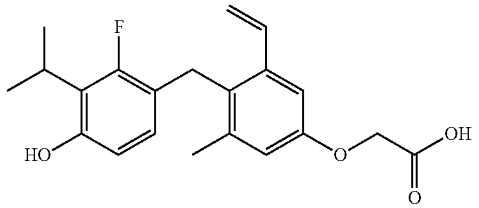

To a solution of Compound 7 (180 mg, 0.4 mmol) and vinyl boron(pinacolate) (92 mg, 0.6 mmol) in water (0.5 mL)/1, 4-dioxane (3 mL) at rt were added Pd(dppf)$Cl_2$ (32 mg, 0.04 mmol) and $K_2CO_3$ (110 mg, 0.8 mmol). The reaction was heated to 120° C. for 2 h in a microwave. The mixture was cooled to rt and NaOH (48 mg, 1.2 mmol) was added. The mixture was stirred at rt for 0.5 h. The reaction mixture was diluted with EtOAc (10 mL), and filtered. The filtrate was acidified to pH~3-4 with 1N HCl, washed with water (5 mL*2), and brine (5 mL*2), dried over $Na_2SO_4$, and concentrated in vacuo. The crude product was purified by Prep-TLC (MeOH/DCM=1/10) to afford Compound 8 (146 mg, 99.4% yield) as a yellow oil.

TLC: DCM/MeOH=1/10 (v/v), Rf=0.24

Example 9

Synthesis of 2-(3-ethyl-4-(2-fluoro-4-hydroxy-3-isopropylbenzyl)-5-methylphenoxy)acetic acid (Compound 9)

9

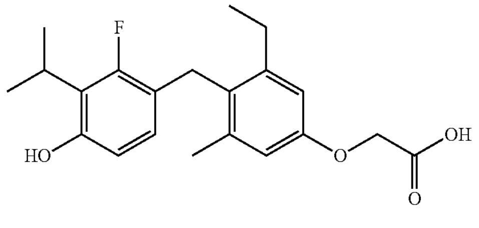

To a solution of Compound 8 (146 mg, 0.4 mmol) in THF (3 mL) at rt was added Pd/C (50 mg); the mixture was stirred overnight at rt under $H_2$ atmosphere. The reaction mixture was filtered through a pad of Celite. The filtrate was concentrated in vacuo and purified by Prep-HPLC to afford Compound 9 (70 mg, 48.6% yield) as a white solid.

TLC: DCM/MeOH=10/1 (v/v), Rf=0.48

LCMS: RT=2.011 min, [M−1]=359.

$^1$H NMR: (400 MHz, DMSO-$d_6$) δ 9.41 (s, 1H), 6.62 (s, 2H), 6.43 (d, J=8.3 Hz, 1H), 6.11 (t, J=8.6 Hz, 1H), 4.61 (s, 2H), 3.76 (s, 2H), 3.47-3.34 (m, 1H), 2.45 (q, J=8.3, 7.5 Hz, 3H), 2.10 (s, 3H), 1.27 (d, J=7.2 Hz, 6H), 1.02 (t, J=7.5 Hz, 3H).

Example 10

Synthesis of 2-(3-ethyl-4-(2-fluoro-4-hydroxy-3-isopropylbenzyl)-5-methylphenoxy)-N-methylacetamide (Compound 10)

10

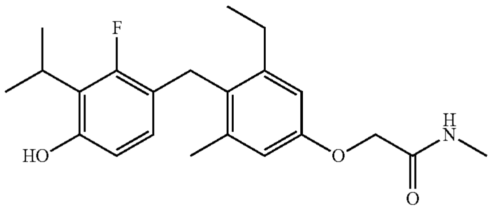

To a solution of Compound 9 (50 mg, 0.14 mmol) in DCM (4 mL) at rt was added oxalyl chloride (18 mg, 0.14 mmol) and a drop of DMF (cat). The mixture was stirred at rt for 1 h, then concentrated in vacuo. The crude acid chloride (50 mg, 0.14 mmol) was dissolved in THF (1 mL0 and added dropwise to a solution of methylamine (12 mg, 0.39 mmol) in THF (3 mL) at 0° C. The mixture was warmed to rt and stirred for 1 h, then concentrated in vacuo. The crude product was purified by Prep-HPLC to afford Compound 10 (20 mg, 40.6% yield) as an off-white solid.

TLC: MeOH/DCM=1/10 (v/v), Rf=0.68

$^1$H NMR: (400 MHz, DMSO-$d_6$) δ 9.42 (s, 1H), 7.99 (s, 1H), 6.69 (q, J=2.8 Hz, 1H), 6.61 (s, 1H), 6.42 (d, J=8.4 Hz, 1H), 6.11 (t, J=8.4 Hz, 1H), 4.56 (s, 1H), 4.42 (s, 1H), 3.76 (d, J=3.6 Hz, 2H), 3.44-3.37 (m, 1H), 2.66 (d, J=4.8 Hz, 2H), 2.45 (dd, J=7.6, 5.2 Hz, 2H), 2.10 (d, J=5.6 Hz, 3H), 1.27 (d, J=7.2 Hz, 6H), 1.03 (td, J=7.6, 4.8 Hz, 3H).

$^{19}$F NMR: (376 MHz, DMSO-$d_6$) δ −120.54, −120.63.

Example 11

Synthesis of ethyl 2-(4-(2-fluoro-4-hydroxy-3-isopropylbenzyl)-3-methyl-5-(prop-1-en-2-yl)phenoxy) acetate (Compound 11)

11

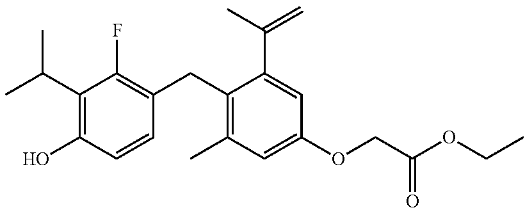

To a solution of Intermediate C2 (530 mg, 1.21 mmol) in 1,4-dioxane (10 mL) at rt were added potassium isopropenyltrifluoroborate (357 mg, 2.42 mmol), $Cs_2CO_3$ (786 mg, 2.42 mmol) and Pd(dppf)$Cl_2$ (88 mg, 0.06 mmol). The reaction was stirred at 120° C. under $N_2$(g) in a microwave for 2 h. The resulting solution of Compound 11 was used without further purification.

TLC: EtOAc/pet. ether=1/5 (v/v), Rf=0.35

LCMS: RT=3.26 min, [M−1]=399.2

Example 12

Synthesis of 2-(4-(2-fluoro-4-hydroxy-3-isopropylbenzyl)-3-methyl-5-(prop-1-en-2-yl)phenoxy)acetic acid (Compound 12)

12

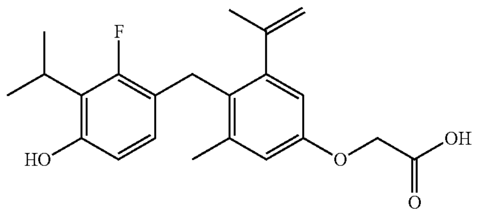

To a solution of Compound 11 (500 mg, 1.25 mmol) in water (5 mL)/THF (1 mL) at rt was added NaOH (149 mg, 3.75 mmol); the resultant mixture was stirred at rt for 1 h. The reaction was acidified to pH~3-4 with 2N HCl and extracted with DCM (30 mL*3). The combined organic phase was concentrated in vacuo and purified by Prep-HPLC to afford Compound 12 (330 mg, 70.9% yield).

TLC: Pet. ether/EtOAc=1/5 (v/v), Rf=0

LCMS: RT=4.09 min, [M−1]=371.1

$^1$H NMR: (400 MHz, DMSO) δ 9.43 (s, 1H), 6.69 (d, J=2.8 Hz, 1H), 6.51 (d, J=2.7 Hz, 1H), 6.44 (d, J=8.4 Hz, 1H), 6.15 (t, J=8.6 Hz, 1H), 5.10-5.02 (m, 1H), 4.64 (d, J=2.3 Hz, 1H), 4.58 (s, 2H), 3.74 (s, 2H), 3.39 (s, 1H), 2.05 (s, 3H), 1.84 (s, 3H), 1.25 (d, J=7.1 Hz, 6H).

Example 13

Synthesis of 2-(4-(2-fluoro-4-hydroxy-3-isopropylbenzyl)-3-isopropyl-5-methylphenoxy)acetic acid (Compound 13)

13

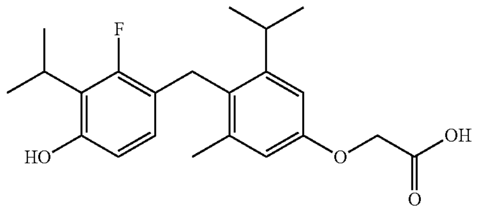

To a solution of Compound 12 (270 mg, 0.72 mmol) in MeOH (5 mL) at rt was added Pd/C (27 mg), the mixture was stirred under $H_2$ atmosphere at 70° C. for 16 h. The reaction was cooled, filtered, concentrated and purified by Prep-HPLC to afford Compound 13 (100 mg, 37.1% yield).

TLC: DCM/MeOH=20/1 (v/v), Rf=0.35

LCMS: RT=4.16 min, [M−1]=373.2

$^1$H NMR: (400 MHz, DMSO) δ 12.88 (s, 1H), 9.42 (d, J=1.4 Hz, 1H), 6.69 (d, J=2.8 Hz, 1H), 6.60 (d, J=2.7 Hz, 1H), 6.43 (d, J=8.3 Hz, 1H), 6.11 (d, J=8.6 Hz, 1H), 4.62 (s, 2H), 3.78 (s, 2H), 3.45-3.36 (m, 1H), 2.97-2.84 (m, 1H), 2.11 (s, 3H), 1.31-1.24 (m, 6H), 1.05 (d, J=6.8 Hz, 6H).

Example 14

Synthesis of methyl 2-(3,5-dichloro-4-(2-fluoro-4-hydroxy-3-isopropylbenzyl)phenoxy)acetate (Compound 14)

14

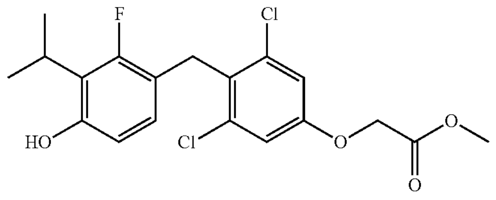

To a solution of Intermediate B2 (23.0 g, 149 mmol) and Intermediate A10 (15.0 g, 53 mmol) in DCE (300 mL) was added $ZnCl_2$ (1M in THF) (133 mmol, 133 mL). The mixture was stirred at 85° C. overnight. The mixture was cooled to rt; water (150 mL) was added, and the resultant mixture was extracted with DCM (100 mL*3). The combined organic phase was washed with brine (100 mL), dried over $Na_2SO_4$, concentrated in vacuo and purified by silica gel column chromatography (EtOAc/pet. ether=1/30 to 1/10) to afford Compound 14 (6.0 g, 28% yield) as a colorless oil.

TLC: EtOAc/pet. ether=1/5 (v/v), $R_f$=0.25

LCMS: RT=4.529 min; [M−1]=398.9

$^1$H NMR: (400 MHz, DMSO-$d_6$) δ 9.54 (s, 1H), 7.18 (s, 2H), 6.48 (d, J=8.4 Hz, 1H), 6.27 (t, J=8.4 Hz, 1H), 4.92 (s, 2H), 4.02 (s, 2H), 3.72 (s, 3H), 3.39 (m, 1H), 1.26 (d, J=6.8 Hz, 6H).

Example 15

Synthesis of 2-(3,5-dichloro-4-(2-fluoro-4-hydroxy-3-isopropylbenzyl)phenoxy)acetic acid (Compound 15)

15

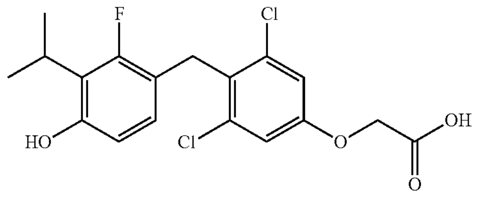

To a solution of Compound 14 (6.0 g, 15 mmol) in THF/$H_2O$ (60 mL/10 mL) at rt was added LiOH·$H_2O$ (1.9 g, 45 mmol). The mixture was stirred at rt for 1 h. The mixture was diluted with water (30 mL), acidified with 1N HCl to pH~3-4 and extracted with EtOAc (15 mL*3). The combined organic phase was washed with brine (30 mL), dried over $Na_2SO_4$ and concentrated in vacuo. The crude product was purified by Prep-HPLC to afford Compound 15 (3.0 g, 17% yield) as a white solid.

TLC: MeOH/DCM=1/10 (v/v), Rf=0.30

LCMS: RT=3.974 min; [M−1]=385.0

$^1$H NMR: (400 MHz, DMSO-$d_6$) δ 13.14 (s, 1H), 9.54 (s, 1H), 7.14 (s, 2H), 6.48 (d, J=8.4 Hz, 1H), 6.27 (t, J=8.4 Hz, 1H), 4.79 (s, 2H), 4.02 (s, 2H), 3.40 (m, 1H), 1.26 (d, J=7.2 Hz, 6H).

$^{19}$F NMR: (376 MHz, DMSO-$d_6$) δ −120.25.

Example 16

Synthesis of 2-(3,5-dichloro-4-(2-fluoro-4-hydroxy-3-isopropylbenzyl)phenoxy)-N-methylacetamide (Compound 16)

16

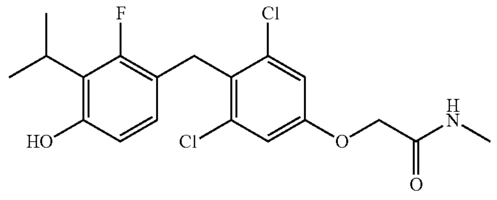

To a mixture of Compound 15 (2.0 g, 5.2 mmol) in DCM (20 mL) was added DMF (cat). The mixture was cooled to 0° C. and oxalyl chloride (1.3 g, 10.4 mmol) was added. The mixture was stirred at rt for 30 min, then concentrated in vacuo to afford the corresponding acid chloride (2.0 g, 95% yield) as a yellow solid. This material was dissolved in DCM (20 mL) and added dropwise to $CH_3NH_2$ (2M/THF) (4.9 mL, 9.8 mmol). The mixture was stirred at rt for 1 h. Water (30 mL) was added and the resultant mixture was extracted with DCM (20 mL*3). The combined organic phase was washed with brine (50 mL), dried over $Na_2SO_4$, concentrated in vacuo and purified by Prep-HPLC to afford Compound 16 (1.1 g, 55% yield) as a white solid.

TLC: DCM/MeOH=10/1 (v/v), Rf=0.45

LCMS: RT=3.974 min; [M−1]=398.0

$^1$H NMR: (400 MHz, DMSO-$d_6$) δ 9.54 (s, 1H), 8.09 (d, J=4.4 Hz, 1H), 7.17 (s, 2H), 6.48 (d, J=8.4 Hz, 1H), 6.28 (t, J=8.4 Hz, 1H), 4.56 (s, 2H), 4.03 (s, 2H), 3.41 (m, 1H), 2.67 (d, J=4.4 Hz, 3H), 1.26 (d, J=7.4 Hz, 6H).

$^{19}$F NMR: (376 MHz, DMSO-$d_6$) δ −120.23.

Example 17

Synthesis of 2-(3,5-dichloro-4-(2-fluoro-4-hydroxy-3-isopropylbenzyl)phenoxy)-N,N-dimethylacetamide (Compound 17)

17

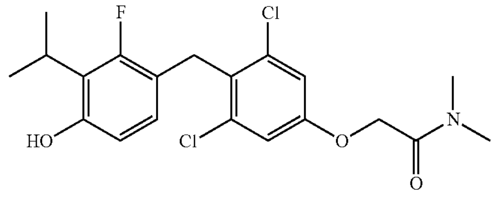

To a mixture of Compound 15 (2.0 g, 5.2 mmol) in DCM (20 mL) was added DMF (cat). The mixture was cooled to 0° C. and oxalyl chloride (1.3 g, 10.4 mmol) was added. The mixture was stirred at rt for 30 min, then concentrated in vacuo to afford the corresponding acid chloride (2.0 g, 95% yield) as a yellow solid. A sample of this material (150 mg, 370 umol) was dissolved in DCM (20 mL) and added dropwise to dimethylamine (2M/THF) (0.37 mL, 740 umol). The mixture was stirred at rt for 1 h. Water (10 mL) was added and resultant mixture was extracted with DCM (10 mL*3). The combined organic phase was washed with brine (20 mL), dried over $Na_2SO_4$, concentrated in vacuo and purified by Prep-HPLC to afford Compound 17 (70 mg, 45% yield) as a white solid.

TLC: DCM/MeOH=10/1 (v/v), Rf=0.45

LCMS: RT=4.109 min; [M−1]=412.1

$^1H$ NMR: (400 MHz, DMSO-$d_6$) δ 9.52 (s, 1H), 7.12 (s, 2H), 6.48 (d, J=8.4 Hz, 1H), 6.27 (t, J=8.6 Hz, 1H), 4.92 (s, 2H), 4.02 (s, 2H), 3.42-3.37 (m, 1H), 2.97 (s, 3H), 2.85 (s, 3H), 1.26 (d, J=7.2 Hz, 6H).

$^{19}F$ NMR: (376 MHz, DMSO-$d_6$) δ −120.28.

Example 18

Synthesis of 2-(3,5-dichloro-4-(2-fluoro-4-hydroxy-3-isopropylbenzyl)phenoxy)-N-ethylacetamide (Compound 18)

18

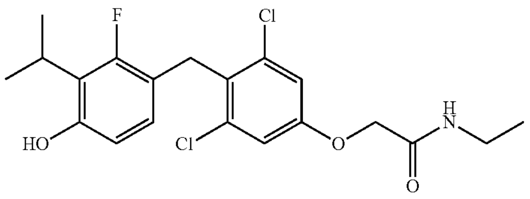

To a solution of Compound 15 (70 mg, 181 umol) in DCM (2 mL) was added oxalyl chloride (69 mg, 542 umol). The mixture was stirred at rt for 1 h. The mixture was concentrated in vacuo; ethylamine in THF (2 mL) was added, the mixture was stirred at rt for 10 min. The resultant solution was concentrated in vacuo and purified by Prep-TLC (DCM/MeOH=10/1) to afford Compound 18 (40 mg, 56.3% yield) as a white solid.

TLC: DCM/MeOH=10/1 (v/v), Rf=0.56

LCMS: RT=2.545 min, [M−1]=412.1

$^1H$ NMR: (400 MHz, DMSO-$d_6$) δ 9.52 (d, J=1.5 Hz, 1H), 8.14 (t, J=5.7 Hz, 1H), 7.16 (s, 2H), 6.47 (d, J=8.3 Hz, 1H), 6.27 (t, J=8.6 Hz, 1H), 4.54 (s, 2H), 4.02 (s, 2H), 3.42-3.35 (m, 1H), 3.20-3.10 (m, 2H), 1.26 (d, J=7.2 Hz, 6H), 1.04 (t, J=7.2 Hz, 3H).

Example 19

Synthesis of 2-(3,5-dichloro-4-(2-fluoro-4-hydroxy-3-isopropylbenzyl)phenoxy)-N-ethyl-N-methylacetamide (Compound 19)

19

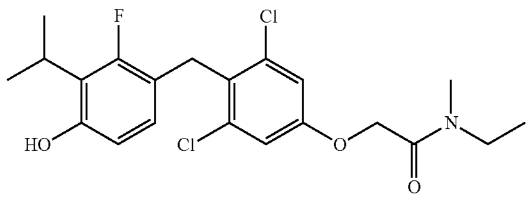

To a solution of Compound 15 (70 mg, 0.18 mmol) in DMF (3 mL) at rt were added HATU (103 mg, 0.27 mmol), DIEA (0.6 mL, 0.36 mmol) and N-methyl-N-ethylamine (0.5 mL, 0.54 mmol). The mixture was stirred at rt for 2 h, then diluted with water (10 mL) and extracted with EtOAc (3 mL*3). The combined organic phase was washed with brine (10 mL), dried over $Na_2SO_4$, and concentrated in vacuo. The crude product was purified by Prep-HPLC to afford Compound 19 (27 mg, 35% yield) as an off-white solid.

TLC: DCM/MeOH=10/1 (v/v), Rf=0.7

$^1H$ NMR: (400 MHz, DMSO-$d_6$) δ 9.56-9.50 (m, 1H), 7.10 (d, J=3.2 Hz, 2H), 6.48 (dd, J=8.4, 1.2 Hz, 1H), 6.27 (t, J=8.4 Hz, 1H), 4.91 (d, J=7.2 Hz, 2H), 4.01 (s, 2H), 3.40 (d, J=7.2 Hz, 1H), 3.30 (dd, J=7.6, 4.0 Hz, 2H), 2.95 (s, 1.5H), 2.82 (s, 1.5H), 1.33-1.20 (m, 6H), 1.14 (s, 1.5H), 1.01 (s, 1.5H).

$^{19}F$ NMR: (376 MHz, DMSO-$d_6$) δ −73.97, −120.27.

Example 20

Synthesis of 2-(3,5-dichloro-4-(2-fluoro-4-hydroxy-3-isopropylbenzyl)phenoxy)-N-(2-fluoroethyl)acetamide (Compound 20)

20

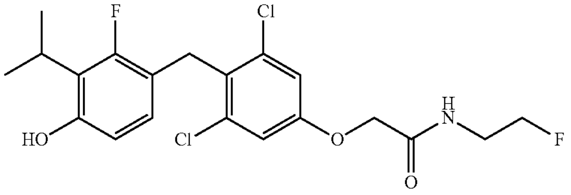

To a solution of Compound 15 (100 mg, 258 umol) in DMF (5 mL) at rt were added HATU (147 mg, 387 umol), DIEA (67 mg, 516 umol) and 2-fluoroethylamine (77 mg, 775 umol). The mixture was stirred at rt for 2 h, diluted with water (10 mL), and extracted with EtOAc (5 mL*3). The combined organic phase was washed with water (10 mL) and brine (10 mL), dried over $Na_2SO_4$, and concentrated in vacuo. The crude product was purified by Prep-TLC (MeOH/DCM=1/10) to afford Compound 20 (50 mg, 43% yield) as a white solid.

TLC: DCM/MeOH=15/1 (v/v), Rf=0.59

LCMS: RT=4.198 min, [M−1]=430.

$^1$H NMR: (400 MHz, DMSO-$d_6$) δ 9.52 (d, J=1.5 Hz, 1H), 8.37 (t, J=5.8 Hz, 1H), 7.17 (s, 2H), 6.47 (dd, J=8.5, 1.1 Hz, 1H), 6.27 (t, J=8.6 Hz, 1H), 4.60 (s, 2H), 4.52 (t, J=5.1 Hz, 1H), 4.40 (t, J=5.1 Hz, 1H), 4.02 (s, 2H), 3.48 (q, J=5.3 Hz, 1H), 3.44-3.38 (m, 1H), 3.38 (s, 1H), 1.29-1.22 (m, 6H).

Example 21

Synthesis of 2-(3,5-dichloro-4-(2-fluoro-4-hydroxy-3-isopropylbenzyl)phenoxy)-N-methoxyacetamide (Compound 21)

21

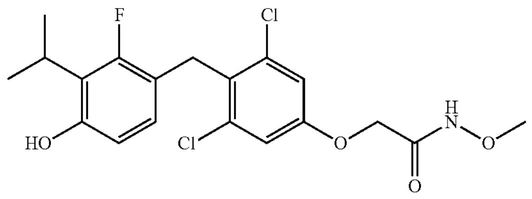

To a solution of Compound 15 (70 mg, 181 umol) in DMF (3 mL) at rt were added HATU (103 mg, 271 umol), DIEA (47 mg, 362 umol) and methoxylamine (45 mg, 542 umol). The mixture was stirred at rt for 2 h, diluted with water (10 mL), and extracted with EtOAc (5 mL*3). The combined organic phase was washed with water (10 mL*3) and brine (10 mL), dried over $Na_2SO_4$, and concentrated in vacuo. The crude product was purified by Prep-HPLC to afford Compound 21 (32 mg, 42% yield) as a white solid.

TLC: DCM/MeOH=15/1 (v/v), $R_f$=0.60

LCMS: RT=4.025 min, [M−1]=414.

$^1$H NMR: (400 MHz, DMSO-$d_6$) δ 11.46 (s, 1H), 9.53 (s, 1H), 7.16 (s, 2H), 6.47 (d, J=8.4 Hz, 1H), 6.26 (t, J=8.6 Hz, 1H), 4.58 (s, 2H), 4.02 (s, 2H), 3.63 (s, 3H), 3.41 (s, 1H), 1.25 (d, J=7.1 Hz, 6H).

Example 22

Synthesis of 2-(3,5-dichloro-4-(2-fluoro-4-hydroxy-3-isopropylbenzyl)phenoxy)-N-methoxy-N-methylacetamide (Compound 22)

22

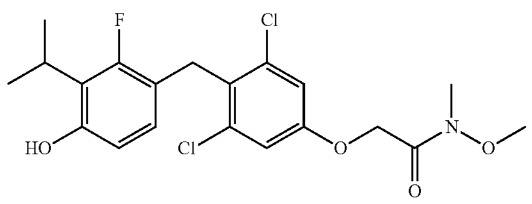

To a solution of Compound 15 (70 mg, 181 umol) in DMF (5 mL) at rt were added HATU (103 mg, 271 umol), DIEA (94 mg, 723 umol) and N,O-dimethylhydroxylamine (53 mg, 542 umol). The mixture was stirred at rt for 2 h, diluted with water (10 mL), and extracted with EtOAc (5 mL*3). The combined organic phase was washed with water (10 mL*3) and brine (10 mL), dried over $Na_2SO_4$, and concentrated in vacuo. The crude product was purified by Prep-HPLC to afford Compound 22 (20 mg, 26% yield) as a white solid.

TLC: DCM/MeOH=15/1 (v/v), $R_f$=0.55

LCMS: RT=4.394 min, [M−1]=428.

$^1$H NMR: (400 MHz, DMSO-$d_6$) δ 9.52 (d, J=1.5 Hz, 1H), 7.12 (s, 2H), 6.48 (d, J=8.4 Hz, 1H), 6.28 (t, J=8.5 Hz, 1H), 5.01 (s, 2H), 4.02 (s, 2H), 3.75 (s, 3H), 3.42-3.37 (m, 1H), 3.13 (s, 3H), 1.29-1.22 (m, 6H).

Example 23

Synthesis of 2-(3,5-dichloro-4-(2-fluoro-4-hydroxy-3-isopropylbenzyl)phenoxy)-N',N'-dimethylacetohydrazide (Compound 23)

23

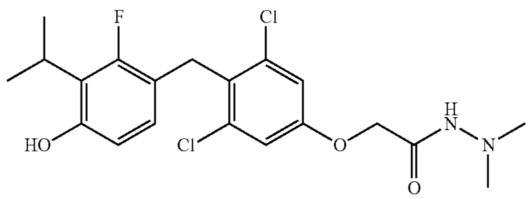

To a solution of Compound 15 (70 mg, 181 umol) in DMF (5 mL) at rt were added HATU (103 mg, 271 umol), DIEA (94 mg, 723 umol) and N,N-dimethylhydrazine (52 mg, 542 umol). The mixture was stirred at rt for 2 h, diluted with water (10 mL), and extracted with EtOAc (5 mL*3). The combined organic phase was washed with water (10 mL*3) and brine (10 mL), dried over $Na_2SO_4$, and concentrated in vacuo. The crude product was purified by Prep-HPLC to afford Compound 23 (12 mg, 15% yield) as a white solid.

TLC: DCM/MeOH=10/1 (v/v), $R_f$=0.65

LCMS: RT=4.031 min, [M−1]=427.

$^1$H NMR: (400 MHz, DMSO-$d_6$) δ 9.52 (d, J=1.5 Hz, 1H), 7.12 (s, 2H), 6.52-6.43 (m, 1H), 6.28 (t, J=8.6 Hz, 1H), 5.01 (s, 2H), 4.02 (s, 2H), 3.75 (s, 3H), 3.41-3.33 (m, 1H), 3.13 (s, 3H), 1.26 (d, J=7.1 Hz, 6H).

Example 24

Synthesis of 2-(3,5-dichloro-4-((3'-(difluoromethoxy)-2-fluoro-6-hydroxy-[1,1'-biphenyl]-3-Yl)methyl)phenoxy)acetic acid (Compound 24)

24

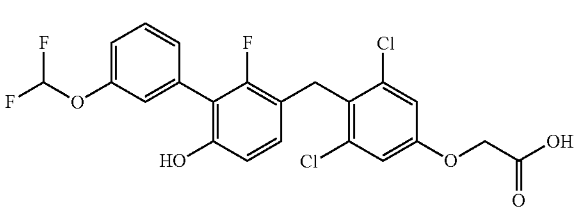

A mixture of Intermediate A11 (150 mg, 0.34 mmol), Intermediate B3 (138 mg, 0.51 mmol), Pd(dppf)$Cl_2$ (22 mg, 0.03 mmol) and $NaHCO_3$(2N) (0.51 mL, 1.02 mmol) in 1,4-dioxane (4 mL) was stirred at 85° C. under $N_2$ overnight.

LiOH·$H_2O$ (aqueous, 2M) (0.51 mL, 1.02 mmol) was added, and the mixture was stirred at rt for 1 h. The solution was adjusted to pH~4 with 1N HCl; the aqueous layer was extracted with EtOAc (20 mL*2). The organic layer was washed with brine (20 mL), dried over $Na_2SO_4$ and concentrated in vacuo. The residue was purified by Prep-HPLC (ACN/water=65:35, v/v) to afford Compound 24 (8 mg, 4.9% yield) as a white solid.

TLC: DCM/MeOH=10/1 (v/v), Rf=0.2

LCMS: RT=3.913 min, [M−1]=485.0

$^1$H NMR: (400 MHz, DMSO-$d_6$) δ 10.04 (s, 1H), 7.48-7.45 (m, 1H), 7.28 (d, J=4.4 Hz, 1H), 7.25 (t, J=62.0 Hz, 1H), 7.19-7.15 (m, 2H), 6.95 (s, 2H), 6.70 (d, J=8.6 Hz, 1H), 6.54 (t, J=8.8 Hz, 1H), 4.26 (s, 2H), 4.06 (s, 2H).

Example 25

Synthesis of 2-(3,5-dichloro-4-((2,2'-difluoro-6-hydroxy-5'-(trifluoromethyl)-[1,1'-biphenyl]-3-yl)methyl)phenoxy)acetic acid (Compound 25)

25

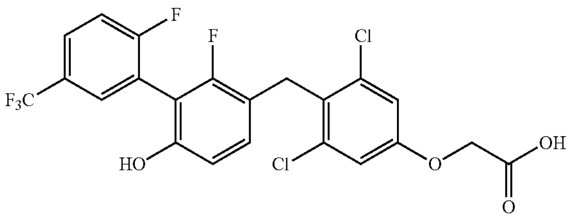

A mixture of 2-fluoro-5-trifluoromethylphenyl boronic acid (69 mg, 332 umol), Intermediate C3 (100 mg, 221 umol), $K_2CO_3$ (92 mg, 664 umol) and Pd(dppf)$Cl_2$ (16 mg, 22 umol) in 1,4-dioxane (2 mL) and water (0.5 mL) was stirred at 100° C. overnight. The mixture was cooled to rt; LiOH·$H_2O$ (28 mg, 664 umol) was added and the resultant mixture was stirred for 20 min. The mixture was acidified to pH~5 with 2N HCl; water. (30 mL) was added, and the mixture was extracted with EtOAc (25 mL*2). The combined organic layer was washed with brine (50 mL), dried over $Na_2SO_4$, concentrated in vacuo and purified by Prep-HPLC to afford Compound 25 (20 mg, 17.8% yield) as a white solid.

TLC: DCM/MeOH=10/1 (v/v), Rf=0.35

LCMS: RT=2.424 min, [M−1]=504.9

$^1$H NMR: (400 MHz, DMSO-$d_6$) δ 13.10 (s, 1H), 10.08 (d, J=1.7 Hz, 1H), 7.88-7.82 (m, 1H), 7.78 (dd, J=6.4, 2.4 Hz, 1H), 7.56 (t, J=9.0 Hz, 1H), 7.16 (s, 2H), 6.72 (d, J=8.6 Hz, 1H), 6.65 (t, J=8.6 Hz, 1H), 4.80 (s, 2H), 4.10 (s, 2H).

Example 26

Synthesis of 2-(3,5-dichloro-4-((5'-(difluoromethoxy)-2,2'-difluoro-6-hydroxy-[1,1'-biphenyl]-3-VI)methyl)phenoxy)acetic acid (Compound 26)

26

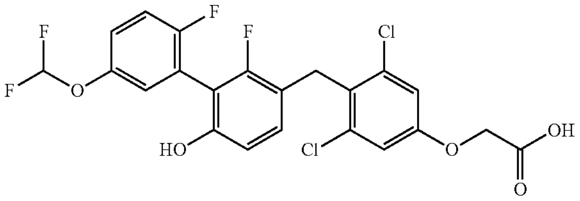

A mixture of Intermediate C3 (50 mg, 111 umol), Intermediate D2 (96 mg, 332 umol), Pd(dppf)$Cl_2$ (8 mg, 11 umol) and $K_2CO_3$ (46 mg, 332 umol) in water (0.3 mL) and 1,4-dioxane (2 mL) was microwaved at 140° C. for 2 h. The mixture was cooled to rt; LiOH·$H_2O$ (14 mg, 331.8 umol) was added and the resultant mixture was stirred for 20 min. The mixture was acidified to pH~5 with 2N HCl; water (30 mL) was added, and the mixture was extracted with EtOAc (25 mL*2). The combined organic phase was washed with brine (50 mL), dried over $Na_2SO_4$, concentrated in vacuo, and purified by Prep-TLC (DCM/MeOH=10/1) and Prep-HPLC to afford Compound 26 (7 mg, 13.4 umol, 12.1% yield) as a white solid.

TLC: DCM/MeOH=10/1 (v/v), Rf=0.35

LCMS: RT=2.050 min, [M−1]=502.9

$^1$H NMR: (400 MHz, DMSO-$d_6$) δ 13.12 (s, 1H), 9.99 (d, J=1.7 Hz, 1H), 7.36 (t, J=9.0 Hz, 1H), 7.23 (t, J=148.2 Hz, 1H), 7.28-7.19 (m, 2H), 7.16 (s, 2H), 6.70 (d, J=8.6 Hz, 1H), 6.62 (t, J=8.6 Hz, 1H), 4.80 (s, 2H), 4.09 (s, 2H).

Example 27

Synthesis of ethyl 2-(3,5-dichloro-4-(2-fluoro-3-(4-fluorobenzyl)-4-hydroxybenzyl)phenoxy)acetate (Compound 27)

27

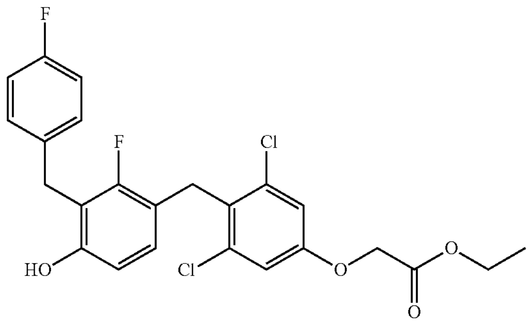

To a solution of Intermediate B6 (444 mg, 2.02 mmol) in DCE (5 mL) at rt were added Intermediate A11 (200 mg, 0.67 mmol) and $ZnCl_2$ (1.0M in THF, 1.5 mL, 1.5 mmol). The reaction was heated to 90° C. overnight. The reaction mixture was diluted with DCM (20 mL), washed with brine (10 mL*2), dried over $Na_2SO_4$, and concentrated in vacuo. The crude product was purified by silica gel column chromatography (pet. ether/EtOAc=5/1) to afford Compound 27 (160 mg, 49.4% yield) as a colorless oil.

TLC: Pet. ether/EtOAc=5/1 (v/v), Rf=0.21

$^1$H NMR: (400 MHz, DMSO-$d_6$) δ 9.81 (s, 1H), 7.23 (dd, J=8.5, 5.7 Hz, 2H), 7.16 (s, 2H), 7.11-7.03 (m, 2H), 6.56 (d, J=8.5 Hz, 1H), 6.40 (t, J=8.7 Hz, 1H), 4.89 (s, 2H), 4.18 (q, J=7.0 Hz, 3H), 4.04 (s, 2H), 3.88 (s, 2H), 1.23-1.18 (m, 3H).

Example 28

Synthesis of 2-(3,5-dichloro-4-(2-fluoro-3-(4-fluorobenzyl)-4-hydroxybenzyl)phenoxy)acetic acid (Compound 28)

28

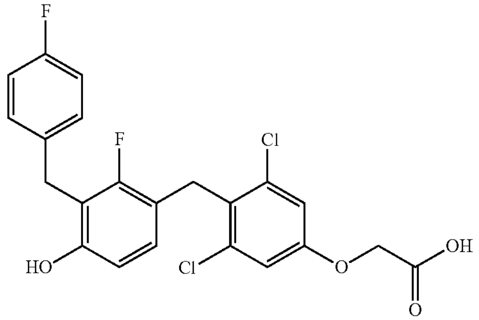

To a solution of Compound 27 (170 mg, 0.35 mmol) in THF (3 mL)/water (1 mL) at rt was added LiOH·$H_2O$ (18 mg, 0.42 mmol); the mixture was stirred at rt for 1 h. The reaction was acidified to pH~3-4 with 1N HCl, then extracted with EtOAc (20 mL). The combined organic phase was washed with brine (20 mL), dried over $Na_2SO_4$, concentrated in vacuo and purified by Prep-HPLC followed by Prep-TLC (DCM/MeOH=5/1) to afford Compound 28 (25 mg, 15% yield) as a white solid.

TLC: DCM/MeOH=5/1 (v/v), Rf=0.31

LCMS: RT=4.137 min, [M−1]=451.

$^1$H NMR: (400 MHz, DMSO-$d_6$) δ 9.81 (s, 1H), 7.27-7.18 (m, 2H), 7.11 (s, 2H), 7.10-7.04 (m, 2H), 6.57 (d, J=8.5 Hz, 1H), 6.40 (t, J=8.7 Hz, 1H), 4.75 (s, 2H), 4.03 (s, 2H), 3.88 (s, 2H).

Example 29

Synthesis of 2-(3,5-dichloro-4-(2-fluoro-3-(1-(4-fluorophenyl)vinyl)-4-hydroxybenzyl)phenoxy)acetic acid (Compound 29)

29

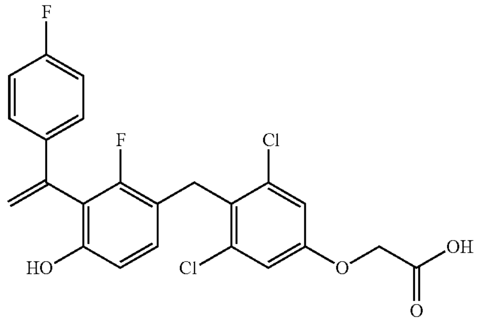

A solution of Intermediate B5 (494 mg, 1.99 mmol), Intermediate C3 (600 mg, 1.33 mmol), Pd(dppf)$Cl_2$ (97.11 mg, 0.13 mmol) and $NaHCO_3$ (2 M, 2 mL) in 1,4-dioxane (7 mL) was stirred at 85° C. overnight. The mixture was concentrated in vacuo. LiOH·$H_2O$ (167 mg, 3.99 mmol) in THF/$H_2O$ (5 mL/1 mL) was added, and the mixture was stirred at rt for 2 h. Water (30 mL) was added, the pH was adjusted to pH~5 with 2N HCl, and the resultant mixture was extracted with EtOAc (25 mL*2). The combined organic phase was washed with brine (50 mL), dried over $Na_2SO_4$, concentrated in vacuo and purified by Prep-TLC (DCM/MeOH=5/1) to afford Compound 29 (200 mg, 32.4% yield) as a yellow solid.

TLC: MeOH/DCM=1/10 (v/v), Rf=0.30

LCMS: RT=3.930 min, [M−1]=463.0

Example 30

Synthesis of 2-(3,5-dichloro-4-(2-fluoro-3-(1-(4-fluorophenyl)ethyl)-4-hydroxybenzyl)phenoxy)acetic acid (Compound 30)

30

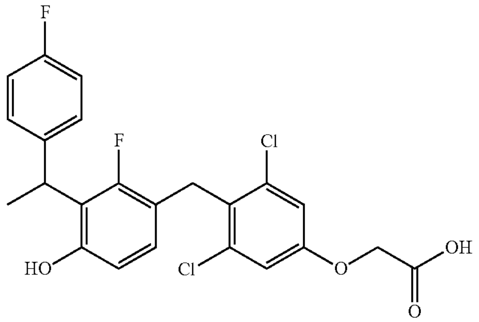

To a solution of Compound 29 (220 mg, 0.47 mmol) in methanol (5 mL) was added Pd/C (200 mg). The mixture was stirred at 60° C. under $H_2$ atmosphere overnight. The mixture was filtered, concentrated in vacuo, and purified by Prep-HPLC to give Compound 30 (20 mg, 9.1% yield) as a yellow solid.

TLC: MeOH/DCM=1/10 (v/v), Rf=0.33

$^1$H NMR: (400 MHz, DMSO-$d_6$) δ 9.74 (s, 1H), 7.28 (dd, J=8.5, 5.6 Hz, 2H), 7.15-7.03 (m, 4H), 6.53 (d, J=8.4 Hz, 1H), 6.35 (t, J=8.5 Hz, 1H), 4.76 (s, 2H), 4.60 (q, J=7.3 Hz, 1H), 4.07-3.92 (m, 2H), 1.63 (d, J=7.3 Hz, 3H).

LCMS: RT=4.060 min, [M−1]=465.0

Example 31

Synthesis of ethyl 2-(3,5-dichloro-4-(2-fluoro-3-(1-(4-fluorophenyl)propyl)-4-hydroxybenzyl)phenoxy)acetate (Compound 31)

31

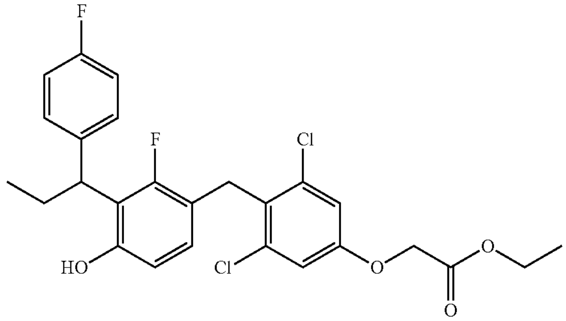

To a solution of Intermediate B8 (80 mg, 322 umol) in DCE (3 mL) at rt were added Intermediate A11 (32 mg, 107 umol) and $ZnCl_2$ (242 umol, 0.2 mL). The mixture was heated to reflux overnight. The mixture was diluted with DCM (5 mL), washed with brine (5 mL), dried over $Na_2SO_4$, and concentrated in vacuo. The crude product was purified by Prep-TLC (pet. ether/EtOAc=5/1) to afford Compound 31 (40 mg, 73% yield) as a colorless oil.

TLC: EtOAc/pet. ether=1/5 (v/v), $R_f$=0.36

Example 32

Synthesis of 2-(3,5-dichloro-4-(2-fluoro-3-(1-(4-fluorophenyl)propyl)-4-hydroxybenzyl)phenoxy) acetic acid (Compound 32)

32

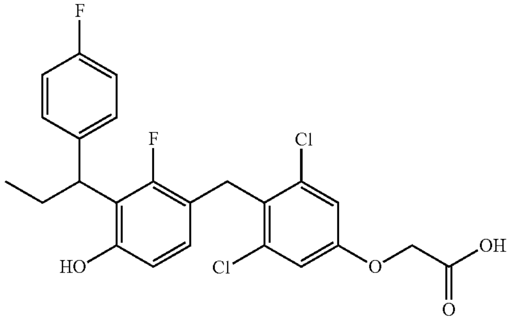

To a solution of Compound 31 (40 mg, 78.5 umol) in THF (5 mL) at rt was added $LiOH{\cdot}H_2O$ (10 mg, 236 umol) in water (1 mL). The mixture was stirred at rt for 2 h, then diluted with water (10 mL), acidified with HCl (1N) to pH~3-4, and extracted with EtOAc (5 mL*3). The combined organic phase was washed with brine (10 mL), dried over $Na_2SO_4$, and concentrated in vacuo. The crude product was purified by Prep-HPLC to afford Compound 32 (4 mg, 10% yield) as an off-white solid.

TLC: DCM/MeOH=10/1 (v/v), $R_f$=0.39

LCMS: RT=2.906 min, [M−1]=479.

$^1$H NMR: (400 MHz, DMSO-$d_6$) δ 13.04 (s, 1H), 9.72 (s, 1H), 7.33 (dd, J=8.5, 5.6 Hz, 2H), 7.12 (s, 2H), 7.11-7.05 (m, 2H), 6.52 (d, J=8.4 Hz, 1H), 6.35 (t, J=8.5 Hz, 1H), 4.76 (s, 2H), 4.33 (t, J=8.0 Hz, 1H), 4.08-3.93 (m, 2H), 2.14 (dd, J=13.5, 6.9 Hz, 2H), 0.83 (t, J=7.3 Hz, 3H).

Example 33

Synthesis of ethyl 2-(3,5-dichloro-4-(2-fluoro-3-(1-(4-fluorophenyl)butyl)-4-hydroxybenzyl)phenoxy) acetate (Compound 33)

33

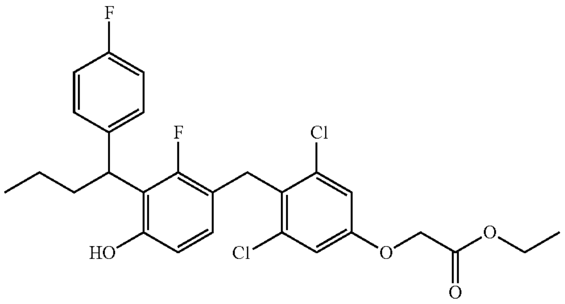

To a solution of Intermediate B10 (130 mg, 496 umol) in DCE (5 mL) at rt were added Intermediate A11 (50 mg, 165 umol) and $ZnCl_2$ (45 mg, 330 umol). The mixture was heated to reflux overnight. The mixture was diluted with DCM (5 mL), washed with brine (10 mL), dried over $Na_2SO_4$, and concentrated in vacuo. The crude product was purified by Prep-TLC (pet. ether/EtOAc=5/1) to afford Compound 33 (40 mg, 46% yield) as a colorless oil.

TLC: EtOAc/pet. ether=1/5 (v/v), $R_f$=0.36

Example 34

Synthesis of 2-(3,5-dichloro-4-(2-fluoro-3-(1-(4-fluorophenyl)butyl)-4-hydroxybenzyl)phenoxy)acetic acid (Compound 34)

34

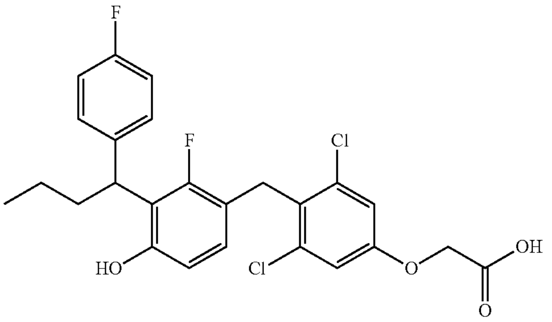

To a solution of Compound 33 (40 mg, 76 umol) in THF (5 mL) at rt was added $LiOH{\cdot}H_2O$ (10 mg, 229 umol) in water (1 mL). The mixture was stirred at rt for 2 h, diluted with water (10 mL), acidified with HCl (1N) to pH~3-4, and extracted with EtOAc (5 mL*3). The combined organic phase was washed with brine (10 mL), dried over $Na_2SO_4$, and concentrated in vacuo. The crude product was purified by Prep-HPLC to afford Compound 34 (5 mg, 13% yield) as an off-white solid.

TLC: DCM/MeOH=10/1 (v/v), $R_f$=0.39

LCMS: RT=3.242 min, [M−1]=493.

$^1$H NMR: (400 MHz, DMSO-$d_6$) δ 9.72 (s, 1H), 7.34 (d, J=8.2 Hz, 2H), 7.10 (d, J=16.5 Hz, 4H), 6.52 (d, J=8.6 Hz, 1H), 6.40-6.29 (m, 1H), 4.86-4.72 (m, 2H), 4.50-4.40 (m, 1H), 4.00 (s, 2H), 2.23-2.10 (m, 1H), 2.09-1.94 (m, 1H), 1.23 (s, 2H), 0.88 (t, J=7.5 Hz, 3H).

Example 35

Synthesis of ethyl 2-(3-chloro-4-(2-fluoro-4-hydroxy-3-isopropylbenzyl)-5-methylphenoxy)acetate (Compound 35)

35

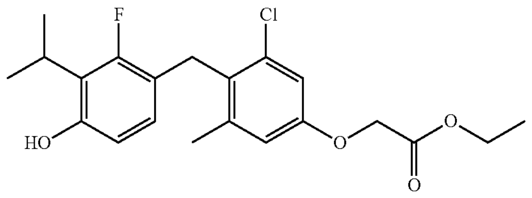

To a solution of Intermediate A14 (1.0 g, 2.21 mmol) in DCE (5 mL) at rt were added Intermediate B2 (0.6 g, 1.47 mmol) and $ZnCl_2$ (4.32 mL, 4.32 mmol). The mixture was heated to reflux overnight. The mixture was diluted with DCM (5 mL), washed with brine (5 mL), dried over $Na_2SO_4$, and concentrated in vacuo. The crude product was purified by silica gel column chromatography (pet. ether/EtOAc=20/1 to 5/1) to afford Compound 35 (320 mg, 37.5% yield) as a colorless oil.

TLC: EtOAc/pet. ether=1/5 (v/v), Rf=0.31

Example 36

Synthesis of 2-(3-chloro-4-(2-fluoro-4-hydroxy-3-isopropylbenzyl)-5-methylphenoxy)acetic acid (Compound 36)

36

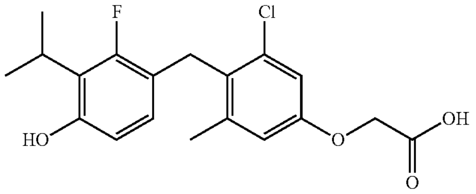

To a solution of Compound 35 (320 mg, 0.8 mmol) in THF (5 mL) at rt was added LiOH·$H_2O$ (102 mg, 2.43 mmol) in water (1 mL). The mixture was stirred at rt for 2 h, diluted with water (10 mL), acidified with HCl (1N) to pH~3-4, and extracted with EtOAc (5 mL*3). The combined organic phase was washed with brine (10 mL), dried over $Na_2SO_4$, and concentrated in vacuo. The crude product was purified by Prep-HPLC to afford Compound 36 (80 mg, 27% yield) as an off-white solid.

TLC: DCM/MeOH=10/1 (v/v), Rf=0.39

LCMS: RT=3.974 min, [M−1]=365.

$^1$H NMR: (400 MHz, DMSO-$d_6$) δ 9.62 (s, 1H), 6.79 (d, J=2.6 Hz, 1H), 6.72 (d, J=2.7 Hz, 1H), 6.47 (d, J=8.4 Hz, 1H), 6.20 (t, J=8.6 Hz, 1H), 4.36 (s, 2H), 3.88 (s, 2H), 3.45-3.33 (m, 1H), 2.13 (s, 3H), 1.26 (d, J=7.1 Hz, 6H).

Example 37

Synthesis of 2-(3-chloro-4-(2-fluoro-4-hydroxy-3-isopropylbenzyl)-5-methylphenoxy)-N-methylacetamide (Compound 37)

37

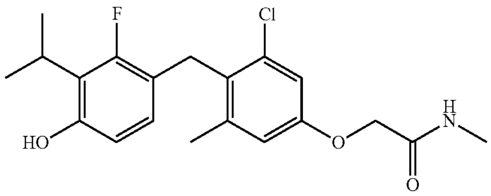

To a solution of Compound 36 (60 mg, 164 umol) in DCM (3 mL) was cooled to 0° C. Oxalyl chloride (42 mg, 327 umol) and DMF (cat) were added. The mixture was stirred at rt for 1 h, then concentrated in vacuo to give the crude acid chloride. One-third of this sample (20 mg, 52 umol) was dissolved in DCM (1 mL) and added dropwise to a solution of methylamine (1 mL) in DCM (3 mL) at 0° C. The mixture was stirred for 1 h at rt, then concentrated in vacuo. The crude product was purified by Prep-TLC (DCM/MeOH=15/1) to afford Compound 37 (15 mg, 76% yield) as an off-white solid.

LCMS: RT=3.969 min, [M−1]=378.

$^1$H NMR: (400 MHz, DMSO-$d_6$) δ 9.48 (s, 1H), 8.04 (s, 1H), 6.95 (s, 1H), 6.86 (s, 1H), 6.45 (d, J=8.5 Hz, 1H), 6.20 (t, J=8.8 Hz, 1H), 4.47 (s, 2H), 3.90 (s, 2H), 3.41-3.36 (m, 1H), 2.66 (d, J=4.7 Hz, 3H), 2.17 (s, 3H), 1.26 (d, J=7.1 Hz, 6H).

Example 38

Synthesis of 2-(3-chloro-4-(2-fluoro-4-hydroxy-3-isopropylbenzyl)-5-methylphenoxy)-N,N-dimethylacetamide (Compound 38)

38

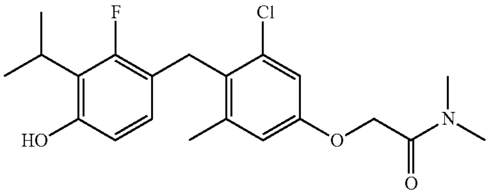

To a solution of Compound 36 (60 mg, 164 umol) in DCM (3 mL) was cooled to 0° C. Oxalyl chloride (42 mg, 327 umol) and DMF (cat) were added. The mixture was stirred at rt for 1 h, then concentrated in vacuo to give the crude acid chloride. One-third of this sample (25 mg, 65 umol) was dissolved in DCM (2 mL) and added dropwise to a solution of dimethylamine (1 mL) in DCM (3 mL) at 0° C. The mixture was stirred for 1 h at rt, then concentrated in vacuo. The crude product was purified by Prep-TLC (DCM/MeOH=15/1) to afford Compound 38 (17 mg, 66.5% yield) as an off-white solid.

LCMS: RT=3.974 min, [M−1]=392.

$^1$H NMR: (400 MHz, DMSO-$d_6$) δ 9.03 (s, 1H), 6.89 (dd, J=13.7, 2.4 Hz, 2H), 6.77 (d, J=2.7 Hz, 1H), 6.63 (d, J=8.2 Hz, 1H), 6.56 (dd, J=8.2, 2.2 Hz, 1H), 4.66 (s, 2H), 3.93 (s, 2H), 3.16-3.09 (m, 1H), 2.19 (s, 3H), 1.10 (d, J=6.9 Hz, 6H).

Example 39

Synthesis of ethyl 2-(3-bromo-5-chloro-4-(2-fluoro-4-hydroxy-3-isopropylbenzyl)phenoxy)acetate (Compound 39)

39

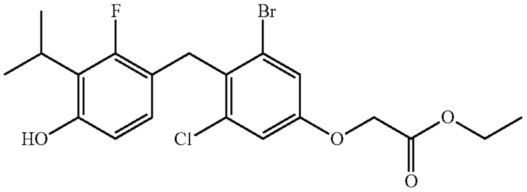

To a solution of Intermediate A17 (820 mg, 2.40 mmol) in DCE (30 mL) at rt were added Intermediate B2 (739 mg, 4.80 mmol) and $ZnCl_2$(s) (817 mg, 6.00 mmol). The reaction was heated to 90° C. and stirred overnight. The reaction mixture was diluted with DCM (20 mL), washed with brine (20 mL), dried over $Na_2SO_4$, and concentrated in vacuo. The crude product was purified by silica gel column chromatography (EtOAc/pet. ether=1/50 to 1/10) to afford Compound 39 (600 mg, 54% yield) as a colorless oil.

TLC: DCM/MeOH=5/1 (v/v), Rf=0.24

LCMS: RT=3.341 min, [M−1]=456.9.

Example 40

Synthesis of 2-(3-bromo-5-chloro-4-(2-fluoro-4-hydroxy-3-isopropylbenzyl)phenoxy)acetic acid (Compound 40)

40

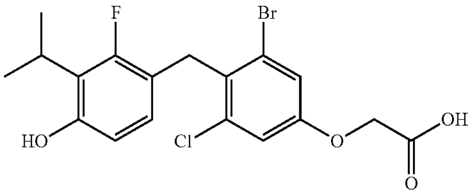

To a mixture of Compound 39 (50 mg, 75% purity, 81.6 umol) in MeOH (3 mL) was added NaOH (10 mg, 245 umol) in water (1 mL). The mixture was stirred at rt for 10 min. The mixture was acidified to pH~5 with 2N HCl; water (10 mL) was added, and the resultant mixture was extracted with EtOAc (15 mL*2). The combined organic phase was washed with brine (50 mL), dried over $Na_2SO_4$, concentrated in vacuo, and purified by Prep-HPLC to afford Compound 40 (15 mg, 45.5% yield) as a white solid.

TLC: EtOAc/pet. ether=1/5 (v/v), $R_f$=0

LCMS: RT=2.372 min, [M−1]=428.9

$^1$H NMR: (400 MHz, DMSO-$d_6$) δ 9.52 (d, J=1.4 Hz, 1H), 7.28 (d, J=2.6 Hz, 1H), 7.17 (d, J=2.6 Hz, 1H), 6.47 (d, J=8.3 Hz, 1H), 6.23 (t, J=8.6 Hz, 1H), 4.79 (s, 2H), 4.06 (s, 2H), 3.42-3.37 (m, 1H), 1.26 (d, J=7.1 Hz, 6H).

Example 41

Synthesis of ethyl 2-(3-chloro-4-(2-fluoro-4-hydroxy-3-isopropylbenzyl)-5-vinylphenoxy)acetate (Compound 41)

41

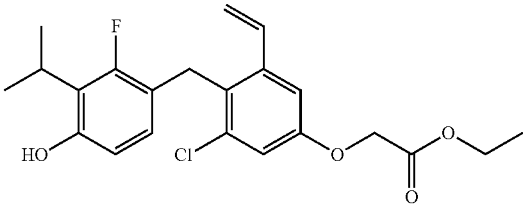

To a mixture of Compound 39 (600 mg, 1.31 mmol) and vinyl boron(pinacolate) (302 mg, 1.96 mmol) in water (1 mL)/1,4-dioxane (3 mL) at rt were added Pd(dppf)$Cl_2$ (106 mg, 0.13 mmol) and $Cs_2CO_3$ (850 mg, 2.62 mmol) under $N_2$(g). The reaction was microwaved at 120° C. for 2 h. The mixture was diluted with EtOAc (20 mL*2), washed with brine (20 mL), dried over $Na_2SO_4$, and concentrated in vacuo to afford Compound 41, which was used without further purification.

TLC: pet. ether/EtOAc=5/1 (v/v), Rf=0.50

LCMS: RT=2.385 min, [M−1]=405.0.

Example 42

Synthesis of 2-(3-chloro-4-(2-fluoro-4-hydroxy-3-isopropylbenzyl)-5-vinylphenoxy)acetic acid (Compound 42)

42

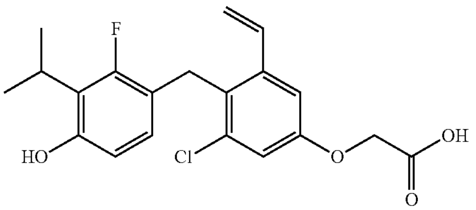

To a solution of Compound 41 (500 mg, 1.23 mmol) in MeOH (5 mL)/water (1 mL) at rt was added LiOH·$H_2O$ (155 mg, 3.69 mmol). The mixture was stirred at rt for 1 h. Water (10 mL) was added, the mixture was adjusted to pH~3-4 with 1N HCl and extracted with EtOAc (10 mL*2). The combined organic phase was washed with brine (20 mL), dried over $Na_2SO_4$, concentrated in vacuo and purified by Prep-TLC (DCM/MeOH=3/1) to afford Compound 42 (220 mg, 47.3% yield) as a colorless oil.

TLC: pet. ether/EtOAc=5/1 (v/v), Rf=0.02

LCMS: RT=1.812 min, [M−1]=377.1.

Example 43

Synthesis of 2-(3-chloro-5-ethyl-4-(2-fluoro-4-hydroxy-3-isopropylbenzyl)phenoxy)acetic acid (Compound 43)

43

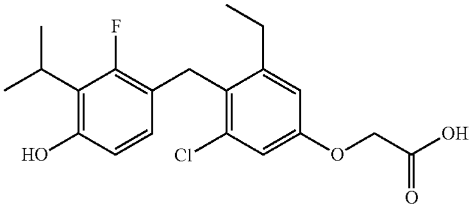

To a solution of Compound 42 (50 mg, 0.13 mmol) in THF (5 mL) at rt was added Pd/C (10 mg); the resultant mixture was stirred at 60° C. for 3 h. The mixture was filtered, concentrated in vacuo and purified by Prep-HPLC to afford Compound 43 (20 mg, 39.6% yield) as a white solid.

TLC: DCM/MeOH=5/1 (v/v), Rf=0.29

LCMS: RT=2.388 min, [M−1]=379.1.

$^1$H NMR: (400 MHz, DMSO-$d_6$) δ 13.02 (s, 1H), 9.46 (d, J=1.2 Hz, 1H), 6.90 (d, J=2.4 Hz, 1H), 6.81 (d, J=2.8 Hz,

1H), 6.45 (d, J=8.4 Hz, 1H), 6.19 (t, J=8.4 Hz, 1H), 4.71 (s, 2H), 3.92 (s, 2H), 3.39 (d, J=7.2 Hz, 1H), 2.51 (d, J=2.0 Hz, 2H), 1.26 (d, J=7.2 Hz, 6H), 1.02 (t, J=7.2 Hz, 3H).

Example 44

Synthesis of 2-(3-chloro-5-ethyl-4-(2-fluoro-4-hydroxy-3-isopropylbenzyl)phenoxy)-N-methylacetamide (Compound 44)

44

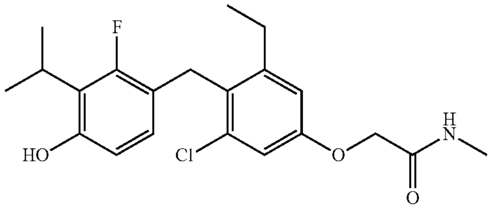

To a solution of Compound 43 (80 mg, 0.21 mmol) in DCM (5 mL) was added oxalyl chloride (40 mg, 0.32 mmol). The mixture was stirred at rt for 1 h. The mixture was concentrated to dryness to afford the crude acid chloride (80 mg, 0.20 mmol), which was dissolved in DCM (5 mL) and added to $CH_3NH_2$/THF (2M, 2 mL). The mixture was stirred at rt for 30 min. The mixture was concentrated to dryness and purified by Prep-TLC (MeOH/DCM=1/15) to afford Compound 44 (21 mg, 26.0% yield) as a white solid.

TLC: Pet. ether/EtOAc=1/1 (v/v), Rf=0.10

LCMS: RT=0.873 min, [M−1]=392.1.

$^1$H NMR: (400 MHz, DMSO-$d_6$) δ 9.52 (s, 1H), 8.08 (d, J=5.2 Hz, 1H), 6.96 (d, J=2.4 Hz, 1H), 6.87 (d, J=2.8 Hz, 1H), 6.47 (d, J=8.4 Hz, 1H), 6.18 (t, J=8.4 Hz, 1H), 4.49 (s, 2H), 3.92 (s, 2H), 3.40 (s, 1H), 2.66 (d, J=4.8 Hz, 3H), 1.26 (d, J=7.2 Hz, 6H), 1.03 (t, J=7.6 Hz, 3H).

Example 45

Synthesis of ethyl 2-(3-chloro-4-(2-fluoro-4-hydroxy-3-isopropylbenzyl)-5-(prop-1-en-2-yl)phenoxy)acetate (Compound 45)

45

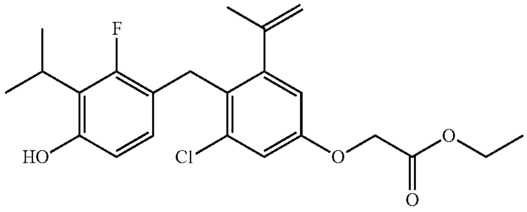

A mixture of Compound 39 (1.0 g, 2.18 mmol), potassium isopropenyl trifluoroborate (805 mg, 5.44 mmol), and Pd(dppf)$Cl_2$ (159.16 mg, 217.52 umol) in 1,4-dioxane (10 mL) and water (1 mL) was microwaved at 120° C. for 2 h. The mixture was cooled to rt, concentrated to dryness, and purified by silica gel column chromatography to afford Compound 45 (610 mg, 66.6% yield) as a white solid.

TLC: EtOAc/pet. ether=1/5 (v/v), Rf=0.39

$^1$H NMR: (400 MHz, DMSO-$d_6$) δ 9.44 (s, 1H), 7.02 (d, J=2.7 Hz, 1H), 6.74 (d, J=2.7 Hz, 1H), 6.45 (d, J=8.4 Hz, 1H), 6.19 (t, J=8.6 Hz, 1H), 5.11 (t, J=1.8 Hz, 1H), 4.84 (s, 2H), 4.68 (s, 1H), 4.18 (q, J=7.1 Hz, 2H), 3.87 (s, 2H), 3.43-3.32 (m, 11H), 1.83 (s, 3H), 1.25 (d, J=7.1 Hz, 6H), 1.21 (t, J=7.1 Hz, 4H).

Example 46

Synthesis of 2-(3-chloro-4-(2-fluoro-4-hydroxy-3-isopropylbenzyl)-5-(prop-1-en-2-yl)phenoxy)acetic acid (Compound 46)

46

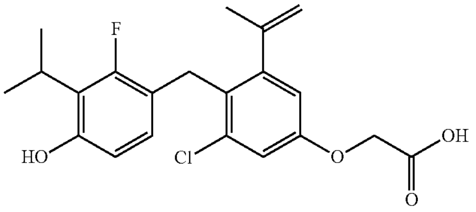

A mixture of Compound 45 (500 mg, 1.23 mmol) and NaOH (148 mg, 3.69 mmol) in water (1 mL) and THF (5 mL) was stirred at rt for 10 min. The mixture was acidified to pH~5 with 2M HCl, water (30 mL) was added, and the mixture was extracted with EtOAc (25 mL*2). The combined organic layer was washed with brine (50 mL), dried over $Na_2SO_4$, concentrated in vacuo and purified by Prep-HPLC to afford Compound 46 (15 mg, 3%) as an off-white solid.

TLC: Pet. ether/EtOAc=1/5 (v/v), Rf=0

LCMS: RT=2.497 min, [M−1]=391.1

$^1$H NMR: (400 MHz, DMSO-$d_6$) δ 9.45 (s, 1H), 6.99 (d, J=2.7 Hz, 1H), 6.72 (d, J=2.7 Hz, 1H), 6.45 (d, J=8.4 Hz, 1H), 6.20 (t, J=8.6 Hz, 1H), 5.11 (t, J=1.9 Hz, 1H), 4.73 (s, 2H), 4.68 (d, J=1.7 Hz, 1H), 3.86 (s, 2H), 3.38-3.37 (m, 1H), 1.83 (s, 3H), 1.25 (d, J=7.0 Hz, 6H).

Example 47

Synthesis of 2-(3-chloro-4-(2-fluoro-4-hydroxy-3-isopropylbenzyl)-5-isopropylphenoxy)acetic acid (Compound 47)

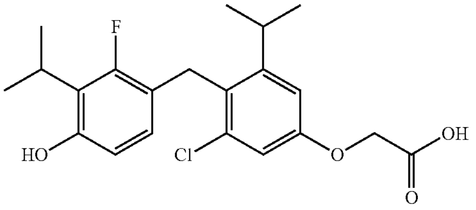 [SMILES: CC(C)c1cc(OCC(=O)O)cc(Cl)c1Cc1ccc(O)c(C(C)C)c1F]

To a solution of Compound 46 (50 mg, 127 umol) in THF (5 mL) at rt was added Pd/C (10 mg); the resulting mixture was stirred at 55° C. under 1 atm of $H_2$(g) overnight. The reaction was filtered, concentrated in vacuo and purified by Prep-HPLC to afford Compound 47 (15 mg, 30% yield).

TLC: DCM/MeOH=10/1 (v/v), Rf=0.35

LCMS: RT=2.662 min, [M−1]=393.1

$^1$H NMR: (400 MHz, DMSO-$d_6$) δ 13.05 (s, 1H), 9.48 (d, J=1.4 Hz, 1H), 6.89 (d, J=2.7 Hz, 1H), 6.86 (d, J=2.7 Hz, 1H), 6.45 (d, J=8.4 Hz, 1H), 6.18 (t, J=8.6 Hz, 1H), 4.72 (s, 2H), 3.95 (s, 2H), 3.44-3.37 (m, 3H), 2.94 (p, J=6.8 Hz, 1H), 1.26 (d, J=7.0 Hz, 6H), 1.05 (d, J=6.8 Hz, 6H).

Example 48

Synthesis of ethyl 2-(3,5-dichloro-4-(2-chloro-4-hydroxy-3-isopropylbenzyl)phenoxy)acetate (Compound 48)

48

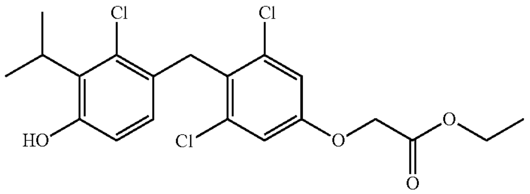

To a solution of Intermediate B12 (300 mg, 1.74 mmol) and Intermediate A11 (174 mg, 0.58 mmol) in chlorobenzene (5 mL) was added $ZnCl_2$ (197 mg, 1.45 mmol). The mixture was stirred at 160° C. under microwave irradiation for 2 h. The mixture was cooled to rt; water (50 mL) was added and the resultant mixture was extracted with DCM (30 mL*3). The combined organic phase was washed with brine (20 mL), dried over $Na_2SO_4$, concentrated in vacuo and purified by Prep-TLC (EtOAc/pet. ether=1/5) to afford Compound 48 (110 mg, 43% yield) as a colorless oil.

TLC: EtOAc/pet. ether=1/5 (v/v), $R_f$=0.25

LCMS: RT=2.60 min, [M−1]=429.0

Example 49

Synthesis of 2-(3,5-dichloro-4-(2-chloro-4-hydroxy-3-isopropylbenzyl)phenoxy)acetic acid (Compound 49)

49

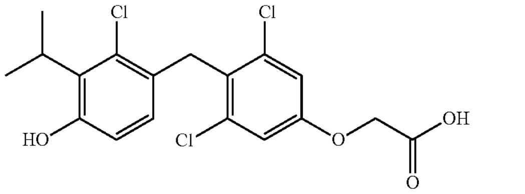

To a solution of Compound 48 (100 g, 0.23 mmol) in $THF/H_2O$ (1 mL/5 mL) at rt was added $LiOH{\cdot}H_2O$ (29 mg, 0.69 mmol). The mixture was stirred at rt for 1 h. The mixture was diluted with water (10 mL), acidified with 1N HCl to pH~3-4, and extracted with EtOAc (15 mL*3). The combined organic phase was washed with brine (30 mL), dried over $Na_2SO_4$, and concentrated in vacuo. The crude product was purified by Prep-HPLC to afford Compound 49 (20 mg, 21% yield) as a white solid.

TLC: MeOH/DCM=1/10 (v/v), Rf=0.30

LCMS: RT=4.42 min, [M−1]=401.0

$^1$H NMR: (400 MHz, DMSO) δ 9.55 (s, 1H), 7.16 (s, 2H), 6.61 (d, J=8.4 Hz, 1H), 6.12 (d, J=8.4 Hz, 1H), 4.80 (s, 2H), 4.09 (s, 2H), 3.72-3.57 (m, 1H), 1.32 (d, J=7.0 Hz, 6H).

Example 50

Synthesis of methyl 2-(3,5-dichloro-4-(4-hydroxy-2-methyl-3-(prop-1-en-2-yl)benzyl)phenoxy)acetate (Compound 50)

50

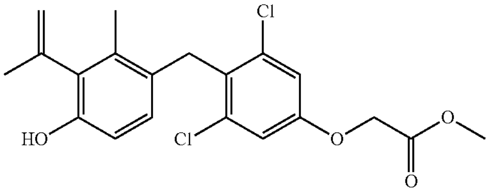

To a mixture of Intermediate C4 (200 mg, 461 umol) and isopropenyl-2-boron(pinacolate) (155 mg, 922 umol) in 1,4-dioxane (2.0 mL) and $H_2O$ (0.2 mL) at rt were added $Pd(dppf)Cl_2{\cdot}CH_2Cl_2$ (41 mg, 46 umol) and $K_2CO_3$ (127 mg, 922 umol) under $N_2$(g). The reaction was heated to 70° C. and stirred overnight. Water (20 mL) was added and the resultant mixture was extracted with EtOAc (10 mL*3). The combined organic phase was washed with brine (20 mL), dried over $Na_2SO_4$, concentrated in vacuo and purified by Prep-TLC (pet. ether/EtOAc=5/1) to afford Compound 50 (40 mg, 22% yield) as a yellow oil.

TLC: Pet. ether/EtOAc=5/1 (v/v), Rf=0.32

Example 51

Synthesis of methyl 2-(3,5-dichloro-4-(4-hydroxy-3-isopropyl-2-methylbenzyl)phenoxy)acetate (Compound 51)

51

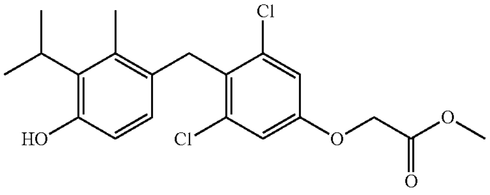

To a solution of Compound 50 (20 mg, 51 mmol) in THF (2.0 mL) was added Raney-Ni (cat.). The mixture was stirred at 70° C. overnight under $H_2$ atmosphere. The mixture was cooled to 0° C. and filtered, then concentrated in vacuo to afford Compound 51 (20 mg, 99% yield) as a yellow oil.

TLC: EtOAc/pet. ether=1/5 (v/v), $R_f$=0.28

Example 52

Synthesis of 2-(3,5-dichloro-4-(4-hydroxy-3-isopropyl-2-methylbenzyl)phenoxy)acetic acid (Compound 52)

52

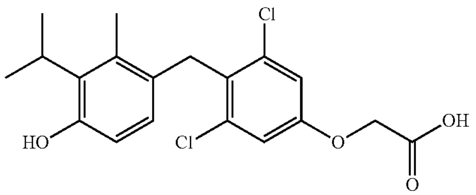

To a solution of Compound 51 (20 mg, 50 umol) in THF/$H_2O$ (1.0 mL/10 mL) at rt was added LiOH·$H_2O$ (7 mg, 150 umol). The mixture was stirred at rt for 1 h. The mixture was diluted with water (20 mL), acidified with 1N HCl to pH~3-4 and extracted with EtOAc (10 mL*3). The combined organic phase was washed with brine (20 mL), dried over $Na_2SO_4$ and concentrated in vacuo. The crude product was purified by Prep-HPLC to afford Compound 52 (3 mg, 16% yield) as a white solid.

TLC: MeOH/DCM=1/10 (v/v), Rf=0.30

LCMS: RT=1.836 min, [M−1]=381.1

$^1$H NMR: (400 MHz, DMSO-$d_6$) δ 8.87 (s, 1H), 7.09 (s, 2H), 6.43 (d, J=8.4 Hz, 1H), 5.97 (d, J=8.4 Hz, 1H), 4.66 (s, 2H), 3.98 (s, 2H), 2.29 (s, 3H), 1.30 (d, J=7.0 Hz, 6H).

Example 53

Synthesis of ethyl 2-(3,5-dichloro-4-(4-hydroxy-3-isopropyl-2-methoxybenzyl)phenoxy)acetate (Compound 53)

53

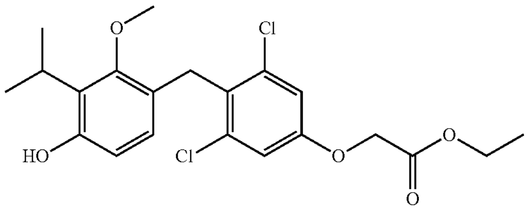

To a solution of Intermediate B14 (200 mg, 0.70 mmol) in DCE (10 mL) at rt were added Intermediate A11 (352 mg, 2.12 mmol) and $ZnCl_2$ (1M in THF, 2 mL). The reaction was heated to 85° C. and stirred overnight. The reaction mixture was diluted with DCM (20 mL), washed with brine (10 mL*2), dried over $Na_2SO_4$, filtered and concentrated in vacuo. The crude product was purified by Prep-TLC (EtOAc/pet. ether=1/5) to afford Compound 53 (50 mg, 17.1% yield) as a white solid.

TLC: Pet. ether/EtOAc=10/1 (v/v), Rf=0.21

$^1$H NMR: (400 MHz, DMSO-$d_6$) δ 9.13 (s, 1H), 7.16 (s, 2H), 6.40 (d, J=8.4 Hz, 1H), 6.06 (d, J=8.4 Hz, 1H), 4.89 (s, 2H), 4.18 (q, J=7.2 Hz, 2H), 4.05 (s, 2H), 3.70 (s, 3H), 3.38-3.34 (m, 1H), 1.30 (d, J=6.8 Hz, 6H), 1.21 (t, J=7.2 Hz, 3H).

Example 54

Synthesis of 2-(3,5-dichloro-4-(4-hydroxy-3-isopropyl-2-methoxybenzyl)phenoxy)acetic acid (Compound 54)

54

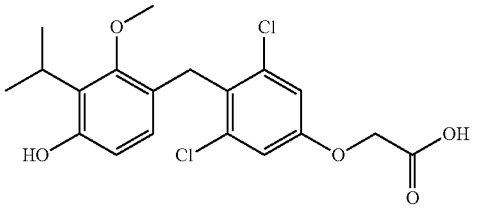

To a solution of Compound 53 (50 mg, 0.12 mmol) in THF (5 mL)/water (0.2 mL) at rt was added LiOH·$H_2O$ (15 mg, 0.36 mmol); the resultant mixture was stirred at rt for 1 h. The reaction was acidified to pH~6-7 with 2N HCl, concentrated in vacuo and purified by Prep-HPLC to afford Compound 54 (25 mg, 51.8% yield) as a white solid.

TLC: DCM/MeOH=5/1 (v/v), Rf=0.24

LCMS: RT=3.931 min, [M−1]=397.0.

$^1$H NMR: (400 MHz, DMSO-$d_6$) δ 9.13 (s, 1H), 7.13 (s, 2H), 6.40 (d, J=8.4 Hz, 1H), 6.07 (d, J=8.4 Hz, 1H), 4.79 (s, 2H), 4.05 (s, 2H), 3.70 (s, 3H), 1.30 (d, J=6.8 Hz, 6H).

Example 55

Synthesis of methyl 2-(3,5-dichloro-4-(2-cyano-4-hydroxy-3-isopropylbenzyl)phenoxy)acetate (Compound 55)

55

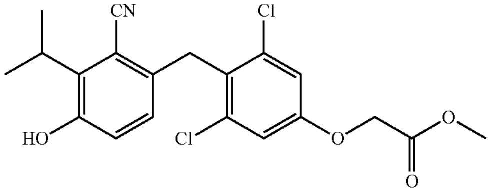

A mixture of Intermediate B16 (150 mg, 0.93 mmol), Intermediate A10 (133 mg, 0.47 mmol), $ZnCl_2$ (160 mg, 1.18 mmol) and DCE (5 mL) was microwaved at 120° C. for 2 h. The mixture was cooled to rt and concentrated to dryness. Water (20 mL) was added, and the resultant mixture was extracted with EtOAc (15 mL*2). The combined organic layer was washed with brine (20 mL), dried over $Na_2SO_4$, and purified by Prep-TLC (pet. ether/EtOAc=10/1) to afford Compound 55 (40 mg, 19.7% yield) as a white solid.

TLC: EtOAc/pet. ether=1/5 (v/v), $R_f$=0.25

Example 56

Synthesis of 2-(3,5-dichloro-4-(2-cyano-4-hydroxy-3-isopropylbenzyl)phenoxy)acetic acid (Compound 56)

56

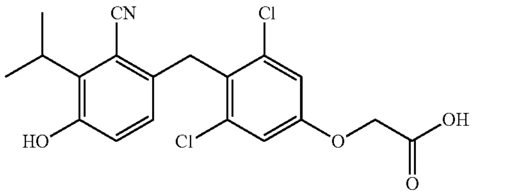

To a solution of Compound 55 (40 mg, 98 mmol) in THF/$H_2O$ (5 mL/1 mL) at rt was added LiOH·$H_2O$ (12 mg, 294 umol). The mixture was stirred at rt for 1 h. The mixture was diluted with water (10 mL), acidified with 1N HCl to pH~3-4 and extracted with EtOAc (15 mL*3). The combined organic phase was washed with brine (30 mL), dried over $Na_2SO_4$, and concentrated in vacuo. The crude product was purified by Prep-HPLC to afford Compound 56 (20 mg, 51.8% yield) as a white solid.

TLC: MeOH/DCM=1/10 (v/v), Rf=0.30

LCMS: RT=1.824 min, [M−1]=392.0

$^1$H NMR: (400 MHz, DMSO-$d_6$) δ 13.14 (s, 1H), 9.92 (s, 1H), 7.17 (s, 2H), 6.96 (d, J=8.5 Hz, 1H), 6.41 (d, J=8.4 Hz, 1H), 4.81 (s, 2H), 4.22 (s, 2H), 3.48-3.42 (m, 1H), 1.36 (d, J=7.1 Hz, 6H).

Example 57

Synthesis of ethyl 2-(2-fluoro-4-(4-hydroxy-3-isopropylbenzyl)-3,5-dimethylphenoxy)acetate (Compound 57)

57

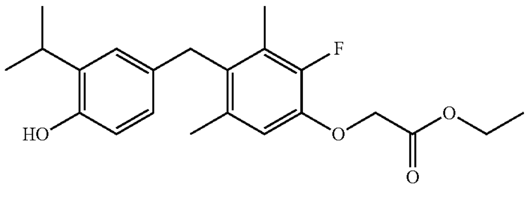

To a solution of Intermediate A24 (198 mg, 1.46 mmol) in DCE (10 mL) at rt were added 2-isopropyl phenol (200 mg, 0.73 mmol) and $ZnCl_2$ (1.82 mmol, 1.82 mL). The reaction was heated to 85° C. for 4 h. The reaction mixture was diluted with DCM (20 mL), washed with brine (10 mL*2), dried over $Na_2SO_4$, and concentrated in vacuo. The crude product was purified by Prep-TLC (EtOAc/pet. ether=1/3) to afford Compound 57 (170 mg, 62.3% yield) as a light yellow oil.

TLC: EtOAc/pet. ether=1/10, Rf=0.88

$^1$H NMR: (400 MHz, DMSO-$d_6$) δ 9.03 (s, 1H), 6.84 (d, J=2.4 Hz, 1H), 6.78 (d, J=8.8 Hz, 1H), 6.62 (d, J=8.0 Hz, 1H), 6.45 (dd, J=8.0, 2.0 Hz, 1H), 4.81 (s, 2H), 4.17 (q, J=7.2 Hz, 2H), 3.81 (s, 2H), 3.12 (p, J=6.8 Hz, 1H), 2.14 (s, 3H), 2.08 (d, J=2.8 Hz, 3H), 1.20 (t, J=7.2 Hz, 3H), 1.09 (d, J=7.2 Hz, 6H).

Example 58

Synthesis of 2-(2-fluoro-4-(4-hydroxy-3-isopropylbenzyl)-3,5-dimethylphenoxy)acetic acid (Compound 58)

58

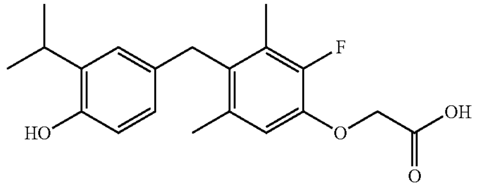

To a solution of Compound 57 (170 mg, 0.45 mmol) in THF (5 mL)/water (0.5 mL) at rt was added LiOH·$H_2O$ (39 mg, 0.91 mmol); the resultant mixture was stirred at rt for 1 h. The reaction was diluted with water (20 mL), acidified to pH~3 with aqueous HCl (1N), and extracted with EtOAc (10 mL*3). The combined organic phase was washed with brine (10 mL*2), dried over $Na_2SO_4$, and concentrated in vacuo. The crude product was purified by Prep-TLC (MeOH/DCM=1/8) to afford Compound 58 (157 mg, 96.8% yield) as a white solid.

TLC: MeOH/DCM=1/10, Rf=0.24

LCMS: RT=3.71 min; [M−1]=345.1

$^1$H NMR: (400 MHz, DMSO-$d_6$) δ 9.09 (s, 1H), 6.86 (s, 1H), 6.73-6.57 (m, 2H), 6.43 (d, J=8.0 Hz, 1H), 4.43 (s, 2H), 3.78 (s, 2H), 3.12 (p, J=6.8 Hz, 1H), 2.11 (s, 3H), 2.07 (s, 3H), 1.10 (d, J=6.8 Hz, 6H).

$^{19}$F NMR: (376 MHz, DMSO-$d_6$) δ −140.89.

Example 59

Synthesis of 2-(2-fluoro-4-(4-hydroxy-3-isopropylbenzyl)-3,5-dimethylphenoxy)-N-methylacetamide (Compound 59)

59

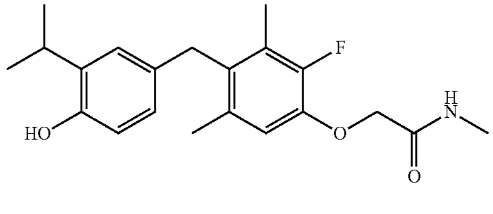

To solution of Compound 58 (150 mg, 0.43 mmol) in DCM (5 mL) at rt was added $SOCl_2$ (154 mg, 1.30 mmol); the resultant solution was stirred at rt for 3 h. The reaction mixture was concentrated in vacuo to afford the acid chloride (157 mg, 99.3% yield) as a white solid. A sample of this material (70 mg, 0.19 mmol) was dissolved in DCM (2 mL), and added dropwise to a solution of methylamine (0.95 mmol, 0.95 mL of 1N aqueous solution) in THF (5 mL). The mixture was stirred overnight. The reaction mixture was diluted with water (20 mL) and extracted with EtOAc (10 mL*3). The combined organic phase was washed with brine (10 mL*2), dried over $Na_2SO_4$, and concentrated in vacuo. The crude product was purified by Prep-TLC (EtOAc/pet. ether=1/3) to afford Compound 59 (21 mg, 30.1% yield) as a white solid.

LCMS: RT=3.68 min; [M−1]=358.1

$^1H$ NMR: (400 MHz, DMSO-$d_6$) δ 9.03 (s, 1H), 7.94 (s, 1H), 6.85 (d, J=2.4 Hz, 1H), 6.79 (d, J=8.8 Hz, 1H), 6.62 (d, J=8.4 Hz, 1H), 6.45 (dd, J=8.4, 2.4 Hz, 1H), 4.49 (s, 2H), 3.81 (s, 2H), 3.12 (p, J=6.8 Hz, 1H), 2.65 (d, J=4.8 Hz, 3H), 2.15 (s, 3H), 2.09 (d, J=2.4 Hz, 3H), 1.10 (d, J=6.8 Hz, 6H).

$^{19}F$ NMR: (376 MHz, DMSO-$d_6$) δ −139.80.

Example 60

Synthesis of 2-(2-fluoro-4-(4-hydroxy-3-isopropylbenzyl)-3,5-dimethylphenoxy)-N,N-dimethylacetamide (Compound 60)

60

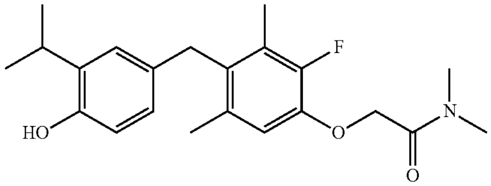

To solution of Compound 58 (150 mg, 0.43 mmol) in DCM (5 mL) at rt was added $SOCl_2$ (154 mg, 1.30 mmol); the resultant solution was stirred at rt for 3 h. The reaction mixture was concentrated in vacuo to afford the acid chloride (157 mg, 99.3% yield) as a white solid. A sample of this material (70 mg, 0.19 mmol) was dissolved in DCM (2 mL), and added dropwise to a solution of dimethylamine (0.95 mmol, 0.48 mL) in THF (5 mL). The mixture was stirred overnight. The reaction mixture was diluted with water (20 mL) and extracted with EtOAc (10 mL*3). The combined organic phase was washed with brine (10 mL*2), dried over $Na_2SO_4$, and concentrated in vacuo. The crude product was purified by Prep-TLC (EtOAc/pet. ether=1/3) to afford Compound 60 (22 mg, 30.0% yield, 98.0% purity) as a white solid.

LCMS: RT=3.76 min; [M−1]=372.2

$^1H$ NMR: (400 MHz, DMSO-$d_6$) δ 9.02 (s, 1H), 6.85 (d, J=2.0 Hz, 1H), 6.76 (d, J=8.8 Hz, 1H), 6.62 (d, J=8.0 Hz, 1H), 6.44 (dd, J=8.0, 2.0 Hz, 1H), 4.83 (s, 2H), 3.80 (s, 2H), 3.11 (q, J=6.8 Hz, 1H), 2.99 (s, 3H), 2.85 (s, 3H), 2.14 (s, 3H), 2.08 (d, J=2.4 Hz, 3H), 1.10 (d, J=6.8 Hz, 6H).

$^{19}F$ NMR: (376 MHz, DMSO-$d_6$) δ −140.69.

Example 61

Synthesis of ethyl 2-(3,5-dichloro-2-fluoro-4-(4-hydroxy-3-isopropylbenzyl)phenoxy)acetate (Compound 61)

61

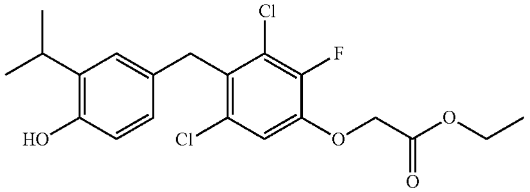

To a solution of Intermediate A29 (500 mg, 1.58 mmol) in DCE (5 mL) at rt were added 2-isopropylphenol (647 mg, 4.74 mmol) and $ZnCl_2$ (3.95 mL, 3.95 mmol). The reaction mixture was heated to 90° C. and stirred for 16 h. The reaction mixture was diluted with DCM (20 mL), washed with brine (40 mL), dried over $Na_2SO_4$, and concentrated in vacuo.

The crude product was purified by silica gel column chromatography (EtOAc/pet. ether=1/8) to afford Compound 61 (377 mg, 57% yield) as a white solid.

TLC: Pet. ether/EtOAc=1/5 (v/v), Rf=0.35

$^1H$ NMR: (400 MHz, DMSO) δ 9.13 (s, 1H), 7.41 (d, J=7.7 Hz, 1H), 6.99-6.96 (m, 1H), 6.70-6.61 (m, 2H), 5.00 (s, 2H), 4.17 (d, J=7.1 Hz, 2H), 4.06 (s, 2H), 1.17 (s, 3H), 1.10 (d, J=6.9 Hz, 6H).

Example 62

Synthesis of 2-(3,5-dichloro-2-fluoro-4-(4-hydroxy-3-isopropylbenzyl)phenoxy)acetic acid (Compound 62)

62

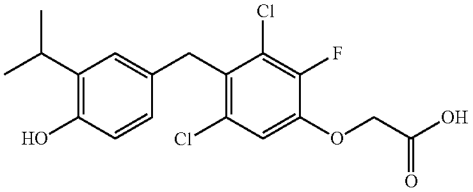

To a solution of Compound 61 (377 mg, 0.90 mmol) in water (10 mL)/THF (1 mL) at rt was added NaOH (108 mg, 2.70 mmol); the mixture was stirred at rt for 1 h. The reaction mixture was acidified to pH~3-4 with 2N HCl, then extracted with DCM (40 mL*3); the combined organic phase was concentrated in vacuo and purified by reversed-phase column chromatography to afford Compound 62 (260 mg, 73% yield).

TLC: Pet. ether/EtOAc=1/5 (v/v), Rf=0

LCMS: RT=2.78 min; [M−1]=385.0

$^1H$ NMR: (400 MHz, DMSO) δ 9.13 (s, 1H), 7.36 (d, J=7.7 Hz, 1H), 6.98 (d, J=1.9 Hz, 1H), 6.66 (t, J=2.0 Hz, 2H), 4.89 (s, 2H), 4.06 (s, 2H), 3.13 (m, 1H), 1.10 (d, J=6.9 Hz, 6H).

Example 63

Synthesis of 2-(3,5-dichloro-2-fluoro-4-(4-hydroxy-3-isopropylbenzyl)phenoxy)-N-methylacetamide (Compound 63)

63

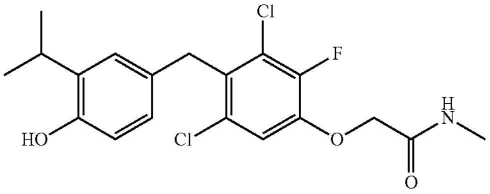

To a solution of Compound 62 (60 mg, 0.15 mmol) in DCM (5 mL) were added oxalyl chloride (57 mg, 0.45 mmol) and DMF (cat.). After stirring at rt for 1 h, the reaction was concentrated in vacuo. The residue was dissolved in DCM (5 mL) and was added to methylamine/THF solution (0.75 mL, 2.0M, 1.5 mmol). After stirring at room temperature for 1 h, the mixture was poured into water (20 mL) and extracted with DCM (30 mL*3); the organic phase was washed with brine (20 mL*2), dried over $Na_2SO_4$, concentrated in vacuo and purified by Prep-TLC (pet. ether: EtOAc=2:1) to afford Compound 63 (33 mg, 55% yield) as a white solid.

TLC: DCM/MeOH=20/1 (v/v), Rf=0.35

LCMS: RT=3.84 min; [M+1]=400.1

$^1H$ NMR: (400 MHz, DMSO) δ 9.13 (s, 1H), 8.02 (s, 1H), 7.29 (d, J=7.6 Hz, 1H), 6.99 (d, J=2.0 Hz, 1H), 6.65 (m, 2H), 4.67 (s, 2H), 4.06 (s, 2H), 3.12 (m, 1H), 2.64 (d, J=4.6 Hz, 3H), 1.11 (d, J=6.9 Hz, 6H).

Example 64

Synthesis of 2-(3,5-dichloro-2-fluoro-4-(4-hydroxy-3-isopropylbenzyl)phenoxy)-N,N-dimethylacetamide (Compound 64)

64

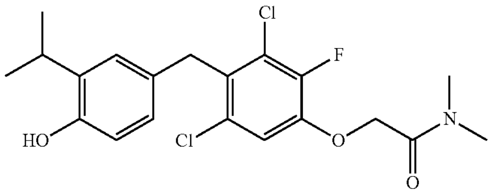

To a solution of Compound 62 (60 mg, 0.15 mmol) in DCM (5 mL) were added oxalyl chloride (57 mg, 0.45 mmol) and DMF (cat.). After stirring at rt for 1 h, the reaction was concentrated in vacuo. The residue was dissolved in DCM (5 mL) and was added to dimethylamine/THF (0.75 mL, 2.0M, 1.5 mmol) in DCM (5 mL). After stirring at room temperature for 1 h, the mixture was poured into water (20 mL) and extracted with DCM (30 mL*3); the organic phase was washed with brine (20 mL), concentrated in vacuo and purified by Prep-TLC (pet. ether:EtOAc=2:1) to afford Compound 64 (42 mg, 68% yield) as a white solid.

TLC: DCM/MeOH=20/1 (v/v), Rf=0.35

LCMS: RT=3.97 min; [M−1]=412.1

$^1H$ NMR: (400 MHz, DMSO) δ 9.13 (s, 1H), 7.32 (d, J=7.8 Hz, 1H), 6.99 (d, J=1.8 Hz, 1H), 6.66 (d, J=2.7 Hz, 2H), 5.05 (s, 2H), 4.05 (s, 2H), 3.19-3.07 (m, 1H), 2.96 (s, 3H), 2.84 (s, 3H), 1.11 (d, J=6.9 Hz, 6H).

Example 65

Synthesis of ethyl 2-(3-bromo-5-chloro-2-fluoro-4-(4-hydroxy-3-isopropylbenzyl)phenoxy)acetate (Compound 65)

65

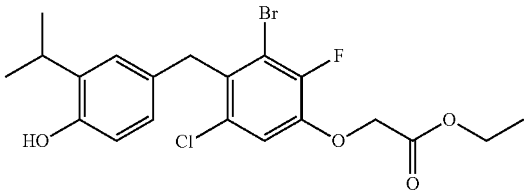

To a solution of Intermediate A34 (1.5 g, 4.2 mmol) and 2-isopropylphenol (1.7 g, 12.6 mmol) in DCE (20.0 mL) was added $ZnCl_2$ (1M/THF) (10.4 mmol, 10.4 mL). The mixture was stirred at 85° C. overnight. The mixture was cooled to rt; water (40 mL) was added and the resultant mixture was extracted with DCM (20 mL*3). The combined organic phase was washed with brine (30 mL), dried over $Na_2SO_4$, concentrated in vacuo and purified by silica gel column chromatography (EtOAc/pet. ether=1/50 to 1/10) to afford Compound 65 (380 mg, 19.8% yield) as a light yellow oil.

TLC: EtOAc/pet. ether=1/5 (v/v), $R_f$=0.30

$^1H$ NMR: (400 MHz, DMSO-$d_6$) δ 9.11 (s, 1H), 7.44 (d, J=7.8 Hz, 1H), 6.97 (s, 1H), 6.65 (d, J=1.2 Hz, 2H), 4.99 (s, 2H), 4.18 (d, J=7.2 Hz, 2H), 4.11 (s, 2H), 3.12 (q, J=6.9 Hz, 1H), 1.21 (t, J=7.2 Hz, 3H), 1.11 (d, J=6.8 Hz, 6H).

Example 66

Synthesis of ethyl 2-(5-chloro-2-fluoro-4-(4-hydroxy-3-isopropylbenzyl)-3-vinylphenoxy)acetate (Compound 66)

66

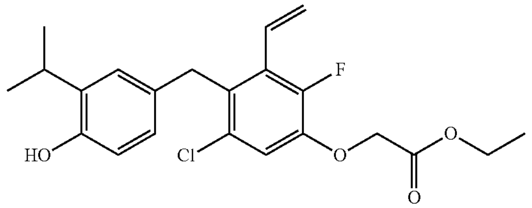

To a mixture of Compound 65 (260 mg, 566 umol) and vinyl boron(pinacolate) (131 mg, 849 umol) in 1,4-dioxane (4.0 mL) and $H_2O$ (0.5 mL) at rt were added Pd(dppf)$Cl_2 \cdot CH_2Cl_2$ (47 mg, 57 umol) and $Cs_2CO_3$ (369 mg, 1.1 mmol). The mixture was microwaved at 120° C. under $N_2$(g) for 3 h. Water (20 mL) was added and the resultant mixture was extracted with EtOAc (10 mL*3). The combined organic phase was washed with brine (20 mL), dried over $Na_2SO_4$, concentrated in vacuo and purified by Prep-TLC (pet. ether/EtOAc=5/1) to afford Compound 66 (140 mg, 60.8% yield) as a yellow solid.

TLC: Pet. ether/EtOAc=5/1 (v/v), Rf=0.32

Example 67

Synthesis of 2-(5-chloro-2-fluoro-4-(4-hydroxy-3-isopropylbenzyl)-3-vinylphenoxy)acetic acid (Compound 67)

67

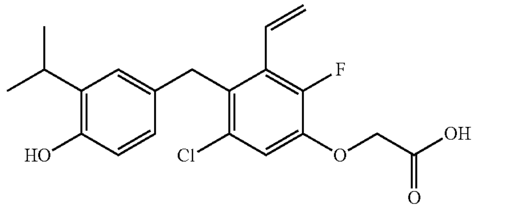

To a solution of Compound 66 (20 mg, 50 umol) in THF/$H_2O$ (2.0 mL/0.5 mL) at rt was added LiOH·$H_2O$ (12 mg, 294 umol). The mixture was stirred at rt for 1 h. The mixture was diluted with water (20 mL), acidified with 1N HCl to pH~3-4 and extracted with EtOAc (10 mL*3). The combined organic phase was washed with brine (20 mL), dried over $Na_2SO_4$ and concentrated in vacuo. The crude product was purified by Prep-HPLC to afford Compound 67 (8 mg, 21.6% yield) as a white solid.

TLC: MeOH/DCM=1/10 (v/v), Rf=0.30

LCMS: RT=1.721 min, [M−1]=377.1

$^1$H NMR: (400 MHz, DMSO-$d_6$) δ 9.07 (s, 1H), 7.18 (d, J=8.0 Hz, 1H), 6.89 (d, J=2.0 Hz, 1H), 6.68-6.58 (m, 2H), 6.56 (dd, J=8.4, 2.4 Hz, 1H), 5.63 (d, J=7.2 Hz, 1H), 5.59 (s, 1H), 4.81 (s, 2H), 3.98 (s, 2H), 3.13 (d, J=7.2 Hz, 1H), 1.10 (d, J=7.2 Hz, 6H).

$^{19}$F NMR: (376 MHz, DMSO-$d_6$) δ −137.31.

Example 68

Synthesis of ethyl 2-(5-chloro-3-ethyl-2-fluoro-4-(4-hydroxy-3-isopropylbenzyl)phenoxy)acetate (Compound 68)

68

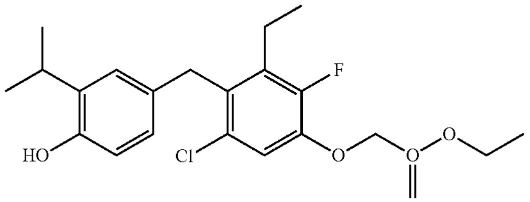

To a solution of Compound 66 (100 mg, 246 umol) in THF (4.0 mL) was added Pd/C (10%) (50 mg). The mixture was purged three times with $H_2$(g) and stirred at 60° C. overnight. The mixture was cooled to 0° C. and filtered, then concentrated in vacuo to afford Compound 68 (100 mg, 99% yield) as a yellow oil.

TLC: EtOAc/pet. ether=1/5 (v/v), $R_f$=0.25

Example 69

Synthesis of 2-(5-chloro-3-ethyl-2-fluoro-4-(4-hydroxy-3-isopropylbenzyl)phenoxy)acetic acid (Compound 69)

69

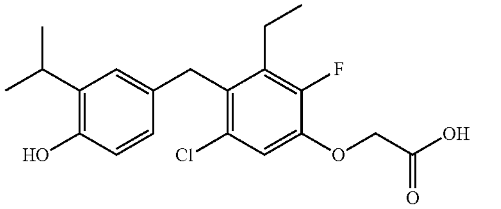

To a solution of Compound 68 (100 mg, 234 umol) in THF/$H_2O$ (2.0 mL/0.5 mL) at rt was added LiOH·$H_2O$ (30 mg, 702 umol). The mixture was stirred at rt for 1 h. The mixture was diluted with water (20 mL), acidified with 1N HCl to pH~3-4 and extracted with EtOAc (10 mL*3). The combined organic phase was washed with brine (20 mL), dried over $Na_2SO_4$ and concentrated in vacuo. The crude product was purified by Prep-HPLC to afford Compound 69 (30 mg, 32.3% yield) as a white solid.

TLC: MeOH/DCM=1/10 (v/v), Rf=0.30

LCMS: RT=1.747 min, [M−1]=379.0

$^1$H NMR: (400 MHz, DMSO-$d_6$) δ 9.06 (s, 1H), 7.11 (d, J=8.0 Hz, 1H), 6.89 (d, J=2.4 Hz, 1H), 6.64 (d, J=8.4 Hz, 1H), 6.55 (dd, J=8.2, 2.2 Hz, 1H), 4.82 (s, 2H), 3.98 (s, 2H), 3.16-3.10 (m, 1H), 2.59 (m, 2H), 1.10 (d, J=6.8 Hz, 6H), 0.90 (t, J=7.6 Hz, 3H).

$^{19}$F NMR: (376 MHz, DMSO-$d_6$) δ −139.73.

Example 70

Synthesis of ethyl 2-(5-chloro-2-fluoro-4-(4-hydroxy-3-isopropylbenzyl)-3-(prop-1-en-2-yl)phenoxy)acetate (Compound 70)

70

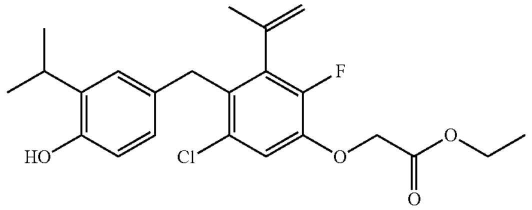

To a mixture of Intermediate C5 (550 mg, 1.2 mmol) and potassium propenyl-2-boron(trifluoride) (354 mg, 2.4 mmol) in 1,4-dioxane (5.0 mL) and $H_2O$ (0.2 mL) at rt were added Pd(dppf)$Cl_2$·$CH_2Cl_2$ (98 mg, 120 umol) and $Cs_2CO_3$ (780 mg, 2.4 mmol) under $N_2$(g). The reaction was heated to 120° C. for 2 h in a sealed tube. The mixture was cooled to rt; water (30 mL) was added and the resultant mixture was extracted with EtOAc (15 mL*3). The combined organic extracts were washed with brine (30 mL), dried over $Na_2SO_4$, concentrated in vacuo and purified by Prep-TLC (EtOAc/pet. ether=1/5) to afford Compound 70 (250 mg, 49.6% yield) as a white solid.

TLC: Pet. ether/EtOAc=5/1 (v/v), Rf=0.23

$^1$H NMR: (400 MHz, DMSO-$d_6$) δ 9.04 (s, 1H), 7.24 (d, J=8.0 Hz, 1H), 6.77 (d, J=2.4 Hz, 1H), 6.64 (d, J=8.0 Hz, 1H), 6.54 (dd, J=8.4, 2.4 Hz, 1H), 5.31 (t, J=1.6 Hz, 1H), 4.94 (s, 2H), 4.80 (t, J=1.6 Hz, 1H), 3.91 (s, 2H), 3.13 (m, 1H), 1.76 (s, 3H), 1.21 (t, J=7.2 Hz, 4H), 1.08 (d, J=6.8 Hz, 6H).

Example 71

Synthesis of 2-(5-chloro-2-fluoro-4-(4-hydroxy-3-isopropylbenzyl)-3-(prop-1-en-2-yl)phenoxy)acetic acid (Compound 71)

71

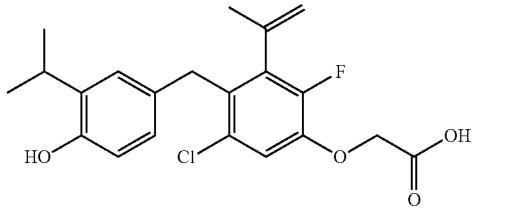

To a solution of Compound 70 (250 mg, 520 umol) in THF/$H_2O$ (2.0 mL/0.5 mL) at rt was added LiOH·$H_2O$ (39 mg, 930 umol). The mixture was stirred at rt for 1 h. The mixture was diluted with water (50 mL), acidified with 1N HCl to pH~3-4, and extracted with EtOAc (20 mL*3). The combined organic phase was washed with brine (50 mL), dried over $Na_2SO_4$, and concentrated in vacuo. The crude product was purified by Prep-HPLC to afford Compound 71 (40 mg, 32.8% yield) as a white solid.

TLC: MeOH/DCM=1/10 (v/v), Rf=0.30

LCMS: RT=1.691 min, [M−1]=391.1

$^1H$ NMR: (400 MHz, DMSO-$d_6$) δ 9.05 (s, 1H), 7.18 (d, J=8.0 Hz, 1H), 6.79 (d, J=2.0 Hz, 1H), 6.63 (d, J=8.0 Hz, 1H), 6.55 (dd, J=8.0, 2.0 Hz, 1H), 5.31 (t, J=2.0 Hz, 1H), 4.84 (s, 2H), 4.81 (t, J=1.2 Hz, 1H), 3.91 (s, 2H), 3.16-3.10 (m, 1H), 1.77 (s, 3H), 1.09 (d, J=6.8 Hz, 6H).

$^{19}F$ NMR: (376 MHz, DMSO-$d_6$) δ −137.45.

Example 72

Synthesis of ethyl 2-(5-chloro-2-fluoro-4-(4-hydroxy-3-isopropylbenzyl)-3-isopropylphenoxy)acetate (Compound 72)

72

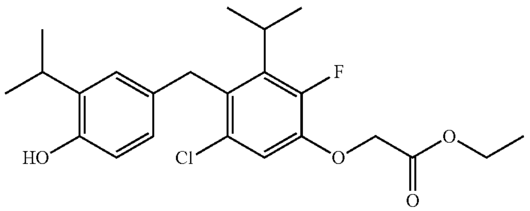

To a solution of Compound 70 (250 mg, 594 umol) in THF (6.0 mL) was added Pd/C (120 mg). The mixture was purged three times with $H_2$ gas and stirred at 60° C. overnight. The mixture was concentrated in vacuo to afford Compound 72 (220 mg, 87.6% yield) as a yellow oil.

TLC: Pet. ether/EtOAc=1/5 (v/v), Rf=0.28

Example 73

Synthesis of 2-(5-chloro-2-fluoro-4-(4-hydroxy-3-isopropylbenzyl)-3-isopropylphenoxy)acetic acid (Compound 73)

73

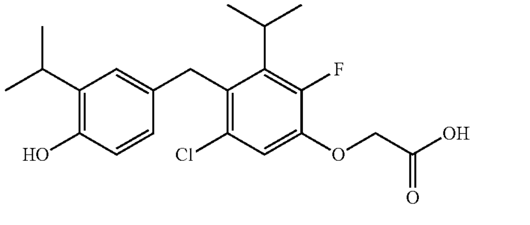

To a solution of Compound 72 (250 mg, 520 umol) in THF/$H_2O$ (2.0 mL/0.5 mL) at rt was added LiOH·$H_2O$ (39 mg, 927 umol). The mixture was stirred at rt for 1 h. The mixture was diluted with water (50 mL), acidified with 1N HCl to pH~3-4 and extracted with EtOAc (20 mL*3). The combined organic phase was washed with brine (50 mL), dried over $Na_2SO_4$ and concentrated in vacuo. The crude product was purified by Prep-HPLC to afford Compound 73 (55 mg, 25.8% yield) as a white solid.

TLC: MeOH/DCM=1/10 (v/v), Rf=0.30

LCMS: RT=1.896 min, [M−1]=393.1

$^1H$ NMR: (400 MHz, DMSO-$d_6$) δ 9.06 (s, 1H), 7.09 (d, J=8.0 Hz, 1H), 6.82 (d, J=2.0 Hz, 1H), 6.66 (d, J=8.0 Hz, 1H), 6.59 (dd, J=8.4, 2.4 Hz, 1H), 4.80 (s, 2H), 4.03 (s, 2H), 3.13 (m, 2H), 1.12 (dd, J=7.2, 1.2 Hz, 6H), 1.09 (d, J=7.2 Hz, 6H).

$^{19}F$ NMR: (376 MHz, DMSO-$d_6$) δ −136.27.

Example 74

Synthesis of ethyl 2-(3-chloro-2-fluoro-4-(4-hydroxy-3-isopropylbenzyl)-5-vinylphenoxy)acetate (Compound 74)

74

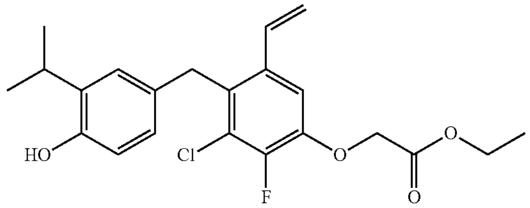

To a mixture of Intermediate C6 (800 mg, 1.7 mmol) and vinylboron(pinacolate) (524 mg, 3.4 mmol) in 1,4-dioxane (6.0 mL) and water (0.5 mL) at rt were added Pd(dppf)$Cl_2$·$CH_2Cl_2$ (139 mg, 170 umol) and $Cs_2CO_3$ (1.1 g, 3.4 mmol). The reaction was heated to 120° C. under $N_2$(g) in a sealed tube for 3 h. The mixture was cooled to rt; water (50 mL) was added and the mixture was extracted with EtOAc (20 mL*3). The combined organic phase was washed with brine (50 mL), dried over $Na_2SO_4$, concentrated in vacuo and purified by Prep-TLC (EtOAc/pet. ether=1/5) to afford Compound 74 (230 mg, 33.2% yield) as a white solid.

TLC: Pet. ether/EtOAc=5/1 (v/v), Rf=0.17

$^1H$ NMR: (400 MHz, DMSO-$d_6$) δ 9.07 (s, 1H), 7.29 (d, J=8.4 Hz, 1H), 6.92-6.90 (m, 1H), 6.62 (d, J=8.0 Hz, 1H), 6.57 (dd, J=8.4, 2.4 Hz, 1H), 5.34 (d, J=10.8 Hz, 1H), 5.01 (s, 2H), 4.17 (q, J=7.2 Hz, 2H), 4.04 (s, 2H), 3.12 (p, J=6.8 Hz, 1H), 1.22-1.18 (t, J=7.4 Hz, 3H), 1.09 (d, J=6.8 Hz, 6H).

Example 75

Synthesis of 2-(3-chloro-2-fluoro-4-(4-hydroxy-3-isopropylbenzyl)-5-vinylphenoxy)acetic acid (Compound 75)

75

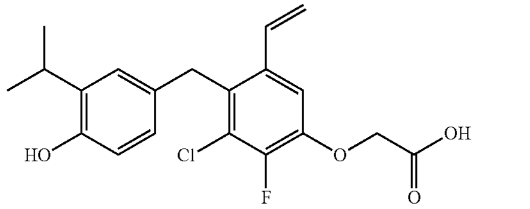

To a solution of Compound 74 (100 mg, 246 umol) in THF/$H_2O$ (2.0 mL/0.5 mL) at rt was added LiOH·$H_2O$ (30 mg, 738 umol). The mixture was stirred at rt for 1 h. The mixture was diluted with water (30 mL), acidified with 1N HCl to pH~3-4 and extracted with EtOAc (20 mL*3). The combined organic phase was washed with brine (50 mL), dried over $Na_2SO_4$ and concentrated in vacuo. The crude product was purified by Prep-HPLC to afford Compound 75 (25 mg, 26.9% yield) as a white solid.

TLC: MeOH/DCM=1/10 (v/v), Rf=0.30

LCMS: RT=1.688 min, [M−1]=378.1

$^1$H NMR: (400 MHz, DMSO-$d_6$) δ 9.07 (s, 1H), 7.27 (d, J=8.4 Hz, 1H), 6.97-6.88 (m, 2H), 6.63 (d, J=8.0 Hz, 1H), 6.57 (dd, J=8.4, 2.4 Hz, 1H), 5.76 (d, J=17.2 Hz, 1H), 5.34 (d, J=11.2 Hz, 1H), 4.92 (s, 2H), 4.05 (s, 2H), 3.16-3.09 (m, 1H), 1.10 (d, J=6.8 Hz, 6H).

$^{19}$F NMR: (376 MHz, DMSO-$d_6$) δ −133.28.

Example 76

Synthesis of ethyl 2-(3-chloro-5-ethyl-2-fluoro-4-(4-hydroxy-3-isopropylbenzyl)phenoxy)acetate (Compound 76)

76

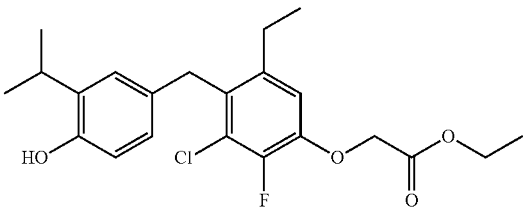

To a solution of Compound 74 (130 mg, 320 umol) in THF (5.0 mL) was added Pd/C (50 mg). The mixture was stirred under $H_2$ atmosphere at 60° C. overnight. The mixture was filtered and concentrated in vacuo to afford Compound 76 (130 mg, 99.2% yield) as a yellow oil.

TLC: Pet. ether/EtOAc=1/5 (v/v), Rf=0.28

Example 77

Synthesis of 2-(3-chloro-5-ethyl-2-fluoro-4-(4-hydroxy-3-isopropylbenzyl)phenoxy)acetic acid (Compound 77)

77

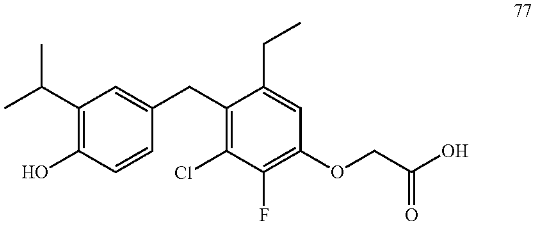 [SMILES: CCc1cc(OCC(=O)O)c(F)c(Cl)c1Cc1ccc(O)c(C(C)C)c1]

To a solution of Compound 76 (130 mg, 318 umol) in THF/$H_2O$ (2.0 mL/0.5 mL) at rt was added LiOH·$H_2O$ (40 mg, 954 umol). The mixture was stirred at rt for 1 h. The mixture was diluted with water (50 mL), acidified with 1N HCl to pH~3-4 and extracted with EtOAc (20 mL*3). The combined organic phase was washed with brine (50 mL), dried over $Na_2SO_4$ and concentrated in vacuo. The crude product was purified by Prep-HPLC to afford Compound 77 (5 mg, 4.1% yield) as a white solid.

TLC: MeOH/DCM=1/10 (v/v), Rf=0.30

LCMS: RT=4.025 min, [M−1]=379.1

$^1$H NMR: (400 MHz, DMSO-$d_6$) δ 9.06 (s, 1H), 6.97 (d, J=8.4 Hz, 1H), 6.89 (d, J=2.4 Hz, 1H), 6.64 (d, J=8.0 Hz, 1H), 6.54 (dd, J=8.4, 2.4 Hz, 1H), 4.83 (s, 2H), 3.99 (s, 2H), 3.16-3.10 (m, 1H), 2.58-2.52 (m, 2H), 1.10 (d, J=7.2 Hz, 6H), 1.00 (t, J=7.6 Hz, 3H).

$^{19}$F NMR: (376 MHz, DMSO-$d_6$) δ −136.31.

Example 78

Synthesis of ethyl 2-(3-chloro-2-fluoro-4-(4-hydroxy-3-isopropylbenzyl)-5-(prop-1-en-2-yl)phenoxy)acetate (Compound 78)

78

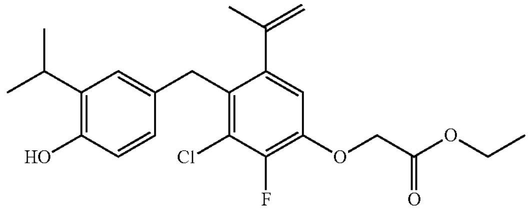

To a mixture of Intermediate C6 (600 mg, 1.3 mmol) and potassium isopropenyl trifluoroborate (354 mg, 2.6 mmol) in 1,4-dioxane (5.0 mL) and $H_2O$ (0.2 mL) at rt were added Pd(dppf)$Cl_2$·$CH_2Cl_2$ (106 mg, 131 umol) and $Cs_2CO_3$ (847 mg, 2.6 mmol). The reaction was heated to 120° C. under $N_2$(g) in a sealed tube for 2 h. The mixture was cooled to rt; water (30 mL) was added and the mixture was extracted with EtOAc (20 mL*3). The combined organic phase was washed with brine (50 mL), dried over $Na_2SO_4$, concentrated in vacuo and purified by Prep-TLC (EtOAc/pet. ether=1/5) to afford Compound 78 (230 mg, 41.9% yield) as a white solid.

TLC: Pet. ether/EtOAc=5/1 (v/v), Rf=0.23

$^1$H NMR: (400 MHz, DMSO-$d_6$) δ 9.03 (s, 1H), 6.92 (d, J=8.4 Hz, 1H), 6.78 (d, J=2.0 Hz, 1H), 6.63 (d, J=8.0 Hz, 1H), 6.54 (dd, J=8.0, 2.4 Hz, 1H), 5.17 (t, J=2.0 Hz, 1H), 4.95 (s, 2H), 4.74 (dd, J=2.0, 1.1 Hz, 1H), 4.19-4.13 (m, 2H), 3.96 (s, 2H), 3.14-3.08 (m, 1H), 1.18 (d, J=7.2 Hz, 3H), 1.08 (d, J=6.8 Hz, 6H)

Example 79

Synthesis of 2-(3-chloro-2-fluoro-4-(4-hydroxy-3-isopropylbenzyl)-5-(prop-1-en-2-yl)phenoxy)acetic acid (Compound 79)

79

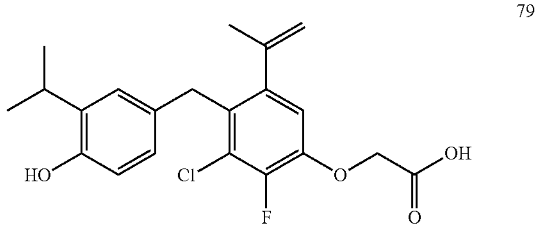 [SMILES: C=C(C)c1cc(OCC(=O)O)c(F)c(Cl)c1Cc1ccc(O)c(C(C)C)c1]

To a solution of Compound 78 (100 mg, 240 umol) in $THF/H_2O$ (2.0 mL/0.5 mL) at rt was added $LiOH \cdot H_2O$ (30 mg, 720 umol). The mixture was stirred at rt for 1 h. The mixture was diluted with water (50 mL), acidified with 1N HCl to pH~3-4 and extracted with EtOAc (20 mL*3). The combined organic phase was washed with brine (50 mL), dried over $Na_2SO_4$ and concentrated in vacuo. The crude product was purified by Prep-HPLC to afford Compound 79 (10 mg, 11.2% yield) as a white solid.

TLC: MeOH/DCM=1/10 (v/v), Rf=0.30

LCMS: RT=2.240 min, [M−1]=391.1

$^1H$ NMR: (400 MHz, DMSO-$d_6$) δ 9.03 (s, 1H), 6.89 (d, J=8.4 Hz, 1H), 6.79 (d, J=2.0 Hz, 1H), 6.62 (d, J=8.4 Hz, 1H), 6.53 (dd, J=8.4, 2.4 Hz, 1H), 5.17 (t, J=2.0 Hz, 1H), 4.85 (s, 2H), 4.77-4.70 (m, 1H), 3.95 (s, 2H), 3.11 (m, 1H), 1.85 (d, J=1.6 Hz, 3H), 1.08 (d, J=6.8 Hz, 6H).

$^{19}F$ NMR: (376 MHz, DMSO-$d_6$) δ −134.85.

Example 80

Synthesis of ethyl 2-(3-chloro-2-fluoro-4-(4-hydroxy-3-isopropylbenzyl)-5-isopropylphenoxy)acetate (Compound 80)

80

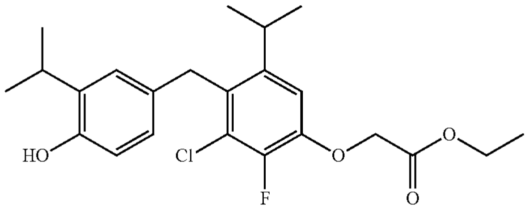

To a solution of Compound 78 (130 mg, 309 umol) in THF (5.0 mL) was added Pd/C (60 mg). The mixture was stirred under $H_2$ atmosphere at 60° C. overnight. The mixture was filtered and concentrated in vacuo to afford Compound 80 (130 mg, 99.2% yield) as a yellow oil.

TLC: Pet. ether/EtOAc=1/5 (v/v), Rf=0.28

Example 81

Synthesis of 2-(3-chloro-2-fluoro-4-(4-hydroxy-3-isopropylbenzyl)-5-isopropylphenoxy)acetic acid (Compound 81)

81

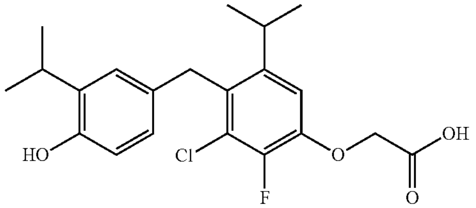

To a solution of Compound 80 (130 mg, 308 umol) in $THF/H_2O$ (2.0 mL/0.5 mL) at rt was added $LiOH \cdot H_2O$ (39 mg, 924 umol). The mixture was stirred at rt for 1 h. The mixture was diluted with water (30 mL), acidified with 1N HCl to pH~3-4 and extracted with EtOAc (10 mL*3). The combined organic phase was washed with brine (20 mL), dried over $Na_2SO_4$ and concentrated in vacuo. The crude product was purified by Prep-HPLC to afford Compound 81 (15 mg, 12.3% yield) as a white solid.

TLC: MeOH/DCM=1/10 (v/v), Rf=0.30

LCMS: RT=1.836 min, [M−1]=393.1

$^1H$ NMR: (400 MHz, DMSO-$d_6$) δ 9.06 (s, 1H), 7.00 (d, J=8.4 Hz, 1H), 6.83 (d, J=2.4 Hz, 1H), 6.65 (d, J=8.0 Hz, 1H), 6.57 (dd, J=8.4, 2.4 Hz, 1H), 4.86 (s, 2H), 4.04 (s, 2H), 3.15-3.06 (m, 2H), 1.07 (dd, J=6.8, 6H), 1.04 (dd, J=6.8, 6H).

$^{19}F$ NMR: (376 MHz, DMSO-$d_6$) δ −136.10.

Example 82

Synthesis of ethyl 2-(3,5-dichloro-2-fluoro-4-(3-(4-fluorobenzyl)-4-hydroxybenzyl)phenoxy)acetate (Compound 82)

82

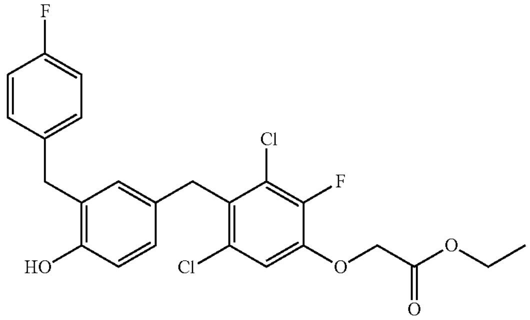

To a solution of Intermediate B6 (385 mg, 1.90 mmol) in DCE (5 mL) at rt were added Intermediate A29 (200 mg, 0.63 mmol) and $ZnCl_2$ (1.0M in THF, 1.4 mL, 1.4 mmol). The reaction was heated to 90° C. overnight. The reaction mixture was diluted with DCM (20 mL), washed with brine (10 mL*2), dried over $Na_2SO_4$, and concentrated in vacuo. The crude product was purified by silica gel column chromatography (pet. ether/EtOAc=5/1) to afford Compound 82 (120 mg, 39.3% yield) as a colorless oil.

TLC: Pet. ether/EtOAc=5/1 (v/v), Rf=0.21

$^1H$ NMR: (400 MHz, DMSO-$d_6$) δ 9.30 (s, 1H), 7.38 (d, J=7.7 Hz, 1H), 7.18 (dd, J=8.6, 5.7 Hz, 2H), 7.11-7.01 (m, 2H), 6.84 (d, J=2.1 Hz, 1H), 6.74 (dd, J=8.3, 2.2 Hz, 1H), 6.69 (d, J=8.2 Hz, 1H), 4.98 (s, 2H), 4.18 (q, J=7.1 Hz, 2H), 4.02 (s, 2H), 3.78 (s, 2H), 1.20 (t, J=7.1 Hz, 3H).

Example 83

Synthesis of 2-(3,5-dichloro-2-fluoro-4-(3-(4-fluorobenzyl)-4-hydroxybenzyl)phenoxy)acetic acid (Compound 83)

83

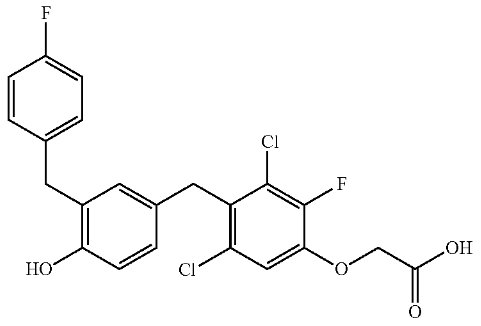

To a solution of Compound 82 (120 mg, 0.25 mmol) in THF (3 mL)/water (1 mL) at rt was added LiOH·$H_2O$ (31 mg, 0.375 mmol); the mixture was stirred at rt for 1 h. The reaction was acidified to pH~3-4 with 1N HCl, then extracted with EtOAc (20 mL). The combined organic phase was washed with brine (20 mL), dried over $Na_2SO_4$, concentrated in vacuo and purified by Prep-HPLC to afford Compound 83 (25 mg, 15.5% yield) as a white solid.

TLC: DCM/MeOH=5/1 (v/v), Rf=0.31

LCMS: RT=3.018 min, [M−1]=451.

$^1$H NMR: (400 MHz, DMSO-$d_6$) δ 9.81 (s, 1H), 7.27-7.18 (m, 2H), 7.11 (s, 2H), 7.10-7.04 (m, 2H), 6.57 (d, J=8.5 Hz, 1H), 6.40 (t, J=8.7 Hz, 1H), 4.75 (s, 2H), 4.03 (s, 2H), 3.88 (s, 2H).

Example 84

Synthesis of ethyl 2-(3,5-dichloro-2-fluoro-4-(3-(1-(4-fluorophenyl)butyl)-4-hydroxybenzyl)phenoxy) acetate (Compound 84)

84

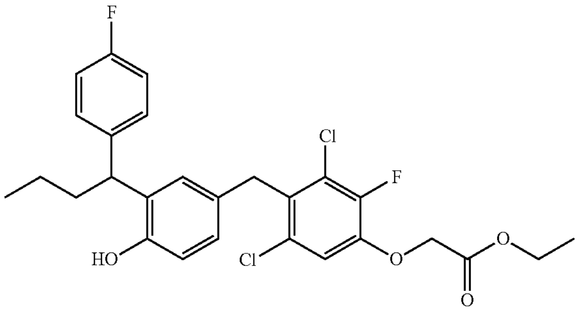

A mixture of Intermediate B18 (244 mg, 1.0 mmol), Intermediate A29 (158 mg, 0.5 mmol) and $ZnCl_2$ (170 mg, 1.25 mmol) in chlorobenzene (5 mL) was stirred at 140° C. overnight. The mixture was cooled to rt, water (10 mL) was added, and the resultant mixture was extracted with DCM (10 mL). The organic layer was dried over $Na_2SO_4$, concentrated in vacuo, and purified by Prep-TLC (pet. ether/EtOAc=5/1) to afford Compound 84 (80 mg, 30.6% yield) as a white solid.

TLC: EtOAc/pet. ether=1/5 (v/v), Rf=0.38

$^1$H NMR: (400 MHz, DMSO-$d_6$) δ 9.21 (s, 1H), 7.40 (d, J=7.6 Hz, 1H), 7.25-7.16 (m, 2H), 7.08-6.99 (m, 3H), 6.70 (d, J=2.2 Hz, 1H), 6.64 (d, J=8.2 Hz, 1H), 4.99 (s, 2H), 4.17 (q, J=7.1 Hz, 4H), 4.05 (s, 2H), 1.89-1.80 (m, 2H), 1.26-1.13 (m, 5H), 0.84 (t, J=7.3 Hz, 3H).

Example 85

Synthesis of 2-(3,5-dichloro-2-fluoro-4-(3-(1-(4-fluorophenyl)butyl)-4-hydroxybenzyl)phenoxy)acetic acid (Compound 85)

85

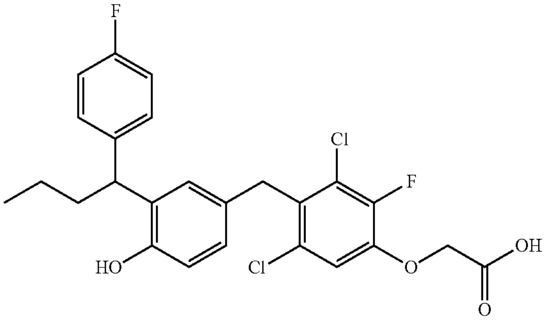

To a solution of Compound 84 (50 mg, 96 umol) in MeOH (3 mL) and water (1 mL) was added LiOH·$H_2O$ (12 mg, 287 umol). The mixture was stirred at rt for 1 h. Water (10 mL) was added; the mixture was acidified to pH~4-5 with 1N HCl, and extracted with DCM (10 mL). The organic phase was dried over $Na_2SO_4$, concentrated in vacuo, and purified by Prep-HPLC to afford Compound 85 (16 mg, 34.0% yield) as a white solid.

TLC: EtOAc/pet. ether=1/5 (v/v), Rf=0

LCMS: RT=2.826 min, [M−1]=493.0/495.0

$^1$H NMR: (400 MHz, DMSO-$d_6$) δ 9.21 (s, 1H), 7.35 (d, J=7.7 Hz, 1H), 7.21 (dd, J=8.7, 5.7 Hz, 2H), 7.08-7.00 (m, 3H), 6.71 (dd, J=8.2, 2.2 Hz, 1H), 6.64 (d, J=8.3 Hz, 1H), 4.89 (s, 2H), 4.22 (t, J=7.9 Hz, 1H), 4.05 (s, 2H), 1.90-1.80 (m, 2H), 1.15 (p, J=7.3 Hz, 2H), 0.84 (t, J=7.3 Hz, 3H).

Example 86

Synthesis of ethyl 2-(3,5-dichloro-4-((3'-(difluoromethoxy)-6-hydroxy-[1,1'-biphenyl]-3-yl)methyl)-2-fluorophenoxy)acetate (Compound 86)

86

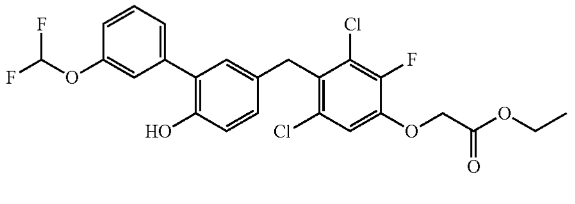

To a solution of Intermediate B19 (150 mg, 0.63 mmol) in DCE (3 mL) at rt were added Intermediate A29 (100 mg, 0.32 mmol) and $ZnCl_2$ (0.8 mmol, 0.8 mL). The reaction was heated to 100° C. and stirred overnight. The reaction mixture was diluted with DCM (20 mL), washed with brine (10 mL*2), dried over $Na_2SO_4$, and concentrated in vacuo. The crude product was purified by Prep-TLC (EtOAc/pet. ether=1/3) to afford Compound 86 (45 mg, 27.6% yield) as a light yellow oil.

TLC: EtOAc/pet. ether=1/3 (v/v), Rf=0.5

$^1$H NMR: (400 MHz, DMSO-$d_6$) δ 9.59 (s, 1H), 7.44-7.41 (m, 2H), 7.35-7.32 (m, 1H), 7.29 (t, J=2.4 Hz, 1H), 7.24 (s, 1H), 7.12-7.08 (m, 2H), 6.91 (d, J=2.4 Hz, 1H), 6.86 (d, J=8.4 Hz, 1H), 4.99 (s, 2H), 4.17 (d, J=7.2 Hz, 2H), 4.14 (s, 2H), 1.20 (d, J=7.2 Hz, 3H).

Example 87

Synthesis of 2-(3,5-dichloro-4-((3'-(difluoromethoxy)-6-hydroxy-[1,1'-biphenyl]-3-yl)methyl)-2-fluorophenoxy)acetic acid (Compound 87)

87

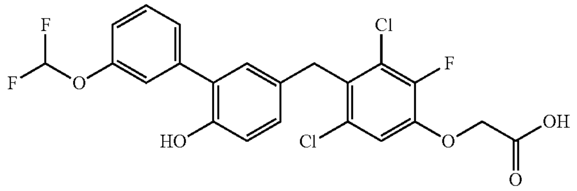

To a solution of Compound 86 (45 mg, 87.3 umol) in water (0.5 mL)/THF (1 mL) at rt was added LiOH·$H_2O$ (7 mg, 175 umol); the resultant mixture was stirred overnight at rt. The reaction mixture was acidified to pH~3 with HCl (1N), extracted with EtOAc (10 mL*3), dried over $Na_2SO_4$, and concentrated in vacuo. The crude product was purified by Prep-TLC (MeOH/DCM=1/10) to afford Compound 87 (24 mg, 53.6% yield, 95% purity) as a white solid.

TLC: MeOH/DCM=1/5 (v/v), $R_f$=0.35

$^1$H NMR: (400 MHz, DMSO-$d_6$) δ 9.71 (s, 1H), 7.45-7.41 (m, 1H), 7.35-7.29 (m, 2H), 7.25 (s, 1H), 7.11-7.06 (m, 3H), 6.90 (s, 2H), 4.42 (s, 2H), 4.11 (s, 2H).

$^{19}$F NMR: (376 MHz, DMSO-$d_6$) δ −81.52, −133.61.

Example 88

Synthesis of ethyl 2-(2,3,5-trichloro-4-(4-hydroxy-3-isopropylbenzyl)phenoxy)acetate (Compound 88)

88

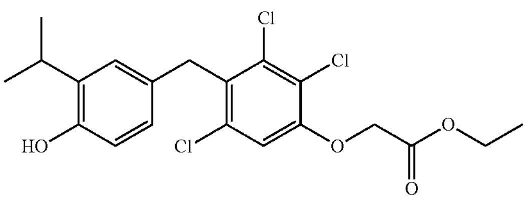

To a solution of Intermediate A42 (115 mg, 0.35 mmol) in DCE (5 mL) at rt were added 2-isopropylphenol (94 mg, 0.70 mmol) and $ZnCl_2$ (1 M, 0.87 mL). The mixture was heated to 90° C. and stirred overnight. The reaction mixture was diluted with DCM (20 mL), washed with brine (10 mL*2), dried over $Na_2SO_4$, and concentrated in vacuo. The crude product was purified by Prep-TLC (pet. ether/EtOAc=5/1) to afford Compound 88 (80 mg, 53.3% yield) as a white solid.

TLC: pet. ether/EtOAc=5/1 (v/v), Rf=0.20.

LCMS: RT=2.302 min, [M−1]=428.9.

$^1$H NMR: (400 MHz, DMSO-$d_6$) δ 9.11 (s, 1H), 7.36 (s, 1H), 6.98 (s, 1H), 6.64 (d, J=1.6 Hz, 2H), 5.03 (s, 2H), 4.18 (q, J=7.2 Hz, 2H), 4.12 (s, 2H), 3.13 (p, J=6.8 Hz, 1H), 1.21 (t, J=7.2 Hz, 3H), 1.10 (d, J=6.8 Hz, 6H).

Example 89

Synthesis of 2-(2,3,5-trichloro-4-(4-hydroxy-3-isopropylbenzyl)phenoxy)acetic acid (Compound 89)

89

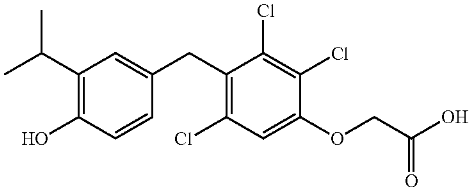

To a solution of Compound 88 (80 mg, 0.18 mmol) in MeOH (3 mL)/water (1 mL) at rt was added LiOH·$H_2O$ (23 mg, 0.54 mmol); the resultant mixture was stirred at rt for 1 h. The reaction was acidified to pH~4-5 with 2N HCl, and extracted with EtOAc (20 mL); the combined organic extracts were washed with brine (10 mL*2), dried over $Na_2SO_4$, concentrated in vacuo and purified by Prep-HPLC to afford Compound 89 (25 mg, 33.1% yield) as a white solid.

TLC: DCM/MeOH=5/1 (v/v), Rf=0.24.

LCMS: RT=1.530 min, [M−1]=400.9.

$^1$H NMR: (400 MHz, DMSO-$d_6$) δ 9.10 (s, 1H), 7.31 (s, 1H), 6.98 (s, 1H), 6.65 (d, J=1.2 Hz, 2H), 4.93 (s, 2H), 4.11 (s, 2H), 3.15-3.10 (m, 1H), 1.11 (d, J=6.8 Hz, 6H).

Example 90

Synthesis of ethyl 2-(3,5-dichloro-4-(4-hydroxy-3-isopropylbenzyl)-2-methylphenoxy)acetate (Compound 90)

90

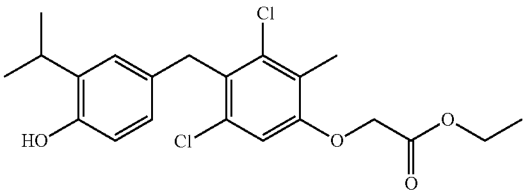

To a solution of Intermediate A47 (200 mg, 0.64 mmol) in DCE (5 mL) at rt were added 2-isopropylphenol (175 mg, 1.28 mmol) and $ZnCl_2$ (1.60 mmol, 1.60 mL). The reaction mixture was heated to 90° C. and stirred overnight. The mixture was diluted with DCM (20 mL), washed with brine (10 mL*2), dried over $Na_2SO_4$, and concentrated in vacuo. The crude product was purified by Prep-TLC (pet. ether/EtOAc=5/1) to afford Compound 90 (120 mg, 45.4% yield) as a colorless oil.

TLC: pet. ether/EtOAc=5/1 (v/v), Rf=0.24

LCMS: RT=2.414 min, [M−1]=408.9.

$^1$H NMR: (400 MHz, DMSO-$d_6$) δ 9.09 (s, 1H), 7.12 (s, 1H), 6.98 (s, 1H), 6.66-6.60 (m, 2H), 4.91 (s, 2H), 4.17 (q, J=7.2 Hz, 2H), 4.07 (s, 2H), 3.12 (p, J=6.8 Hz, 1H), 2.25 (s, 3H), 1.22-1.19 (m, 3H), 1.10 (d, J=6.8 Hz, 6H).

Example 91

Synthesis of 2-(3,5-dichloro-4-(4-hydroxy-3-isopropylbenzyl)-2-methylphenoxy)acetic acid (Compound 91)

91

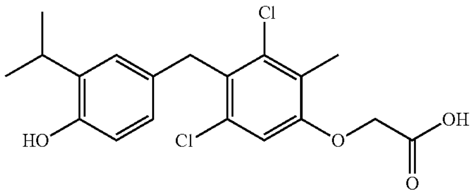

To a solution of Compound 90 (120 mg, 0.29 mmol) in MeOH (3 mL)/water (1 mL) at rt was added LiOH·$H_2O$ (37 mg, 0.87 mmol); the mixture was stirred at rt for 1 h. The reaction was acidified to pH~4-5 with 2N HCl, and extracted with EtOAc (20 mL); the combined extracts were washed with brine (10 mL*2), dried over $Na_2SO_4$, concentrated in vacuo and purified by Prep-HPLC to afford Compound 91 (26 mg, 22.7% yield) as a white solid.

TLC: DCM/MeOH=5/1 (v/v), Rf=0.31.

LCMS: RT=1.656 min, [M−1]=381.0.

$^1$H NMR: (400 MHz, DMSO-$d_6$) δ 13.05 (s, 1H), 9.07 (s, 1H), 7.07 (s, 1H), 6.99 (s, 1H), 6.63 (s, 2H), 4.81 (s, 2H), 4.07 (s, 2H), 3.12 (p, J=6.8 Hz, 1H), 2.24 (s, 3H), 1.11 (d, J=6.8 Hz, 6H).

Example 92

Synthesis of ethyl 2-(2-fluoro-4-(2-fluoro-4-hydroxy-3-isopropylbenzyl)-3,5-dimethylphenoxy) acetate (Compound 92)

92

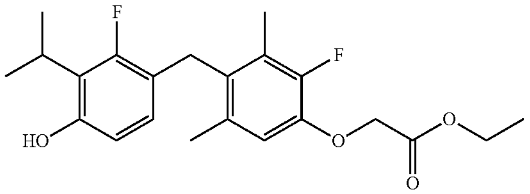

To a solution of Intermediate A24 (449 mg, 2.91 mmol) in chlorobenzene (20 mL) at rt were added Intermediate B2 (400 mg, 1.46 mmol) and $ZnCl_2$ (258 mg, 1.89 mmol). The reaction was heated to 130° C. and stirred overnight. The reaction mixture was diluted with DCM (20 mL), washed with brine (10 mL*2), dried over $Na_2SO_4$, and concentrated in vacuo. The crude product was purified by prep-TLC (EtOAc/pet. ether=1/3) to afford Compound 92 (200 mg, 35.0% yield) as a light yellow oil.

$^1$H NMR: (400 MHz, DMSO-$d_6$) δ 9.49 (s, 1H), 6.80 (d, J=8.8 Hz, 1H), 6.45 (d, J=8.4 Hz, 1H), 6.13 (t, J=8.6 Hz, 1H), 4.82 (s, 2H), 4.18 (q, J=7.2 Hz, 2H), 3.76 (s, 2H), 3.40-3.38 (m, 1H), 2.10 (s, 3H), 2.05 (d, J=2.4 Hz, 3H), 1.26 (d, J=7.2 Hz, 6H), 1.21 (t, J=7.2 Hz, 3H).

$^{19}$F NMR: (376 MHz, DMSO-$d_6$) δ −120.40, −140.40.

Example 93

Synthesis of 2-(2-fluoro-4-(2-fluoro-4-hydroxy-3-isopropylbenzyl)-3,5-dimethylphenoxy)acetic acid (Compound 93)

93

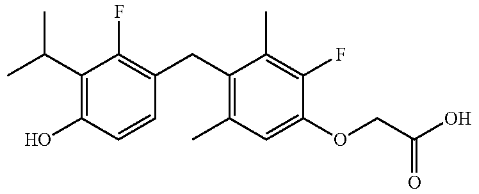

To a solution of Compound 92 (200 mg, 0.51 mmol) in THF (5 mL)/water (0.5 mL) at rt was added LiOH·$H_2O$ (22 mg, 0.51 mmol); the resultant mixture was stirred at rt for 1 h. The reaction was diluted with water (20 mL), acidified to pH~3 with aqueous HCl (1N), and extracted with EtOAc (10 mL*3). The combined organic phase was washed with brine (10 mL*2), dried over $Na_2SO_4$, and concentrated in vacuo. The crude product was purified by Prep-TLC (MeOH/DCM=1/8) to afford Compound 93 (170 mg, 84.2% yield) as a white solid.

TLC: MeOH/DCM=1/10, Rf=0.24

LCMS: RT=3.96 min; [M−1]=363.1

$^1$H NMR: (400 MHz, DMSO-$d_6$) δ 9.54 (s, 1H), 6.71 (d, J=8.8 Hz, 1H), 6.46 (d, J=8.4 Hz, 1H), 6.13 (t, J=8.4 Hz, 1H), 4.52 (s, 2H), 3.74 (s, 2H), 3.52-3.22 (m, 1H), 2.08 (s, 3H), 2.03 (d, J=2.4 Hz, 3H), 1.26 (d, J=7.2 Hz, 6H).

$^{19}$F NMR: (376 MHz, DMSO-$d_6$) δ −120.51, −140.69.

Example 94

Synthesis of 2-(2-fluoro-4-(2-fluoro-4-hydroxy-3-isopropylbenzyl)-3,5-dimethylphenoxy)-N-methylacetamide (Compound 94)

94

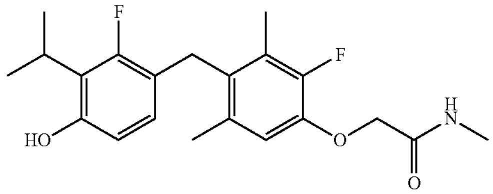

To solution of Compound 93 (130 mg, 0.36 mmol) in DCM (5 mL) at rt was added $SOCl_2$ (128 mg, 1.08 mmol); the resultant solution was stirred at rt for 3 h. The reaction mixture was concentrated in vacuo to afford the acid chloride (130 mg, 95.1% yield) as a white solid. A sample of this material (65 mg, 0.17 mmol) was dissolved in DCM (2 mL), and added dropwise to a solution of methylamine (1.02 mmol, 1.02 mL of 1.0M) in THF (5 mL). The mixture was stirred overnight. The reaction mixture was diluted with water (20 mL) and extracted with EtOAc (10 mL*3). The combined organic phase was washed with brine (10 mL*2), dried over $Na_2SO_4$, and concentrated in vacuo. The crude product was purified by Prep-TLC (EtOAc/pet. ether=1/3) to afford Compound 94 (31 mg, 48.3% yield) as a white solid.

LCMS: RT=3.96 min; [M−1]=376.1

$^1$H NMR: (400 MHz, DMSO-$d_6$) δ 9.46 (d, J=1.2 Hz, 1H), 7.92 (s, 1H), 6.80 (d, J=8.4 Hz, 1H), 6.54-6.37 (m, 1H), 6.14 (t, J=8.8 Hz, 1H), 4.50 (s, 2H), 3.77 (s, 2H), 3.41-3.36 (m, 1H), 2.66 (d, J=4.4 Hz, 3H), 2.11 (s, 3H), 2.05 (d, J=2.4 Hz, 3H), 1.26 (dd, J=7.2, 0.8 Hz, 6H).

$^{19}$F NMR: (376 MHz, DMSO-$d_6$) δ −120.39, −139.71.

Example 95

Synthesis of 2-(2-fluoro-4-(2-fluoro-4-hydroxy-3-isopropylbenzyl)-3,5-dimethylphenoxy)-N,N-dimethylacetamide (Compound 95)

95

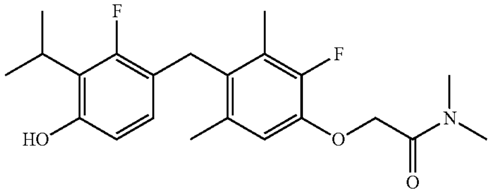

To solution of Compound 93 (130 mg, 0.36 mmol) in DCM (5 mL) at rt was added $SOCl_2$ (128 mg, 1.08 mmol); the resultant solution was stirred at rt for 3 h. The reaction mixture was concentrated in vacuo to afford the acid chloride (130 mg, 95.1% yield) as a white solid. A sample of this material (65 mg, 0.17 mmol) was dissolved in DCM (2 mL), and added dropwise to a solution of dimethylamine (1.02 mmol, 0.5 mL of 2N) in THF (5 mL). The mixture was stirred overnight. The reaction mixture was diluted with water (20 mL) and extracted with EtOAc (10 mL*3). The combined organic phase was washed with brine (10 mL*2), dried over $Na_2SO_4$, and concentrated in vacuo. The crude product was purified by Prep-TLC (EtOAc/pet. ether=1/3) to afford Compound 95 (31 mg, 41.9% yield) as a white solid.

LCMS: RT=4.04 min; [M−1]=390.2

$^1$H NMR: (400 MHz, DMSO-$d_6$) δ 9.46 (d, J=1.6 Hz, 1H), 6.77 (d, J=8.8 Hz, 1H), 6.45 (dd, J=8.4, 0.8 Hz, 1H), 6.14 (t, J=8.8 Hz, 1H), 4.84 (s, 2H), 3.76 (s, 2H), 3.41-3.36 (m, 1H), 3.00 (s, 3H), 2.85 (s, 3H), 2.10 (s, 3H), 2.04 (d, J=2.4 Hz, 3H), 1.26 (dd, J=7.2, 0.8 Hz, 6H).

$^{19}$F NMR: (376 MHz, DMSO-$d_6$) δ −120.43, −140.60.

Example 96

Synthesis of ethyl 2-(3,5-dichloro-2-fluoro-4-(2-fluoro-4-hydroxy-3-isopropylbenzyl)phenoxy)acetate (Compound 96)

96

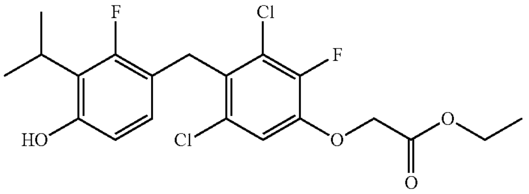

To a solution of Intermediate A29 (5.0 g, 15.8 mmol) in chlorobenzene (25 mL) at rt were added Intermediate B2 (7.3 g, 47.5 mmol) and $ZnCl_2$ (5.4 g, 39.6 mmol). The reaction mixture was heated to 130° C. and stirred for 6 h. The reaction mixture was diluted with DCM (20 mL), washed with brine (40 mL), dried over $Na_2SO_4$, and concentrated in vacuo. The crude product was purified by silica gel column chromatography (EtOAc/pet. ether=1/10) to afford Compound 96 (2.4 g, 34% yield) as a white solid.

TLC: Pet. ether/EtOAc=1/5 (v/v), Rf=0.35

$^1$H NMR: (400 MHz, DMSO) δ 9.56 (s, 1H), 7.44 (d, J=7.7 Hz, 1H), 6.48 (d, J=8.4 Hz, 1H), 6.29 (t, J=8.6 Hz, 1H), 5.01 (s, 2H), 4.18 (q, J=7.1 Hz, 2H), 4.04 (s, 2H), 3.38 (m, 1H), 1.25 (m, 6H), 1.22 (m, 3H).

Example 97

Synthesis of 2-(3,5-dichloro-2-fluoro-4-(2-fluoro-4-hydroxy-3-isopropylbenzyl)phenoxy)acetic acid (Compound 97)

97

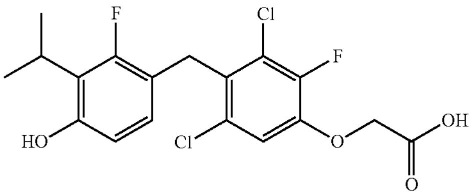

To a solution of Compound 96 (4.5 g, 10.3 mmol) in water (30 mL)/THF (10 mL) at rt was added NaOH (1.2 g, 31.2 mmol); the resultant mixture was stirred at rt for 1 h. The reaction was acidified to pH~3-4 with 2N HCl, and extracted with DCM (40 mL*3); the combined organic phase was washed with brine (100 mL), dried over $Na_2SO_4$, and concentrated in vacuo to afford Compound 97 (4.0 g, 95% yield).

TLC: Pet. ether/EtOAc=1/5 (v/v), Rf=0

LCMS: RT=4.16 min; [M−1]=403.0

$^1$H NMR: (400 MHz, DMSO) δ 9.56 (s, 1H), 7.38 (d, J=7.7 Hz, 1H), 6.48 (d, J=8.4 Hz, 1H), 6.29 (t, J=8.6 Hz, 1H), 4.91 (s, 2H), 4.04 (s, 2H), 1.25 (d, J=7.0 Hz, 6H).

Example 98

Synthesis of 2-(3,5-dichloro-2-fluoro-4-(2-fluoro-4-hydroxy-3-isopropylbenzyl)phenoxy)-N-methylacetamide (Compound 98)

98

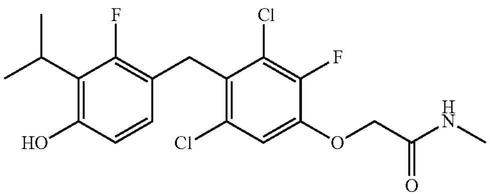

To a solution of Compound 97 (2.1 g, 5.18 mmol) in DCM (20 mL) were added oxalyl chloride (1.9 g, 15.5 mmol) and DMF (cat.). After stirring at rt for 1 h, the reaction mixture was concentrated in vacuo. The residue was dissolved in DCM (20 mL) and was added to methylamine/THF solution (25 mL of 2N, 51.8 mmol). After stirring at room temperature for 1 h, the mixture was poured into water (20 mL) and extracted with DCM (30 mL*3). The combined organic phase was washed with brine (20 mL*2), dried over $Na_2SO_4$, and concentrated in vacuo to afford Compound 98 (1.4 g, 51% yield) as a white solid.

TLC: DCM/MeOH=20/1 (v/v), Rf=0.35

LCMS: RT=4.14 min; [M−1]=416.0

$^1$H NMR: (400 MHz, DMSO) δ 9.55 (d, J=1.3 Hz, 1H), 8.02 (d, J=4.2 Hz, 1H), 7.32 (d, J=7.7 Hz, 1H), 6.48 (d, J=8.3 Hz, 1H), 6.30 (t, J=8.6 Hz, 1H), 4.68 (s, 2H), 4.04 (s, 2H), 3.43-3.35 (m, 1H), 2.70-2.62 (d, 3H), 1.26 (d, J=7.0 Hz, 6H).

Example 99

Synthesis of 2-(3,5-dichloro-2-fluoro-4-(2-fluoro-4-hydroxy-3-isopropylbenzyl)phenoxy)-N,N-dimethylacetamide (Compound 99)

99

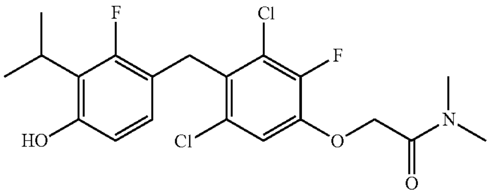

To a solution of Compound 97 (50 mg, 0.12 mmol) in DCM (5 mL) were added oxalyl chloride (45 mg, 0.36 mmol) and DMF (cat.). After stirring at rt for 1 h, the reaction was concentrated in vacuo. The residue was dissolved in DCM (5 mL) and was added to dimethylamine/THF solution (0.6 mL, 2M, 1.2 mmol) in DCM (5 mL). After stirring at room temperature for 1 h, the mixture was poured into water (20 mL) and extracted with DCM (30 mL*3). The organic phase was washed with brine (20 mL), dried over $Na_2SO_4$, concentrated in vacuo and purified by Prep-TLC (pet. ether/EtOAc=2:1) to afford Compound 99 (20 mg, 39% yield) as a white solid.

TLC: DCM/MeOH=20/1 (v/v), Rf=0.35

LCMS: RT=4.28 min; [M−1]=430.1

$^1$H NMR: (400 MHz, DMSO) δ 9.57 (s, 1H), 7.35 (d, J=7.8 Hz, 1H), 6.50 (d, J=1.8 Hz, 1H), 6.31 (t, 1H), 5.06 (s, 2H), 4.03 (s, 2H), 3.40 (m, 1H), 2.96 (s, 3H), 2.84 (s, 3H), 1.26 (d, J=6.9 Hz, 6H).

Example 100

Synthesis of ethyl 2-(3,5-dichloro-4-((5'-(difluoromethoxy)-2,2'-difluoro-6-hydroxy-[1,1'-biphenyl]-3-yl)methyl)-2-fluorophenoxy)acetate (Compound 100)

100

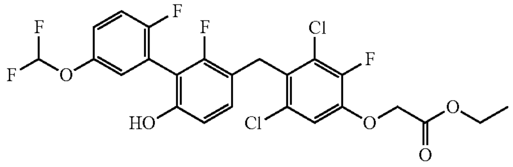

To a mixture of Intermediate D2 (150 mg, 0.45 mmol), Intermediate C7 (137 mg, 0.30 mmol) and Pd(dppf)$Cl_2 \cdot CH_2Cl_2$ (12 mg, 10 umol) in 1,4-dioxane (3 mL) and water (0.3 mL) at rt was added $K_2CO_3$ (124 mg, 0.9 mmol). The reaction was heated to 80° C. under $N_2$(g) overnight. The solution of Compound 100 was used without further purification.

Example 101

Synthesis of 2-(3,5-dichloro-4-((5'-(difluoromethoxy)-2,2'-difluoro-6-hydroxy-[1,1'-biphenyl]-3-yl)methyl)-2-fluorophenoxy)acetic acid (Compound 101)

101

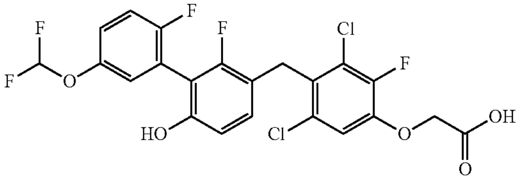

To a solution of Compound 100 (40 mg, 0.07 mmol) in water (5 mL)/THF (1 mL) at rt was added NaOH (8 mg, 0.21 mmol); the mixture was stirred at rt for 1 h. The reaction was acidified to pH~3-4 with 2N HCl, concentrated in vacuo and purified by Prep-HPLC to afford Compound 101 (30 mg, 78.3% yield).

LCMS: RT=2.045 min, [M−1]=520.8

$^1$H NMR: (400 MHz, DMSO) δ 10.02 (s, 1H), 7.45-7.32 (m, 2.54H), 7.29-7.18 (m, 2.49H), 7.04 (s, 0.23H), 6.74-6.62 (m, 2H), 4.89 (s, 2H), 4.11 (s, 2H).

Example 102

Synthesis of ethyl 2-(3,5-dichloro-2-fluoro-4-(2-fluoro-3-(4-fluorobenzyl)-4-hydroxybenzyl)phenoxy)acetate (Compound 102)

102

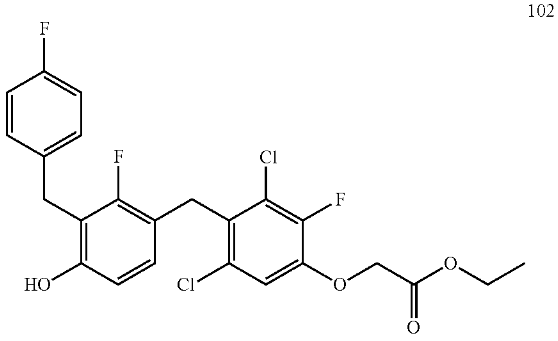 [SMILES: CCOC(=O)COc1cc(Cl)c(Cc2ccc(O)c(Cc3ccc(F)cc3)c2F)c(Cl)c1F]

To a solution of Intermediate B6 (200 mg, 0.90 mmol) in DCE (5 mL) at rt were added Intermediate A29 (191 mg, 0.60 mmol) and $ZnCl_2$ (206 mg, 1.50 mmol). The reaction was heated to 90° C. overnight, then cooled to room temperature, and diluted with DCM (20 mL). The resultant solution was washed with brine (10 mL*2), dried over $Na_2SO_4$, and concentrated in vacuo. The crude product was purified by Prep-TLC (pet. ether/EtOAc=5/1) to afford Compound 102 (180 mg, 59.5% yield) as a colorless oil.

TLC: Pet. ether/EtOAc=5/1 (v/v), Rf=0.21

LCMS: RT=2.433 min, [M−1]=497.0.

Example 103

Synthesis of 2-(3,5-dichloro-2-fluoro-4-(2-fluoro-3-(4-fluorobenzyl)-4-hydroxybenzyl)phenoxy)acetic acid (Compound 103)

103

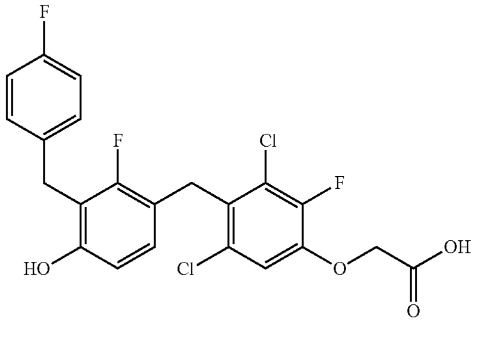

To a solution of Compound 102 (180 mg, 0.36 mmol) in MeOH (7 mL)/Water (1 mL) was added $LiOH{\cdot}H_2O$ (45 mg, 1.08 mmol); the mixture was stirred at rt for 1 h. The reaction was acidified to pH~4-5 with 2N HCl and extracted with EtOAc (20 mL). The combined organic extracts were washed with brine (20 mL), dried over $Na_2SO_4$, concentrated in vacuo and purified by Prep-HPLC and Prep-TLC (DCM/MeOH=5/1) to afford Compound 103 (20 mg, 11.8% yield) as a white solid.

TLC: DCM/MeOH=5/1 (v/v), Rf=0.31

LCMS: RT=2.480 min, [M−1]=469.0.

$^1$H NMR: (400 MHz, DMSO-$d_6$) δ 13.15 (s, 1H), 9.84 (s, 1H), 7.38 (d, J=8 Hz, 1H), 7.25-7.19 (m, 2H), 7.13-7.03 (m, 2H), 6.57 (d, J=8.4 Hz, 1H), 6.43 (t, J=8.8 Hz, 1H), 4.90 (s, 2H), 4.06 (s, 2H), 3.88 (s, 2H).

Example 104

Synthesis of 2-(3,5-dichloro-2-fluoro-4-(2-fluoro-3-(4-fluorobenzyl)-4-hydroxybenzyl)phenoxy)-N-methylacetamide (Compound 104)

104

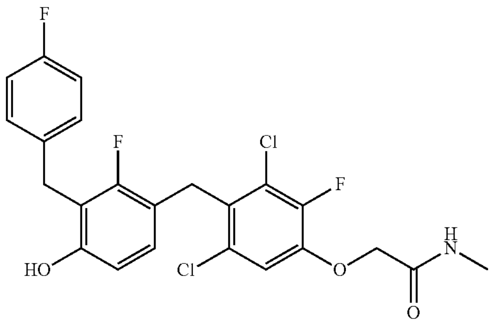

A solution of Compound 102 (70 mg, 0.14 mmol) and aqueous methylamine (0.21 mL of 2N in THF, 0.42 mmol) in THF (5 mL) was stirred at 75° C. overnight in a sealed tube. Water (10 mL) was added, and the resultant mixture was extracted with EtOAc (15 mL*2). The combined organic phase was washed with brine (10 mL*2), dried over $Na_2SO_4$ and concentrated in vacuo. The crude product was purified by Prep-HPLC to afford Compound 104 (12 mg, 17.0% yield) as a white solid.

TLC: Pet. ether/EtOAc=1/1 (v/v), Rf=0.24

LCMS: RT=2.458 min, [M−1]=482.0.

$^1$HNMR: (400 MHz, DMSO-$d_6$) δ 9.84 (d, J=1.6 Hz, 1H), 8.02 (d, J=4.8 Hz, 1H), 7.31 (d, J=7.6 Hz, 1H), 7.24-7.21 (m, 2H), 7.11-7.04 (m, 2H), 6.59-6.54 (m, 1H), 6.43 (t, J=8.4 Hz, 1H), 4.68 (s, 2H), 4.06 (s, 2H), 3.88 (s, 2H), 2.65 (d, J=4.8 Hz, 3H).

Example 105

Synthesis of ethyl 2-(3,5-dichloro-2-fluoro-4-(2-fluoro-3-(1-(4-fluorophenyl)vinyl)-4-hydroxybenzyl)phenoxy)acetate (Compound 105)

105

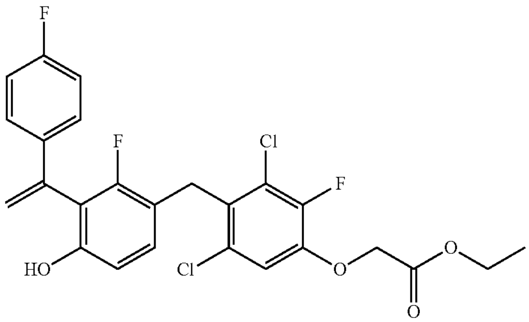

To a mixture of Intermediate C7 (300 mg, 0.6 mmol), Intermediate B5 (316 mg, 1.2 mmol) and $Pd(dppf)Cl_2$ (23 mg, 0.03 mmol) in 1,4-dioxane (10 mL) at rt was added 2N $NaHCO_3$ (0.9 mL, 1.8 mmol). The mixture was heated to 90° C. and stirred overnight. The resulting solution of Compound 105 was used without further purification.

TLC: EtOAc/pet. ether=1/10 (v/v), Rf=0.55

Example 106

Synthesis of 2-(3,5-dichloro-2-fluoro-4-(2-fluoro-3-(1-(4-fluorophenyl)vinyl)-4-hydroxybenzyl)phenoxy)acetic acid (Compound 106)

106

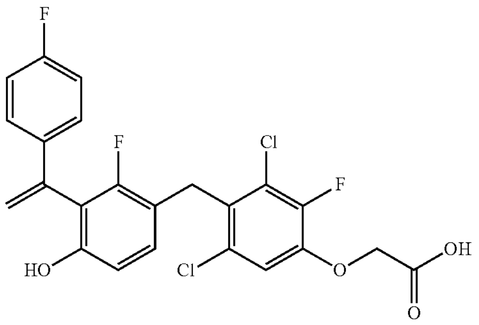

To a solution of Compound 105 (300 mg, 0.58 mmol) in THF/$H_2O$ (2 mL/5 mL) at rt was added LiOH·$H_2O$ (42 mg, 1.74 mmol). The mixture was stirred at rt for 1 h. The mixture was diluted with water (30 mL), acidified with 1N HCl to pH~3-4 and extracted with EtOAc (15 mL*3). The combined organic phase was washed with brine (30 mL), dried over $Na_2SO_4$ and concentrated in vacuo. The crude product was purified by Prep-HPLC to afford Compound 106 (150 mg, 52.9% yield) as a white solid.

TLC: MeOH/DCM=1/10 (v/v), Rf=0.30

LCMS: RT=1.80 min, [M−1]=481.0

Example 107

Synthesis of 2-(3,5-dichloro-2-fluoro-4-(2-fluoro-3-(1-(4-fluorophenyl)ethyl)-4-hydroxybenzyl)phenoxy)acetic acid (Compound 107)

107

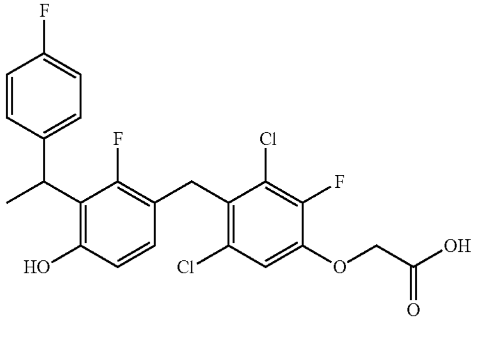

To a solution of Compound 106 (150 mg, 0.31 mmol) in THF (10 mL) was added Pd/C (10%) (15 mg). The reaction mixture was stirred at 55° C. under hydrogen atmosphere overnight. The mixture was cooled to rt and filtered, then concentrated in vacuo and purified by Prep-HPLC to afford Compound 107 (20 mg, 13% yield).

LCMS: RT=4.338 min, [M−1]=483.0

$^1$H NMR: (400 MHz, DMSO) δ 13.54-12.93 (m, 1H), 9.77 (s, 1H), 7.37 (d, J=7.7 Hz, 1H), 7.28 (m, 2H), 7.08 (t, J=8.9 Hz, 2H), 6.54 (d, J=8.4 Hz, 1H), 6.37 (t, J=8.6 Hz, 1H), 4.89 (s, 2H), 4.60 (q, J=7.0 Hz, 1H), 4.09-3.93 (m, 2H), 1.63 (d, J=7.3 Hz, 3H).

Example 108

Synthesis of ethyl 2-(3-chloro-2-fluoro-4-(2-fluoro-4-hydroxy-3-isopropylbenzyl)-5-methylphenoxy)acetate (Compound 108)

108

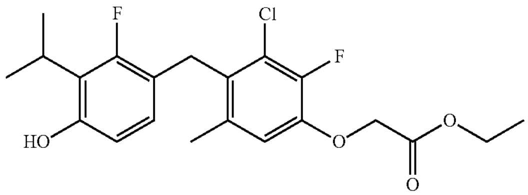

To a solution of Intermediate A52 (300 mg, 1.02 mmol) in DCE (8 mL) at rt were added Intermediate B2 (470 mg, 3.06 mmol) and $ZnCl_2$ (416 mg, 3.06 mmol). The reaction was heated to 90° C. overnight. The reaction mixture was diluted with DCM (20 mL), washed with brine (2*10 mL), dried over $Na_2SO_4$, and concentrated in vacuo. The crude product was purified by silica gel column chromatography (pet. ether/EtOAc=100/1-5/1) to afford Compound 108 (130 mg, 31% yield) as a colorless oil.

TLC: pet. ether/EtOAc=5/1 (v/v), Rf=0.24.

$^1$H NMR: (400 MHz, DMSO-$d_6$) δ 9.51 (d, J=1.6 Hz, 1H), 7.05 (d, J=8.4 Hz, 1H), 6.46 (dd, J=8.4, 1.2 Hz, 1H), 6.21 (t, J=8.4 Hz, 1H), 4.91 (s, 2H), 4.18 (q, J=7.2 Hz, 2H), 3.92 (s, 2H), 3.39 (q, J=7.2 Hz, 1H), 2.15 (s, 3H), 1.27-1.25 (m, 5H), 1.20 (d, J=7.2 Hz, 3H).

Example 109

Synthesis of 2-(3-chloro-2-fluoro-4-(2-fluoro-4-hydroxy-3-isopropylbenzyl)-5-methylphenoxy)acetic acid (Compound 109)

109

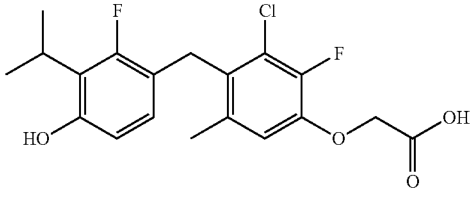

To a solution of Compound 108 (60 mg, 0.14 mmol) in THF (5 mL)/water (1 mL) at rt was added LiOH·$H_2O$ (35 mg, 0.84 mmol); the mixture was stirred at rt overnight. The reaction was acidified to pH~4-5 with 2N HCl, then extracted with EtOAc (5 mL). The combined organic phase was washed with brine (5 mL), dried over $Na_2SO_4$, and concentrated in vacuo. The crude product was purified by Prep-HPLC afford Compound 109 (30 mg, 53.5% yield) as a white solid.

TLC: DCM/MeOH=5/1 (v/v), Rf=0.36.

LCMS: RT=3.985 min, [M−1]=383.1.

$^1$H NMR: (400 MHz, DMSO-$d_6$) δ 13.09 (s, 1H), 9.50 (d, J=1.6 Hz, 1H), 7.02 (d, J=8.4 Hz, 1H), 6.47 (dd, J=8.4, 1.2 Hz, 1H), 6.21 (t, J=8.4 Hz, 1H), 4.81 (s, 2H), 3.91 (s, 2H), 3.42-3.37 (m, 1H), 2.15 (s, 3H), 1.28-1.23 (m, 6H).

Example 110

Synthesis of 2-(3-chloro-2-fluoro-4-(2-fluoro-4-hydroxy-3-isopropylbenzyl)-5-methylphenoxy)-N-methylacetamide (Compound 110)

110

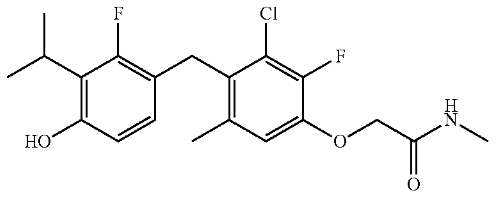

To a solution of Compound 109 (60 mg, 0.16 mmol) in DCM (5 mL) were added oxalyl chloride (40 mg, 0.31 mmol) and DMF (0.2 mL). The mixture was stirred at rt for 1 h. The mixture was concentrated in vacuo to afford the corresponding acid chloride (60 mg, 95.2% yield) as a colorless oil. This intermediate was dissolved in DCM (5 mL); $CH_3NH_2$/THF (2M, 1 mL) was added, and the mixture was stirred at rt for 30 min. The mixture was poured into water (20 mL) and extracted with DCM (30 mL*2); the combined organic phase was dried over $Na_2SO_4$, concentrated in vacuo and purified by Prep-HPLC to afford Compound 110 (25 mg, 41.1% yield) as a white solid.

TLC: Pet. ether/EtOAc=3/1 (v/v), Rf=0.13.

LCMS: RT=3.988 min, [M−1]=396.1.

$^1$H NMR: (400 MHz, DMSO-$d_6$) δ 9.51 (d, J=1.6 Hz, 1H), 7.98 (d, J=5.6 Hz, 1H), 7.00 (d, J=8.4 Hz, 1H), 6.46 (dd, J=8.4, 1.2 Hz, 1H), 6.21 (t, J=8.4 Hz, 1H), 4.59 (s, 2H), 3.92 (s, 2H), 3.42-3.36 (m, 1H), 2.65 (d, J=4.8 Hz, 3H), 2.16 (s, 3H), 1.28-1.23 (m, 6H).

Example 111

Synthesis of ethyl 2-(5-chloro-2-fluoro-4-(2-fluoro-4-hydroxy-3-isopropylbenzyl)-3-methylphenoxy) acetate (Compound 111)

111

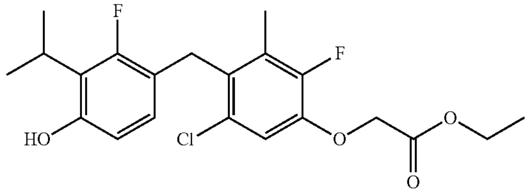

To a solution of Intermediate A57 (1.0 g, 3.4 mmol) in DCE (10.0 mL) at rt were added Intermediate B2 (1.6 g, 10.2 mmol) and $ZnCl_2$ (8.5 mmol, 8.5 mL of 1M in THF). The reaction was heated to 85° C. and stirred overnight. The reaction mixture was cooled to rt; water (60 mL) was added and the mixture was extracted with DCM (30 mL*3). The combined organic phase was washed with brine (100 mL), dried over $Na_2SO_4$ and concentrated in vacuo. The crude product was purified by silica gel column chromatography (EtOAc/pet. ether=1/100 to 1/10) to afford Compound 111 (550 mg, 39.3% yield) as a white solid.

TLC: Pet. ether/EtOAc=5/1 (v/v), Rf=0.20

$^1$H NMR: (400 MHz, DMSO-$d_6$) δ 9.52 (s, 1H), 7.16 (d, J=7.6 Hz, 1H), 6.48 (dd, J=8.4, 0.8 Hz, 1H), 6.23 (t, J=8.8 Hz, 1H), 4.93 (s, 2H), 4.19 (d, J=6.8 Hz, 2H), 3.93 (s, 2H), 1.27 (d, J=7.2 Hz, 6H), 1.18 (t, J=7.2 Hz, 6H).

Example 112

Synthesis of 2-(5-chloro-2-fluoro-4-(2-fluoro-4-hydroxy-3-isopropylbenzyl)-3-methylphenoxy)acetic acid (Compound 112)

112

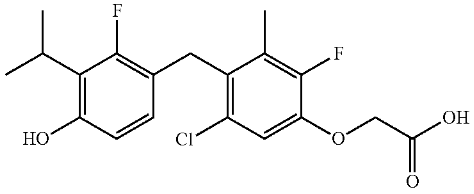

To a solution of Compound 111 (550 mg, 1.3 mmol) in THF/$H_2O$ (10.0 mL/1.0 mL) at rt was added LiOH·$H_2O$ (164 mg, 3.9 mmol). The mixture was stirred at rt for 1 h. The mixture was diluted with water (50 mL), acidified with 1N HCl to pH~3-4 and extracted with EtOAc (20 mL*3). The combined organic phase was washed with brine (50 mL), dried over $Na_2SO_4$ and concentrated in vacuo. The crude product was purified by Prep-HPLC twice to afford Compound 112 (40 mg, 8.0% yield) as a white solid.

TLC: MeOH/DCM=1/10 (v/v), Rf=0.30

LCMS: RT=2.324 min, [M−1]=383.0

$^1$H NMR: (400 MHz, DMSO-$d_6$) δ 9.52 (s, 1H), 7.12 (d, J=8.0 Hz, 1H), 6.48 (d, J=8.4 Hz, 1H), 6.23 (t, J=8.4 Hz, 1H), 4.83 (s, 2H), 3.93 (s, 2H), 2.11 (d, J=2.8 Hz, 3H), 1.27 (d, J=6.8 Hz, 6H).

$^{19}$F NMR: (376 MHz, DMSO-$d_6$) δ −120.35, −137.25.

Example 113

Synthesis of 2-(5-chloro-2-fluoro-4-(2-fluoro-4-hydroxy-3-isopropylbenzyl)-3-methylphenoxy)-N-methylacetamide (Compound 113)

113

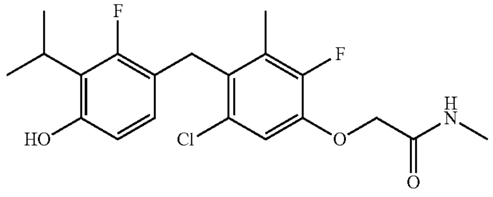

To a mixture of Compound 112 (100 mg, 260 umol) in DCM (2.0 mL) was added DMF (0.1 mL). The mixture was cooled to 0° C. and oxalyl chloride (65 mg, 520 mmol) was added. The mixture was stirred at rt for 30 min. The mixture was concentrated in vacuo to afford the crude acid chloride (100 mg, 96.2% yield) as a yellow solid. A solution of this intermediate (100 mg, 248 umol) in DCM (2.0 mL) was added to $CH_3NH_2$ (2M, in THF) (248 uL, 496 umol). The mixture was stirred at rt for 1 h. Water (30 mL) was added and the resultant mixture was extracted with DCM (20 mL*3). The combined organic phase was washed with brine (30 mL), dried over $Na_2SO_4$, concentrated in vacuo and purified by Prep-HPLC to afford Compound 113 (10 mg, 10.1% yield) as a white solid.

TLC: DCM/MeOH=10/1 (v/v), Rf=0.45

LCMS: RT=4.053 min, [M−1]=396.0

$^1H$ NMR: (400 MHz, DMSO-$d_6$) δ 9.53 (s, 1H), 8.04-7.96 (d, J=6.8 Hz, 1H), 7.12 (d, J=6.8 Hz, 1H), 6.50 (d, J=8.4 Hz, 1H), 6.26 (t, J=8.4 Hz, 1H), 4.62 (s, 2H), 3.95 (s, 2H), 3.41 (s, 1H), 2.68 (d, J=4.8 Hz, 3H), 2.13 (d, J=2.8 Hz, 3H), 1.29 (d, J=7.2 Hz, 6H).

$^{19}F$ NMR: (376 MHz, DMSO-$d_6$) δ −120.32, −136.48.

Example 114

Synthesis of ethyl 2-(3-chloro-2-fluoro-4-(4-hydroxy-3-isopropylbenzyl)-5-methylphenoxy)acetate (Compound 114)

114

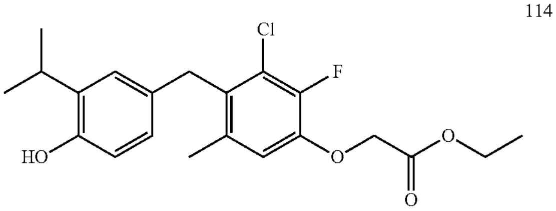 [SMILES: CCOC(=O)COc1cc(C)c(Cc2ccc(O)c(C(C)C)c2)c(Cl)c1F]

To a solution of Intermediate A52 (500 mg, 1.69 mmol) and 2-isopropylphenol (461 mg, 3.39 mmol) in DCE (10 mL) was added $ZnCl_2$ (577 mg, 4.24 mmol). The mixture was stirred at 90° C. overnight. The mixture was cooled to rt; water (15 mL) was added, and the mixture was extracted with DCM (10 mL*3). The combined organic phase was washed with brine (10 mL), dried over $Na_2SO_4$, concentrated in vacuo and purified by Prep-TLC (EtOAc/pet. ether=1/5) to afford Compound 114 (258 mg, 38.6% yield) as a light yellow solid.

TLC: EtOAc/pet. ether=1/3 (v/v), $R_f$=0.25

$^1H$ NMR: (400 MHz, DMSO-$d_6$) δ 9.06 (s, 1H), 7.02 (d, J=8.4 Hz, 1H), 6.90 (d, J=2.0 Hz, 1H), 6.64 (d, J=8.0 Hz, 1H), 6.56 (dd, J=8.4, 2.4 Hz, 1H), 4.90 (s, 2H), 4.18 (q, J=7.2 Hz, 2H), 3.96 (s, 2H), 3.13 (p, J=6.9 Hz, 1H), 2.19 (s, 3H), 1.21 (t, J=7.2 Hz, 3H), 1.11 (d, J=6.8 Hz, 7H).

Example 115

Synthesis of 2-(3-chloro-2-fluoro-4-(4-hydroxy-3-isopropylbenzyl)-5-methylphenoxy)acetic acid (Compound 115)

115

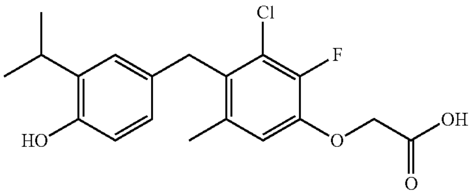

To a solution of Compound 114 (100 mg, 253 umol) in $THF/H_2O$ (3 mL/1.5 mL) at rt was added $LiOH{\cdot}H_2O$ (32 mg, 760 umol). The mixture was stirred at rt for 1 h. The mixture was diluted with water (10 mL), acidified with 1N HCl to pH~3-4 and extracted with EtOAc (5 mL*3). The combined organic phase was washed with brine (10 mL), dried over $Na_2SO_4$ and concentrated in vacuo. The crude product was purified by Prep-HPLC to afford Compound 115 (56 mg, 60.2% yield) as a white solid.

TLC: Pet. ether/ethyl acetate=1/1 (v/v), Rf=0.08

LCMS: RT=3.73 min, [M−1]=365.10

$^1H$ NMR: (400 MHz, DMSO-$d_6$) δ 6.90 (d, J=2.2 Hz, 1H), 6.55 (d, J=2.2 Hz, 1H), 4.79 (s, 2H), 3.94 (s, 2H), 3.12 (t, J=6.9 Hz, 1H), 2.18 (s, 3H), 1.09 (d, J=6.9 Hz, 6H).

Example 116

Synthesis of 2-(3-chloro-2-fluoro-4-(2-fluoro-4-hydroxy-3-isopropylbenzyl)-5-methylphenoxy)-N-methylacetamide (Compound 116)

116

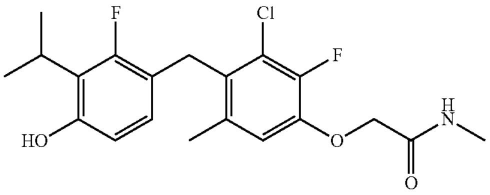

To a solution of Compound 114 (100 mg, 253 umol) in THF (3 mL) in a sealed tube at rt was added methylamine (2 mL of 2N in THF). The mixture was stirred at 75° C. overnight. The mixture was diluted with water (10 mL) and extracted with EtOAc (5 mL*3). The combined organic phase was washed with brine (10 mL), dried over $Na_2SO_4$ and concentrated in vacuo. The crude product was purified by Prep-HPLC to afford Compound 116 (63 mg, 65.6% yield) as a white solid.

TLC: Pet. ether/ethyl acetate=1/1 (v/v), Rf=0.16

LCMS: RT=3.69 min, [M+1]=380.15

$^1H$ NMR: (400 MHz, DMSO-$d_6$) δ 9.05 (s, 1H), 7.98 (s, 1H), 6.97 (d, J=8.3 Hz, 2H), 6.92 (s, 1H), 6.64 (d, J=8.2 Hz, 1H), 4.58 (s, 2H), 3.97 (s, 2H), 3.13 (M, 1H), 2.66 (d, J=4.6 Hz, 3H), 2.20 (s, 3H), 1.11 (d, J=6.9 Hz, 6H).

Example 117

Synthesis of ethyl 2-(5-chloro-2-fluoro-4-(4-hydroxy-3-isopropylbenzyl)-3-methylphenoxy)acetate (Compound 117)

117

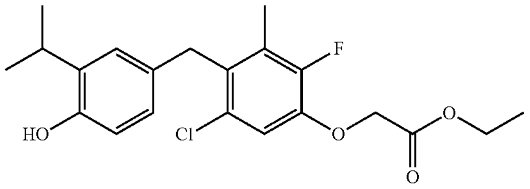

To a solution of Intermediate A57 (1.0 g, 3.4 mmol) in DCE (10.0 mL) at rt were added 2-isopropylphenol (1.4 g, 10.2 mmol) and $ZnCl_2$ (8.5 mmol, 8.5 mL). The reaction was heated to 85° C. and stirred overnight. The reaction mixture was cooled to rt; water (60 mL) was added and the resultant mixture was extracted with DCM (30 mL*3). The combined organic phase was washed with brine (100 mL), dried over $Na_2SO_4$ and concentrated in vacuo. The crude product was purified by silica gel column chromatography (EtOAc/pet. ether=1/100 to 1/10) to afford Compound 117 (500 mg, 37.4% yield) as a white solid.

TLC: Pet. ether/EtOAc=5/1 (v/v), Rf=0.20

LCMS: RT=2.151 min, [M−1]=393.0

$^1$H NMR: (400 MHz, DMSO-$d_6$) δ 9.12 (s, 1H), 7.17 (d, J=8.0 Hz, 1H), 6.93 (d, J=2.4 Hz, 1H), 6.66 (d, J=8.4 Hz, 1H), 6.58 (dd, J=8.4, 2.4 Hz, 1H), 4.94 (s, 2H), 4.19 (q, J=7.2 Hz, 2H), 3.98 (s, 2H), 3.17-3.11 (m, 1H), 2.15 (d, J=6.4 Hz, 3H), 1.23 (t, J=7.2 Hz, 3H), 1.12 (d, J=6.8 Hz, 6H).

Example 118

Synthesis of 2-(5-chloro-2-fluoro-4-(4-hydroxy-3-isopropylbenzyl)-3-methylphenoxy)acetic acid (Compound 118)

118

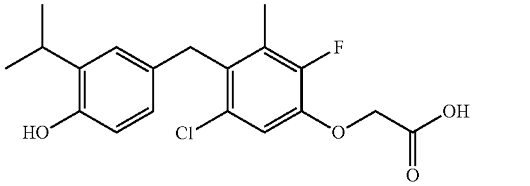

To a solution of Compound 117 (500 mg, 1.26 mmol) in THF/$H_2O$ (10.0 mL/1.0 mL) at rt was added LiOH·$H_2O$ (159 mg, 3.78 mmol). The mixture was stirred at rt for 1 h. The mixture was diluted with water (50 mL), acidified with 1N HCl to pH~3-4, and extracted with EtOAc (20 mL*3). The combined organic phase was washed with brine (50 mL), dried over $Na_2SO_4$ and concentrated in vacuo. The crude product was purified twice by Prep-HPLC to afford Compound 118 (50 mg, 11% yield) as a white solid.

TLC: MeOH/DCM=1/10 (v/v), Rf=0.30

LCMS: RT=1.564 min, [M−1]=365.0

$^1$H NMR: (400 MHz, DMSO-$d_6$) δ 9.08 (s, 1H), 7.12 (d, J=8.0 Hz, 1H), 6.93 (d, J=2.0 Hz, 1H), 6.66 (d, J=8.4 Hz, 1H), 6.58 (dd, J=8.4 2.4 Hz, 1H), 4.83 (s, 2H), 3.98 (s, 2H), 3.15 (p, J=6.8 Hz, 1H), 2.15 (d, J=2.8 Hz, 3H), 1.13 (d, J=6.8 Hz, 6H).

$^{19}$F NMR: (376 MHz, DMSO-$d_6$) δ −137.35.

Example 119

Synthesis of 2-(5-chloro-2-fluoro-4-(4-hydroxy-3-isopropylbenzyl)-3-methylphenoxy)-N-methylacetamide (Compound 119)

119

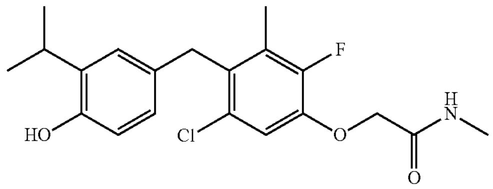

To a mixture of Compound 118 (100 mg, 260 umol) in DCM (2.0 mL) was added a drop of DMF; the mixture was cooled to 0° C. and oxalyl chloride (138 mg, 1.1 mmol) was added. The mixture was stirred at rt for 30 min. The mixture was concentrated in vacuo to afford the crude acid chloride (200 mg, 95.2% yield) as a yellow solid. This material was dissolved in DCM (2.0 mL) and added dropwise to methylamine (2M in THF) (0.5 mL, 1.0 mmol). The resultant mixture was stirred at rt for 1 h. Water (30 mL) was added and the mixture was extracted with DCM (20 mL*3). The combined organic phase was washed with brine (30 mL), dried over $Na_2SO_4$, concentrated in vacuo and purified by Prep-HPLC to afford Compound 119 (15 mg, 7.6% yield) as a white solid.

TLC: DCM/MeOH=10/1 (v/v), Rf=0.45

LCMS: RT=1.536 min, [M−1]=378.0

$^1$H NMR: (400 MHz, DMSO-$d_6$) δ 9.08 (s, 1H), 7.99 (s, 1H), 7.10 (d, J=8.0 Hz, 1H), 6.94 (d, J=2.4 Hz, 1H), 6.66 (d, J=8.4 Hz, 1H), 6.58 (dd, J=8.4, 2.4 Hz, 1H), 4.60 (s, 2H), 3.99 (s, 2H), 3.15 (p, J=7.0 Hz, 1H), 2.67 (d, J=4.8 Hz, 3H), 2.15 (d, J=2.8 Hz, 3H), 1.13 (d, J=6.8 Hz, 6H).

$^{19}$F NMR: (376 MHz, DMSO-$d_6$) δ −136.57.

Example 120

Synthesis of ethyl 2-(5-chloro-2-fluoro-4-(2-fluoro-4-hydroxy-3-isopropylbenzyl)-3-(prop-1-en-2-yl)phenoxy)acetate (Compound 120)

120

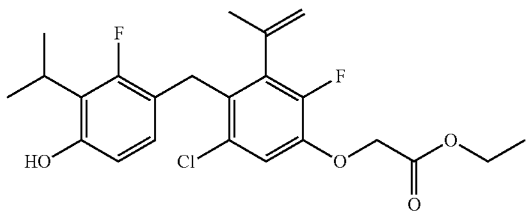

To a mixture of Intermediate C8 (260 mg, 544 umol), and potassium propenyl-2-boron(trifluoride) (161 mg, 1.1 mmol) in 1,4-dioxane (5.0 mL) and water (0.2 mL) at rt were added Pd(dppf)$Cl_2$·$CH_2Cl_2$ (44 mg, 54 umol) and $Cs_2CO_3$ (355 mg, 1.1 mmol) under $N_2$(g). The mixture was heated to 120° C. for 2 h in a sealed tube. The mixture was cooled to rt. Water (30 mL) was added and the mixture was extracted with EtOAc (15 mL*3). The combined organic phase was washed with brine (30 mL), dried over $Na_2SO_4$, filtered and concentrated in vacuo. Purification by Prep-TLC (EtOAc/pet. ether=1/5) afforded Compound 120 (90 mg, 37.7% yield) as a white solid.

TLC: Pet. ether/EtOAc=5/1 (v/v), Rf=0.23

$^1$H NMR: (400 MHz, DMSO-$d_6$) δ 9.49 (d, J=1.2 Hz, 1H), 7.26 (d, J=8.0 Hz, 1H), 6.47 (d, J=8.4 Hz, 1H), 6.22 (t, J=8.4 Hz, 1H), 5.29-5.25 (m, 1H), 4.95 (s, 2H), 4.78-4.75 (m, 1H), 4.18 (t, J=7.2 Hz, 2H), 3.85 (s, 2H), 3.40-3.36 (m, 1H), 1.78 (t, J=1.2 Hz, 3H), 1.24 (d, J=1.2 Hz, 9H).

Example 121

Synthesis of 2-(5-chloro-2-fluoro-4-(2-fluoro-4-hydroxy-3-isopropylbenzyl)-3-(prop-1-en-2-yl)phenoxy)acetic acid (Compound 121)

121

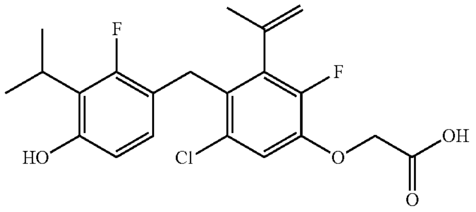

To a solution of Compound 120 (90 mg, 205 umol) in THF/$H_2O$ (2.0 mL/0.5 mL) at rt was added LiOH·$H_2O$ (26 mg, 615 umol). The mixture was stirred at rt for 1 h. The mixture was diluted with water (30 mL), acidified with 1N HCl to pH~3-4, and extracted with EtOAc (10 mL*3). The combined organic phase was washed with brine (20 mL), dried over $Na_2SO_4$ and concentrated in vacuo. The crude product was purified by Prep-HPLC to afford Compound 121 (15 mg, 17.8% yield) as a white solid.

TLC: MeOH/DCM=1/10 (v/v), Rf=0.30

LCMS: RT=1.925 min, [M−1]=410.1

$^1$H NMR: (400 MHz, DMSO-$d_6$) δ 9.51 (s, 1H), 7.17 (d, J=7.6 Hz, 1H), 6.47 (d, J=8.4 Hz, 1H), 6.23 (t, J=8.4 Hz, 1H), 5.27 (d, J=2.0 Hz, 1H), 4.79 (s, 2H), 4.76 (s, 1H), 3.85 (s, 2H), 1.78 (s, 3H), 1.25 (d, J=7.2 Hz, 6H).

$^{19}$F NMR: (376 MHz, DMSO-$d_6$) δ −120.40, −137.72.

Example 122

Synthesis of ethyl 2-(5-chloro-2-fluoro-4-(2-fluoro-4-hydroxy-3-isopropylbenzyl)-3-isopropylphenoxy) acetate (Compound 122)

122

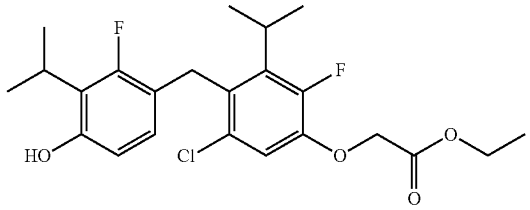

To a solution of Compound 120 (140 mg, 319 umol) in THF (2.0 mL) was added Pd/C (70 mg). The mixture was purged three times with $H_2$ gas and stirred at 60° C. overnight under $H_2$ atmosphere. The mixture was filtered and concentrated in vacuo to afford Compound 122 (120 mg, 85.3% yield) as a yellow oil.

TLC: Pet. ether/EtOAc=1/5 (v/v), Rf=0.20

Example 123

Synthesis of 2-(5-chloro-2-fluoro-4-(2-fluoro-4-hydroxy-3-isopropylbenzyl)-3-isopropylphenoxy) acetic acid (Compound 123)

123

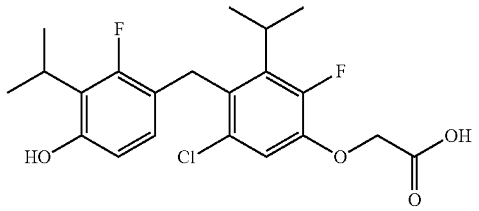

To a solution of Compound 122 (120 mg, 272 umol) in THF/$H_2O$ (2.0 mL/0.5 mL) at rt was added LiOH·$H_2O$ (39 mg, 816 umol). The mixture was stirred at rt for 1 h. The mixture was diluted with water (30 mL), acidified with 1N HCl to pH~3-4 and extracted with EtOAc (10 mL*3). The combined organic phase was washed with brine (30 mL), dried over $Na_2SO_4$ and concentrated in vacuo. The crude product was purified by Prep-HPLC to afford Compound 123 (10 mg, 8.5% yield) as a white solid.

TLC: MeOH/DCM=1/10 (v/v), Rf=0.30

LCMS: RT=2.136 min, [M−1]=411.1

$^1$H NMR: (400 MHz, DMSO-$d_6$) δ 9.52 (s, 1H), 7.11 (d, J=7.8 Hz, 1H), 6.49 (d, J=8.4 Hz, 1H), 6.24 (t, J=8.4 Hz, 1H), 4.81 (s, 2H), 3.97 (s, 2H), 3.01 (q, J=6.8 Hz, 1H), 1.26 (d, J=7.2 Hz, 6H), 1.13 (d, J=6.8 Hz, 6H).

$^{19}$F NMR: (376 MHz, DMSO-$d_6$) δ −120.43, −136.14.

Example 124

Synthesis of 2-(4-(2-fluoro-4-hydroxy-3-isopropylbenzyl)-3,5-dimethylphenoxy)-N-methylacetamide (Compound 124)

124

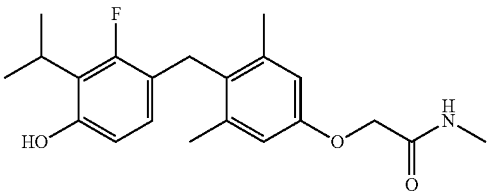

To a mixture of acid Compound 2 (90 mg, 0.26 mmol) in DCM (2.0 mL) was added oxalyl chloride (66 mg, 0.52 mmol) at 0° C. The mixture was stirred at rt for 30 min. The mixture was concentrated in vacuum to afford crude product acid chloride (90 mg, 95% yield) as yellow solid. A solution of acid chloride (90 mg, 0.25 mmol) in DCM (2.0 mL) was added to methylamine (2 M/THF) (2.0 mL, 4.00 mmol). The mixture was stirred at rt for 1 h. Water (15 mL) was added, and the mixture was extracted with DCM (10 mL*3). The combined organic phase was washed by brine (20 mL), dried over $Na_2SO_4$, concentrated in vacuum, and purified by Prep-HPLC to afford Compound 124 (15 mg, 17% yield) as white solid LCMS: T=1.60 min, [M−1]=358.1

$^1$H NMR (400 MHz, DMSO-$d_6$) δ 9.42 (d, J=1.4 Hz, 1H), 7.97 (d, J=5.3 Hz, 1H), 6.68 (s, 2H), 6.43 (dd, J=8.4, 1.0 Hz, 1H), 6.12 (t, J=8.6 Hz, 1H), 4.41 (s, 2H), 3.75 (s, 2H), 3.38 (p, J=7.0 Hz, 1H), 2.66 (d, J=4.7 Hz, 3H), 2.12 (s, 6H), 1.26 (dd, J=7.1, 1.0 Hz, 6H).

Example 125A

Synthesis of ethyl 2-(2,3-difluoro-4-(4-hydroxy-3-isopropylbenzyl)-5-methylphenoxy)acetate (Compound 125)

125

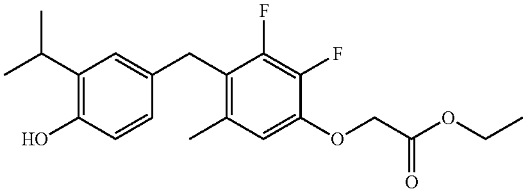

To a solution of Intermediate A60 (800 mg, 4.6 mmol) in DMF (10 mL) at rt was added $K_2CO_3$ (762 mg, 5.51 mmol) and ethyl 2-bromoacetate (767 mg, 4.59 mmol). The mixture was stirred at rt overnight, diluted with water (30 mL) and was extracted with EtOAc (20 mL*3). The combined organic phase was washed by brine (10 mL), dried over $Na_2SO_4$, concentrated under reduce pressure to a white solid. DCM (10 mL) was added, and the resulting solution was cooled to 0° C. Thionyl chloride (686 mg, 5.76 mmol) was added dropwise. The mixture was stirred at rt for 2 h and concentrated under vacuum. The resulting yellow solid was dissolved in DCE (10 mL) and 2-isopropylphenol (1.5 g, 10.77 mmol) and $ZnCl_2$ (1 M/THF, 8.9 mL) were added. The reaction was heated to 85° C. overnight and was cooled to rt. Water (30 mL) was added and the mixture was extracted with DCM (20 mL*3). The combined organic layer was washed with brine (30 mL), dried over $Na_2SO_4$ and concentrated in vacuum. The crude product was purified by silica gel column (EtOAc/pet. ether=1/50 to 1/20) to afford Compound 125 (600 mg, 44% yield) as light-yellow oil.

$^1$H NMR (400 MHz, DMSO-$d_6$) δ 9.09 (s, 1H), 6.92 (s, 1H), 6.83-6.79 (m, 1H), 6.64 (s, 2H), 4.87 (s, 2H), 4.16 (q, J=7.1 Hz, 2H), 3.80 (s, 2H), 3.12 (q, J=6.9 Hz, 1H), 2.17 (s, 3H), 1.20 (t, J=7.1 Hz, 3H), 1.10 (d, J=6.9 Hz, 6H).

Example 126

Synthesis of 2-(2,3-difluoro-4-(4-hydroxy-3-isopropylbenzyl)-5-methylphenoxy)acetic acid (Compound 126)

126

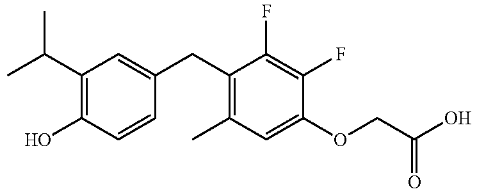

To Compound 125 (600 mg, 1.59 mmol) in water (1 mL) and THF (6 mL) was added LiOH·$H_2O$ (200 mg, 4.76 mmol). The mixture was stirred at rt for 1 h. Water (30 mL) was added, and the mixture was acidified to pH=4-5 with 1 M HCl. The mixture was extracted with EtOAc (20 mL*3). The combined organic phase was washed by brine (30 mL), dried over $Na_2SO_4$, concentrated in vacuum and 200 mg crude was purified by Prep-HPLC (MeCN/$H_2O$) to afford Compound 126 (120 mg, 21% yield) as white solid.

LCMS: T=1.4 min, [M−1]=349.1

$^1$H NMR (400 MHz, DMSO-$d_6$) δ 9.10 (s, 1H), 6.95 (d, J=1.9 Hz, 1H), 6.83-6.79 (m, 1H), 6.69-6.62 (m, 2H), 4.79 (s, 2H), 3.82 (d, J=2.1 Hz, 2H), 3.15 (p, J=6.9 Hz, 1H), 2.20 (s, 3H), 1.13 (d, J=6.9 Hz, 6H).

Example 127

Synthesis of ethyl 2-(2,5-difluoro-4-(4-hydroxy-3-isopropylbenzyl)-3-methylphenoxy)acetate (Compound 127)

127

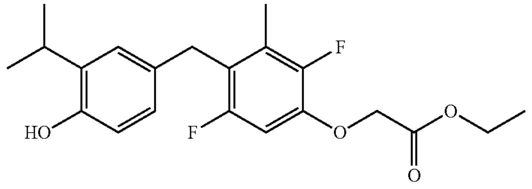

To a solution of Intermediate A64 (276 mg, 990.39 μmol) and 2-isopropylphenol (405 mg, 2.97 mmol) in DCE (3 mL) was added $ZnCl_2$ (338 mg, 2.48 mmol). The mixture was stirred at 85° C. overnight and was cooled to rt. The mixture was partitioned between water (30 mL) and DCM (30 mL). The organic phase was washed with brine (30 mL), dried over $Na_2SO_4$, concentrated under vacuum and purified by Prep-TLC (pet. ether/EtOAc=5/1) to afford Compound 127 (80 mg, 21% yield) as white solid.

$^1$H NMR (400 MHz, DMSO-$d_6$) δ 9.08 (s, 1H), 6.95 (dd, J=11.3, 7.1 Hz, 1H), 6.91 (s, 1H), 6.63 (d, J=3.4 Hz, 2H), 4.88 (d, J=11.9 Hz, 2H), 4.17 (q, J=7.1 Hz, 2H), 3.80 (s, 2H), 3.13 (p, J=6.9 Hz, 1H), 2.13 (d, J=2.6 Hz, 3H), 1.18-1.15 (m, 3H), 1.10 (d, J=6.9 Hz, 6H).

Example 128

Synthesis of 2-(2,5-difluoro-4-(4-hydroxy-3-isopropylbenzyl)-3-methylphenoxy)acetic acid (Compound 128)

128

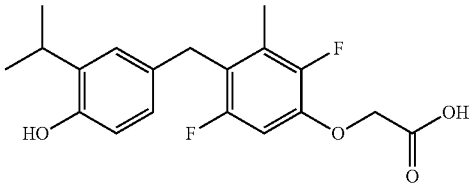

To a solution of Compound 127 (80 mg, 0.21 mmol) in THF/water (2/0.5 mL) was added NaOH (17 mg, 0.43 mmol). The mixture was stirred at rt 1 h. The mixture was diluted with water (5 mL), acidified to pH=3-4 with 1N HCl, and was extracted with EtOAc (3 mL*2). The organic phase was washed by brine (30 mL), dried by $Na_2SO_4$, concentrated under reduced vacuum and purified by Prep-HPLC to afford Compound 128 (15 mg, 20% yield) as a white solid.

LCMS: T=1.424 min [M−1]=349.0

$^1$H NMR (400 MHz, DMSO-$d_6$) δ 9.06 (s, 1H), 6.96-6.88 (m, 2H), 6.63 (d, J=2.1 Hz, 2H), 4.78 (s, 2H), 3.80 (s, 2H), 3.13 (p, J=6.9 Hz, 1H), 2.13 (d, J=2.5 Hz, 3H), 1.11 (d, J=6.9 Hz, 6H).

Example 129

Synthesis of 2-(4-(2-fluoro-4-hydroxy-3-isopropylbenzyl)-3-methyl-5-(prop-1-en-2-yl)phenoxy)-N-methylacetamide (Compound 129)

129

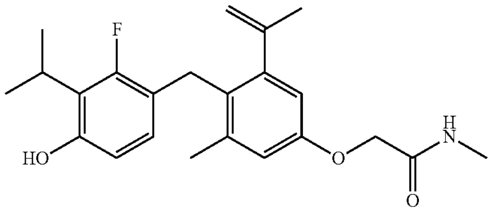

To a mixture of Compound 12 (130 mg, 0.35 mmol) in DCM (5.0 mL) was added oxalyl chloride (132 mg, 1.0 mmol) at 0° C. The mixture was stirred at rt for 30 min and concentrated in vacuum the resulting yellow solid was dissolved in DCM (2.0 mL) and was added to methylamine (2 M/THF) (750 uL, 1.56 mmol). The mixture was stirred at rt for 2 h. Water (10 mL) was added, and the mixture was extracted with DCM (10 mL*3). The combined organic phase was washed by brine (30 mL), dried over $Na_2SO_4$, concentrated in vacuum and purified by Prep-TLC (DCM/MeOH=10/1) to afford Compound 129 (12 mg, 19% yield) as white solid.

LCMS: T=4.170 min, [M−1]=384.2

$^1$H NMR: (400 MHz, DMSO-$d_6$) δ 9.41 (d, J=1.4 Hz, 1H), 8.01 (d, J=5.0 Hz, 1H), 6.77 (d, J=2.8 Hz, 1H), 6.61 (d, J=2.7 Hz, 1H), 6.43 (d, J=8.3 Hz, 1H), 6.15 (t, J=8.6 Hz, 1H), 5.10-5.04 (m, 1H), 4.65 (d, J=2.0 Hz, 1H), 4.43 (s, 2H), 3.75 (s, 2H), 3.39 (s, 1H), 2.66 (d, J=4.4 Hz, 4H), 2.06 (s, 3H), 1.85 (s, 3H), 1.25 (d, J=7.0 Hz, 8H).

Example 130

Synthesis of 2-(4-(2-fluoro-4-hydroxy-3-isopropylbenzyl)-3-methyl-5-(prop-1-en-2-yl)phenoxy)-N,N-dimethylacetamide (Compound 130)

130

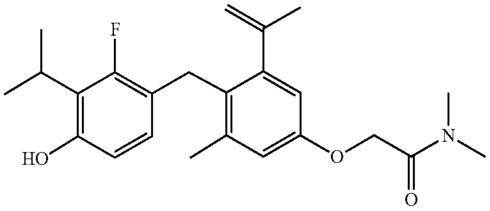

To a mixture of Compound 12 (130 mg, 0.35 mmol) in DCM (5 mL) was added oxalyl chloride (132 mg, 1.0 mmol) at 0° C. The mixture was stirred at rt for 30 min and was concentrated in vacuum. The resulting yellow solid was dissolved in DCM (5 mL) added to dimethylamine (1 M/THF, 1 mL, 1.0 mmol). The mixture was stirred at rt for 2 h. Water (10 mL) was added, and the mixture was extracted with DCM (10 mL*3). The combined organic phase was washed by brine (30 mL), dried over $Na_2SO_4$, concentrated in vacuum and purified by Prep-TLC (DCM/MeOH=10/1) to afford Compound 130 (22 mg, 24% yield) as a white solid.

LCMS: T=4.228 min, [M−1]=398.2

$^1$H NMR (400 MHz, DMSO-$d_6$) δ 9.41 (d, J=1.4 Hz, 1H), 6.71 (d, J=2.7 Hz, 1H), 6.55 (d, J=2.8 Hz, 1H), 6.44 (d, J=8.4 Hz, 1H), 6.15 (t, J=8.6 Hz, 1H), 5.06 (t, J=2.0 Hz, 1H), 4.75 (s, 2H), 4.64 (t, J=1.7 Hz, 1H), 3.74 (s, 2H), 3.40 (d, J=7.4 Hz, 1H), 3.00 (s, 3H), 2.85 (s, 3H), 2.05 (s, 3H), 1.85 (s, 3H), 1.30-1.21 (m, 6H).

Example 131

Synthesis of 2-(4-(2-fluoro-4-hydroxy-3-isopropylbenzyl)-3-isopropyl-5-methylphenoxy)-N-methylacetamide (Compound 131)

131

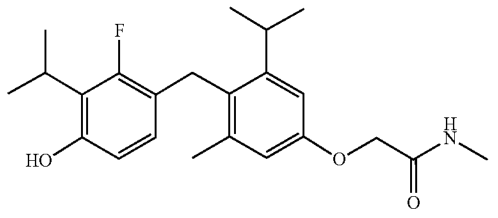

To a mixture of Compound 13 (130 mg, 0.35 mmol) in DCM (5 mL) was added oxalyl chloride (132 mg, 1.0 mmol) at 0° C. The mixture was stirred at rt for 30 min and concentrated in vacuum. The resulting yellow solid was dissolved in DCM (3 mL) and methylamine (1 M/THF, 0.51 mL) was added. The mixture was stirred at rt for 2 h. Water (10 mL) was added, and the mixture was extracted with DCM (10 mL*3). The combined organic phase was washed by brine (30 mL), dried over $Na_2SO_4$, concentrated in vacuum and purified by Prep-TLC (pet.ether:EtOAc=1:2) to afford Compound 131 (20 mg, 51% yield) as a white solid.

LCMS: T=4.142 min, [M−1]=386.2

$^1$H NMR (400 MHz, DMSO-$d_6$) δ 9.44 (d, J=1.4 Hz, 1H), 8.03 (d, J=5.1 Hz, 1H), 6.77 (d, J 15=2.7 Hz, 1H), 6.67 (d, J=2.7 Hz, 1H), 6.43 (d, J=8.4 Hz, 1H), 6.10 (t, J=8.6 Hz, 1H), 4.42 (s, 2H), 3.79 (s, 2H), 3.39 (q, J=7.1 Hz, 1H), 2.99-2.85 (m, 1H), 2.66 (d, J=4.6 Hz, 3H), 2.12 (s, 3H), 1.27 (d, J=7.0 Hz, 6H), 1.06 (d, J=6.7 Hz, 6H).

Example 132

Synthesis of 2-(4-(2-fluoro-4-hydroxy-3-isopropylbenzyl)-3-isopropyl-5-methylphenoxy)-N,N-dimethylacetamide (Compound 132)

132

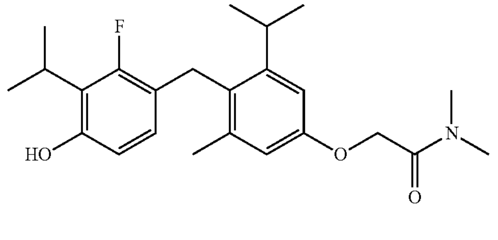

To a mixture of Compound 13 (80 mg, 0.21 mmol) in DCM (5 mL) was added oxalyl chloride (81 mg, 0.64 mmol) at 0° C. The mixture was stirred at rt for 30 min and was concentrated in vacuum. The resulting yellow solid was dissolved in DCM (3 mL) and dimethylamine (1 M, 510 uL) was added and the mixture was stirred at rt for 1 h. Water (10 mL) was added and the mixture was extracted with DCM (10 mL*3). The combined organic phase was washed by brine (30 mL), dried over $Na_2SO_4$, concentrated in vacuum and purified by Prep-TLC (Pet.ether:EtOAc=1:2) to afford Compound 132 (25 mg, 61% yield) as a white solid.

LCMS: T=4.198 min, [M−1]=400.2

$^1$H NMR: (400 MHz, DMSO-$d_6$) δ 9.43 (s, 1H), 6.71 (d, J=2.8 Hz, 1H), 6.62 (d, J=2.8 Hz, 1H), 6.43 (d, J=8.4 Hz, 1H), 6.10 (t, J=8.6 Hz, 1H), 4.73 (s, 2H), 3.78 (s, 2H), 3.39 (d, J=7.2 Hz, 1H), 3.01 (s, 3H), 2.96-2.87 (m, 1H), 2.85 (s, 3H), 2.11 (s, 3H), 1.27 (d, J=7.0 Hz, 6H), 1.05 (d, J=6.7 Hz, 6H).

Example 133

Synthesis of 2-(2,3-difluoro-4-(4-hydroxy-3-isopropylbenzyl)-5-methylphenoxy)-N-methylacetamide (Compound 133)

133

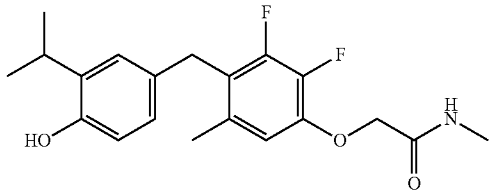

To a mixture of Compound 126 (100 mg, 0.33 mmol) in DCM (2.0 mL) was added oxalyl chloride (54 mg, 0.43 mmol) at 0° C. The mixture was stirred at rt for 30 min. The mixture was concentrated in vacuum. The resulting yellow solid was dissolved in DCM (2.0 mL) and methylamine (2 M/THF, 1 mL) was added. The mixture was stirred at rt for 1 h. Water (20 mL) was added, and the mixture was extracted with DCM (20 mL*3). The combined organic phase was washed by brine (30 mL), dried over $Na_2SO_4$, concentrated in vacuum and purified by Prep-HPLC to afford Compound 133 (25 mg, 24% yield) as white solid.

LCMS: T=1.42 min, [M−1]=362.1

$^1$H NMR (400 MHz, DMSO-$d_6$) δ 9.08 (s, 1H), 7.96 (s, 1H), 6.93 (d, J=1.9 Hz, 1H), 6.81-6.75 (m, 1H), 6.67-6.60 (m, 2H), 4.55 (s, 2H), 3.81 (d, J=2.1 Hz, 2H), 3.12 (q, J=7.0 Hz, 1H), 2.64 (d, J=4.6 Hz, 3H), 2.18 (s, 3H), 1.11 (d, J=6.9 Hz, 6H).

Example 134

Synthesis of 2-(2,5-difluoro-4-(4-hydroxy-3-isopropylbenzyl)-3-methylphenoxy)-N-methylacetamide (Compound 134)

134

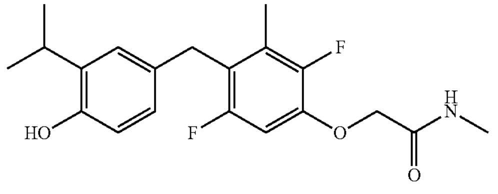

To a mixture of Compound 128 (50 mg, 0.29 mmol) in DMF (2 mL) was added methylamine (2 M, 428 μL), HATU (162 mg, 428 μmol) and DIPEA (73 mg, 0.57 mmol). The mixture was stirred at rt for 2 h. Water (20 mL) was added, and the mixture was extracted with EtOAc (10 mL*3). The combined organic phase was washed by brine (30 mL), dried over $Na_2SO_4$, concentrated in vacuum, and purified by Prep-HPLC to afford Compound 134 (30 mg, 29% yield) as white solid.

LCMS: T=2.176 min, [M+1]=364.0

$^1$H NMR (400 MHz, DMSO-$d_6$) δ 9.07 (s, 1H), 7.92 (s, 1H), 6.95-6.84 (m, 2H), 6.66-6.59 (m, 2H), 4.55 (s, 2H), 3.82-3.78 (m, 2H), 3.13 (p, J=7.0 Hz, 1H), 2.65 (d, J=4.6 Hz, 3H), 2.14 (d, J=2.5 Hz, 3H), 1.11 (d, J=6.9 Hz, 6H).

Example 135

Synthesis of 2-(3-chloro-4-(2-fluoro-4-hydroxy-3-isopropylbenzyl)-5-vinylphenoxy)-N-methylacetamide (Compound 135)

135

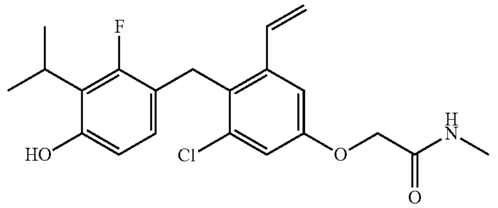

To a mixture of acid Compound 42 (130 mg, 0.34 mmol) in DCM (2.0 mL) was added oxalyl chloride (87 mg, 0.69 mmol) at 0° C. The mixture was stirred at rt for 30 min. The mixture was concentrated in vacuum. The resulting yellow solid was dissolved in DCM (5 mL) and methylamine (2 M/THF) (2.0 mL, 4.00 mmol) was added. The mixture was stirred at rt for 1 h. Water (15 mL) was added, and the mixture was extracted with DCM (10 mL*3). The combined organic phase was washed by brine (20 mL), dried over $Na_2SO_4$, concentrated in vacuum and purified by Prep-TLC (DCM/MeOH=10/1) and Prep-HPLC to afford Compound 135 (40 mg, 31% yield) as white solid.

LCMS: T=2.28 min, [M+1]=392.0

$^1$H NMR (400 MHz, DMSO-$d_6$) δ 9.48 (d, J=1.5 Hz, 1H), 8.07 (d, J=4.9 Hz, 1H), 7.17 (d, J=2.6 Hz, 1H), 7.08 (d, J=2.6 Hz, 1H), 6.80 (dd, J=17.2, 11.0 Hz, 1H), 6.44 (dd, J=8.5, 1.1 Hz, 1H), 6.19 (t, J=8.6 Hz, 1H), 5.75 (dd, J=17.2, 1.3 Hz, 1H), 5.34 (dd, J=11.0, 1.2 Hz, 1H), 4.55 (s, 2H), 3.98 (s, 2H), 3.42-3.35 (m, 1H), 2.67 (d, J=4.7 Hz, 3H), 1.26 (dd, J=7.1, 0.9 Hz, 6H).

Example 136

Synthesis of 2-(3-chloro-4-(2-fluoro-4-hydroxy-3-isopropylbenzyl)-5-vinylphenoxy)-N,N-dimethylacetamide (Compound 136)

136

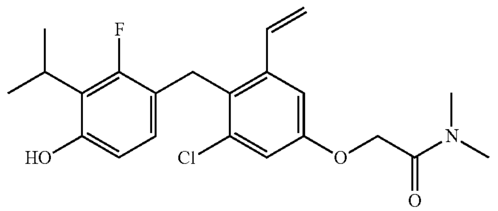

To a mixture of acid Compound 42 (120 mg, 0.32 mmol) in DCM (2.0 mL) was added oxalyl chloride (80 mg, 0.64 mmol) at 0° C. The mixture was stirred at rt for 30 min. The mixture was concentrated in vacuum. The resulting yellow solid was dissolved in DCM (2.0 mL) and dimethylamine (2 M/THF) (2.0 mL, 4.00 mmol) was added. The mixture was stirred at rt for 1 h. Water (15 mL) was added, and the mixture was extracted with DCM (10 mL*3). The combined organic phase was washed by brine (20 mL), dried over $Na_2SO_4$, concentrated in vacuum, and purified by Prep-HPLC to afford Compound 136 (35 mg, 28.5% yield) as a white solid.

LCMS: T=3.23 min, [M+1]=406.1

$^1$H NMR (400 MHz, DMSO-$d_6$) δ 9.48 (d, J=1.4 Hz, 1H), 7.10 (d, J=2.7 Hz, 1H), 7.03 (d, J 5=2.6 Hz, 1H), 6.78 (dd, J=17.3, 11.0 Hz, 1H), 6.45 (dd, J=8.5, 1.1 Hz, 1H), 6.19 (t, J=8.6 Hz, 1H), 5.74 (dd, J=17.2, 1.3 Hz, 1H), 5.32 (dd, J=11.0, 1.2 Hz, 1H), 4.89 (s, 2H), 3.97 (s, 2H), 3.38 (p, J=6.7 Hz, 1H), 3.00 (s, 3H), 2.85 (s, 3H), 1.26 (dd, J=7.1, 0.9 Hz, 6H).

Example 137

Synthesis of 2-(3-chloro-5-ethyl-4-(2-fluoro-4-hydroxy-3-isopropylbenzyl)phenoxy)acetamide (Compound 137)

137

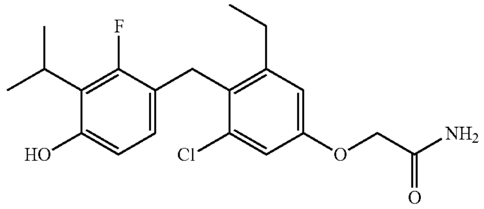

To a solution of Compound 43 (200 mg, 525 μmol) in DMF (5 mL) was added HATU (300 mg, 788 μmol) DIPEA (136 mg, 1.1 mmol, 183 μL) and NH3 (0.5 M, 3.2 mL). The mixture was stirred at rt 2 h. The mixture was diluted with water (30 mL) and extracted with EtOAc (30 mL). The organic phases was washed by water (30 mL*3), brine (30 mL), concentrated under vacuum and purified by Prep-HPLC to the product Compound 137 (8 mg, 21 μmol, 4% yield) as white solid.

LCMS: T=1.88 min, [M+1]=380.2

$^1$H NMR (400 MHz, DMSO-$d_6$) δ 9.46 (s, 1H), 7.29 (s, 2H) 6.91 (d, J=2.6 Hz, 1H), 6.80 (d, J=2.7 Hz, 1H), 6.45 (d, J=8.4 Hz, 1H), 6.19 (t, J=8.5 Hz, 1H), 4.83 (s, 2H), 3.91 (s, 2H), 3.42-3.38 (m, 1H), 1.26 (d, J=7.1 Hz, 6H), 1.02 (t, J=7.5 Hz, 3H).

Example 138

Synthesis of 2-(3-chloro-5-ethyl-4-(2-fluoro-4-hydroxy-3-isopropylbenzyl)phenoxy)-N,N-dimethylacetamide (Compound 138)

138

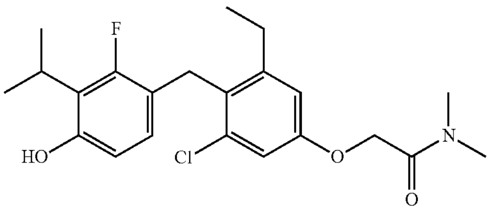

To a solution of acid Compound 43 (105 mg, 0.28 mmol) in DMF (3 mL) was added HATU (157 mg, 0.41 mmol) and dimethylamine (2 M, 0.4 mL). The mixture was stirred at rt 2 h. The mixture was diluted with water (30 mL) and extracted with EtOAc (20 mL*2).

The combined organic phase was washed by water (30 mL*3), brine (20 mL) and concentrated under vacuum. The residue was purified by Prep-HPLC to afford Compound 138 (15 mg, 13% yield) as a white solid.

LCMS: T=1.88 min, [M+1]=408.1

$^{1}$H NMR (400 MHz, DMSO-$d_6$) δ 9.46 (s, 1H), 6.91 (d, J=2.6 Hz, 1H), 6.80 (d, J=2.7 Hz, 1H), 6.45 (d, J=8.4 Hz, 1H), 6.19 (t, J=8.5 Hz, 1H), 4.83 (s, 2H), 3.91 (s, 2H), 3.42-3.38 (m, 1H), 2.99 (s, 3H), 2.85 (s, 3H), 1.26 (d, J=7.1 Hz, 6H), 1.02 (t, J=7.5 Hz, 3H).

Example 139

Synthesis of 2-(3-chloro-5-ethyl-4-(2-fluoro-4-hydroxy-3-isopropylbenzyl)phenoxy)-N,N-dimethylacetamide (Compound 139)

139

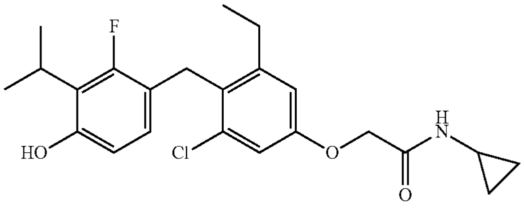

To a solution of acid Compound 43 (150 mg, 0.39 mmol) in DMF (5 mL) was added HATU (225 mg, 0.59 mmol), DIPEA (102 mg, 0.79 mmol) and cyclopropanamine (67 mg, 1.18 mmol). The mixture was stirred at rt 2 h. The mixture was diluted with water (30 mL) and extracted with EtOAc (30 mL). The organic phase was washed by water (30 mL*3), brine (30 mL), concentrated under vacuum and purified by Prep-HPLC to afford Compound 139 (22 mg, 13% yield) as white solid.

LCMS: T=2.0 min, [M+1]=420.1

$^{1}$H NMR (400 MHz, DMSO-$d_6$) δ 9.46 (s, 1H), 8.13 (d, J=4.3 Hz, 1H), 6.93 (d, J=2.6 Hz, 1H), 6.84 (d, J=2.6 Hz, 1H), 6.44 (d, J=8.4 Hz, 1H), 6.18 (t, J=8.6 Hz, 1H), 4.46 (s, 2H), 3.92 (s, 2H), 3.43-3.37 (m, 1H), 2.70 (dt, J=7.5, 3.7 Hz, 1H), 2.52 (s, 2H), 1.26 (d, J=7.1 Hz, 6H), 1.02 (t, J=7.5 Hz, 3H), 0.66-0.62 (m, 2H), 0.48 (dt, J=7.1, 4.5 Hz, 2H).

Example 140

Synthesis of 2-(5-chloro-2-fluoro-4-(2-fluoro-4-hydroxy-3-isopropylbenzyl)-3-isopropylphenoxy) acetic acid (Compound 140)

140

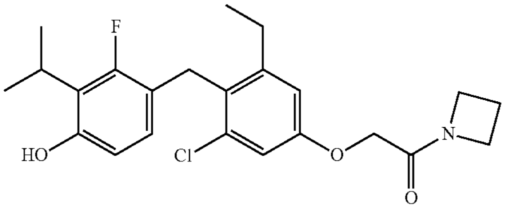

To a solution of acid Compound 43 (200 mg, 0.53 mmol) in DMF (5 mL) was added HATU (300 mg, 0.79 mmol), DIPEA (136 mg, 1.05 mmol) and azetidine (90 mg, 1.58 mmol). The mixture was stirred at rt 2 h. The mixture was diluted with water (30 mL) and extracted with EtOAc (30 mL*2). The organic phase was washed by water (30 mL*3), brine (30 mL), concentrated under vacuum and purified by Prep-HPLC to afford Compound 140 (70 mg, 31% yield) as white solid.

LCMS: T=3.74 min, [M+1]=420.25

$^{1}$HNMR: $^{1}$H NMR (400 MHz, DMSO-$d_6$) δ 9.47 (d, J=1.4 Hz, 1H), 6.91 (d, J=2.7 Hz, 1H), 6.81 (d, J=2.6 Hz, 1H), 6.45 (d, J=8.4 Hz, 1H), 6.18 (t, J=8.6 Hz, 1H), 4.60 (s, 2H), 4.23 (t, J=7.7 Hz, 2H), 3.94-3.89 (m, 4H), 3.43-3.39 (m, 1H), 2.25 (q, J=7.7 Hz, 2H), 1.26 (d, J=7.1 Hz, 6H), 1.02 (t, J=7.5 Hz, 3H).

Example 141

Synthesis of 2-(3-chloro-5-ethyl-4-(2-fluoro-4-hydroxy-3-isopropylbenzyl)phenoxy)-N-cyclohexylacetamide (Compound 141)

141

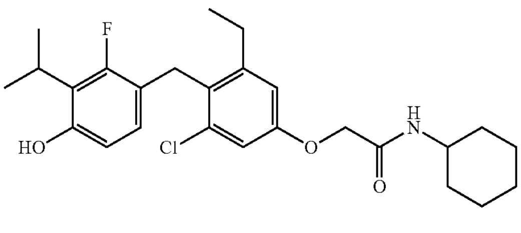

To a solution of Compound 43 (150 mg, 0.39 mmol) in DCM (5 mL) was added oxalyl dichloride (75 mg, 0.59 mmol). The mixture was stirred at rt 30 minutes. The mixture was concentrated to dryness to afford acid chloride (130 mg, 83% yield) as yellow oil. A solution of cyclohexanamine (65 mg, 0.65 mmol) and TEA (67 mg, 0.66 mmol) in DCM (5 mL) was added acid chloride (130 mg, 0.33 mmol) at 0° C. The mixture was stirred at rt 30 minutes.

The mixture was concentrated to dryness and purified by Prep-HPLC to afford Compound 141 (35 mg, 22% yield) as white solid.

LCMS: T=2.6 min, [M−1]=460.1

$^1$H NMR (400 MHz, DMSO-$d_6$) δ 9.47 (d, J=1.4 Hz, 1H), 7.90 (d, J=8.1 Hz, 1H), 6.94 (d, J=2.7 Hz, 1H), 6.84 (d, J=2.7 Hz, 1H), 6.44 (dd, J=8.4, 1.1 Hz, 1H), 6.17 (t, J=8.6 Hz, 1H), 4.48 (s, 2H), 3.92 (s, 2H), 3.63 (d, J=5.6 Hz, 1H), 3.43-3.35 (m, 1H), 2.52 (s, 1H), 2.47 (s, 1H), 1.70 (dd, J=13.3, 6.8 Hz, 4H), 1.56 (d, J=12.8 Hz, 1H), 1.31-1.22 (m, 10H), 1.13 (t, J=12.6 Hz, 1H), 1.02 (t, J=7.5 Hz, 3H).

Example 142

Synthesis of 2-(3-chloro-5-ethyl-4-(2-fluoro-4-hydroxy-3-isopropylbenzyl)phenoxy)-N-(3,4-dimethylisoxazol-5-yl)acetamide (Compound 142)

142

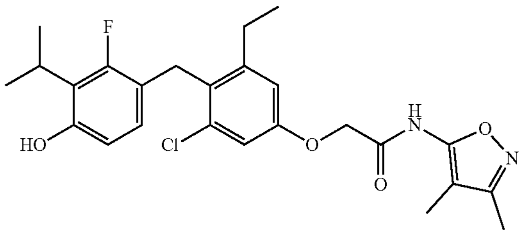

To a mixture of Compound 43 (15 mg, 0.40 mmol) in DCM (2.0 mL) was added oxalyl dichloride (100 mg, 079 mmol) at 0° C. The mixture was stirred at rt for 30 min. The mixture was concentrated in vacuum The resulting yellow solid was dissolved in DCM (2.0 mL) and 5-amino-3.4-dimethylisoxazole (84 mg, 0.75 mmol) and pyridine (149 mg, 1.88 mmol) were added at 0° C. The mixture was stirred at rt for 1 h. Water (15 mL) was added, and the mixture was extracted with DCM (10 mL*3). The combined organic phase was washed by brine (20 mL), dried over $Na_2SO_4$, concentrated in vacuum, and purified by Prep-HPLC to afford Compound 142 (10 mg, 5% yield) as a white solid.

LCMS: T=1.56 min, [M+1]=475.1

$^1$H NMR: (400 MHz, DMSO-$d_6$) δ 10.68 (s, 1H), 9.47 (d, J=1.4 Hz, 1H), 7.00 (d, J=2.6 Hz, 1H), 6.90 (d, J=2.6 Hz, 1H), 6.45 (d, J=8.4 Hz, 1H), 6.18 (t, J=8.6 Hz, 1H), 4.80 (s, 2H), 3.93 (s, 2H), 3.38 (p, J=7.1 Hz, 1H), 2.53 (d, J=7.5 Hz, 2H), 2.15 (s, 3H), 1.78 (s, 3H), 1.26 (d, J=7.0 Hz, 6H), 1.04 (t, J=7.5 Hz, 3H).

Example 143

Synthesis of 2-(3-chloro-2-fluoro-4-(4-hydroxy-3-isopropylbenzyl)-5-methylphenoxy)-N-methylacetamide (Compound 143)

143

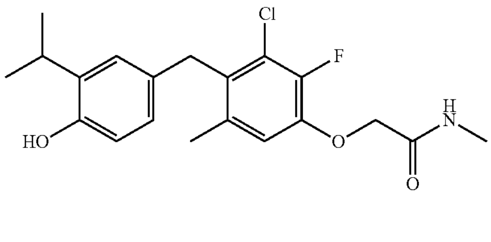

To a solution of Compound 115 (100 mg, 0.25 mmol) in THF (3 mL) at rt was added methylamine (2M/THF, 2 mL) and HATU (142 mg, 0.38 mmol), the resulting mixture was stirred at rt 16 h. The mixture was diluted with water (20 mL) and extracted with EtOAc (20 mL*2). The organic phases was washed by water (30 mL*3), brine (30 mL), dried over $Na_2SO_4$, concentrated and purified by Prep-TLC (pet. ether/EtOAc=1/1) to afford Compound 143 (63 mg, 65% yield).

LCMS: T=3.7 min, [M+1]=380.15

$^1$H NMR: (400 MHz, DMSO-$d_6$) δ 9.05 (s, 1H), 7.98 (s, 1H), 6.97 (d, J=8.3 Hz, 2H), 6.92 (s, 1H), 6.64 (d, J=8.2 Hz, 1H), 4.58 (s, 1H), 3.97 (s, 2H), 3.13 (dt, J=13.7, 6.8 Hz, −2H), 2.66 (d, J=4.6 Hz, 8H), 2.20 (s, −3H), 1.11 (d, J=6.9 Hz, −1H).

Example 144

Synthesis of 2-(3,5-dichloro-4-(2-fluoro-4-hydroxy-3-isopropylbenzyl)phenoxy)acetamide (Compound 144)

144

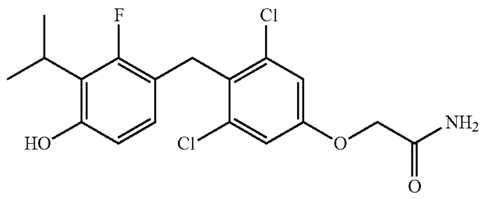

To a mixture of Compound 15 (310 mg, 0.80 mmol) in DCM (2 mL) was added oxalyl dichloride (152 mg, 1.20 mmol) at 0° C. The mixture was stirred at rt for 30 min. The mixture was concentrated in vacuum. The resulting yellow solid was dissolved in DCM (3 mL) and was added to $NH_3/H_2O$ (2 mL). The mixture was stirred at rt for 1 h. Water (20 mL) was added, and the mixture was extracted with DCM (10 mL*3). The combined organic phase was washed by brine (30 mL), dried over $Na_2SO_4$, concentrated in vacuum, and purified by Prep-HPLC to Compound 144 (70 mg, 49% yield) as a white solid LCMS: T=1.648 min, [M−1]=384.0

$^1$H NMR: (400 MHz, DMSO-$d_6$) δ 9.52 (s, 1H), 7.51 (d, J=62.2 Hz, 2H), 7.15 (s, 2H), 6.47 (dd, J=8.4, 1.0 Hz, 1H), 6.27 (t, J=8.6 Hz, 1H), 4.52 (s, 2H), 4.02 (s, 2H), 3.41-3.35 (m, 1H), 1.26 (dd, J=7.1, 0.9 Hz, 6H).

Example 145

Synthesis of ethyl 2-(5-chloro-2,3-difluoro-4-(4-hydroxy-3-isopropylbenzyl)phenoxy)acetate (Compound 145)

145

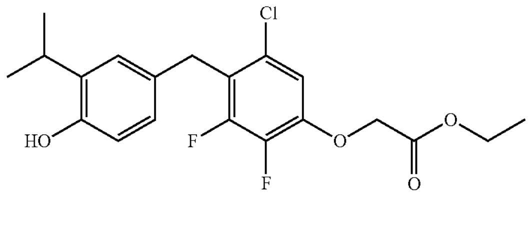

Intermediate A70 (1.5 g, 5.02 mmol), 2-isopropylphenol (1.40 g, 10.0 mmol, 1.35 mL) and $ZnCl_2$ (1 M, 12.5 mL) in DCE (15 mL) was stirred at 85° C. overnight and was cooled down to rt. The mixture was diluted with $H_2O$ (50 mL), extracted with DCM (25 mL*2). The combined organic layer was washed with water (25 mL*2), brine (50 mL), dried over $Na_2SO_4$, purified with silica gel column (Pet. ether to Pet. ether/EtOAc=10/1) to afford product Compound 145 (900 mg, 45% yield) as a colorless oil.

$^1H$ NMR: (400 MHz, DMSO-$d_6$) δ 9.13 (s, 1H), 7.23 (dd, J=7.2, 2.2 Hz, 1H), 6.98 (d, J=2.2 Hz, 1H), 6.73 (dd, J=8.1, 2.2 Hz, 1H), 6.66 (d, J=8.1 Hz, 1H), 4.97 (s, 2H), 4.19-4.14 (m, 2H), 3.91 (d, J=2.3 Hz, 2H), 3.12 (q, J=6.9 Hz, 1H), 1.21 (d, J=7.2 Hz, 3H), 1.11 (d, J=6.9 Hz, 6H).

Example 146

Synthesis of 2-(5-chloro-2,3-difluoro-4-(4-hydroxy-3-isopropylbenzyl)phenoxy)acetic acid (Compound 146)

146

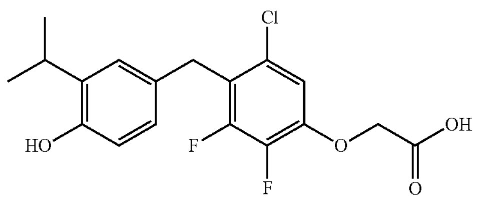

To a solution of Compound 145 (900 mg, 1.81 mmol) in methanol (9 mL) was added NaOH (217 mg, 5.42 mmol) in water (1 mL). The mixture was stirred at rt for 5 mins. The mixture was acidified to pH=4-5 with 2M HCl and $H_2O$ (30 mL) was added. The mixture was extracted with EtOAc (25 mL*2). The combined organic layer was washed with brine (50 mL), dried over $Na_2SO_4$, purified by Prep-HPLC to afford Compound 146 (400 mg, 59% yield) as a white solid.

LCMS: T=1.513, [M−1]=369.0

$^1H$ NMR: (400 MHz, DMSO-$d_6$) δ 13.19 (s, 1H), 9.12 (s, 1H), 7.20-7.16 (m, 1H), 6.99 (d, J=2.1 Hz, 1H), 6.73 (dd, J=8.2, 2.2 Hz, 1H), 6.66 (d, J=8.2 Hz, 1H), 4.87 (d, J=0.8 Hz, 2H), 3.91 (d, J=2.3 Hz, 2H), 3.17-3.10 (m, 1H), 1.11 (dd, J=6.9, 0.7 Hz, 6H).

Example 147

Synthesis of ethyl 2-(3-chloro-2,5-difluoro-4-(4-hydroxy-3-isopropylbenzyl)phenoxy)acetate (Compound 147)

147

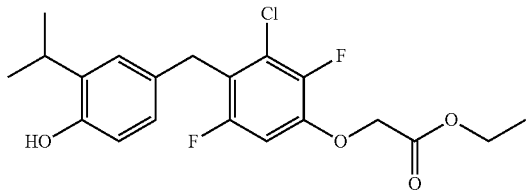

To a solution of Intermediate A73 (200 mg, 0.67 mmol) in DCE (5 ml) at rt was added 2-isopropylphenol (182 mg, 1.34 mmol) and $ZnCl_2$ (228 mg, 1.67 mmol). The reaction was heated to 80° C. and stirred overnight. The reaction mixture was diluted with $H_2O$ (20 mL) and was extracted DCM (10 mL*2). The combined organic phase was washed with brine (20 mL*2), dried over $Na_2SO_4$, concentrated under reduce pressure. The crude product was purified by silica gel column (Pet. ether/EtOAc=50/1 to 10/1) to afford compound 147 (140 mg, 53% yield) as a white solid.

LCMS: T=2.073 min, [M−1]=397.1

Example 148

Synthesis of 2-(3-chloro-2,5-difluoro-4-(4-hydroxy-3-isopropylbenzyl)phenoxy)acetic acid (Compound 148)

148

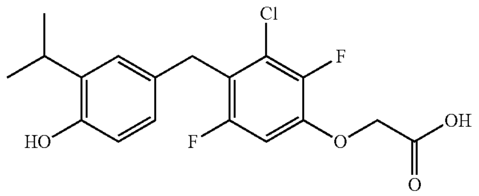

To a solution of compound 147 (125 mg, 0.31 mmol) in MeOH (3 mL)/water (0.5 mL) at rt was added $LiOH·H_2O$ (39 mg, 0.94 mmol). The mixture was stirred at rt 1 h. The reaction was acidified to pH=4-5 with 2 N HCl, extracted with EtOAc (30 mL), washed with brine (10 mL*2), dried over $Na_2SO_4$, concentrated and washed by hexane to afford Compound 148 (110 mg, 87% yield) as a yellow solid.

LCMS: T=1.480 min, [M−1]=369.0

$^1H$ NMR: (400 MHz, DMSO-$d_6$) δ 9.15 (s, 1H), 7.10 (dd, J=11.4, 7.1 Hz, 1H), 6.98 (d, J=2.2 Hz, 1H), 6.71 (dd, J=8.1, 2.2 Hz, 1H), 6.65 (d, J=8.2 Hz, 1H), 4.70 (s, 2H), 3.89 (d, J=2.1 Hz, 2H), 3.12 (p, J=6.9 Hz, 1H), 1.11 (d, J=7.0 Hz, 6H).

Example 149

Synthesis of 2-(5-chloro-2-fluoro-4-(2-fluoro-4-hydroxy-3-isopropylbenzyl)-3-isopropylphenoxy)acetic acid (Compound 149)

149

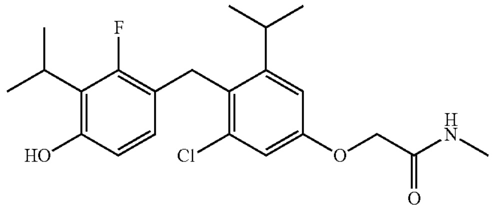

To a solution of Compound 47 (200 mg, 0.51 mmol) in DCM (2.0 mL) was added oxalyl chloride (129 mg, 1.01 mmol). The mixture was stirred at rt for 2 h and concentrated to dryness. The resulting yellow solid was dissolved in DCM (2.0 mL) and methylamine (2 M, in THF) (121 μL, 0.24 mmol) was added. The mixture was stirred at rt for 1 h. Water (30 mL) was added, and the mixture was extracted with DCM (20 mL*3). The combined organic phase was washed by brine (30 mL), dried over $Na_2SO_4$, concentrated in vacuum and purified by Prep-HPLC to Compound 149 (20 mg, 20% yield) as white solid

LCMS: T=2.710, (M−1)=406.2

$^1$H NMR: (400 MHz, DMSO-$d_6$) δ 9.49 (d, J=1.4 Hz, 1H), 8.08 (d, J=4.9 Hz, 1H), 6.94 (q, J=2.6 Hz, 2H), 6.45 (dd, J=8.5, 1.1 Hz, 1H), 6.18 (t, J=8.6 Hz, 1H), 4.49 (s, 2H), 3.96 (s, 2H), 3.39 (d, J=7.2 Hz, 1H), 2.95 (p, J=6.8 Hz, 1H), 2.67 (d, J=4.7 Hz, 3H), 1.32-1.17 (m, 6H), 1.06 (d, J=6.7 Hz, 6H).

Example 150

Synthesis of 2-(3-chloro-4-(2-fluoro-4-hydroxy-3-isopropylbenzyl)-5-isopropylphenoxy)-N,N-dimethylacetamide (Compound 150)

150

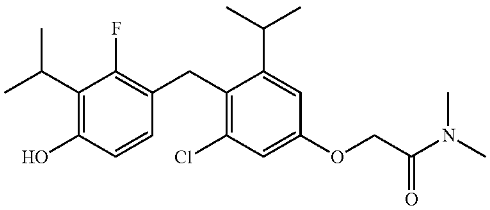

To a mixture of Compound 47 (200 mg, 0.51 mmol) in DCM (2 mL) was added oxalyl chloride (128 mg, 1.01 mmol) at 0° C. The mixture was stirred at rt for 30 min. The mixture was concentrated in vacuum. The resulting solid was dissolved in DCM (2 mL) and dimethylamine (2 M/THF, 1 mL) was added. The mixture was stirred at rt for 1 h. Water (30 mL) was added, and the mixture was extracted with DCM (20 mL*3). The combined organic phase was washed by brine (30 mL), dried over $Na_2SO_4$, concentrated in vacuum and purified by Prep-HPLC to Compound 150 (25 mg, 25% yield) as white solid LCMS: T=2.856 min, [M−1]=420.1

$^1$H NMR: (400 MHz, DMSO-$d_6$) δ 9.48 (s, 1H), 6.90 (d, J=2.6 Hz, 1H), 6.86 (d, J=2.7 Hz, 1H), 6.46 (d, J=8.4 Hz, 1H), 6.18 (t, J=8.6 Hz, 1H), 4.83 (s, 2H), 3.95 (s, 2H), 3.35 (s, 1H), 3.00 (s, 3H), 2.96-2.90 (m, 1H), 2.85 (s, 3H), 1.26 (d, J=7.1 Hz, 6H), 1.05 (d, J=6.8 Hz, 6H).

Example 151

Synthesis of 2-(3-chloro-4-(2-fluoro-4-hydroxy-3-isopropylbenzyl)-5-(prop-1-en-2-yl)phenoxy)-N-methylacetamide (Compound 151)

151

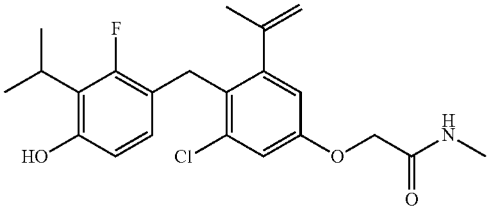

To a mixture of Compound 46 (100 mg, 0.25 mmol) in DCM (3 mL) was added oxalyl chloride (65 mg, 0.51 mmol) at 0° C. The mixture was stirred at rt for 30 min. The mixture was concentrated in vacuum. The resulting yellow solid was dissolved in DCM (2 mL) and was added to methylamine (2 M/THF, 2 mL). The mixture was stirred at rt for 1 h. Water (20 mL) was added, and the mixture was extracted with DCM (20 mL*3). The combined organic phase was washed by brine (30 mL), dried over $Na_2SO_4$, concentrated in vacuum and purified by Prep-HPLC to afford Compound 151 (25 mg, 30% yield) as white solid.

LCMS: T=2.590 min, [M−1]=406.2

$^1$H NMR: (400 MHz, DMSO-$d_6$) δ 9.45 (s, 1H), 8.07 (d, J=5.0 Hz, 1H), 7.04 (d, J=2.7 Hz, 1H), 6.78 (d, J=2.7 Hz, 1H), 6.45 (d, J=8.4 Hz, 1H), 6.20 (t, J=8.6 Hz, 1H), 5.12 (s, 1H), 4.68 (s, 1H), 4.50 (s, 2H), 3.87 (s, 2H), 3.38-3.36 (m, 1H), 2.66 (d, J=4.6 Hz, 3H), 1.84 (s, 3H), 1.25 (d, J=7.1 Hz, 6H).

Example 152

Synthesis of 2-(3-chloro-4-(2-fluoro-4-hydroxy-3-isopropylbenzyl)-5-(prop-1-en-2-yl)phenoxy)-N,N-dimethylacetamide (Compound 152)

152

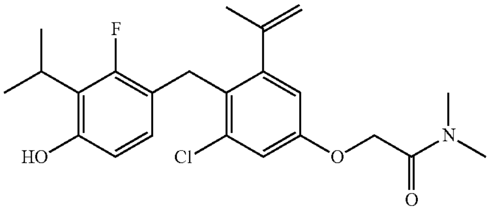

To a mixture of Compound 46 (100 mg, 0.25 mmol) in DCM (3 mL) was added oxalyl chloride (65 mg, 0.51 mmol) at 0° C. The mixture was stirred at rt for 2 h and concentrated in vacuum. The resulting yellow solid was dissolved in THF (3 mL) and was added to dimethylamine (2 M/THF) (0.61 mL, 1.22 mmol). The mixture was stirred at rt for 1 h. Water (30 mL) was added, and the mixture was extracted with DCM (20 mL*3). The combined organic phase was washed by brine (30 mL), dried over $Na_2SO_4$, concentrated in vacuum and purified by Prep-HPLC to afford Compound 152 (35 mg, 34% yield) as white solid.

LCMS: T=2.73 min, [M+1]=420.1

$^1$H NMR: (400 MHz, DMSO-$d_6$) δ 9.44 (d, J=1.3 Hz, 1H), 6.99 (d, J=2.6 Hz, 1H), 6.72 (d, J=2.7 Hz, 1H), 6.46 (d, J=8.3 Hz, 1H), 6.20 (s, 1H), 5.10 (t, J=1.9 Hz, 1H), 4.85 (s, 2H), 4.68 (d, J=1.9 Hz, 1H), 3.86 (s, 2H), 3.38 (s, 1H), 2.99 (s, 3H), 2.85 (s, 3H), 1.83 (s, 3H), 1.25 (d, J=7.1 Hz, 6H).

Example 153

Synthesis of 2-(5-chloro-2,3-difluoro-4-(4-hydroxy-3-isopropylbenzyl)phenoxy)-N-methylacetamide (Compound 153)

153

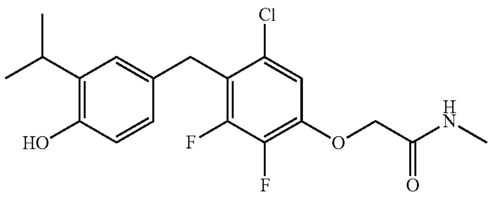

To a mixture of Compound 146 (200 mg, 0.54 mmol) in DCM (5 mL) was added oxalyl chloride (103 mg, 0.81 mmol) at 0° C. The mixture was stirred at rt for 30 min and was concentrated in vacuum. The resulting yellow solid was dissolved in DCM (5 mL) and methylamine (2 M/THF) (0.51 mL, 1.03 mmol) was added. The mixture was stirred at rt for 1 h, diluted with water (30 mL) extracted with DCM (20 mL*3). The combined organic phase was washed with brine (30 mL), dried over $Na_2SO_4$, concentrated in vacuum and purified by Prep-HPLC to afford Compound 153 (100 mg, 49% yield) as white solid.

LCMS: T=1.471 min, [M+1]=383.9

$^1$H NMR: (400 MHz, DMSO-$d_6$) δ 9.13 (s, 1H), 8.00 (d, J=5.0 Hz, 1H), 7.12 (dd, J=7.2, 2.1 Hz, 1H), 7.00 (d, J=2.1 Hz, 1H), 6.73 (dd, J=8.1, 2.2 Hz, 1H), 6.66 (d, J=8.2 Hz, 1H), 4.65 (s, 2H), 3.91 (d, J=2.4 Hz, 2H), 3.13 (p, J=6.9 Hz, 1H), 2.64 (d, J=4.6 Hz, 3H), 1.11 (d, J=6.9 Hz, 6H).

Example 154

Synthesis of 2-(3-chloro-2,5-difluoro-4-(4-hydroxy-3-isopropylbenzyl)phenoxy)-N-methylacetamide (Compound 154)

154

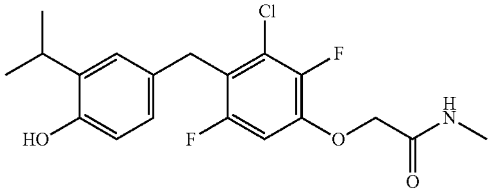

To a mixture of Compound 148 (55 mg, 0.15 mmol) in DCM (2 mL) was added oxalyl chloride (28 mg, 0.22 mmol) at 0° C. The mixture was stirred at rt for 30 min and was concentrated in vacuum. The resulting brown oil was dissolved in DCM (2 mL) and was added to methylamine (2 M, in THF) (2 mL, 2.92 mmol). The mixture was stirred at rt for 1 h, diluted with water (30 mL) and extracted with DCM (20 mL*3). The combined organic phase was washed by brine (30 mL), dried over $Na_2SO_4$, concentrated in vacuum and purified by Prep-HPLC to afford Compound 154 (20 mg, 33% yield) as a white solid.

LCMS: T=1.466 min, [M+1]=384.0

$^1$H NMR: (400 MHz, DMSO-$d_6$) δ 9.13 (s, 1H), 8.00 (d, J=5.2 Hz, 1H), 7.13 (dd, J=11.2, 7.1 Hz, 1H), 6.99 (d, J=2.2 Hz, 1H), 6.72 (dd, J=8.1, 2.2 Hz, 1H), 6.65 (d, J=8.2 Hz, 1H), 4.63 (s, 2H), 3.90 (d, J=2.1 Hz, 2H), 3.13 (p, J=6.9 Hz, 1H), 2.64 (d, J=4.6 Hz, 3H), 1.11 (d, J=7.0 Hz, 6H).

Example 155

Synthesis of 2-(3-chloro-2-fluoro-4-(4-hydroxy-3-isopropylbenzyl)-5-vinylphenoxy)-N-methylacetamide (Compound 155)

155

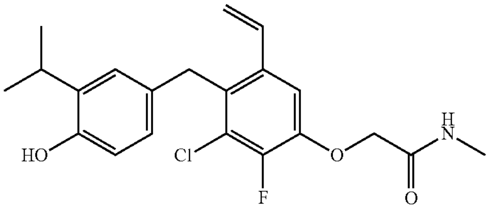

To a mixture of Compound 75 (160 mg, 0.44 mmol) in DCM (2.0 mL) was added oxalyl chloride (112 mg, 0.44 mmol) at 0° C. The mixture was stirred at rt for 30 min and was concentrated in vacuum. The resulting brown solid was dissolved in DCM (2.0 mL) and methylamine (2 M/THF, 1 mL) was added. The mixture was stirred at rt for 1 h, diluted with water (20 mL) and extracted with DCM (20 mL*3). The combined organic phase was washed by brine (30 mL), dried over $Na_2SO_4$, concentrated in vacuum and purified by Prep-HPLC to afford Compound 155 (15 mg, 17% yield) as a white solid.

LCMS: T=1.59 min, [M−1]=390.1

$^1$H NMR: (400 MHz, DMSO-$d_6$) δ 9.08 (s, 1H), 7.96 (s, 1H), 6.93 (d, J=1.9 Hz, 1H), 6.81-6.75 (m, 1H), 6.67-6.60 (m, 2H), 4.55 (s, 2H), 3.81 (d, J=2.1 Hz, 2H), 3.12 (q, J=7.0 Hz, 1H), 2.64 (d, J=4.6 Hz, 3H), 2.18 (s, 3H), 1.11 (d, J=6.9 Hz, 6H).

Example 156

Synthesis of 2-(3-chloro-2-fluoro-4-(4-hydroxy-3-isopropylbenzyl)-5-vinylphenoxy)-N,N-dimethylacetamide (Compound 156)

156

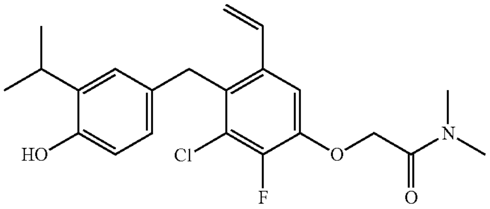

To a mixture of Compound 75 (160 mg, 0.44 mmol) in DCM (2.0 mL) was added oxalyl chloride (112 mg, 0.44 mmol) at 0° C. The mixture was stirred at rt for 30 min and was concentrated in vacuum. The resulting brown solid was dissolved in DCM (2.0 mL) and was added to dimethylamine (2 M/THF, 1 mL). The mixture was stirred at rt for 1 h. Water (20 mL) was added, and the mixture was extracted with DCM (20 mL*3). The combined organic phase was washed by brine (30 mL), dried over $Na_2SO_4$, concentrated in vacuum and purified by Prep-HPLC to afford Compound 156 (30 mg, 32% yield) as white solid.

LCMS: T=1.74 min, [M−1]=404.1

$^1$H NMR (400 MHz, DMSO-$d_6$) δ 9.05 (s, 1H), 7.23 (d, J=8.3 Hz, 1H), 6.98-6.86 (m, 2H), 6.62 (d, J=8.2 Hz, 1H), 6.56 (dd, J=8.3, 2.1 Hz, 1H), 5.71 (d, J=17.2 Hz, 1H), 5.33 (d, J=11.0 Hz, 1H), 5.03 (s, 2H), 4.03 (s, 2H), 3.12 (p, J=7.0 Hz, 1H), 3.00 (s, 3H), 2.84 (s, 3H), 1.09 (d, J=6.9 Hz, 6H).

Example 157

Synthesis of 2-(3-chloro-5-ethyl-2-fluoro-4-(4-hydroxy-3-isopropylbenzyl)phenoxy)-N-methylacetamide (Compound 157)

157

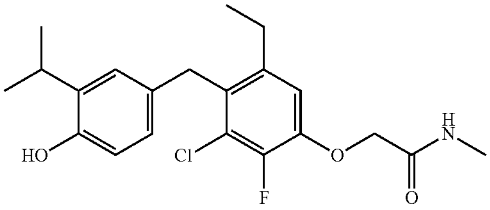

To a mixture of Compound 77 (150 mg, 0.39 mmol) in DCM (2.0 mL) was added oxalyl chloride (100 mg, 0.79 mmol) at 0° C. The mixture was stirred at rt for 30 min and was concentrated in vacuum. The resulting yellow oil was dissolved in DCM (2.0 mL) and methylamine (2 M/THF, 1 mL) was added. The mixture was stirred at rt for 1 h, diluted with water (20 mL), and extracted with DCM (20 mL*3). The combined organic phase was washed by brine (30 mL), dried over $Na_2SO_4$, concentrated in vacuum and purified by Prep-HPLC to afford Compound 157 (30 mg, 32% yield) as a white solid.

LCMS: T=1.68 min, [M−1]=392.1

$^1$H NMR: (400 MHz, DMSO-$d_6$) δ 9.04 (s, 1H), 8.00 (s, 1H), 6.95 (d, J=8.4 Hz, 1H), 6.88 (d, J=2.2 Hz, 1H), 6.63 (d, J=8.2 Hz, 1H), 6.53 (dd, J=8.2, 2.3 Hz, 1H), 4.60 (s, 2H), 3.99 (s, 2H), 3.13 (p, J=6.9 Hz, 1H), 2.65 (d, J=4.7 Hz, 3H), 2.58-2.52 (m, 2H), 1.10 (d, J=6.9 Hz, 6H), 1.00 (t, J=7.5 Hz, 3H).

Example 158

Synthesis of 2-(3-chloro-5-ethyl-2-fluoro-4-(4-hydroxy-3-isopropylbenzyl)phenoxy)-N,N-dimethylacetamide (Compound 158)

158

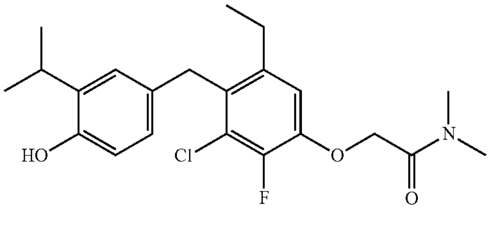

To a mixture of Compound 77 (150 mg, 0.39 mmol) in DCM (2.0 mL) was added oxalyl chloride (100 mg, 0.79 mmol) at 0° C. The mixture was stirred at rt for 30 min and was concentrated in vacuum. The resulting yellow oil was dissolved in DCM (2.0 mL) and dimethylamine (2 M/THF, 1 mL) was added. The mixture was stirred at rt for 1 h, diluted with water (20 mL), and was extracted with DCM (20 mL*3). The combined organic phase was washed by brine (30 mL), dried over $Na_2SO_4$, concentrated in vacuum and purified by Prep-HPLC to afford Compound 158 (25 mg, 31% yield) as white solid.

LCMS: T=1.71 min, [M−1]=406.2

$^1$H NMR: (400 MHz, DMSO-$d_6$) δ 9.03 (s, 1H), 6.94 (d, J=8.5 Hz, 1H), 6.88 (d, J=2.2 Hz, 1H), 6.63 (d, J=8.1 Hz, 1H), 6.53 (dd, J=8.3, 2.2 Hz, 1H), 4.95 (s, 2H), 3.98 (s, 2H), 3.13 (p, J=6.9 Hz, 1H), 2.99 (s, 3H), 2.84 (s, 3H), 2.56-2.51 (m, 2H), 1.10 (d, J=6.8 Hz, 6H), 0.99 (t, J=7.5 Hz, 3H).

Example 159

Synthesis of 2-(5-chloro-2-fluoro-4-(4-hydroxy-3-isopropylbenzyl)-3-vinylphenoxy)-N-methylacetamide (Compound 159)

159

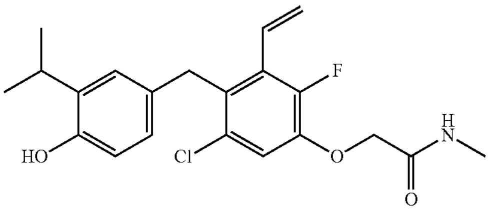

To a mixture of Compound 67 (350 mg, 0.92 mmol) in DCM (5 mL) was added oxalyl chloride (176 mg, 1.00 mmol) at 0° C. The mixture was stirred at rt for 30 min and was concentrated in vacuum. The resulting yellow solid was dissolved in DCM (2 mL) and was added to methylamine (2 M/THF, 2 mL). The mixture was stirred at rt for 20 min, diluted with water (10 mL), and was extracted with DCM (50 mL*2). The combined organic phase was washed by brine (10 mL), dried over $Na_2SO_4$, concentrated in vacuum and purified by Prep-TLC (DCM:MeOH=10/1) to afford Compound 159 (20 mg, 29% yield) as a white solid.

LCMS: T=1.592 min, [M−1]=390.1

$^1$H NMR: (400 MHz, DMSO-$d_6$) δ 9.05 (s, 1H), 7.98 (d, J=5.0 Hz, 1H), 7.17 (d, J=7.7 Hz, 1H), 6.89 (d, J=2.2 Hz, 1H), 6.68-6.54 (m, 3H), 5.67-5.56 (m, 2H), 4.61 (s, 2H), 3.99 (s, 2H), 3.12 (p, J=6.9 Hz, 1H), 2.66 (d, J=4.7 Hz, 3H), 1.09 (d, J=6.9 Hz, 6H).

Example 160

Synthesis of 2-(5-chloro-2-fluoro-4-(4-hydroxy-3-isopropylbenzyl)-3-vinylphenoxy)-N,N-dimethylacetamide (Compound 160)

160

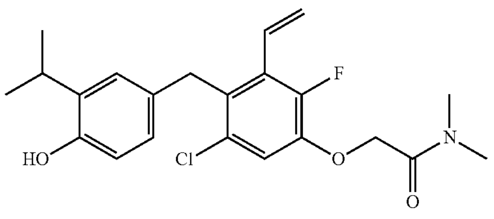

To a mixture of Compound 67 (200 mg, 0.52 mmol) in DCM (5 mL) was added oxalyl chloride (99 mg, 0.78 mmol) at 0° C. The mixture was stirred at rt for 30 min and was concentrated in vacuum. The resulting yellow solid was dissolved in DCM (2 mL) and was added to dimethylamine (2 M/THF, 2 mL). The mixture was stirred at rt for 20 min, diluted with water (10 mL), and was extracted with DCM (50 mL*2). The combined organic phase was washed by brine (10 mL), dried over $Na_2SO_4$, concentrated in vacuum and purified by Prep-TLC (DCM:MeOH=10/1) to afford Compound 160 (70 mg, 31.5% yield) as a white solid.

LCMS: RT=1.695 min, [M+1]=406.1

$^1$H NMR: $^1$H NMR (400 MHz, DMSO-d6) δ 9.04 (s, 1H), 7.18 (d, J=7.8 Hz, 1H), 6.89 (d, J=2.2 Hz, 1H), 6.67-6.54 (m, 3H), 5.65-5.57 (m, 2H), 4.98 (s, 2H), 3.98 (s, 2H), 3.12 (p, J=6.9 Hz, 1H), 2.98 (s, 3H), 2.85 (s, 3H), 1.10 (d, J=6.9 Hz, 6H).

Example 161

Synthesis of 2-(3-chloro-2-fluoro-4-(4-hydroxy-3-isopropylbenzyl)-5-vinylphenoxy)-N-ethylacetamide (Compound 161)

161

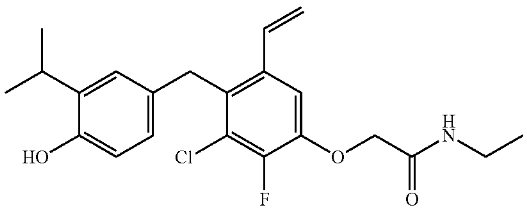

To a mixture of Compound 67 (250 mg, 0.66 mmol) in DCM (5 mL) was added oxalyl chloride (89 mg, 1.9 mmol) at 0° C. The mixture was stirred at rt for 30 min and was concentrated in vacuum. The resulting yellow solid was dissolved in DCM (2 mL) and was added to ethylamine (1 M/THF, 2 mL). The mixture was stirred at rt for 20 min, diluted with water (10 mL), and was extracted with DCM (50 mL*2). The combined organic phase was washed by brine (10 mL), dried over $Na_2SO_4$, concentrated in vacuum and purified by Prep-TLC (DCM:MeOH=10/1) to afford Compound 161 (30 mg, 11% yield) as a white solid.

LCMS: RT=1.802 min, [M+1]=406.1

$^1$H NMR: $^1$H NMR (400 MHz, DMSO-d6) δ 9.06 (s, 1H), 8.11 (s, 1H), 7.23 (d, J=8.3 Hz, 1H), 6.97-6.88 (m, 2H), 6.62 (d, J=8.2 Hz, 1H), 6.58 (s, 1H), 5.71 (d, J=17.2 Hz, 1H), 5.33 (d, J=11.0 Hz, 1H), 4.66 (s, 2H), 4.04 (s, 2H), 3.14 (dq, J=13.8, 6.9 Hz, 3H), 1.09 (d, J=6.9 Hz, 6H), 1.02 (t, J=7.2 Hz, 3H).

Example 162

Synthesis of 2-(3-chloro-2-fluoro-4-(4-hydroxy-3-isopropylbenzyl)-5-vinylphenoxy)-N-(2-fluoroethyl)acetamide (Compound 162)

162

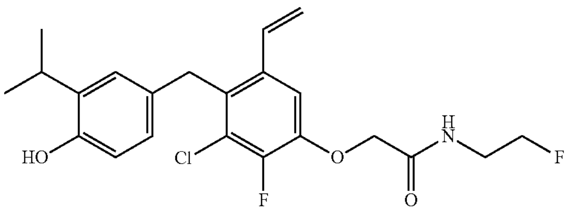

To a mixture of Compound 67 (378 mg, 1 mmol) and 2-fluoroethan-1-amine (192 mg, 3 mmol) in THF (10 mL) was added HATU (582 mg, 1 mmol) and DIPEA (262 mg, 2 mmol). The mixture was stirred at rt for 2 h. The mixture was diluted with water (30 mL) and extracted with EtOAc (20 mL*2). The organic phase was washed by brine (30 ml), dried over $Na_2SO_4$, concentrated in vacuum, and purified by Prep-HPLC to afford Compound 162 (105 mg, 24% yield) as white solid.

LCMS: RT=1.718 min, [M+1]=424.0

$^1$H NMR: $^1$H NMR (400 MHz, DMSO-d6) δ 9.07 (s, 1H), 8.35 (t, J=5.6 Hz, 1H), 7.24 (d, J=8.4 Hz, 1H), 7.00-6.87 (m, 2H), 6.62 (d, J=8.2 Hz, 1H), 6.57 (d, J=8.2 Hz, 1H), 5.72 (d, J=18.4 Hz, 1H), 5.33 (d, J=10.5 Hz, 1H), 4.73 (s, 2H), 4.50 (t, J=5.0 Hz, 1H), 4.38 (t, J=5.1 Hz, 1H), 4.04 (s, 2H), 3.47 (d, J=5.3 Hz, 1H), 3.41 (d, J=5.3 Hz, 1H), 3.11 (p, J=6.9 Hz, 1H), 1.09 (d, J=6.9 Hz, 6H).

Example 163

Synthesis of 2-(3,5-dichloro-2-cyano-4-(4-hydroxy-3-isopropylbenzyl)phenoxy)acetic acid (Compound 163)

163

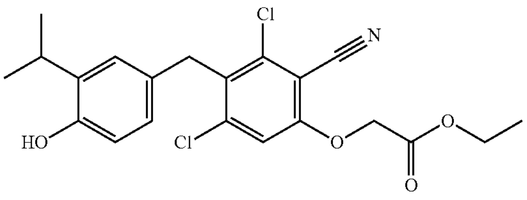

To a solution of Intermediate C10 (30 mg, 79 μmol) in DMF (2 mL) was added $K_2CO_3$ (22 mg, 157 μmol) and ethyl 2-bromoacetate (15 mg, 86.78 μmol). The reaction mixture was stirred for 1 h. Water (20 mL) was added, and the mixture was extracted with EtOAc (15 mL*3). The combined organic phase was washed by brine (30 mL), dried over $Na_2SO_4$ and concentrated in vacuum to afford compound 13 (25 mg, 68% yield) as a yellow oil. To a mixture of compound 13 (25 mg, 54 μmol) in DCM (0.5 mL) was added HCl/1,4-dioxane (54 μmol, 2 mL). The mixture was stirred at rt for 1 h and was concentrated in vacuum to afford Compound 163 (20 mg, 88% yield) as colorless oil.

Example 164

Synthesis of 2-(3,5-dichloro-2-cyano-4-(4-hydroxy-3-isopropylbenzyl)phenoxy)acetic acid (Compound 164)

164

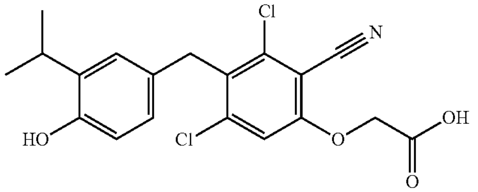

To a mixture of Compound 163 (20 mg, 47 μmol) in THF (1 mL) and water (0.5 mL) was added $LiOH \cdot H_2O$ (6 mg, 142 μmol). The mixture was stirred at rt for 1 h. The reaction was acidified to pH=5 with aqueous HCl (0.5 N) and extracted with EtOAc (10 mL*3). The combined organic phase was washed by brine (30 mL), dried over $Na_2SO_4$, concentrated in vacuum and purified by Prep-HPLC to afford Compound 164 (15 mg, 80% yield) as a white solid.

LCMS: T=1.513 min, [M−1]=392.0

$^1$H NMR: (400 MHz, DMSO-$d_6$) δ 13.31 (s, 1H), 9.14 (s, 1H), 7.49 (s, 1H), 6.97 (s, 1H), 6.65 (d, J=1.8 Hz, 2H), 5.01 (s, 2H), 4.10 (s, 2H), 3.13 (p, J=6.9 Hz, 1H), 1.11 (d, J=6.7 Hz, 6H).

Example 165

Synthesis of ethyl 2-(3,5-dichloro-4-(4-hydroxy-3-isopropylbenzyl)-2-methoxyphenoxy)acetate (Compound 165)

165

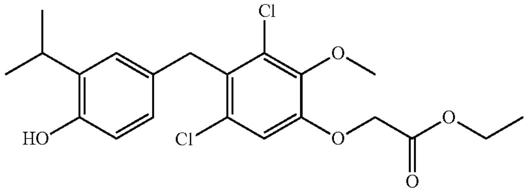

To a solution of Intermediate A80 (378 mg, 1.15 mmol) in DCE (5 mL) at rt was added 2-isopropylphenol (314 mg, 2.31 mmol) and $ZnCl_2$ (393 mg, 2.88 mmol). The reaction was heated to 90° C. overnight. The reaction mixture was diluted with $H_2O$ (20 mL) and was extracted EtOAc (10 mL*2). The combined organic phase was washed with brine (10 mL*2), dried over $Na_2SO_4$, and was concentrated under reduce pressure. The crude product was purified by Prep- TLC (pet. ether/EtOAc=5/1) to afford Compound 165 (195 mg, 40% yield) as a white solid.

LCMS: T=2.179 min, [M−1]=425.0

Example 166

Synthesis of 2-(3,5-dichloro-4-(4-hydroxy-3-isopropylbenzyl)-2-methoxyphenoxy)acetic acid (Compound 166)

166

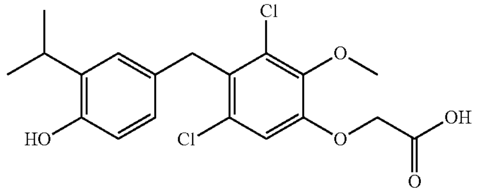

To a solution of Compound 165 (195 mg, 0.46 mmol) in MeOH (5 mL)/water (0.5 mL) at rt was added $LiOH \cdot H_2O$ (57 mg, 1.37 mmol). The mixture was stirred at rt 1 h. The reaction was acidified to pH=4-5 with 2 N HCl and was extracted with EtOAc (50 mL). The combined organic phase was washed with brine (20 mL*2), dried over $Na_2SO_4$, concentrated and purified by Prep-HPLC to afford Compound 166 (180 mg, 95% yield) as a white solid.

LCMS: T=1.592 min, [M−1]=397.0

$^1$H NMR: (400 MHz, DMSO-$d_6$) δ 9.06 (s, 1H), 7.17 (s, 1H), 6.97 (d, J=2.0 Hz, 1H), 6.67 (dd, J=8.4, 2.0 Hz, 1H), 6.63 (d, J=8.0 Hz, 1H), 4.84 (s, 2H), 4.04 (s, 2H), 3.80 (s, 3H), 3.13 (p, J=6.8 Hz, 1H), 1.10 (d, J=6.8 Hz, 6H).

Example 167

Synthesis of 2-(3,5-dichloro-4-(4-hydroxy-3-isopropylbenzyl)-2-methoxyphenoxy)-N-methylacetamide (Compound 167)

167

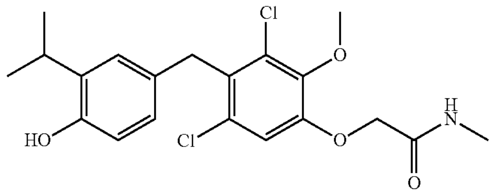

To a solution of Compound 166 (90 mg, 225.41 umol) in DCM (2 mL) was added $(COCl)_2$ (43 mg, 338 umol). The mixture was stirred at rt for 1 h and concentrated. The resulting colorless oil was dissolved in DCM (3 mL) and methylamine (2 M, 2.2 mL) was added. The mixture was stirred at rt for 30 min, concentrated to dryness, and purified by Prep-HPLC to afford product Compound 167 (52 mg, 123 umol, 57% yield) as a white solid.

LCMS: T=2.285 min, [M+1]=412.0

$^1$H NMR: (400 MHz, DMSO-$d_6$) δ 9.07 (s, 1H), 7.93 (d, J=4.8 Hz, 1H), 7.14 (s, 1H), 6.98 (d, J=2.0 Hz, 1H), 6.67 (dd, J=8.4, 2.0 Hz, 1H), 6.63 (d, J=8.0 Hz, 1H), 4.61 (s, 2H), 4.05

(s, 2H), 3.80 (s, 3H), 3.13 (p, J=6.8 Hz, 1H), 2.66 (d, J=4.8 Hz, 3H), 1.10 (d, J=6.8 Hz, 6H).

Example 168

Thyroid-Hormone Reporter-Gene Assays

Compounds were tested for thyroid-hormone receptor activity using TR reporter-gene assays. Reporter cells used in the assays express a TR-receptor hybrid (either TRα or TRβ) in which the native N-terminal DNA binding domain (DBD) has been replaced with that of the yeast Gal4 DBD. The reporter gene, firefly luciferase, is functionally linked to the Gal4 upstream activation sequence (UAS). Both cell lines were derived from human embryonic kidney (HEK293).

Step 1: A suspension of reporter cells was prepared in cell recovery medium containing 10% charcoal-stripped FBS, and dispensed into assay plates. The plates were pre-incubated for 6 hours in a cell culture incubator (37° C./5% $CO_2$/85% humidity).

Step 2: Test compound master stocks and triiodothyronine were diluted in DMSO to generate solutions at "1,000×-concentration" relative to each final treatment concentration. These intermediate stocks were subsequently diluted directly into compound screening medium containing 10% charcoal-stripped FBS to generate "2×-concentration" treatment media (containing 0.2, 0.4 or 0.8% DMSO).

Step 3: At the end of the pre-incubation period, culture media were discarded from the assay plates, and all wells received 100 μl of compound screening medium. 100 μl of each of the previously prepared "2×-concentration" treatment media were dispensed into duplicate assay wells, thereby achieving the desired final treatment concentrations. The final concentration of DMSO in all assay wells was 0.1, 0.2 or 0.4%. Assay plates were incubated for 24 hr in a cell culture incubator (37° C./5% $CO_2$/85% humidity).

Step 4: At the 24 h assay endpoint, treatment media were discarded and 100 μl/well of luciferase detection reagent was added. Relative luminometer units (RLUs) were quantified from each assay well. The performance of the TRα and TRβ assays was validated using the reference agonist triiodothyronine (T3).

The results of these assays are presented in Table 2 below, wherein data are reported as $EC_{50}$ values determined for TRα and TRβ receptors, and the selectivity index (SI) is calculated as $EC_{50}$ (TRα)/$EC_{50}$ (TRβ). To this end, $EC_{50}$ and SI values are expressed as follows:

Potency: +$EC_{50}$>1,000 nM
++ 100 nM<$EC_{50}$≤1,000 nM
+++ 10 nM<$EC_{50}$≤100 n M
++++$EC_{50}$≤10 nM
ND Not determined
Selectivity: + T3-SI≤3×
++ 3×<T3-SI≤30×
+++ T3-SI>30×
ND Not determined

TABLE 2

| Activity Data | | | |
|---|---|---|---|
| CPD. NO. | TRα | TRβ | T3-SI |
| T3 | ++++ | +++ | + |
| 2 | + | ++ | ++ |
| 3 | + | ++ | ++ |
| 6 | +++ | ++++ | ++ |
| 9 | +++ | +++ | ++ |

TABLE 2-continued

| Activity Data | | | |
|---|---|---|---|
| CPD. NO. | TRα | TRβ | T3-SI |
| 12 | +++ | ++++ | ++ |
| 13 | ++++ | ++++ | ++ |
| 15 | +++ | +++ | ++ |
| 22 | +++ | +++ | ++ |
| 24 | ++ | +++ | ++ |
| 25 | +++ | ++++ | ++ |
| 26 | ++ | +++ | ++ |
| 28 | +++ | +++ | ++ |
| 30 | +++ | ++++ | ++ |
| 32 | ++ | +++ | ++ |
| 34 | + | ++ | ++ |
| 36 | +++ | +++ | ++ |
| 40 | ++++ | ++++ | ++ |
| 43 | +++ | +++ | ++ |
| 46 | +++ | ++++ | ++ |
| 47 | ++++ | ++++ | ++ |
| 49 | ++ | +++ | ++ |
| 52 | + | + | ++ |
| 54 | + | ++ | ++ |
| 56 | + | + | ++ |
| 58 | ++ | +++ | +++ |
| 62 | ++ | +++ | +++ |
| 67 | ++ | +++ | ++ |
| 69 | + | ++ | ++ |
| 71 | + | + | ++ |
| 73 | + | ++ | +++ |
| 75 | ++ | +++ | +++ |
| 77 | +++ | +++ | ++ |
| 79 | ++ | +++ | +++ |
| 81 | +++ | +++ | ++ |
| 83 | ++ | +++ | +++ |
| 85 | + | ++ | +++ |
| 87 | + | + | +++ |
| 89 | +++ | +++ | ++ |
| 91 | ++ | +++ | +++ |
| 93 | ++ | +++ | +++ |
| 97 | +++ | ++++ | ++ |
| 101 | + | ++ | ++ |
| 103 | +++ | +++ | +++ |
| 107 | +++ | +++ | ++ |
| 109 | +++ | ++++ | +++ |
| 112 | +++ | ++++ | ++ |
| 115 | ++ | +++ | ++ |
| 118 | ++ | +++ | +++ |
| 121 | + | ++ | ++ |
| 123 | ++ | +++ | ++ |
| 125 | + | + | ++ |
| 133 | +++ | +++ | ++ |
| 142 | ++ | +++ | ++ |
| 143 | ++ | +++ | +++ |
| 147 | + | ++ | +++ |
| 148 | + | + | ++ |
| 163 | ++ | +++ | +++ |
| 164 | + | + | ++ |
| 165 | ++ | ++ | ++ |
| 167 | +++ | +++ | ++ |

As indicated by the above experiments, compounds of the present invention show improved TRβ selectivity when compared to the natural agonist T3 as well as improved potency when compared to T3.

While replacement of hydrogen atoms with halogens can sometimes lead to enhancements/improvements in drug properties, it is not obvious that any specific such replacement might be beneficial. For example, Table 3 shows the results of replacing several of the hydrogen atoms on JD-21 (Devereaux et al., ChemMedChem 2016, 11, 1-8, DOI: 10.1002/cmdc.201600408), as well as results for several comparative compounds (i.e., Comparative Cpds. A and B), with fluorine atoms, along with comparative data for several representative compounds of this disclosure (i.e., Cpd. Nos. 15 and 62).

TABLE 3

| Activity Data | | | | |
|---|---|---|---|---|
| Cpd. No. | Structure | $EC_{50}$-TRα | $EC_{50}$-TRβ | T3-SI |
| JD-21 | 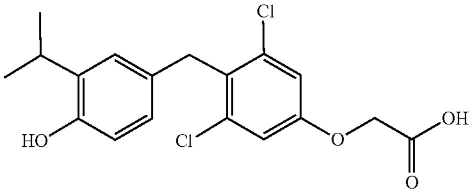 [SMILES: CC(C)c1cc(Cc2c(Cl)cc(OCC(=O)O)cc2Cl)ccc1O] | 190 nM | 79 nM | 14 |
| 15 | 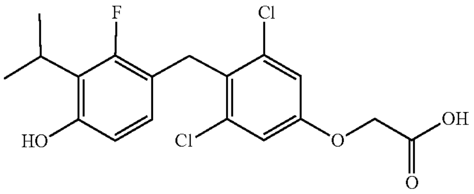 [SMILES: CC(C)c1c(O)ccc(Cc2c(Cl)cc(OCC(=O)O)cc2Cl)c1F] | 43 nM | 14 nM | 6.8 |
| Comparative Cpd. A | 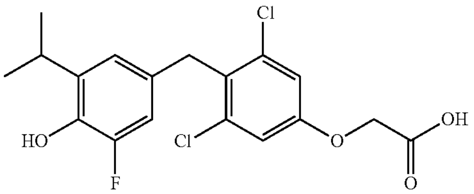 [SMILES: CC(C)c1cc(Cc2c(Cl)cc(OCC(=O)O)cc2Cl)cc(F)c1O] | 3,000 nM | 870 nM | 16 |
| Comparative Cpd. B | 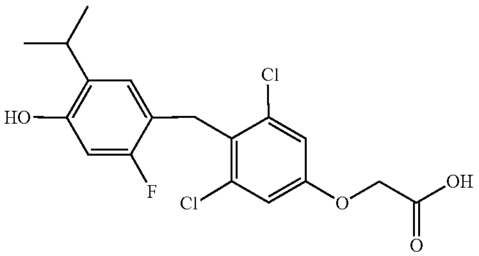 [SMILES: CC(C)c1cc(Cc2c(Cl)cc(OCC(=O)O)cc2Cl)c(F)cc1O] | 790 nM | 250 nM | 9.4 |
| 62 | 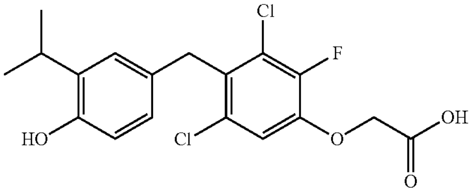 | 360 nM | 28 nM | 38 |

As indicated in Table 3, replacement of the 2'-H on the "outer-ring" of JD-21 (to give the compound of Example 15) improves potency at both TRα and TRβ receptors, but suppresses TRβ selectivity slightly. When the H-to-F replacement is made instead at the 4'- or 5'-positions on the outer-ring, potency is lost against both receptors. On the other hand, if one of the "inner-ring" hydrogen atoms is replaced with F (to give the compound of Example 62) both TRβ potency and TRβ-selectivity are improved. The effects of these modifications are not predictable a priori.

Example 169

In Vivo Activity

Animal Studies

Compounds of the current invention may be tested for thyroid-hormone receptor agonist activity in an in vivo model according to the following protocol.

Male Sprague-Dawley rats (~6 weeks old) are placed on a high cholesterol chow (HC Chow; 1.5% Cholesterol, 0.5% choline) for at least 10 days. Animals are weighed on Day −1. Test compounds are formulated in 1% NMP/1% solutol and dosed orally (PO), subcutaneously (SC) or intraperitoneally (IP) for 7 days, with each daily dose based on the body weight on that day. On Day 1 and Day 7, approximately 24 hrs after the first and last dose, respectively, blood samples are obtained via the saphenous vein, processed for serum and frozen at −80° C. Serum samples are analyzed for total cholesterol, LDL cholesterol and/or triglycerides using a clinical chemistry analyzer. If desired, test compound levels may be determined in these same samples by LCMS, comparing peak area to authentic standards. The rats are then anesthetized with isoflurane and an additional blood sample collected from the inferior vena cava or via cardiac puncture. Samples were again processed for serum, then analyzed for T3/T4/TSH levels by ELISA. Rats are terminated by exsanguination or pneumothorax; organs are harvested and weighed. Organ weight data are reported both as absolute values and as a percent of final body weight.

Compounds of the current invention may be tested for thyroid-hormone mediated remyelination according to the following protocol.

Eight week old, male and female iCKO-Myrf mice are treated with 100 OIL (20 mg/mL) tamoxifen i.p. daily for 5 days to induce oligodendrocyte depletion through deletion of Myrf from the mature oligodendrocytes (Koenning et al. 2012 J. Neuroscience). Test compounds are formulated into the food or formulated in 1% NMP/1% solutol and dosed PO, SC or IP starting at week 2, 5 or 12 after tamoxifen induction. Dosing frequency may be daily (QD), every other day (Q2D), three times a week (QIW) or weekly (QW). The functional impact of central demyelination is measured by subjecting the mice to an accelerating rotorod technique where the time at which the mice fall off of a rotating rod is indicative of their neuromuscular function. Mice are subjected to the rotorod protocol weekly, every other week or at specific times during the study. Loss of myelination is associated with decreased time such that a nadir in ability occurs around 12 weeks after tamoxifen treatment. Partial recovery occurs from 12-24 weeks. Mice are sacrificed at 24 weeks after tamoxifen induction and brain and spinal cord tissues examined for remyelination using histologic analysis.

Compounds of the current invention may be tested for thyroid-hormone mediated inhibition of fibrosis according to the following protocol.

Adult male, C57Bl/6 mice are induced with pulmonary fibrosis through a single oropharangeal (OP) administration of 1.5-2 U/kg of bleomycin. Test compounds are formulated in 1% NMP/1% solutol and dosed PO, SC or IP, QD starting at day −1 (prophylactic) or Day 7 (therapeutic) after bleomycin administration. On Day 21, mice are anesthetized and blood drawn via cardiac puncture. Lungs are excised and weighed, subjected broncheoalveolar lavage, inflated and fixed for histologic analysis. Lung samples are embedded in paraffin and stained with hematoxylin and eosin and Masson's trichrome stain. A pathologist evaluates degree of fibrosis using the Ashcroft's score to quantify fibrosis. A minimum of 10 sites per lung are assessed and an average score reported for each lung.

Tissue Distribution Studies

For tissue concentration studies in male C57Bl/6 mice, test compounds are formulated as NMP/solutol/PBS solution, at a concentration of 0.05 mg/mL and dosed at 2 mL/kg with the targeted dose of 0.100 mg/kg via SC injection or oral dosing. Plasma, brain, liver, lung, kidney, heart and other selected tissue samples are collected at 1, 4 and 24 hr (for AUC determination) or 1 hr (single time point) post-dose with three animals per time point. Tissue homogenates and plasma concentrations of test compounds are determined using LC-MS/MS with lower limits of quantitation of 0.0200 ng/mL or 0.100 ng/g. The pharmacokinetic parameters are determined by non-compartmental methods using WinNonlin. Area under the drug curves (AUC) values are determined by trapezoidal approximation; tissue-to-tissue ratios are determined by comparing AUC values.

TABLE 4

| Compound No. | AUC(4-hr) Liver* | AUC(4-hr) Heart* | L/H ratio |
|---|---|---|---|
| T3 | 395 | 120 | 2.5 |
| 15 | 580 | 25.8 | 22.5 |
| 62 | 550 | 24.4 | 22.5 |

*in ng-hr/g of tissue

Cardiotoxicity is a limiting safety event for many thyroid hormone agonists; one strategy for improving the safety of thyromimetics is to restrict tissue distribution to limit drug exposure in the heart. The results in Table 4 indicate that compounds of the present invention can produce elevated drug levels in target tissues like the liver, while reducing levels in toxicity-target tissues like the heart, providing an improved liver-to-heart drug exposure ratio and presumably suppressing cardiotoxicity.

Amide prodrugs of the present invention can be processed by fatty-acid amide hydrolase enzyme (FAAH), the levels of which are elevated in tissues like the brain. Thus, amide prodrugs have the ability to selectively elevate brain levels of the corresponding parent acid, as demonstrated in FIG. 1. FIG. 1 depicts brain levels of Compound 15 recorded after PO dosing (0.1 mg/kg) of Compound 15 itself, or the corresponding amide prodrugs Compound 16 and 17. Compound 16 (Formula (I): $X^1$=Cl, $X^2$=Cl, $Y^1$=F, $Y^2$=H, $R^2$=iPr, $R^1$=NHMe), a brain-targeted prodrug of Compound 15 (Formula (I): $X^1$=Cl, $X^2$=Cl, $Y^1$=F, $Y^2$=H, $R^2$=iPr, $R^1$=OH), shows a dramatic increase in brain concentration of the parent acid when compared to dosing the parent acid Compound 15 itself. Compound 17 (Formula (I): $X^1$=Cl, $X^2$=Cl, $Y^1$=F, $Y^2$=H, $R^2$=iPr, $R^1$=$NMe_2$) also shows an increase in the brain concentration of the parent acid Compound 15 when compared to dosing the parent acid Compound 15 itself, though the effect is less dramatic in this case. As indicated in FIG. 1, in each case levels of the parent acid are measured ("BLOQ"=below level of quantitation; "LOQ"=level of quantitation). As a consequence, Compounds 16 and 17 are expected to have superior potency in targeting indications for which brain drug levels are predictive of activity.

Gene Activation

Adult male Sprague-Dawley rats or C57BL/6 mice are dosed orally with test compounds at up to 3 dose levels (e.g. 1×, 3× and 10× higher than the $ED_{50}$ values obtained in the cholesterol lowering studies described above). At predefined times, 4, 8 or 24 hrs after test compound administration, rodents are anesthetized and blood drawn for plasma samples to measure drug concentrations. Samples of multiple organs including, but not limited to, liver, brain, kidney, heart, lung, skeletal muscle, pituitary and testes, are harvested and processed for RNA analysis. Samples are analyzed either by RNA-Seq after RNA isolation or by targeted gene analysis using an appropriate platform such as Quantigene™ which does not require RNA isolation. Multiple genes are used to represent a T3-mediated gene signature in each tissue; different genes are used for each tissue and all are normalized to multiple housekeeping genes that account for any variability in overall RNA quality.

Conversion Studies

Amides of Formula II may be converted to active agonist acids of Formula IV through the action of amidases such as FAAH. Similarly, esters of Formula III may be converted to active agonist acids of Formula IV through the action of various esterases. This in vivo conversion can be demonstrated through pharmacokinetics studies which measure the level of test compounds as described below:

The pharmacokinetics of test compounds are evaluated following IV, PO or SC administration to fasted male Sprague-Dawley rats (N=3/route/dose). Test compounds are dosed as clear solutions in NMP/solutol/PBS, at a concentration of 0.1 mg/mL as a single dose via IV injection (0.1 mg/kg) or orally (1 mg/kg) or subcutaneous injection (SC, 0.1 mg/kg). Blood samples are collected into K2EDTA tubes at pre-dose, 0.083, 0.25, 0.5, 1, 2, 4, 8, and 24 hours post-dose administration. Plasma concentrations of test compounds are determined using LC-MS/MS with a lower limit of quantitation of 0.0200 ng/mL. The pharmacokinetic parameters are determined by non-compartmental methods using WinNonlin.

All of the U.S. patents, U.S. patent application publications, U.S. patent applications, foreign patents, foreign patent applications and non-patent publications referred to in this specification and/or listed in the Application Data Sheet are incorporated herein by reference, in their entirety. In addition, the terms used in the following claims should not be construed as limited to the specific embodiments disclosed in the specification, but should be construed to include all possible embodiments along with the full scope of equivalents to which such claims are entitled.

The invention claimed is:

1. A compound having the structure of Formula (I):

(I)

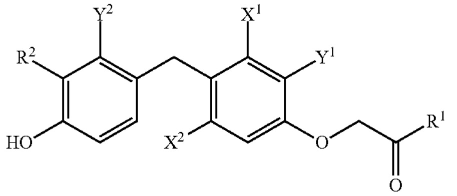

or a pharmaceutically acceptable hydrate, solvate, isotope, or salt thereof, wherein:

$X^1$ is lower alkyl, lower alkenyl, lower haloalkyl, or halo;

$X^2$ is lower alkyl, lower alkenyl, lower haloalkyl, or halo;

$Y^1$ and $Y^2$ are each, independently, H, cyano, halogen, lower alkyl, or lower alkoxy, wherein at least one of $Y^1$ and $Y^2$ is not H;

$R^1$ is —$NR^{1a}R^{1b}$ or —$OR^{1c}$;

$R^{1a}$ and $R^{1b}$ are each, independently, H, lower alkyl, lower alkenyl, lower alkynyl, carbocycle, carbocyclealkyl, heterocycle, or heterocyclealkyl, or $R^{1a}$ and $R^{1b}$ taken together with the nitrogen atom to which they are attached form heterocycle;

$R^{1c}$ is H, lower alkyl, carbocycle, heterocycle, carbocyclealkyl, or heterocyclealkyl; and $R^2$ is lower alkyl, lower alkenyl, carbocycle, heterocycle, carbocyclealkyl, or heterocyclealkyl;

wherein $R^{1a}$, $R^{1b}$, $R^{1c}$, and $R^2$ are each, independently, optionally substituted with one or more halo, lower alkyl, lower haloalkyl, cyano, —OR', —NR'R", =O, =S, —$S(O)_2R'$ or —$S(O)_2OR'$, wherein R' and R" are each, independently, H, lower alkyl, or lower haloalkyl.

2. The compound of claim 1, or a pharmaceutically acceptable hydrate, solvate, isotope, or salt thereof, wherein $R^2$ is lower alky 1 optionally substituted with one or more halo, cyano, —OR', —NR'R", =O, =S, —$S(O)_2R'$ or —$S(O)_2OR'$, wherein R' and R" are each, independently, H, lower alkyl, or lower haloalkyl.

3. The compound of claim 2, or a pharmaceutically acceptable hydrate, solvate, isotope, or salt thereof, wherein $R^2$ is unsubstituted lower alkyl.

4. The compound of claim 3 having the structure of Formula (II-A):

(II-A)

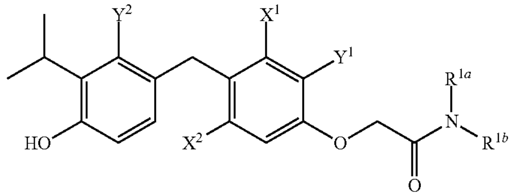

or a pharmaceutically acceptable hydrate, solvate, isotope, or salt thereof, wherein:

$X^1$ is lower alkyl, lower alkenyl, lower haloalkyl, or halo;

$X^2$ is lower alkyl, lower alkenyl, lower haloalkyl, or halo;

$Y^1$ and $Y^2$ are each, independently, H, cyano, halogen, lower alkyl, or lower alkoxy, wherein at least one of $Y^1$ and $Y^2$ is not H; and $R^{1a}$ and $R^{1b}$ are each, independently, H, lower alkyl, lower alkenyl, lower alkynyl, carbocycle, carbocyclealkyl, heterocycle, or heterocyclealkyl, or $R^{1a}$ and $R^{1b}$ taken together with the nitrogen atom to which they are attached form heterocycle;

wherein $R^{1a}$ and $R^{1b}$ are each, independently, optionally substituted with one or more halo, cyano, —OR', —NR'R", =O, =S, —$S(O)_2R'$ or —$S(O)_2OR'$, wherein R' and R" are each, independently, H, lower alkyl, or lower haloalkyl.

5. The compound of claim 4, or a pharmaceutically acceptable hydrate, solvate, isotope, or salt thereof, wherein $R^{1a}$ is lower alkyl and $R^{1b}$ is H.

6. The compound of claim 4, or a pharmaceutically acceptable hydrate, solvate, isotope, or salt thereof, wherein $X^1$ is lower alkyl.

7. The compound of claim 4, or a pharmaceutically acceptable hydrate, solvate, isotope, or salt thereof, wherein $X^1$ is halo.

8. The compound of claim 4, or a pharmaceutically acceptable hydrate, solvate, isotope, or salt thereof, wherein $X^2$ is lower alkyl.

9. The compound of claim 4, or a pharmaceutically acceptable hydrate, solvate, isotope, or salt thereof, wherein $X^2$ is halo.

10. The compound of claim 4, or a pharmaceutically acceptable hydrate, solvate, isotope, or salt thereof, wherein $X^1$ is Cl and $X^2$ is Cl.

11. The compound of claim 4, or a pharmaceutically acceptable hydrate, solvate, isotope, or salt thereof, wherein $Y^1$ is halogen.

12. The compound of claim 11, or a pharmaceutically acceptable hydrate, solvate, isotope, or salt thereof, wherein $Y^1$ is F.

13. The compound of claim 4, or a pharmaceutically acceptable hydrate, solvate, isotope, or salt thereof, wherein $Y^1$ is H.

14. The compound of claim 4, or a pharmaceutically acceptable hydrate, solvate, isotope, or salt thereof, wherein $Y^2$ is halogen.

15. The compound of claim 14, or a pharmaceutically acceptable hydrate, solvate, isotope, or salt thereof, wherein $Y^2$ is F.

16. The compound of claim 4, or a pharmaceutically acceptable hydrate, solvate, isotope, or salt thereof, wherein $Y^2$ is H.
17. The compound of claim 1, or a pharmaceutically acceptable hydrate, solvate, isotope, or salt thereof, having the structure of any one of the following compounds:
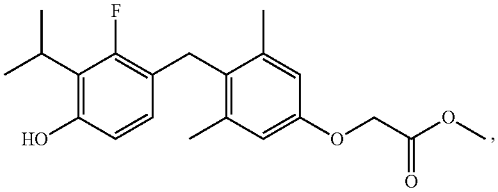,
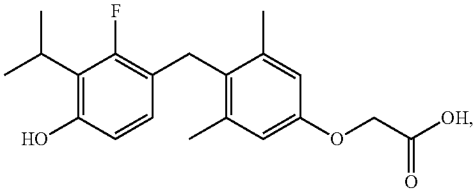,
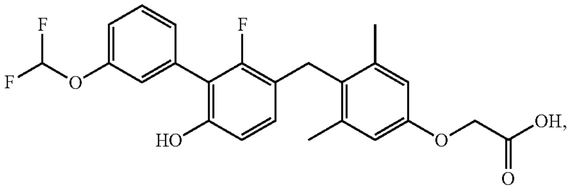,
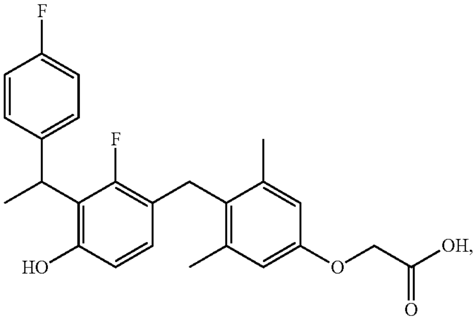,
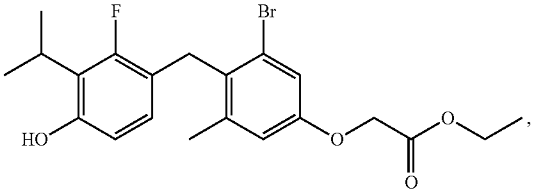,
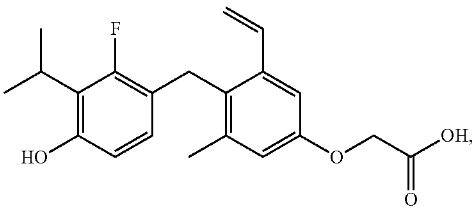,
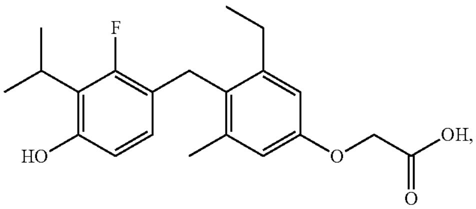,
-continued
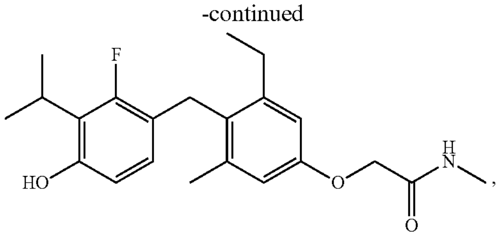,
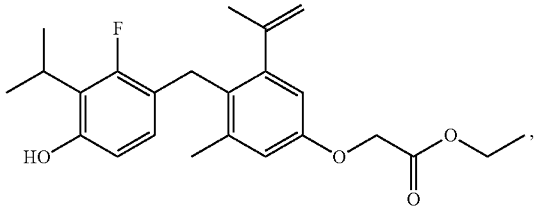,
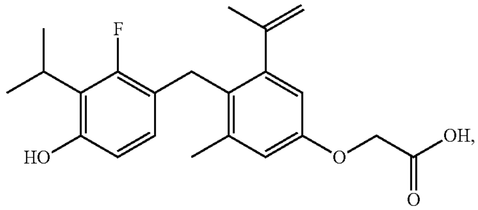,
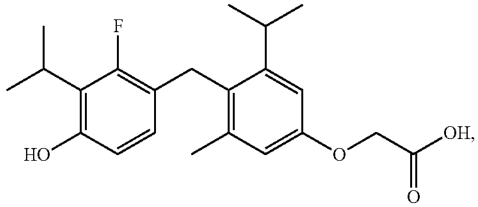,
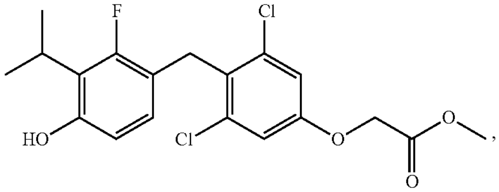,
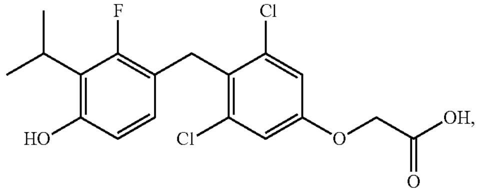,
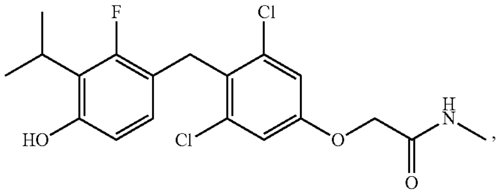,
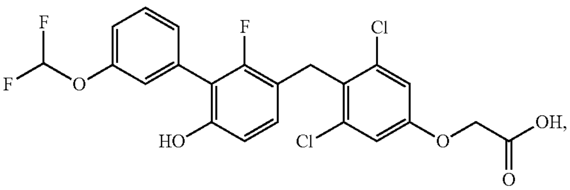, -continued
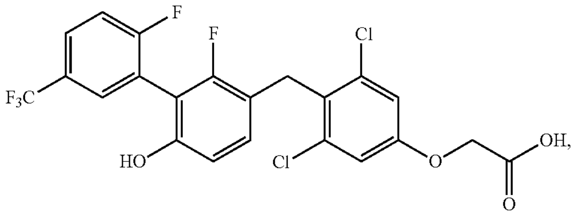
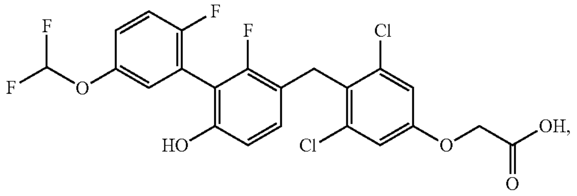
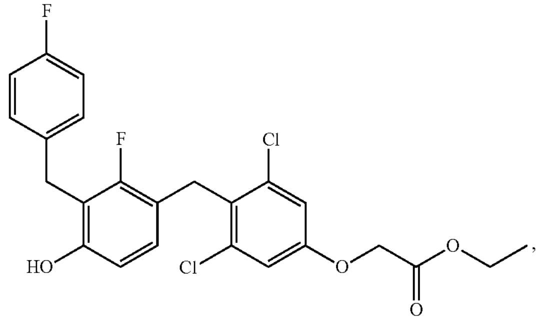
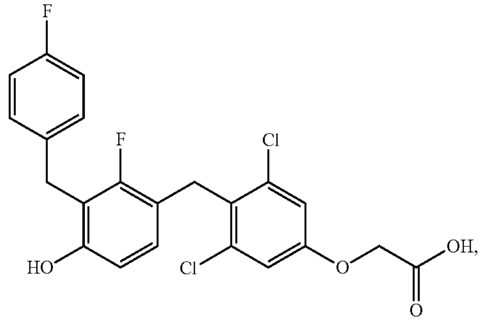
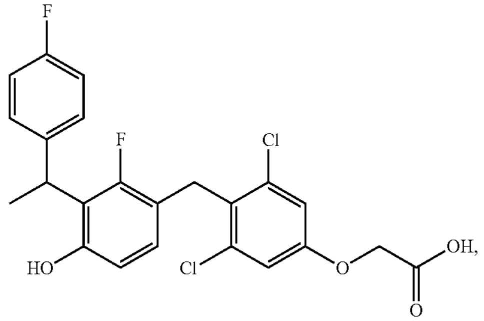
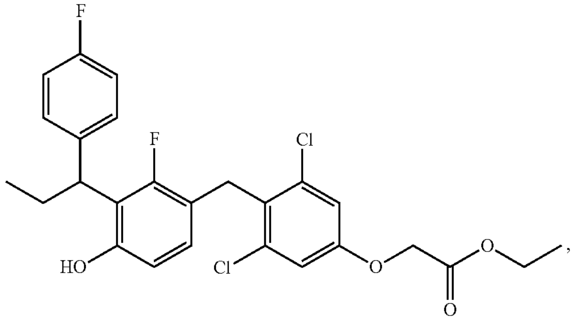
-continued
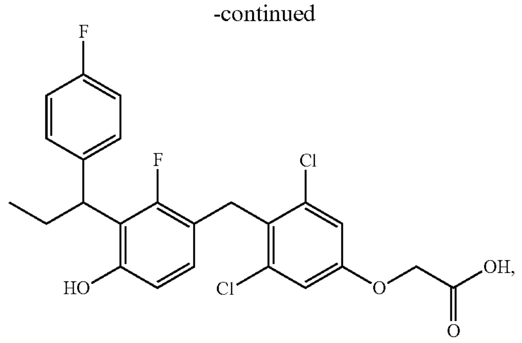
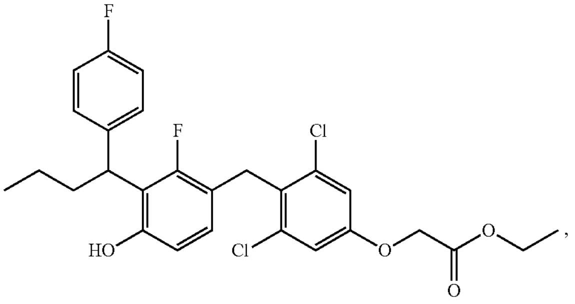
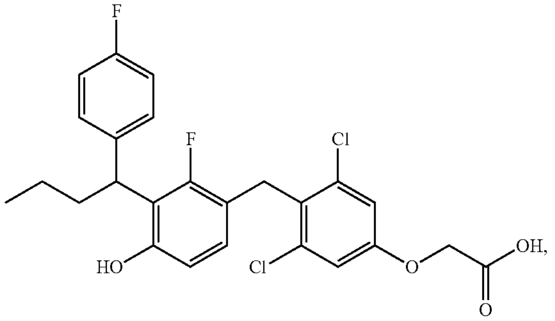
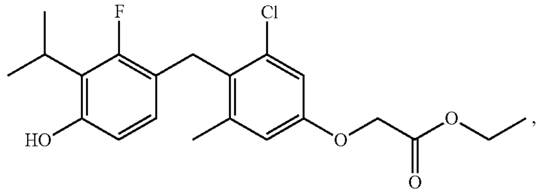
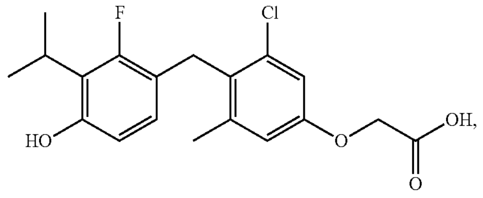
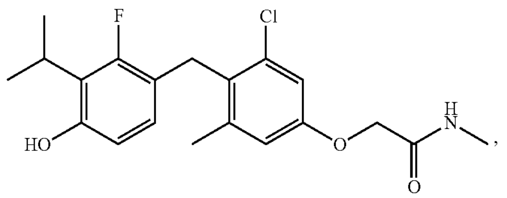
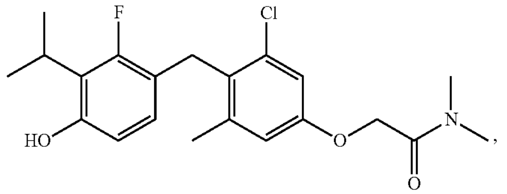

-continued
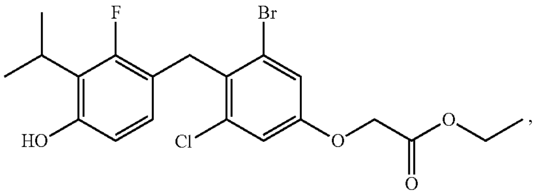
,
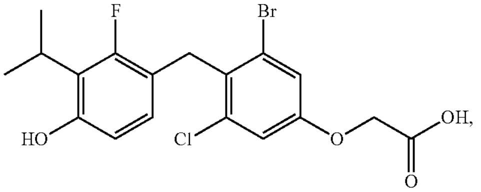
,
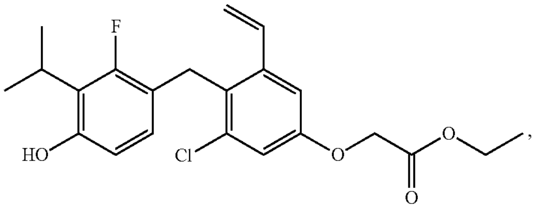
,
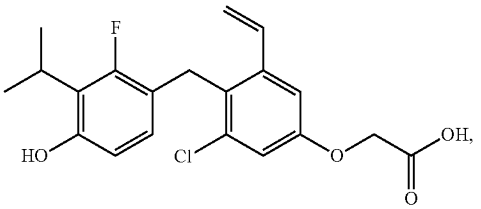
,
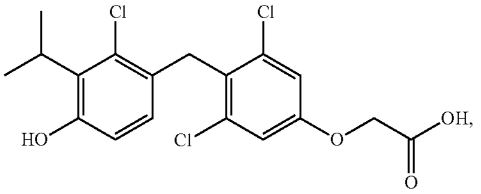
,
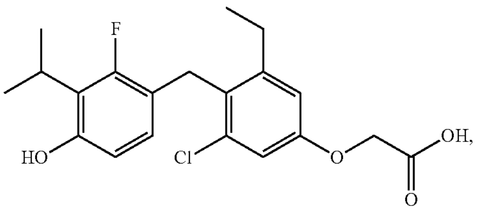
,
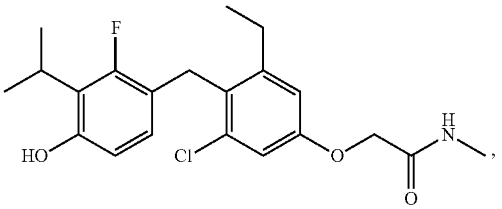
,
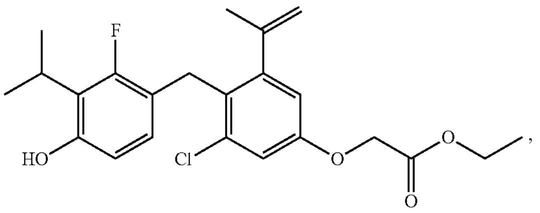
,
-continued
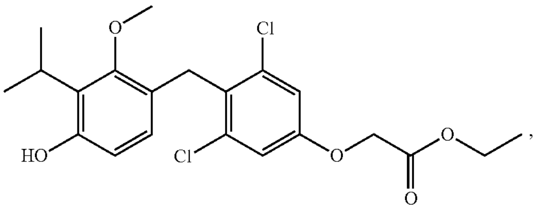
,
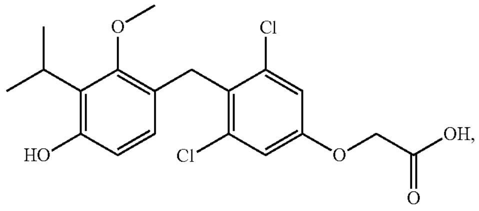
,
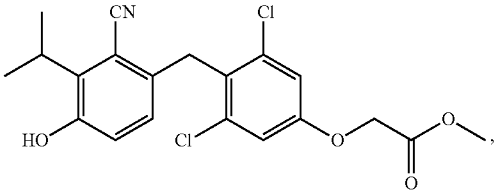
,
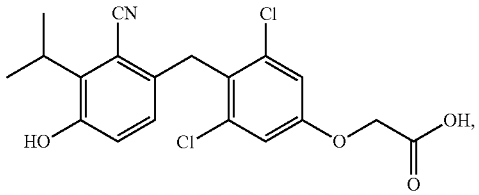
,
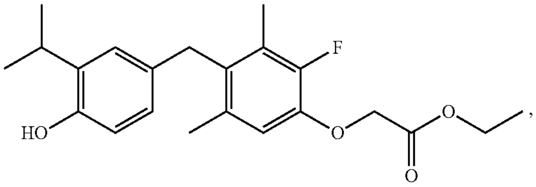
,
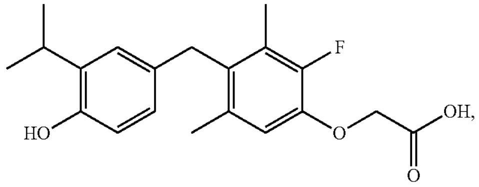
,
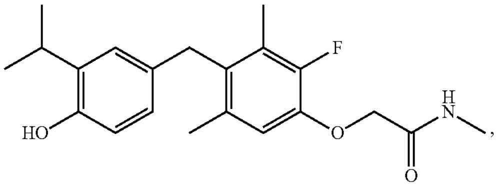
,
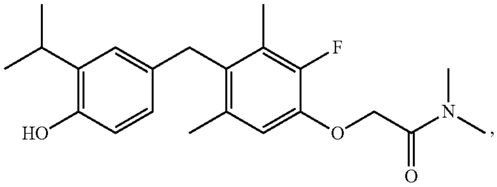
, -continued
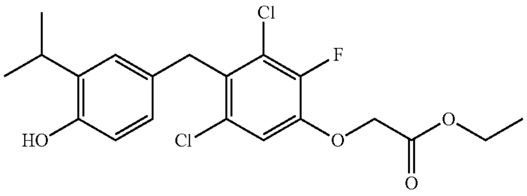
,
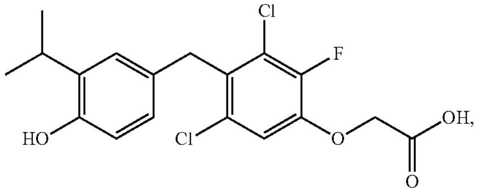
,
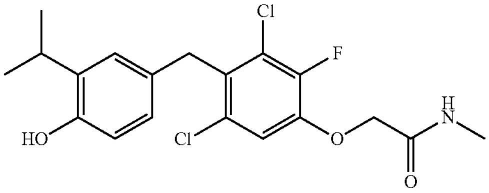
,
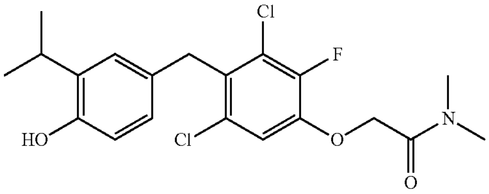
,
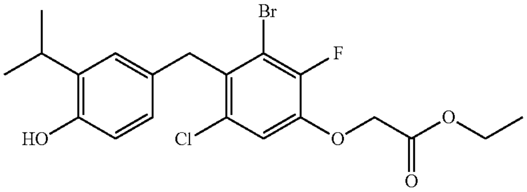
,
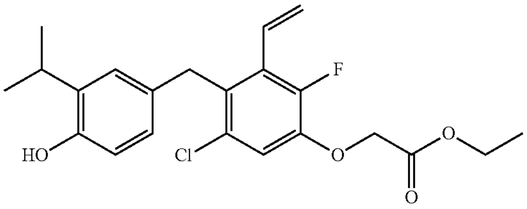
,
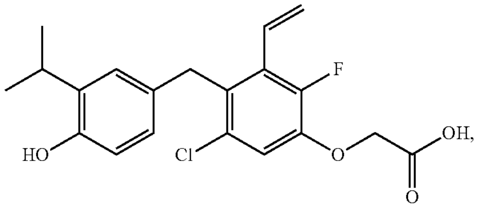
,
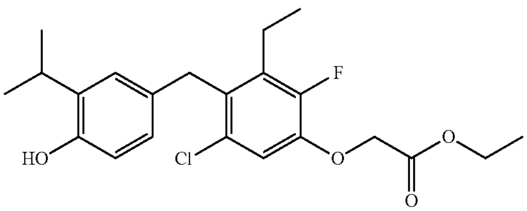
,
-continued
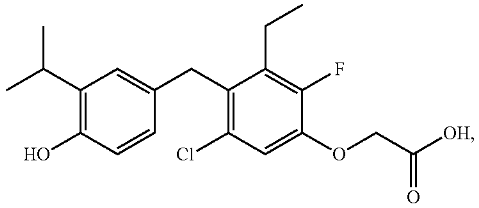
,
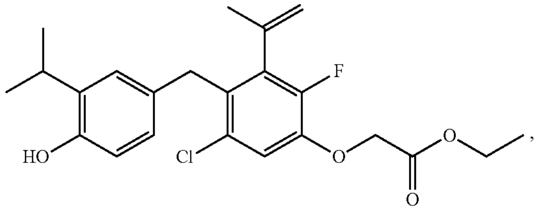
,
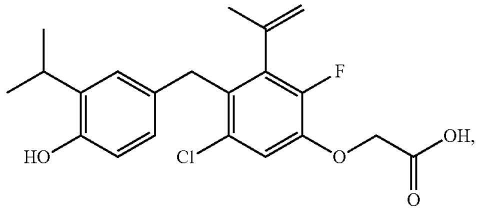
,
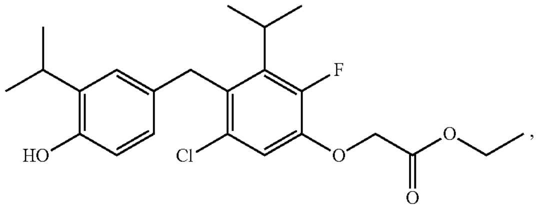
,
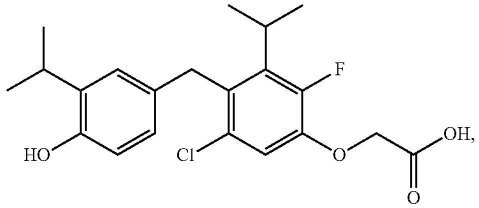
,
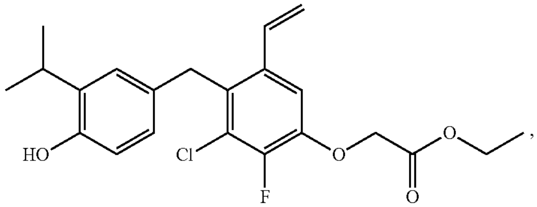
,
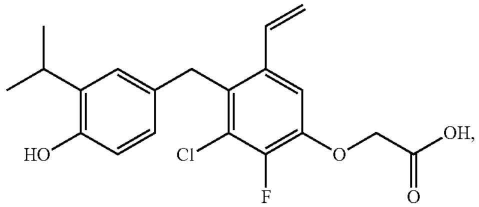
,
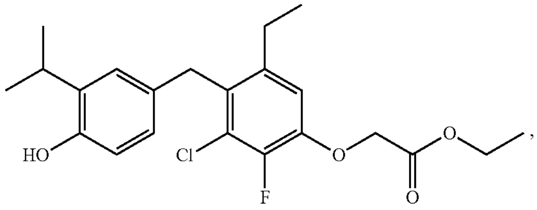
, -continued
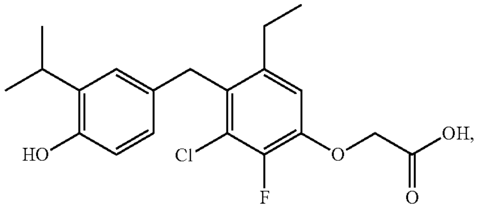
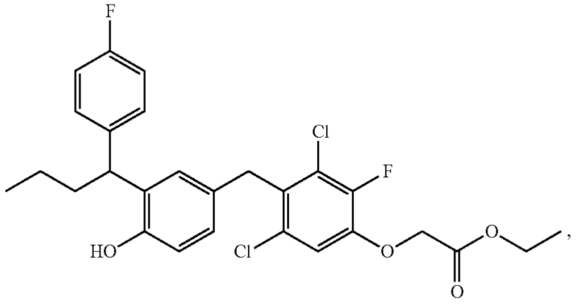
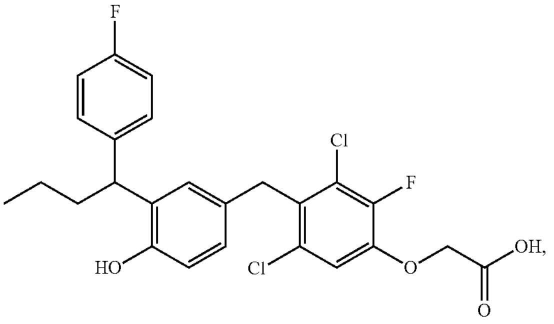
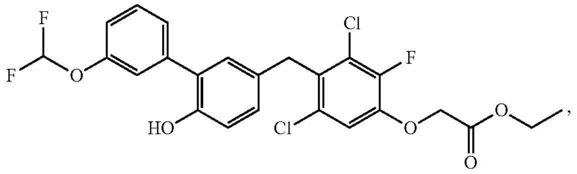
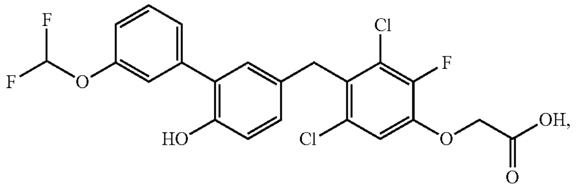
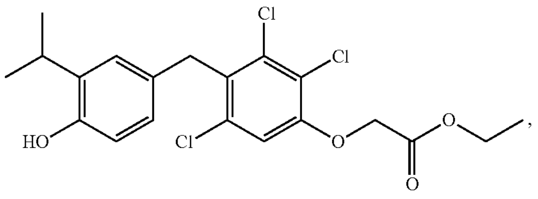
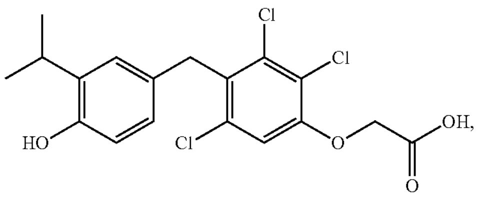
-continued
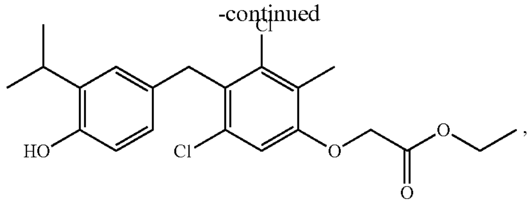
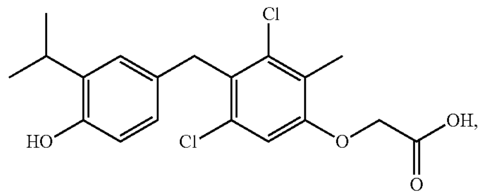
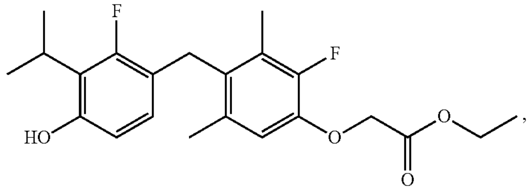
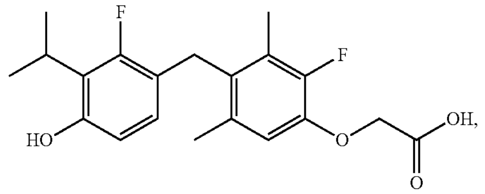
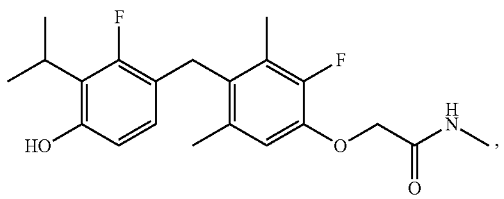
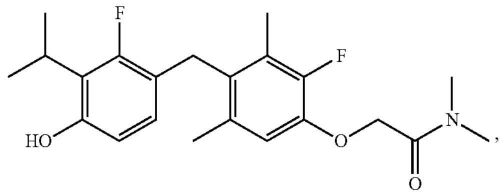
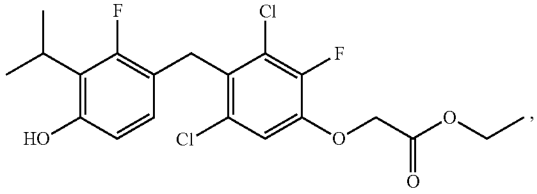
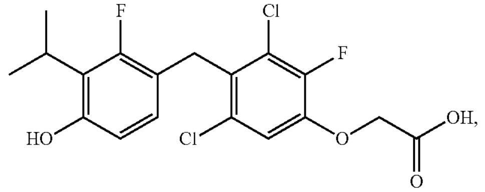
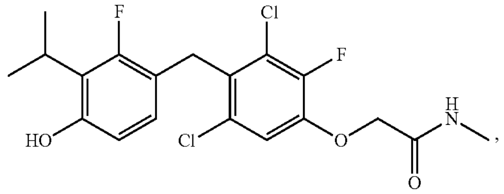

-continued
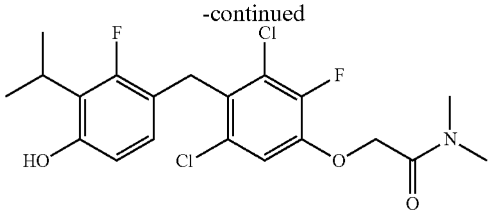,
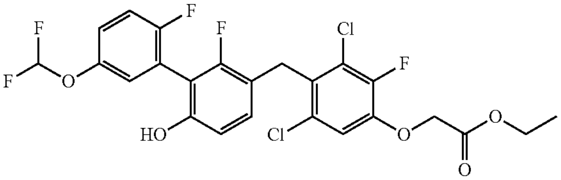,
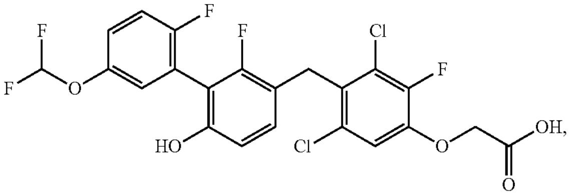
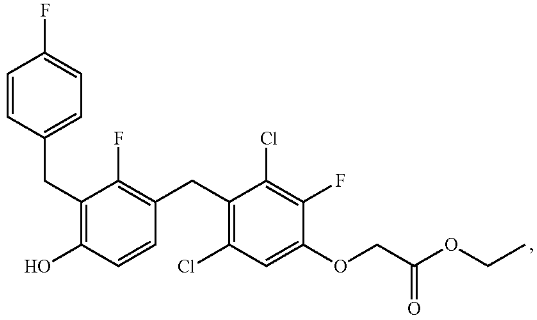,
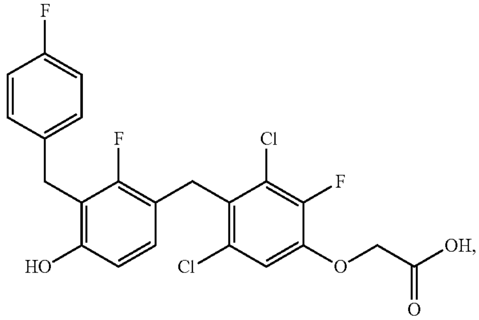
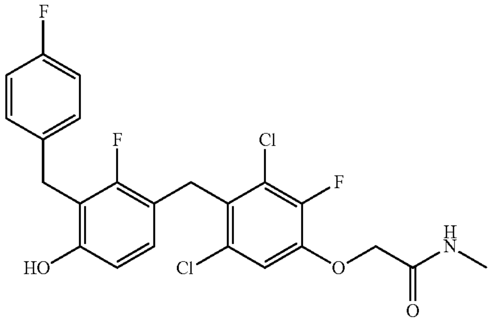,
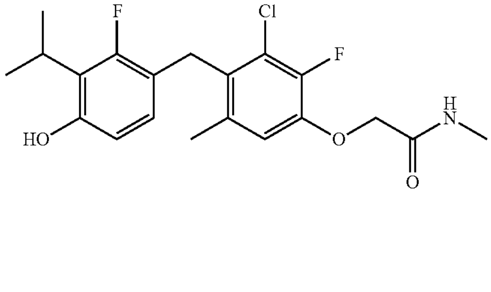,
-continued
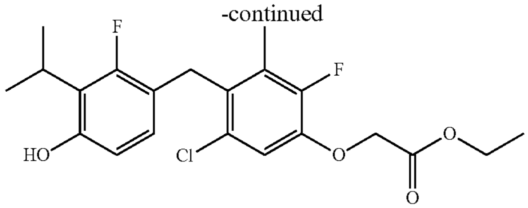,
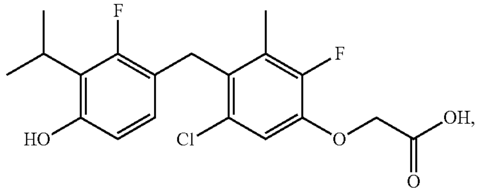
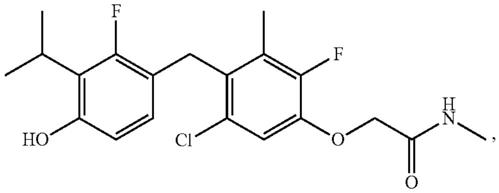,
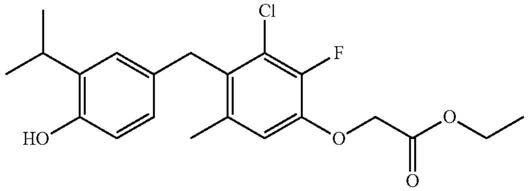,
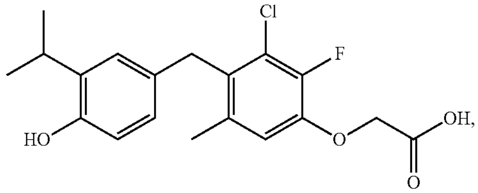
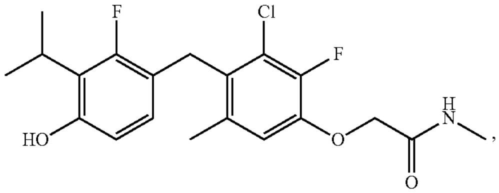,
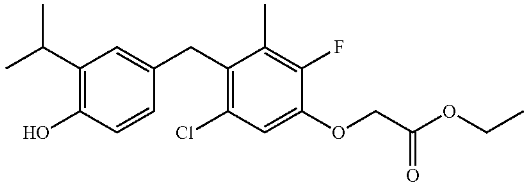,
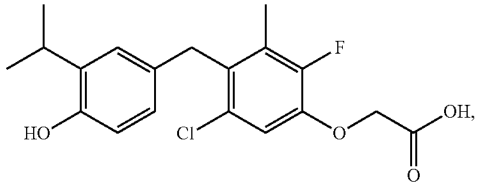
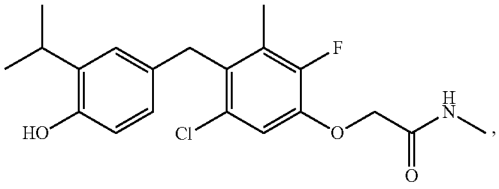, -continued
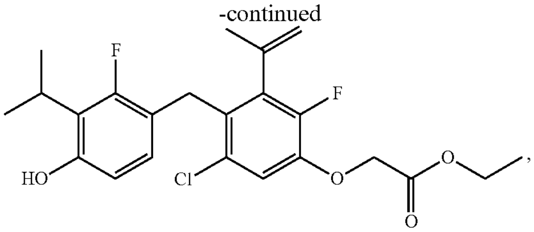
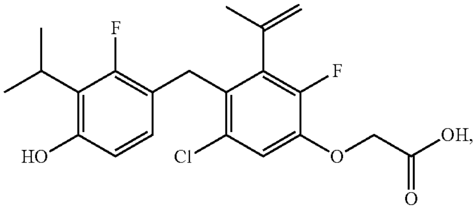
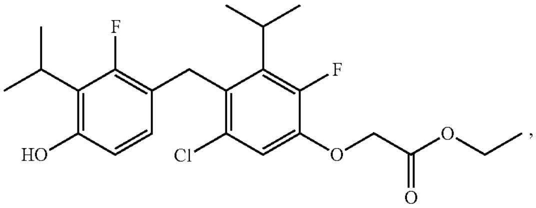
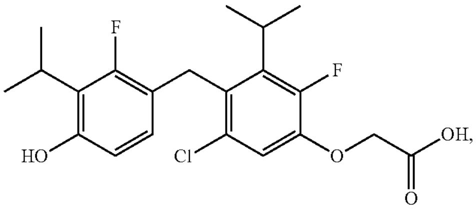
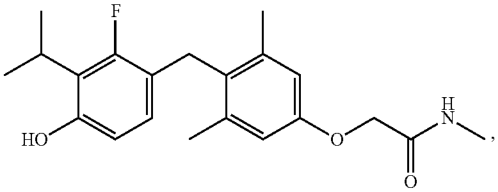
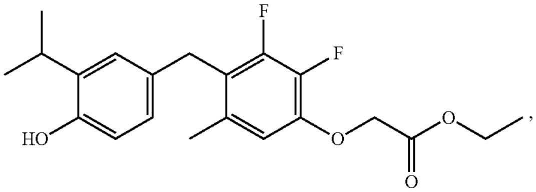
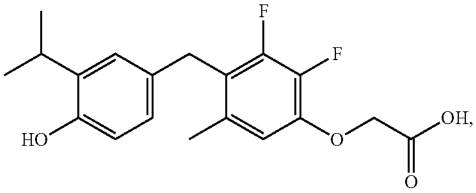
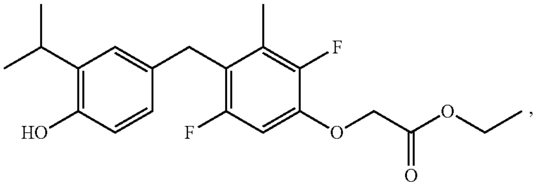
-continued
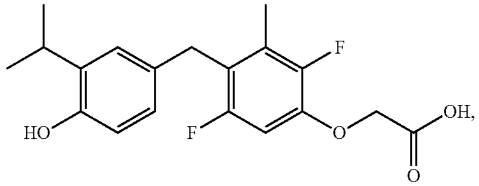
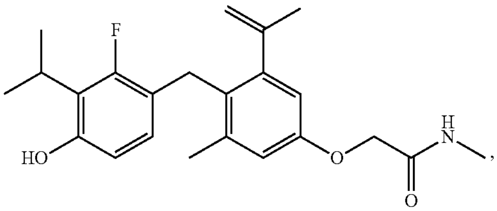
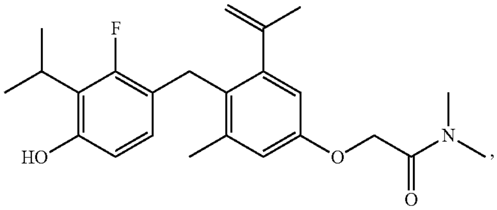
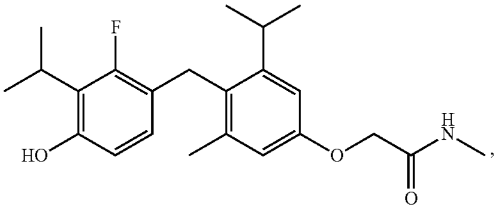
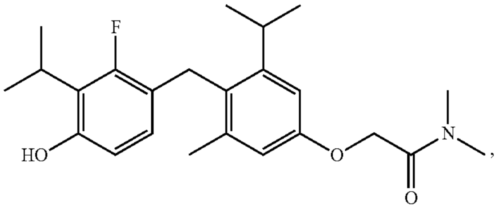
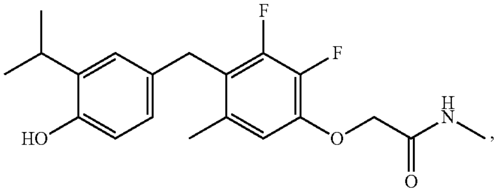
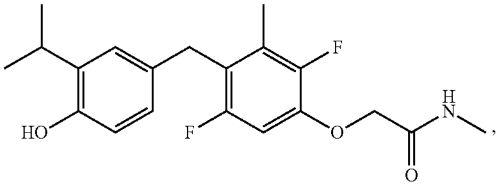
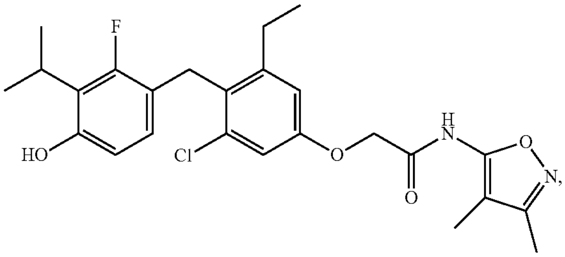

-continued
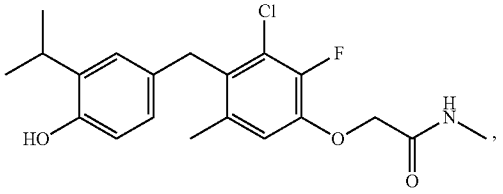
,
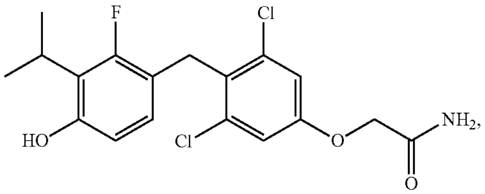
,
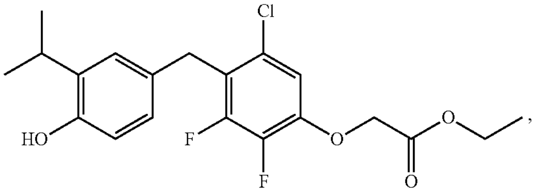
,
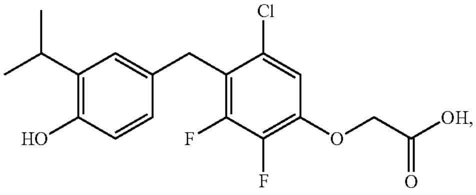
,
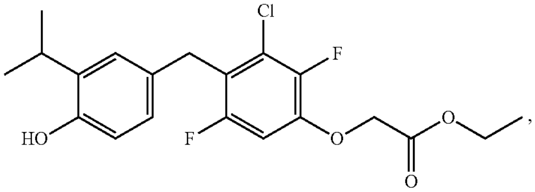
,
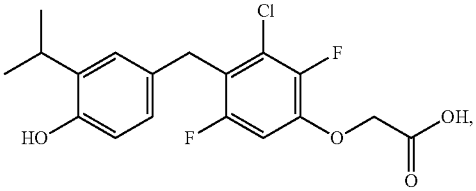
,
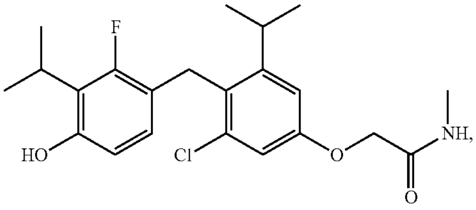
,
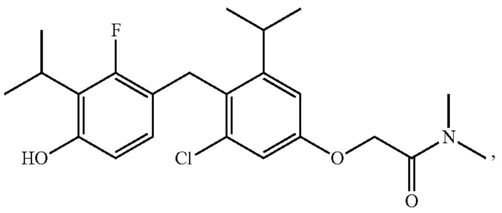
,
-continued
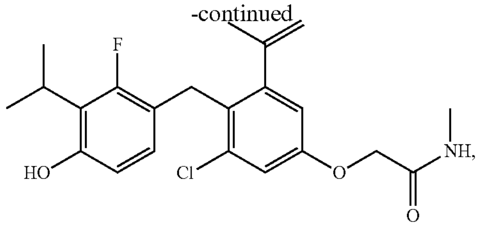
,
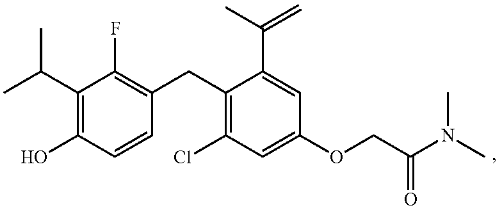
,
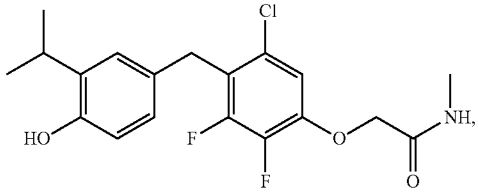
,
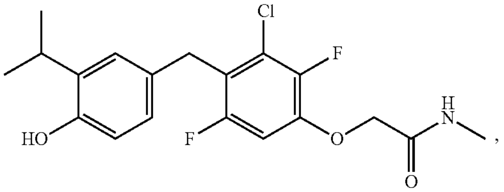
,
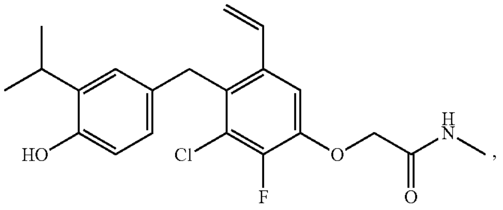
,
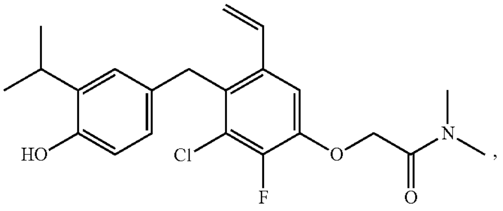
,
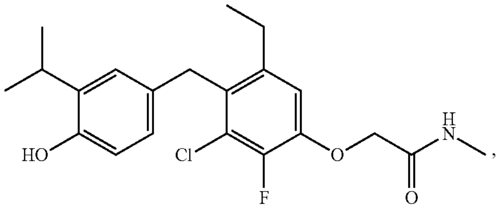
,
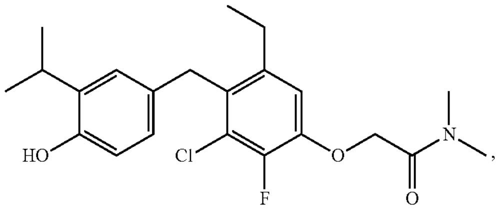
, -continued
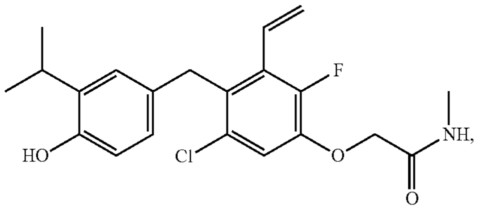
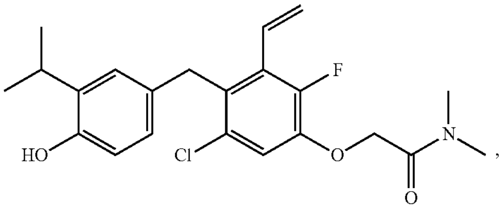
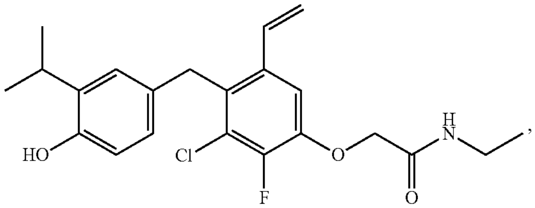
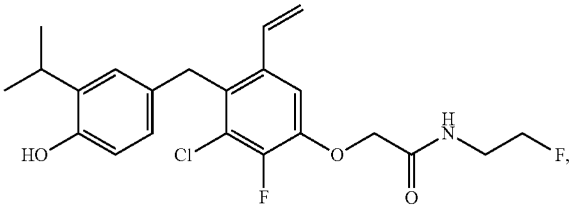
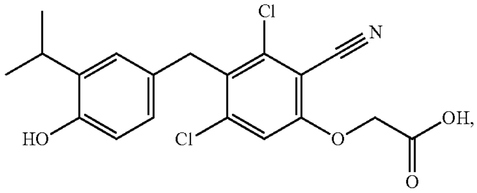
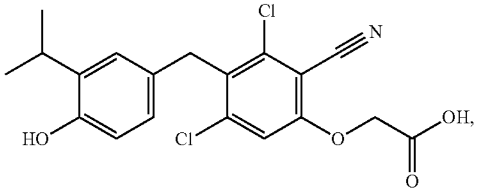
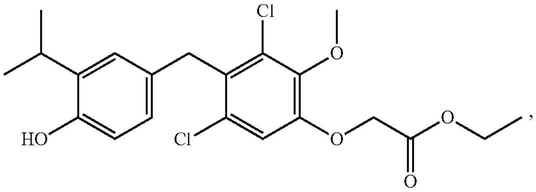
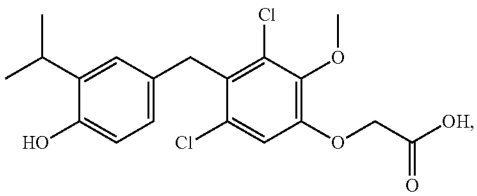
-continued
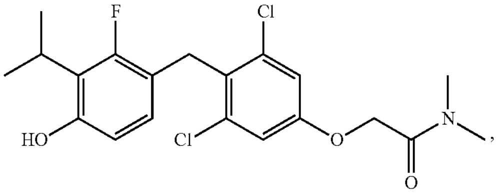
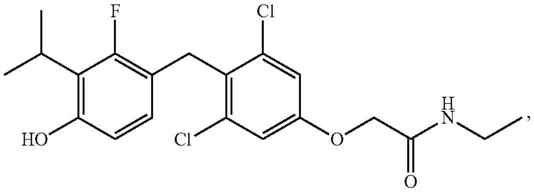
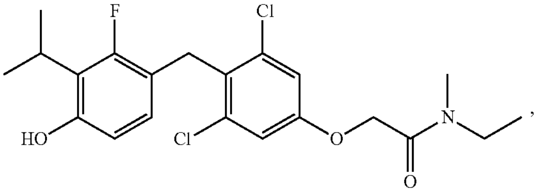
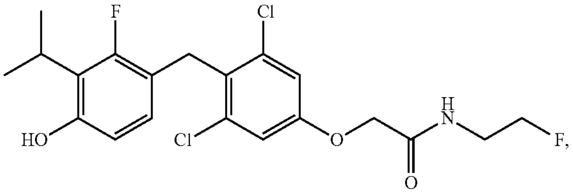
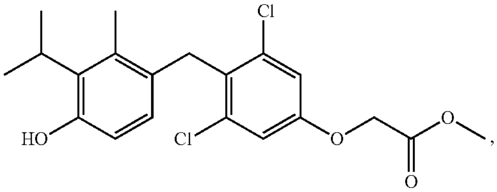
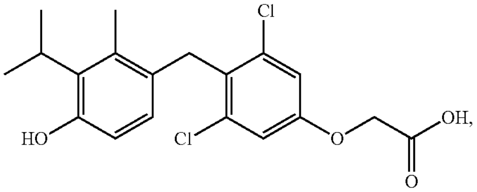
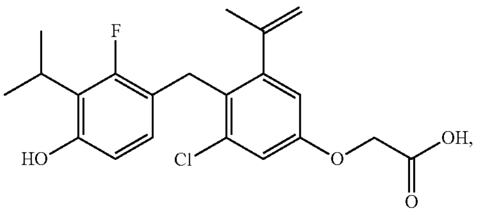
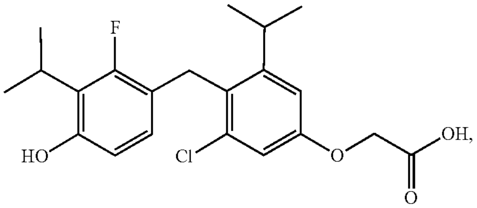

-continued
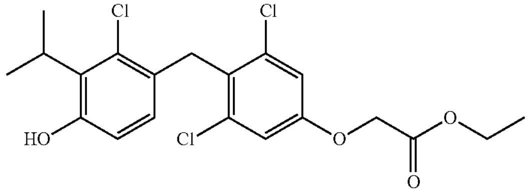
,
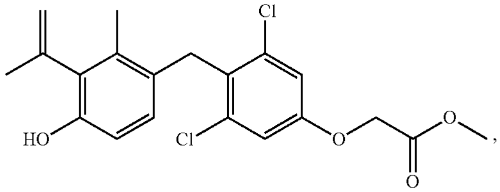
,
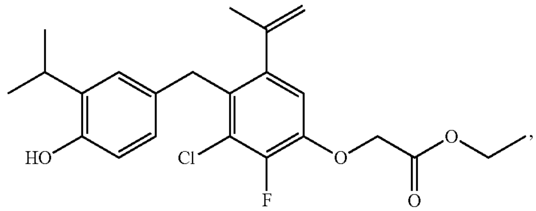
,
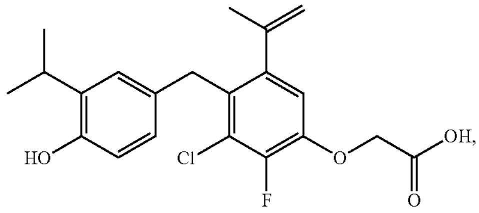
,
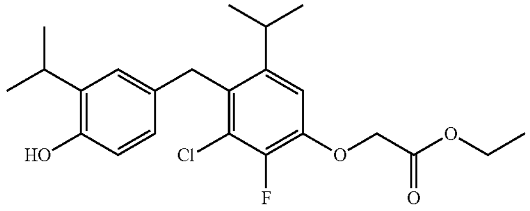
,
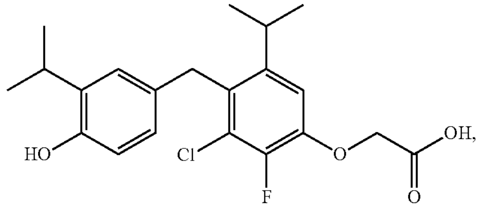
,
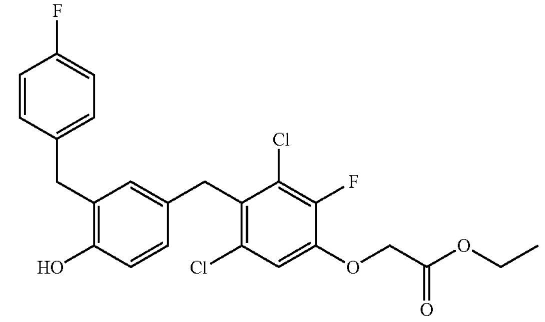
,
-continued
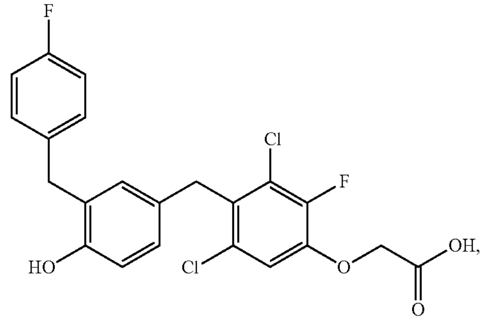
,
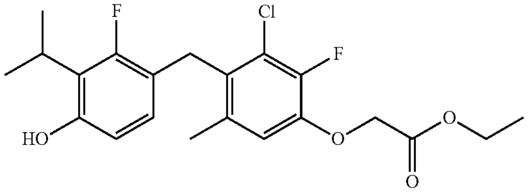
,
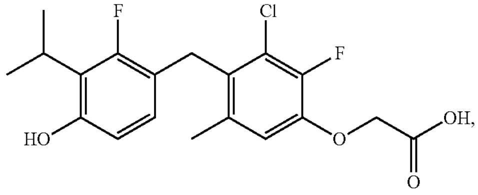
,
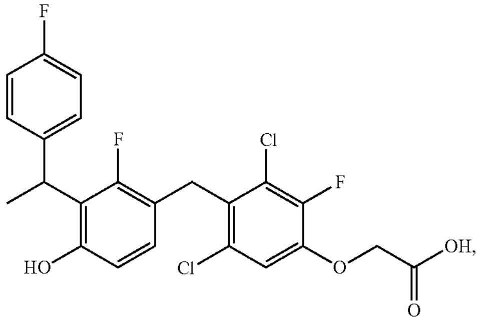
,
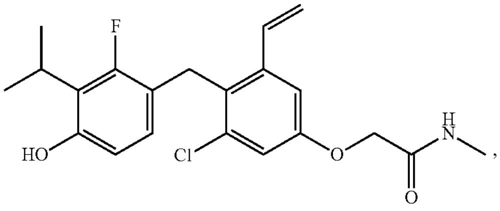
,
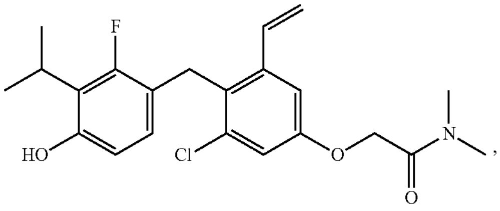
,
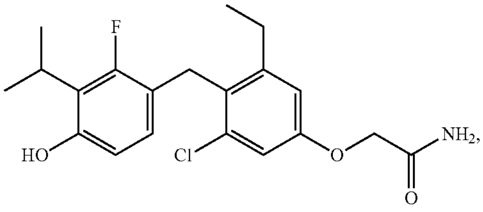
, -continued

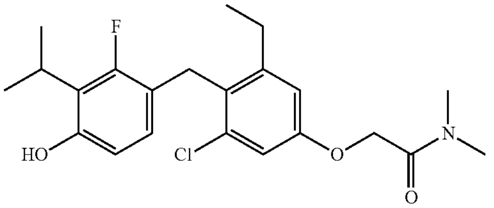

,

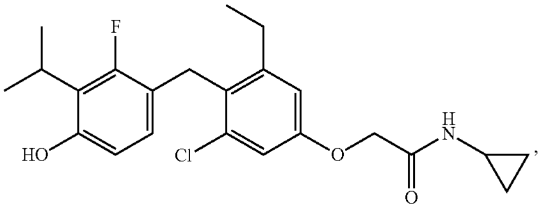

,

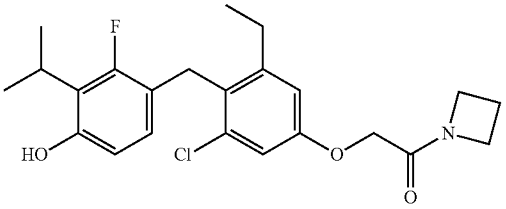

,

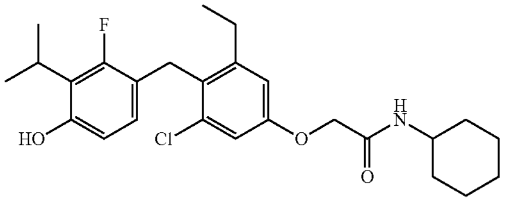

, and

-continued

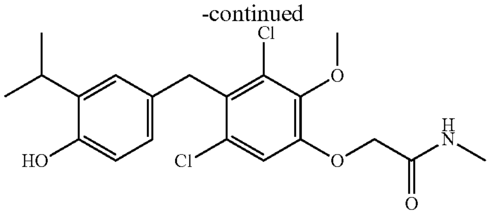

.

18. A pharmaceutical composition comprising a compound of claim 1, or a pharmaceutically acceptable hydrate, solvate, isotope, or salt thereof, and a pharmaceutically acceptable excipient.

19. A method of treating a subject having a neurodegenerative disease comprising administering to the subject in need thereof a pharmaceutically effective amount of a compound of claim 1, or a pharmaceutically acceptable salt thereof.

20. The method of claim 19, wherein the neurodegenerative disease is adult Refsum disease, Alexander disease, Alzheimer's disease, Balo concentric sclerosis, Canavan disease, central pontine myelinolysis, cerebral palsy, cerebrotendineous xanthomatosis, chronic inflammatory demyelinating polyneuropathy, Devic's syndrome, diffuse myelinoclastic sclerosis, idiopathic inflammatory demyelinating disease, infantile Refsum disease, Krabbe disease, Leber hereditary optic neuropathy, Marburg multiple sclerosis, Marchiafava-Bignarni disease, metachromatic leukodystrophy, multifocal motor neuropathy, paraproteinemic demyelinating polyneuropathy, Pelizaeus-Merzbacher disease, peroneal muscular atrophy, progressive multifocal leukoencephalopathy, transverse myelitis, tropical spastic paraparesis, van der Knaap disease, X-linked adrenoleukodystrophy, or Zellweger syndrome.

* * * * *